(12) United States Patent
Taniguchi et al.

(10) Patent No.: US 8,575,167 B2
(45) Date of Patent: Nov. 5, 2013

(54) SPIRO COMPOUNDS HAVING STEAROYL-COA DESATURASE ACTION

(75) Inventors: Takahiko Taniguchi, Osaka (JP); Kenichi Miyata, Ibaraki (JP); Osamu Kubo, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 885 days.

(21) Appl. No.: 12/449,320

(22) PCT Filed: Feb. 5, 2008

(86) PCT No.: PCT/JP2008/051849
§ 371 (c)(1),
(2), (4) Date: Aug. 3, 2009

(87) PCT Pub. No.: WO2008/096746
PCT Pub. Date: Aug. 14, 2008

(65) Prior Publication Data
US 2010/0069351 A1 Mar. 18, 2010

(30) Foreign Application Priority Data

Feb. 6, 2007 (JP) ................................. 2007-027404
May 25, 2007 (JP) ................................. 2007-139645

(51) Int. Cl.
| | | |
|---|---|---|
| A61K 31/50 | (2006.01) |
| C07D 401/00 | (2006.01) |
| A61P 3/04 | (2006.01) |
| A61P 3/06 | (2006.01) |
| A61P 7/12 | (2006.01) |
| A61P 9/12 | (2006.01) |
| A61P 9/04 | (2006.01) |
| A61P 9/00 | (2006.01) |
| A61P 9/10 | (2006.01) |

(52) U.S. Cl.
USPC ..................................... 514/252.04; 544/238

(58) Field of Classification Search
USPC ............ 544/238; 514/252.03, 252.05, 252.04
See application file for complete search history.

(56) References Cited

U.S. PATENT DOCUMENTS 4,624,952 A 11/1986 Biziere et al.

FOREIGN PATENT DOCUMENTS

| WO | 00/23444 | 4/2000 |
|---|---|---|
| WO | 01/42241 | 6/2001 |
| WO | 2003/029245 | 4/2003 |
| WO | 2005/011653 | 2/2005 |
| WO | 2005/011654 | 2/2005 |
| WO | 2005/011655 | 2/2005 |
| WO | 2005/011656 | 2/2005 |
| WO | 2005/011657 | 2/2005 |
| WO | 2006/023630 | 3/2006 |
| WO | 2006/034279 | 3/2006 |
| WO | 2006/034312 | 3/2006 |
| WO | 2006/034338 | 3/2006 |
| WO | 2006/034440 | 3/2006 |
| WO | 2006/034441 | 3/2006 |
| WO | 2006/034446 | 3/2006 |
| WO | 2006/053024 | 5/2006 |
| WO | 2006/086445 | 8/2006 |
| WO | 2006/086447 | 8/2006 |
| WO | 2006/101521 | 9/2006 |
| WO | 2006/125178 | 11/2006 |
| WO | 2006/125179 | 11/2006 |
| WO | 2006/125180 | 11/2006 |
| WO | 2006/125181 | 11/2006 |
| WO | 2006/130986 | 12/2006 |

OTHER PUBLICATIONS

Bhattacharya, et al., J. Nutritional Biochem. 17 (2006) 789-810.*
Martin-Fuentes, et al., Lipids (2009) 44: 115-123.*
Wang, et al., J. Lipid Research, 45, 972-980, May 2004.*
Major, et al., J. Lipid Research, vol. 49, 2008, 1456-1465.*
Brown, et al., Circulation, Sep. 30, 2008, 118(14): 1467-1475.*
Liu, et al., Adv. Nutr., vol. 2, 15-22, 2011.*
Cohen, et al., J. Nutrition, 2004, 2455S-2463S.*
International Search Report issued Apr. 15, 2008 in the International (PCT) Application of which the present application is the U.S. National Stage. PCT/JP2008/051849.

* cited by examiner

*Primary Examiner* — James O Wilson
*Assistant Examiner* — Cecilia M Jaisle
(74) *Attorney, Agent, or Firm* — Wenderoth, Lind & Ponack, L.L.P.

(57) ABSTRACT

The present invention aims to provide a novel SCD inhibitor. The present invention relate to SCD inhibitor comprising A compound represented by the formula (I)

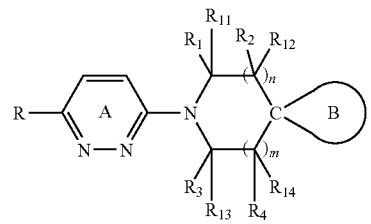

wherein
R is an optionally substituted cyclic group or an optionally substituted carbamoyl group, provided that R is not an optionally substituted 7-pyrido[2,3-d]pyrimidyl group;
ring A is an optionally further substituted pyridazine ring;
$R_1$, $R_2$, $R_3$, $R_4$, $R_{11}$, $R_{12}$, $R_{13}$ and $R_{14}$ are each independently a hydrogen atom or a substituent, or $R_1$ and $R_{11}$ in combination, $R_2$ and $R_{12}$ in combination, $R_3$ and $R_{13}$ in combination, or $R_4$ and $R_{14}$ in combination optionally form an oxo group, or $R_2$ and $R_4$ in combination optionally form a bond or an alkylene cross-linkage;
m and n are each independently an integer of 0 to 2;
ring B is an optionally substituted ring, provided that the two atoms constituting ring B, which are adjacent to the spiro carbon atom, are not oxygen atoms at the same time,
or a salt thereof, or a prodrug thereof.

11 Claims, No Drawings

SPIRO COMPOUNDS HAVING STEAROYL-CoA DESATURASE ACTION

This application is a U.S. national stage of International Application No. PCT/JP2008/051849 filed Feb. 5, 2008.

TECHNICAL FIELD

The present invention relates to a novel compound having a stearoyl-CoA desaturase (hereinafter sometimes to be abbreviated as SCD) action. In addition, the present invention relates to an agent for the prophylaxis or treatment of hyperlipidemia, diabetes, diabetic complications, obesity, lipid metabolism abnormality, fatty liver, metabolic syndrome, hypertension, cardiac failure, arteriosclerosis, arteriosclerosis-associated disease, cardiovascular disease and the like, which comprises a compound having a SCD inhibitory action or a prodrug thereof.

BACKGROUND OF THE INVENTION

Being one of the enzymes localized in endoplasmic reticulum, SCD is a rate determining enzyme of monounsaturated fatty acid synthesis, and introduces a double bond into the Δ9-Δ10 position of saturated fatty acid. SCD has selectivity for palmitic acid and stearic acid, and converts them to palmitoleic acid and oleic acid (J Biol. Chem. 1976 Aug. 25; 251 (16): 5095-5103; Prog Lipid Res. 1995; 34(2): 139-150). The products resulting from these enzyme reactions are most abundantly contained in various fats such as phospholipid, triglyceride, cholesterol ester, wax ester and the like (Prostaglandins Leukot Essent Fatty Acids. 1995 October; 53(4): 279-286; J Lipid Res. 2002 December; 43(12): 2146-2154). In addition, monounsaturated fatty acid is not only a constituent factor of fat but also plays an important role as a mediator of intercellular signaling, cell differentiation, apoptosis and the like (Dev Neurosci. 1992; 14(1): 61-68; FEBS Lett. 1999 Jul. 2; 454(1-2): 42-46; J Lipid Res. 1999 September; 40(9): 1549-1558; Diabetes. 1999 October; 48(10): 2007-2014; Immunology. 2002 December; 107(4): 435-43; Proc Natl Acad Sci USA. 2003 Mar. 18; 100(6): 3077-3082). Since monovalent unsaturated fatty acid have a wide variety of functions, variation in the SCD activity is considered to possibly influence various metabolic pathways relating to diabetes, obesity, abnormal lipid metabolism, fatty liver, metabolic syndrome, arteriosclerosis-associated disease and cardiovascular disease.

As SCD genes, two types (SCD1, SCD2) in rat (GenBank ACCESSION No.: NM_139192; GenBank ACCESSION No.: NM_031841), and four types in mouse (SCDs 1, 2, 3, and 4) (GenBank ACCESSION No.: NM_009127; GenBank ACCESSION No.: NM_009128; GenBank ACCESSION No.: NM_024450; GenBank ACCESSION No.: NM_183216) are cloned.

SCD1 is expressed in various tissues, and characteristically regulated by dietary factor and hormone factor including insulin, cholesterol and polyvalent unsaturated fatty acid (Curr Opin Lipidol. 2003 June; 14(3): 255-261). In human, 2 kinds (SCD1 and SCD5) of genes have been cloned (GenBank ACCESSION NO.: NM_005063; GenBank ACCESSION NO.: NM_001037582), amino acid sequence homology between human SCD1 and mouse SCD1 is as high as 85% (Biochem J. 1999 May 15; 340 (Pt 1): 255-264; Gene. 2003 Apr. 24; 309(1): 11-21).

The SCD activity increases in human and animals with fatty liver, but deletion of SCD1 was found to improve both the high-fat diet induced fatty liver and hereditary fatty liver (Proc Natl Acad Sci USA. 2002 Aug. 20; 99(17): 11482-11486; J Biol Chem. 2000 Sep. 29; 275(39): 30132-30138). It has been confirmed that SCD1 lack mouse shows resistance to diet-induced obesity, promoted energy consumption, decrease in visceral fat, and enhanced insulin signal (Proc Natl Acad Sci USA. 2002 Aug. 20; 99(17):11482-11486; J Lipid Res. 2004 September; 45(9): 1674-1682; Proc Natl Acad Sci USA. 2003 Sep. 16; 100(19): 11110-11115).

SCD1/leptin double knockout mouse is significantly non-obese as compared to control leptin deficient mouse, and shows a remarkable increase in the energy consumption amount and a significant decrease in the liver triglyceride storage and VLDL production. Therefore, suppression of SCD1 expression is considered to be an important constituent factor of a metabolic action of leptin (Science. 2002 Jul. 12; 297(5579): 240-243).

Additionally, SCD1 is involved in the differentiation of adipocytes, and suggested to be also involved in food ingestion and lipolysis. Since inhibition of acetyl-CoA carboxylase 2, glycerol-3-phosphate acyltransferase, fatty acid synthase and the like involved in fatty acid synthesis cascade like SCD1 affords improvement of abnormal lipid metabolism and resistance to obesity (Science. 2001 Mar. 30; 291(5513): 2558-2559; Science. 2000 Jun. 30; 288(5475): 2299-2300; Proc Natl Acad Sci USA. 2002 Jul. 9; 99(14): 9498-9502; Nat Genet. 2000 May; 25(1): 6-7), control of cascade involving SCD1 is considered to be suitable as a target of disease treatment.

Metabolic syndrome drawing attention in these days refers to a syndrome where a single individual shows plural symptoms of abnormal lipid metabolism, high blood pressure, abnormal sugar metabolism and the like, resulting from common onset basis such as visceral fat accumulation, insulin resistance and the like. Thus, it is a pathology with a high onset risk of cardiovascular disease and type 2 diabetes (JAMA. 2001; 285: 2486-2497; Circulation 2004; 109: 433-438; Diabet. Med. 1998; 15: 539-553; The Journal of the Japanese Society of Internal Medicine 2005; 94: 188-203). According to the current guidelines, the basis of the treatment of metabolic syndrome is considered to be the improvement of lifestyle. Since prevention of the onset of cardiovascular events by the administration of statin medicaments and fibrate medicaments has been reported (Am J Transplant. 2005 December; 5(12): 2929-2936; Lancet. 2005 Nov. 26; 366 (9500): 1849-1861), a novel medicament having an SCD inhibitory action targeting plural risk factors of metabolic syndrome is considered to be necessary also from the aspects of treatment efficiency and medical economy.

As a therapeutic drug for SCD-mediated diseases, patent document 1 (WO2006/034338) discloses a compound represented by the following formula:

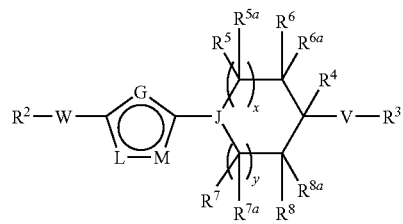

wherein
x and y are each independently 0, 1, 2 or 3;
G is —C(R$^4$)=, —C(R$^4$)=C(R$^4$)— or the like;
J is N or C(R$^{10}$);

L and M are each independently —N= or —C(R⁴)=, provided that when G is —C(R⁴)= or —C(R⁴)=C(R⁴)—, then both L and M should not be —C(R⁴)=;
V is a bond, —N(R¹)— or the like;
W is —N(R¹)C(O)—, —C(O)N(R¹)— or the like;
R¹ is a hydrogen atom or the like;
R² is a C$_{1-12}$ alkyl group or the like;
R³ is a hydrogen atom, a C$_{1-12}$ alkyl group, C$_{3-12}$ cycloalkyl, aryl, a C$_{3-12}$ heterocyclic group, a poly-cyclic structure having 2 to 4 rings, or the like;
R⁴ is independently a hydrogen atom or the like;
R⁵, R$^{5a}$, R⁶, R$^{6a}$, R⁷, R$^{7a}$, R⁸ and R$^{8a}$ are each independently a hydrogen atom, a C$_{1-3}$ alkyl group or the like; and
R¹⁰ is independently a hydrogen atom or the like.

In addition, patent documents 2 to 16 (WO2006/086447; WO2006/034446; WO2006/034441; WO2006/034312; WO2006/034279; WO2005/011657; WO2005/011656; WO2005/011655; WO2005/011654; WO2005/011653; WO2006/101521; WO2006/125178; WO2006/125179; WO2006/125180; WO2006/125181) disclose compounds having a structure similar to those of the compound represented by the above-mentioned formula.

However, these documents do not disclose that the compound of the present invention is used as a SCD inhibitor.

Patent document 17 (WO2006/086445) discloses a method for the treatment of side effects of body weight gain associated with drug therapy, which comprises administering an SCD1 inhibitor.

Patent document 18 (WO2006/130986) discloses a compound represented by the following formula:

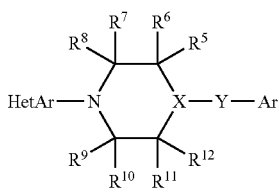

wherein
X—Y is N—C(O) or the like;
Ar is phenyl or the like;
HetAr is an optionally fused 5-membered aromatic heterocycle; and
R⁵, R⁶, R⁷, R⁸, R⁹, R¹⁰, R¹¹ and R¹² are each independently a hydrogen atom, a C$_{1-3}$ alkyl group or the like.

However, this document does not disclose the compound of the present invention which is used as a SCD inhibitor.

Patent document 19 (WO2006/053024) discloses a lactam compound represented by the following formula:

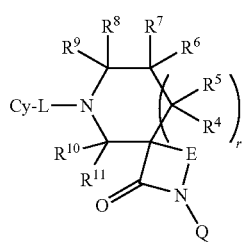

wherein
Cy is aryl, heteroaryl or the like, each of which is optionally substituted;

L is (CR¹²R¹³)$_{q1}$ or the like;
Q is —(CR¹R²)m-A;
A is aryl, heteroaryl or the like, each of which is optionally substituted;
E is —(CR$^{3a}$R$^{3b}$)$_{n1}$;
R¹ and R² are each independently H or a C$_{1-8}$ alkyl group;
R$^{3a}$ and R$^{3b}$ are each independently H or the like;
R⁴, R⁵, R⁶, R⁷, R⁸, R⁹, R¹⁰ and R¹¹ are each independently H or the like;
m is 0, 1, 2 or 3;
R¹² and R¹³ are each independently H or the like;
n1 is 1, 2, 3 or 4;
q1 is 0, 1 or 2; and
r is 0, 1 or 2.

Patent document 20 (WO2001/042241) discloses a pyrimidine derivative represented by the following formula:

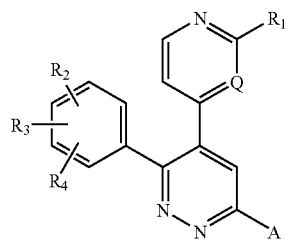

wherein
A is a halogen atom, phenyl or the like;
R₁ is a hydrogen atom or the like;
R₂, R₃ and R₄ are each independently a halogen atom or the like; and
Q is CH or N.

Patent document 21 (U.S. Pat. No. 4,624,952) discloses a heterocycle derivative represented by the following formula:

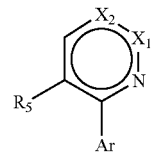

wherein
X₁ and X₂ are each independently N or the like;
Ar is an optionally substituted phenyl group; and
R₅ is a hydrogen atom or the like.

Patent document 22 (WO2000/023444) discloses a pyridopyrimidine derivative represented by the following formula:

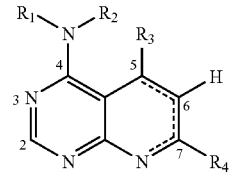

wherein
R₁ and R² are each independently a hydrogen atom or the like;
R³ is an alkenyl group or the like;
R⁴ is alkenyl, aryl, —R$^C$R$^D$R$^E$ or the like;

$R^C$ is aryl, heterocycle or the like;
$R^D$ is aryl, heterocycle or the like; and
$R^E$ is void, or aryl, heterocycle or the like.

However, these documents do not disclose that these compounds are SCD inhibitors.

patent document 1: WO2006/034338
patent document 2: WO2006/086447
patent document 3: WO2006/034446
patent document 4: WO2006/034441
patent document 5: WO2006/034312
patent document 6: WO2006/034279
patent document 7: WO2005/011657
patent document 8: WO2005/011656
patent document 9: WO2005/011655
patent document 10: WO2005/011654
patent document 11: WO2005/011653
patent document 12: WO2006/101521
patent document 13: WO2006/125178
patent document 14: WO2006/125179
patent document 15: WO2006/125180
patent document 16: WO2006/125181
patent document 17: WO2006/086445
patent document 18: WO2006/130986
patent document 19: WO2006/053024
patent document 20: WO2001/042241
patent document 21: U.S. Pat. No. 4,624,952 specification
patent document 22: WO2000/023444

DISCLOSURE OF THE INVENTION

Problems to be Solved by the Invention

SCD is an important regulatory factor of lipid homeostasis and body weight control, and is considered a promising target of a therapeutic drug for hyperlipidemia, diabetes, diabetic complications, obesity, lipid metabolism abnormality, fatty liver, metabolic syndrome, hypertension, cardiac failure, arteriosclerosis, arteriosclerosis-associated diseases and cardiovascular diseases. Thus, the development of a medicament that specifically inhibits SCD is desired.

Means of Solving the Problems

The present inventors have conducted intensive studies in view of the above-mentioned problems and found that the following compound represented by the formula [I] has a superior SCD inhibitory action and shows a blood triglyceride lowering action and the like, which resulted in the completion of the present invention. Accordingly, the present invention provides the following.

[1] A compound represented by the formula (I)

wherein
R is an optionally substituted cyclic group or an optionally substituted carbamoyl group, provided that R is not an optionally substituted 7-pyrido[2,3-d]pyrimidyl group; ring A is an optionally further substituted pyridazine ring; $R_1$, $R_2$, $R_3$, $R_4$, $R_{11}$, $R_{12}$, $R_{13}$ and $R_{14}$ are each independently a hydrogen atom or a substituent, or $R_1$ and $R_{11}$ in combination, $R_2$ and $R_{12}$ in combination, $R_3$ and $R_{13}$ in combination, or $R_4$ and $R_{14}$ in combination optionally form an oxo group, or $R_2$ and $R_4$ in combination optionally form a bond or an alkylene cross-linkage;

m and n are each independently an integer of 0 to 2;

ring B is an optionally substituted ring, provided that the two atoms constituting ring B, which are adjacent to the spiro carbon atom, are not oxygen atoms at the same time, or a salt thereof (hereinafter sometimes to be abbreviated as compound (I)).

[2] The compound of the above-mentioned [1], wherein R is an optionally substituted 5-membered nitrogen-containing aromatic heterocyclic group.

[3] The compound of the above-mentioned [1], wherein m and n are each independently 0 or 1.

[4] The compound of the above-mentioned [1], wherein ring B is an optionally substituted non-aromatic fused ring.

[5] The compound of the above-mentioned [4], wherein the optionally substituted non-aromatic fused ring is an optionally substituted 5- or 6-membered non-aromatic ring condensed with a benzene ring or a 5- or 6-membered aromatic heterocycle.

[6] The compound of the above-mentioned [1], wherein ring B is an optionally substituted monocyclic non-aromatic heterocycle.

[7] The compound of the above-mentioned [1], wherein $R_1$, $R_2$, $R_3$, $R_4$, $R_{11}$, $R_{12}$, $R_{13}$ and $R_{14}$ are all hydrogen atoms.

[8] 1'-[6-(3-methyl-1,2,4-thiadiazol-5-yl)pyridazin-3-yl]spiro[1-benzofuran-3,4'-piperidine], 1'-[6-(3-methyl-1,2,4-oxadiazol-5-yl)pyridazin-3-yl]-3H-spiro[2-benzofuran-1,3'-pyrrolidine], 1'-[6-(3-methyl-1,2,4-oxadiazol-5-yl)pyridazin-3-yl]spiro[1-benzofuran-3,3'-pyrrolidine], {5-[6-(1'H-spiro[1-benzofuran-3,4'-piperidin]-1'-yl)pyridazin-3-yl]-1,2,4-oxadiazol-3-yl}methanol, 1'-[6-(4-methyl-4,5-dihydro-1,3-thiazol-2-yl)pyridazin-3-yl]spiro[1-benzofuran-3,4'-piperidine], {3-[6-(1'H-spiro[1-benzofuran-3,4'-piperidin]-1'-yl)pyridazin-3-yl]-1,2,4-oxadiazol-5-yl}methanol, 1'-[6-(5-methyl-1,2,4-oxadiazol-3-yl)pyridazin-3-yl]-3H-spiro[2-benzofuran-1,3'-pyrrolidine], {5-[6-(1'H,3H-spiro[2-benzofuran-1,3'-pyrrolidin]-1'-yl)pyridazin-3-yl]-1,2,4-oxadiazol-3-yl}methanol, {5-[6-(1'H-spiro[1-benzofuran-3,3'-pyrrolidin]-1'-yl)pyridazin-3-yl]-1,2,4-oxadiazol-3-yl}methanol, 1-methyl-1'-[6-(3-methyl-1,2,4-oxadiazol-5-yl)pyridazin-3-yl]spiro[indole-3,3'-pyrrolidin]-2(1H)-one, or 1'-[6-(3-methyl-1,2,4-oxadiazol-5-yl)pyridazin-3-yl]-3H-spiro[1-benzofuran-2,3'-pyrrolidine]
or a salt thereof.

[9] A prodrug of the compound of the above-mentioned [1].
[10] A SCD inhibitor comprising the compound of the above-mentioned [1] or a prodrug thereof.
[11] A medicament comprising the compound of the above-mentioned [1] or a prodrug thereof.
[12] The medicament of the above-mentioned [11], which is an agent for the prophylaxis and/or treatment of obesity, diabetes, hypertension, hyperlipidemia, cardiac failure, diabetic complications or metabolic syndrome.
[13] A method of inhibiting a SCD in a mammal, which comprising administering the compound of the above-mentioned [1] or a prodrug thereof to the mammal.
[14] A method for the prophylaxis and/or treatment of obesity, diabetes, hypertension, hyperlipidemia, cardiac failure, diabetic complications or metabolic syndrome in a mammal, which comprising administering the compound of the above-mentioned [1] or a prodrug thereof to the mammal.

[15] Use of the compound of the above-mentioned [1] or a prodrug thereof, for the production of a SCD inhibitor.

[16] Use of the compound of the above-mentioned [1] or a prodrug thereof, for the production of an agent for the prophylaxis and/or treatment of obesity, diabetes, hypertension, hyperlipidemia, cardiac failure, diabetic complications or metabolic syndrome.

Effect of the Invention

Compound (I) shows an SCD inhibitory action (particularly SCD-1 inhibitory action), and is considered to show a fatty acid desaturation inhibitory action, an insulin signal enhancing action, suppression of body weight gain and a visceral fat-decreasing action based on a promoted energy consumption, plasma and liver triglyceride lowering action, cholesterol ester and lipoprotein synthesis inhibitory action, and cholesterol efflux improving effect via ATP-binding cassette transporter A1 (ABCA1). Accordingly, compound (I) is highly useful as a prophylactic or therapeutic agent for hyperlipidemia (including hypercholesterolemia, high LDL-cholesterolemia, low HDL-cholesterolemia and hypertriglycerid (TG)emia and the like, particularly hypertriglyceridemia), diabetes (including type 1 diabetes, type 2 diabetes, gestational diabetes, obese diabetes and the like, particularly type 2 diabetes), diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, lipid metabolism abnormality, fatty liver, metabolic syndrome, hypertension, cardiac failure, arteriosclerosis (e.g., atherosclerosis), arteriosclerosis-associated disease, fatal myocardial infarction, sudden cardiac death, nonfatal myocardial infarction, angina pectoris decubitus, effort angina pectoris, destabilized angina pectoris, cardiovascular disorder (cardiovascular disease including cerebral thrombus, cerebral embolism, cerebral hemorrhage, subarachnoid hemorrhage, TIA (transient cerebral ischemic attack; Transient ischemic attack)) and the like.

DETAILED DESCRIPTION OF THE INVENTION

The definition of each symbol in the formula (I) is described in detail in the following.

Examples of the "halogen atom" used in the present specification include a fluorine, chlorine, bromine and iodine atoms. Of these, a fluorine and chlorine atoms are preferable.

The "$C_{1-3}$ alkylenedioxy group" in the present specification means, unless otherwise specified, methylenedioxy, ethylenedioxy, trimethylendioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

R is an optionally substituted cyclic group or an optionally substituted carbamoyl group, provided that R is not an optionally substituted 7-pyrido[2,3-d]pyrimidyl group.

Examples of the "cyclic group" of the "optionally substituted cyclic group" for R include an alicyclic hydrocarbon group, an aromatic hydrocarbon group, an aromatic heterocyclic group, a non-aromatic heterocyclic group and the like.

Examples of the "alicyclic hydrocarbon group" include a saturated or unsaturated $C_{3-12}$ alicyclic hydrocarbon group, specifically, a cycloalkyl group, a cycloalkenyl group, a cycloalkadienyl group and the like.

Preferable examples of the cycloalkyl group include a $C_{3-10}$ cycloalkyl group, for example, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferable examples of the cycloalkenyl group include a $C_{3-10}$ cycloalkenyl group, for example, 2-cyclopenten-1-yl, 3-cyclopenten-1-yl, 2-cyclohexen-1-yl, 3-cyclohexen-1-yl and the like.

Preferable examples of the cycloalkadienyl group include a $C_{4-10}$ cycloalkadienyl group, for example, 2,4-cyclopentadien-1-yl, 2,4-cyclohexadien-1-yl, 2,5-cyclohexadien-1-yl and the like.

These cycloalkyl group, cycloalkenyl group, cycloalkadienyl group are each optionally condensed with a benzene ring. Examples of the fused ring group include indanyl, indenyl, dihydronaphthyl, tetrahydronaphthyl, fluorenyl and the like.

Examples of the "aromatic hydrocarbon group" include a $C_{6-14}$ aryl group and the like. Preferable examples of the $C_{6-14}$ aryl group include phenyl, naphthyl, anthryl, phenanthryl, acenaphthyl, biphenylyl and the like. Of these, phenyl, naphthyl and the like are preferable, and phenyl is more preferable.

Examples of the aromatic heterocyclic group include a 5- to 7-membered monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 5- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the "aromatic heterocyclic group" include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), oxazolyl (e.g., 2-oxazolyl, 4-oxazolyl, 5-oxazolyl), isoxazolyl, thiazolyl (e.g., 2-thiazolyl, 4-thiazolyl, 5-thiazolyl), isothiazolyl, oxadiazolyl (e.g., 1,2,4-oxadiazol-5-yl, 1,3,4-oxadiazol-2-yl), thiadiazolyl (e.g., 1,2,4-thiadiazol-5-yl, 1,3,4-thiadiazol-2-yl), triazolyl (e.g., 1,2,4-triazol-1-yl, 1,2,4-triazol-3-yl, 1,2,4-triazol-5-yl, 1,2,3-triazol-1-yl, 1,2,3-triazol-2-yl, 1,2,3-triazol-4-yl), tetrazolyl (e.g., tetrazol-1-yl, tetrazol-5-yl), quinolyl (e.g., 2-quinolyl, 3-quinolyl, 4-quinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl), benzimidazolyl (e.g., benzimidazol-1-yl, benzimidazol-2-yl), indolyl (e.g., indol-1-yl, indol-3-yl), 1H-indazolyl (e.g., 1H-indazol-3-yl), 1H-pyrrolopyrazinyl (e.g., 1H-pyrrolo[2,3-b]pyrazin-2-yl), 1H-pyrrolopyridinyl (e.g., 1H-pyrrolo[2,3-b]pyridin-6-yl), 1H-imidazopyridinyl (e.g., 1H-imidazo[4,5-b]pyridin-2-yl, 1H-imidazo[4,5-c]pyridin-2-yl), 1H-imidazopyrazinyl (e.g., 1H-imidazo[4,5-b]pyrazin-2-yl), triazinyl, isoquinolyl, benzoxadiazolyl, benzothiadiazolyl, benztriazolyl and the like.

Examples of the non-aromatic heterocyclic group include a 5- to 7-membered monocyclic non-aromatic heterocyclic group containing, as a ring-constituting atom besides carbon atoms, 1 to 4 hetero atoms selected from an oxygen atom, a sulfur atom and a nitrogen atom, and a fused non-aromatic heterocyclic group. Examples of the fused non-aromatic heterocyclic group include a group derived from a fused ring wherein a ring corresponding to the 5- to 7-membered monocyclic non-aromatic heterocyclic group and 1 or 2 rings selected from a 5- or 6-membered aromatic or non-aromatic heterocycle containing 1 or 2 nitrogen atoms (e.g., pyrrole, imidazole, pyrazole, pyrazine, pyridine, pyrimidine), a 5-membered aromatic or non-aromatic heterocycle containing one sulfur atom (e.g., thiophene) and a benzene ring are condensed, a group wherein the above-mentioned group is partially saturated, and the like.

Preferable examples of the "non-aromatic heterocyclic group" include pyrrolidinyl (e.g., 1-pyrrolidinyl), piperidinyl (e.g., piperidino), morpholinyl (e.g., morpholino), thiomorpholinyl (e.g., thiomorpholino), piperazinyl (e.g., 1-piperazinyl), hexamethyleniminyl (e.g., hexamethylenimin-1-yl), oxazolidinyl (e.g., oxazolidin-3-yl), thiazolidinyl (e.g., thiazolidin-3-yl), imidazolidinyl (e.g., imidazolidin-1-yl, imidazolidin-3-yl), imidazolinyl (e.g., imidazolin-1-yl, imidazolin-2-yl), oxazolinyl (e.g., oxazolin-2-yl), thiazolinyl (e.g., thiazolin-2-yl), oxazinyl (e.g., oxazin-2-yl), tetrahydrofuranyl, azepanyl, tetrahydropyridinyl (e.g., 1,2,3,6-tetrahydropyridin-1-yl), dihydrobenzofuranyl and the like.

The "cyclic group" of the "optionally substituted cyclic group" for R is preferably a $C_{6-14}$ aryl group, an aromatic heterocyclic group or a non-aromatic heterocyclic group, more preferably a $C_{6-14}$ aryl group or an aromatic heterocyclic group, more preferably an aromatic heterocyclic group.

The $C_{6-14}$ aryl group is preferably phenyl.

The aromatic heterocyclic group is preferably a 5-membered nitrogen-containing aromatic heterocyclic group such as thiadiazolyl, pyrazolyl, oxadiazolyl, imidazolyl and the like, more preferably oxadiazolyl.

The non-aromatic heterocyclic group is preferably oxazolinyl or thiazolinyl.

Examples of the "substituent" of the "optionally substituted cyclic group" for R include a substituent selected form the group consisting of
(1) a halogen atom (e.g., fluorine, chlorine, bromine, iodine; preferably fluorine),
(2) a lower alkyl group (e.g., a $C_{1-6}$ alkyl group such as methyl, ethyl, propyl, isopropyl, butyl, isobutyl, sec-butyl, tert-butyl, pentyl, hexyl and the like, and the like),
(3) a cycloalkyl group (e.g., a $C_{3-6}$ cycloalkyl group such as cyclopropyl, cyclobutyl, cyclopentyl, cyclohexyl and the like, and the like),
(4) a lower alkenyl group (e.g., a $C_{2-6}$ alkenyl group such as vinyl, allyl, isopropenyl, butenyl, isobutenyl and the like, and the like),
(5) a lower alkynyl group (e.g., a $C_{2-6}$ alkynyl group such as ethynyl, 1-propynyl, propargyl and the like, and the like),
(6) an aralkyl group (e.g., a $C_{7-12}$ aralkyl group such as benzyl, α-methylbenzyl, phenethyl and the like, and the like),
(7) an aryl group (e.g., a $C_{6-10}$ aryl group such as phenyl, naphthyl and the like, and the like, preferably phenyl group),
(8) a lower alkoxy group (e.g., a $C_{1-6}$ alkoxy group such as methoxy, ethoxy, propoxy, isopropoxy, butoxy, isobutoxy, sec-butoxy, tert-butoxy and the like, and the like),
(9) an aryloxy group (e.g., a $C_{6-10}$ aryloxy group such as phenoxy and the like, and the like),
(10) a formyl group or a lower alkanoyl group (e.g., a $C_{1-6}$ alkyl-carbonyl group such as acetyl, propionyl, butyryl, isobutyryl and the like, and the like),
(11) an arylcarbonyl group (e.g., a $C_{6-10}$ aryl-carbonyl group such as benzoyl, naphthoyl and the like, and the like),
(12) a formyloxy group or a lower alkanoyloxy group (e.g., a $C_{1-6}$ alkyl-carbonyloxy group such as cetyloxy, propionyloxy, butyryloxy, isobutyryloxy and the like, and the like),
(13) an arylcarbonyloxy group (e.g., a $C_{6-10}$ aryl-carbonyloxy group such as benzoyloxy, naphthoyloxy and the like, and the like),
(14) a carboxy group,
(15) a lower alkoxycarbonyl group (e.g., a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl and the like, and the like),
(16) an aralkyloxycarbonyl group (e.g., a $C_{7-12}$ aralkyloxycarbonyl group such as benzyloxycarbonyl and the like, and the like),
(17) a carbamoyl group,
(18) a mono-lower alkylcarbamoyl group (e.g., a mono-$C_{1-6}$ alkyl-carbamoyl group such as methylcarbamoyl, ethylcarbamoyl, propylcarbamoyl, isopropylcarbamoyl, butylcarbamoyl and the like, and the like),
(19) a di-lower alkylcarbamoyl group (e.g., a di-$C_{1-6}$ alkylcarbamoyl group such as dimethylcarbamoyl, diethylcarbamoyl, dipropylcarbamoyl, diisopropylcarbamoyl, dibutylcarbamoyl, N-ethyl-N-methylcarbamoyl and the like, and the like),
(20) a mono-, di- or tri-halogeno-lower alkyl group (e.g., a mono-, di- or tri-halogeno-$C_{1-6}$ alkyl group such as chloromethyl, dichloromethyl, trifluoromethyl, 2,2,2-trifluoroethyl and the like, and the like),
(21) an oxo group,
(22) an amidino group,
(23) an imino group,
(24) an amino group,
(25) a mono-lower alkylamino group (e.g., a mono-$C_{1-6}$ alkylamino group such as methylamino, ethylamino, propylamino, isopropylamino, butylamino and the like, and the like),
(26) a di-lower alkylamino group (e.g., a di-$C_{1-6}$ alkylamino group such as dimethylamino, diethylamino, dipropylamino, diisopropylamino, dibutylamino, N-ethyl-N-methylamino and the like, and the like),
(27) a 3- to 8-membered aromatic heterocyclic group containing, besides carbon atoms and one nitrogen atom, 1 to 3 hetero atoms selected from a nitrogen atom, an oxygen atom and a sulfur atom (e.g., pyridyl, pyrazinyl, pyrrolyl, imidazolyl, pyrazolyl, oxadiazolyl, isoxazolyl, triazolyl, tetrazolyl, thiazolyl, isothiazolyl, thiadiazolyl, pyridazinyl, thienyl, benzimidazolyl, indolyl etc.),

(28) a 3- to 8-membered non-aromatic heterocyclic group containing, besides carbon atoms and one nitrogen atom, 1 to 3 hetero atoms selected from a nitrogen atom, an oxygen atom and a sulfur atom (e.g., aziridinyl, azetidinyl, pyrrolidinyl, pyrrolinyl, piperidinyl, morpholinyl, dihydropyridyl, tetrahydropyridyl, piperazinyl, thiazolidinyl, tetrahydropyranyl, tetrahydrofuryl, hexahydropyrimidinyl etc.),

(29) an alkylenedioxy group (e.g., a $C_{1-3}$ alkylenedioxy group such as methylenedioxy, ethylenedioxy and the like, and the like),

(30) a hydroxy group,

(31) a nitro group,

(32) a cyano group,

(33) a mercapto group,

(34) a sulfo group,

(35) a sulfino group,

(36) a phosphono group,

(37) a sulfamoyl group,

(38) a mono-lower alkylsulfamoyl group (e.g., a mono-$C_{1-6}$ alkylsulfamoyl group such as N-methylsulfamoyl, N-ethylsulfamoyl, N-propylsulfamoyl, N-isopropylsulfamoyl, N-butylsulfamoyl and the like, and the like),

(39) a di-lower alkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl and the like, and the like),

(40) a lower alkylthio group (e.g., a $C_{1-6}$ alkylthio group such as methylthio, ethylthio, propylthio, isopropylthio, butylthio, sec-butylthio, tert-butylthio and the like, and the like),

(41) an arylthio group (e.g., a $C_{6-10}$ arylthio group such as phenylthio, naphthylthio and the like, and the like),

(42) a lower alkylsulfinyl group (e.g., a $C_{1-6}$ alkylsulfinyl group methylsulfinyl, ethylsulfinyl, propylsulfinyl, butylsulfinyl and the like, and the like),

(43) an arylsulfinyl group (e.g., a $C_{6-10}$ arylsulfinyl group such as phenylsulfinyl, naphthylsulfinyl and the like, and the like),

(44) a lower alkylsulfonyl group (e.g., a $C_{1-6}$ alkylsulfonyl group such as methylsulfonyl, ethylsulfonyl, propylsulfonyl, butylsulfonyl and the like, and the like),

(45) an arylsulfonyl group (e.g., a $C_{6-10}$ arylsulfonyl group such as phenylsulfonyl, naphthylsulfonyl and the like, and the like)

and the like (in the present specification, to be referred as Substituent Group (a)).

The "cyclic group" of the "optionally substituted cyclic group" for R optionally has 1 to 5, preferably 1 to 3 of the above-mentioned substituents at substitutable positions. When the number of the substituents is not less than 2, the respective substituents may be the same or different. These substituents are optionally further substituted by Substituent Group (a).

Preferable examples of the substituent for the "cyclic group" of the "optionally substituted cyclic group" for R include:

(A)

(a) a $C_{1-6}$ alkyl group (preferably methyl, ethyl, propyl), (b) a amino group optionally mono- or di-substituted by $C_{1-6}$ alkyl group(s) (preferably methyl);

(B)

a $C_{1-6}$ alkyl group (preferably methyl, ethyl, propyl);

(C)

(a) a $C_{1-6}$ alkyl group (preferably methyl, ethyl, propyl) optionally substituted by 1 to 3 substituents selected from
 (i) a hydroxy group,
 (ii) a $C_{1-6}$ alkoxy group (preferably methoxy),
 (iii) a $C_{1-6}$ alkyl-carbonyloxy group (preferably acetyloxy), and
 (iv) a carboxy group, (b) an amino group optionally mono- or di-substituted by $C_{1-6}$ alkyl group(s) (preferably methyl), and (c) a $C_{7-12}$ aralkyl group (preferably benzyl); and the like.

Preferable examples of the "optionally substituted cyclic group" for R include:

(A)

an optionally substituted 5-membered nitrogen-containing aromatic heterocyclic group (preferably thiadiazolyl, pyrazolyl, oxadiazolyl, imidazolyl, more preferably oxadiazolyl);

(B)

a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted;

(C)

a $C_{6-14}$ aryl group (preferably phenyl), an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) or a non-aromatic heterocyclic group (preferably oxazolinyl, thiazolinyl), each of which is optionally substituted;

(D)

a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) [preferably an aromatic heterocyclic group], each of which is optionally substituted by 1 to 3 substituents selected from (a) a $C_{1-6}$ alkyl group (preferably methyl, ethyl, propyl), and
(b) an amino group optionally mono- or di-substituted by $C_{1-6}$ alkyl group(s) (preferably methyl);

(E)

an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) optionally substituted by 1 to 3 $C_{1-6}$ alkyl groups (preferably methyl, ethyl, propyl);

(F)

a $C_{6-14}$ aryl group (preferably phenyl), an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) or a non-aromatic heterocyclic group (preferably oxazolinyl, thiazolinyl), each of which is optionally substituted by 1 to 3 substituents selected from (a) a $C_{1-6}$ alkyl group (preferably methyl, ethyl, propyl) optionally substituted by 1 to 3 substituents selected from
 (i) a hydroxy group,
 (ii) a $C_{1-6}$ alkoxy group (preferably methoxy),
 (iii) a $C_{1-6}$ alkyl-carbonyloxy group (preferably acetyloxy), and
 (iv) a carboxy group, (b) an amino group optionally mono- or di-substituted by $C_{1-6}$ alkyl group(s) (preferably methyl), and (c) an $C_{7-12}$ aralkyl group (preferably benzyl), and the like.

The "optionally substituted carbamoyl group" for R optionally has 1 or 2 substituents. When it is substituted by 2 substituents, the respective substituents may be the same or different. Examples of the substituent include an "optionally substituted hydrocarbon group", an "optionally substituted heterocyclic group" and the like. When the "optionally substituted carbamoyl group" is substituted by 2 substituents, the substituents optionally form, together with the adjacent nitrogen atom, an optionally substituted nitrogen-containing heterocycle (in this case, R is an "optionally substituted nitrogen-containing heterocyclylcarbonyl group").

Examples of the "hydrocarbon group" of the "optionally substituted hydrocarbon group" include an aliphatic hydrocarbon group, an alicyclic hydrocarbon group, an aromatic hydrocarbon group, an aromatic-aliphatic hydrocarbon group, an alicyclic-aliphatic hydrocarbon group and the like.

Examples of the aliphatic hydrocarbon group include a linear or branched $C_{1-15}$ aliphatic hydrocarbon group, specifically an alkyl group, an alkenyl group, an alkynyl group and the like.

Preferable examples of the alkyl group include a $C_{1-10}$ alkyl group, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a $C_{1-6}$ alkyl group is preferable.

Preferable examples of the alkenyl group include a $C_{2-10}$ alkenyl group, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a $C_{2-6}$ alkenyl group is preferable.

Preferable examples of the alkynyl group include a $C_{2-10}$ alkynyl group, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, a $C_{2-6}$ alkynyl group is preferable.

Examples of the alicyclic hydrocarbon group include those similar to the "alicyclic hydrocarbon group" exemplified as "cyclic group" of the "optionally substituted cyclic group" for R.

Examples of the aromatic hydrocarbon group include those similar to the "aromatic hydrocarbon group" exemplified as "cyclic group" of the "optionally substituted cyclic group" for R.

Examples of the aromatic-aliphatic hydrocarbon group include a $C_{7-13}$ aromatic-aliphatic hydrocarbon group, specifically, an aralkyl group, an arylalkenyl group and the like.

Preferable examples of the aralkyl group include a $C_{7-13}$ aralkyl group, for example, a $C_{6-10}$ aryl-$C_{1-3}$ alkyl group such as benzyl, phenethyl, phenylpropyl, naphthylmethyl, benzhydryl and the like.

Preferable examples of the arylalkenyl group include a $C_{8-13}$ arylalkenyl group, for example, a $C_{6-10}$ aryl-$C_{2-3}$ alkenyl group such as styryl and the like.

Examples of the alicyclic-aliphatic hydrocarbon group include a $C_{4-13}$ alicyclic-aliphatic hydrocarbon group, specifically, a cycloalkylalkyl group, a cycloalkylalkenyl group, a cycloalkenylalkyl group, a cycloalkenylalkenyl group and the like.

Preferable examples of the cycloalkylalkyl group include a $C_{4-13}$ cycloalkylalkyl group, for example, a $C_{3-10}$ cycloalkyl-$C_{1-3}$ alkyl group such as cyclopropylmethyl, cyclopropylethyl, cyclopentylmethyl, cyclopentylethyl, cyclohexylmethyl, cyclohexylethyl and the like.

Preferable examples of the cycloalkylalkenyl group include a $C_{5-13}$ cycloalkylalkenyl group, for example, a $C_{3-10}$ cycloalkyl-$C_{2-3}$ alkenyl group such as cyclopropylethenyl, cyclopentylethenyl, cyclohexylethenyl and the like.

Preferable examples of the cycloalkenylalkyl group include a $C_{4-13}$ cycloalkenylalkyl group, for example, a $C_{3-10}$ cycloalkenyl-$C_{1-3}$ alkyl group such as 2-cyclopenten-1-ylmethyl, 3-cyclopenten-1-ylmethyl, 2-cyclohexen-1-ylmethyl, 3-cyclohexen-1-ylmethyl and the like.

Preferable examples of the cycloalkenylalkenyl group include a $C_{5-13}$ cycloalkenylalkenyl group, for example, a $C_{3-10}$ cycloalkenyl-$C_{2-3}$ alkenyl group such as 2-cyclopenten-1-ylethenyl, 3-cyclopenten-1-ylethenyl, 2-cyclohexen-1-ylethenyl, 3-cyclohexen-1-ylethenyl and the like.

Examples of the "substituent" of the "optionally substituted hydrocarbon group" include those exemplified in the above-mentioned Substituent Group (a).

The "hydrocarbon group" of the "optionally substituted hydrocarbon group" optionally has 1 to 5, preferably 1 to 3 of the above-mentioned substituents at substitutable positions. When the number of the substituents is not less than 2, the respective substituents may be the same or different. These substituents are optionally further substituted by substituent(s) selected from Substituent Group (a).

Examples of the "heterocyclic group" of the "optionally substituted heterocyclic group", which is exemplified as the "substituent" of the "optionally substituted carbamoyl group" for R, include an aromatic heterocyclic group, a non-aromatic heterocyclic group and the like.

Examples of the "aromatic heterocyclic group" and "non-aromatic heterocyclic group" include those similar to the "aromatic heterocyclic group" and "non-aromatic heterocyclic group", which is exemplified as "cyclic group" of the "optionally substituted cyclic group" for R.

Examples of the "substituent" of the "optionally substituted heterocyclic group" include those exemplified in the above-mentioned Substituent Group (a).

The "heterocyclic group" of the "optionally substituted heterocyclic group" optionally has 1 to 5, preferably 1 to 3 of the above-mentioned substituents at substitutable positions. When the number of the substituents is not less than 2, the respective substituents may be the same or different. These substituents are optionally further substituted by substituent(s) selected from Substituent Group (a).

Preferable examples of the substituent for "carbamoyl group" of the "optionally substituted carbamoyl group" for R include (A) an optionally substituted $C_{1-6}$ alkyl group (preferably methyl, ethyl, propyl, isopropyl, butyl, sec-butyl, isopentyl), (B) an optionally substituted $C_{3-10}$ cycloalkyl group (preferably cyclopropyl), (C) an optionally substituted $C_{6-14}$ aryl group (preferably phenyl), (D) an optionally substituted aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like), (E) an optionally substituted non-aromatic heterocyclic group (preferably a 5- or 6-membered non-aromatic heterocyclic group such as pyrrolidinyl, piperidinyl and the like) and the like.

More preferable examples of the substituent include
(A) a $C_{1-6}$ alkyl group (preferably methyl, ethyl, propyl, isopropyl, butyl, sec-butyl, isopentyl) optionally substituted by 1 to 3 substituents selected from
- (a) a $C_{6-10}$ aryl group (preferably phenyl) optionally substituted by 1 to 3 substituents selected from
  - (i) a $C_{1-6}$ alkyl group (preferably methyl) optionally substituted by 1 to 3 $C_{1-6}$ alkoxy groups (preferably methoxy),
  - (ii) a $C_{1-6}$ alkylsulfonyl group (preferably methylsulfonyl), and
  - (iii) a sulfamoyl group,
- (b) an aromatic heterocyclic group (preferably thienyl, thiazolyl, imidazolyl, triazolyl, isoxazolyl, pyridyl, indolyl) optionally substituted by 1 to 3 substituents selected from
  - (i) a halogen atom (preferably a fluorine atom, a chlorine atom),
  - (ii) a $C_{1-6}$ alkyl group (preferably methyl),
  - (iii) a $C_{6-10}$ aryl group (preferably phenyl),
  - (iv) an aromatic heterocyclic group (preferably thienyl), and
  - (v) a non-aromatic heterocyclic group (preferably morpholinyl),
- (c) a non-aromatic heterocyclic group (preferably pyrrolidinyl, morpholinyl, thiazolidinyl, tetrahydropyranyl, tetrahydrofuryl) optionally substituted by 1 to 3 substituents selected from
  - (i) a $C_{1-6}$ alkyl group (preferably methyl) optionally substituted by 1 to 3 $C_{6-10}$ aryl groups (preferably phenyl), and
  - (ii) an oxo group,
- (d) a $C_{3-6}$ cycloalkyl group (preferably cyclopropyl, cyclohexyl),
- (e) a hydroxy group,
- (f) a $C_{1-6}$ alkoxy group (preferably ethoxy, isopropoxy),
- (g) a $C_{6-10}$ aryloxy group (preferably phenoxy),
- (h) a $C_{1-6}$ alkoxy-carbonyl group (preferably methoxycarbonyl),
- (i) a $C_{6-10}$ aryl-carbonyl group (preferably benzoyl),
- (j) a $C_{1-6}$ alkylsulfonyl group (preferably methylsulfonyl),
- (k) a $C_{6-10}$ arylsulfonyl group (preferably phenylsulfonyl),
- (l) an aromatic heterocyclesulfonyl group (preferably pyridylsulfonyl),
- (m) a $C_{1-6}$ alkylsulfonylamino group (preferably methylsulfonylamino) optionally substituted by 1 to 3 halogen atoms (preferably a fluorine atom),
- (n) a halogen atom (preferably a fluorine atom), and
- (o) a cyano group, (B) a $C_{3-10}$ cycloalkyl group (preferably cyclopropyl) optionally substituted by 1 to 3 $C_{6-10}$ aryl groups (preferably phenyl), (C) a $C_{6-14}$ aryl group (preferably phenyl) optionally substituted by 1 to 3 $C_{1-6}$ alkyl groups (preferably methyl) optionally substituted by 1 to 3 non-aromatic heterocyclic groups (preferably morpholinyl), (D) an aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like) optionally substituted by 1 to 3 substituents selected from
- (a) a $C_{1-6}$ alkyl group (preferably methyl) optionally substituted by 1 to 3 $C_{6-10}$ aryl groups (preferably phenyl) optionally substituted by 1 to 3 halogen atoms (preferably a fluorine atom), and
- (b) a $C_{1-6}$ alkoxy group (preferably methoxy), (E) a non-aromatic heterocyclic group (preferably a 5- or 6-membered non-aromatic heterocyclic group such as pyrrolidinyl, piperidinyl and the like) optionally substituted by 1 to 3 substituents selected from
- (a) a $C_{1-6}$ alkyl group (preferably methyl) optionally substituted by 1 to 3 $C_{6-10}$ aryl groups (preferably phenyl), and
- (b) a $C_{1-6}$ alkyl-carbonyl group (preferably acetyl) optionally substituted by 1 to 3 halogen atoms (preferably a fluorine atom), and the like.

Examples of the "nitrogen-containing heterocycle" of the "optionally substituted nitrogen-containing heterocycle" formed by, together with the adjacent nitrogen atom, the two substituent of the "optionally substituted carbamoyl group" include a 5- to 7-membered nitrogen-containing heterocycle containing, as a ring-constituting atom besides carbon atom, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

Examples of the "substituent" of the above-mentioned "optionally substituted nitrogen-containing heterocycle" include those exemplified in the above-mentioned Substituent Group (a).

The "nitrogen-containing heterocycle" of the "optionally substituted nitrogen-containing heterocycle" optionally has 1 or 2 substituents. When it is substituted by 2 substituents, the respective substituents may be the same or different. These substituents are optionally further substituted by substituent(s) selected from Substituent Group (a).

Preferable examples of the substituent for the "nitrogen-containing heterocycle" of the "optionally substituted nitrogen-containing heterocyclylcarbonyl group" for R include
(a) a $C_{1-6}$ alkyl group (preferably methyl, ethyl) optionally substituted by 1 to 3 substituents selected from
  (i) a halogen atom (preferably a fluorine atom),
  (ii) a $C_{6-10}$ aryl group (preferably phenyl),
  (iii) a $C_{1-6}$ alkylsulfonyl group (preferably methylsulfonyl), and
  (iv) an aromatic heterocyclic group (preferably pyridyl),
(b) a $C_{6-10}$ aryl group (preferably phenyl),
(c) a $C_{6-10}$ aryloxy group (preferably phenoxy),
(d) a $C_{6-10}$ aryl-carbonyl group (preferably benzoyl),
(e) a $C_{6-10}$ arylsulfonyl group (preferably phenylsulfonyl),
(f) an aromatic heterocyclic group (preferably pyridyl, pyrazinyl),
(g) an aromatic heterocyclyloxy group (preferably pyridyloxy),
(h) a non-aromatic heterocyclic group (preferably hexahydropyrimidinyl) optionally substituted by 1 to 3 oxo groups and the like.

The "optionally substituted carbamoyl group" for R is preferably
(1) a carbamoyl group optionally mono- or di-substituted by substituent(s) selected from
  (A) an optionally substituted $C_{1-6}$ alkyl group (preferably methyl, ethyl, propyl, isopropyl, butyl, sec-butyl, isopentyl),
  (B) an optionally substituted $C_{3-10}$ cycloalkyl group (preferably cyclopropyl),
  (C) an optionally substituted $C_{6-14}$ aryl group (preferably phenyl),
  (D) an optionally substituted aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like), and
- (E) an optionally substituted non-aromatic heterocyclic group (preferably a 5- or 6-membered non-aromatic heterocyclic group such as pyrrolidinyl, piperidinyl and the like), or (2) an optionally substituted nitrogen-containing heterocyclylcarbonyl group (preferably 1-pyrrolidinylcarbonyl, 1-piperidinocarbonyl, 1-piperazinylcarbonyl, morpholinocarbonyl), more preferably (1) a carbamoyl group optionally mono- or di-substituted by substituent(s) selected from
- (A) a $C_{1-6}$ alkyl group (preferably methyl, ethyl, propyl, isopropyl, butyl, sec-butyl, isopentyl) optionally substituted by 1 to 3 substituents selected from
  - (a) a $C_{6-10}$ aryl group (preferably phenyl) optionally substituted by 1 to 3 substituents selected from
    - (i) a $C_{1-6}$ alkyl group (preferably methyl) optionally substituted by 1 to 3 $C_{1-6}$ alkoxy groups (preferably methoxy),
    - (ii) a $C_{1-6}$ alkylsulfonyl group (preferably methylsulfonyl), and
    - (iii) a sulfamoyl group,
  - (b) an aromatic heterocyclic group (preferably thienyl, thiazolyl, imidazolyl, triazolyl, isoxazolyl, pyridyl, indolyl) optionally substituted by 1 to 3 substituents selected from
    - (i) a halogen atom (preferably a fluorine atom, a chlorine atom),
    - (ii) a $C_{1-6}$ alkyl group (preferably methyl),
    - (iii) a $C_{6-10}$ aryl group (preferably phenyl),
    - (iv) an aromatic heterocyclic group (preferably thienyl), and
    - (v) a non-aromatic heterocyclic group (preferably morpholinyl),
  - (c) a non-aromatic heterocyclic group (preferably pyrrolidinyl, morpholinyl, thiazolidinyl, tetrahydropyranyl, tetrahydrofuryl) optionally substituted by 1 to 3 substituents selected from
    - (i) a $C_{1-6}$ alkyl group (preferably methyl) optionally substituted by 1 to 3 $C_{6-10}$ aryl groups (preferably phenyl), and
    - (ii) an oxo group,
  - (d) a $C_{3-6}$ cycloalkyl group (preferably cyclopropyl, cyclohexyl),
  - (e) a hydroxy group,
  - (f) a $C_{1-6}$ alkoxy group (preferably ethoxy, isopropoxy),
  - (g) a $C_{6-10}$ aryloxy group (preferably phenoxy),
  - (h) a $C_{1-6}$ alkoxy-carbonyl group (preferably methoxycarbonyl),
  - (i) a $C_{6-10}$ aryl-carbonyl group (preferably benzoyl),
  - (j) a $C_{1-6}$ alkylsulfonyl group (preferably methylsulfonyl),
  - (k) a $C_{6-10}$ arylsulfonyl group (preferably phenylsulfonyl),
  - (l) an aromatic heterocyclesulfonyl group (preferably pyridylsulfonyl),
  - (m) a $C_{1-6}$ alkylsulfonylamino group (preferably methylsulfonylamino) optionally substituted by 1 to 3 halogen atoms (preferably a fluorine atom),
  - (n) a halogen atom (preferably a fluorine atom), and
  - (o) a cyano group,
- (B) a $C_{3-10}$ cycloalkyl group (preferably cyclopropyl) optionally substituted by 1 to 3 $C_{6-10}$ aryl groups (preferably phenyl),
- (C) a $C_{6-14}$ aryl group (preferably phenyl) optionally substituted by 1 to 3 $C_{1-6}$ alkyl groups (preferably methyl) optionally substituted by 1 to 3 non-aromatic heterocyclic groups (preferably morpholinyl),
- (D) an aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like) optionally substituted by 1 to 3 substituents selected from
  - (a) a $C_{1-6}$ alkyl group (preferably methyl) optionally substituted by 1 to 3 $C_{6-10}$ aryl groups (preferably phenyl) optionally substituted by 1 to 3 halogen atoms (preferably a fluorine atom), and
  - (b) a $C_{1-6}$ alkoxy group (preferably methoxy), and
- (E) a non-aromatic heterocyclic group (preferably a 5- or 6-membered non-aromatic heterocyclic group such as pyrrolidinyl, piperidinyl and the like) optionally substituted by 1 to 3 substituents selected from
  - (a) a $C_{1-6}$ alkyl group (preferably methyl) optionally substituted by 1 to 3 $C_{6-10}$ aryl groups (preferably phenyl), and
  - (b) a $C_{1-6}$ alkyl-carbonyl group (preferably acetyl) optionally substituted by 1 to 3 halogen atoms (preferably a fluorine atom), or (2) a nitrogen-containing heterocyclylcarbonyl group (preferably 1-pyrrolidinylcarbonyl, 1-piperidinocarbonyl, 1-piperazinylcarbonyl, morpholinocarbonyl) optionally substituted by 1 to 3 substituents selected from
- (a) a $C_{1-6}$ alkyl group (preferably methyl, ethyl) optionally substituted by 1 to 3 substituents selected from
  - (i) a halogen atom (preferably a fluorine atom),
  - (ii) a $C_{6-10}$ aryl group (preferably phenyl),
  - (iii) a $C_{1-6}$ alkylsulfonyl group (preferably methylsulfonyl), and
  - (iv) an aromatic heterocyclic group (preferably pyridyl),
- (b) a $C_{6-10}$ aryl group (preferably phenyl),
- (c) a $C_{6-10}$ aryloxy group (preferably phenoxy),
- (d) a $C_{6-10}$ aryl-carbonyl group (preferably benzoyl),
- (e) a $C_{6-10}$ arylsulfonyl group (preferably phenylsulfonyl),
- (f) an aromatic heterocyclic group (preferably pyridyl, pyrazinyl),
- (g) an aromatic heterocyclyloxy group (preferably pyridyloxy), and
- (h) a non-aromatic heterocyclic group (preferably hexahydropyrimidinyl) optionally substituted by 1 to 3 oxo groups.

In one embodiment, R is preferably an optionally substituted 5-membered nitrogen-containing aromatic heterocyclic group (preferably thiadiazolyl, pyrazolyl, oxadiazolyl, imidazolyl, more preferably oxadiazolyl).

In another embodiment, R is preferably
(1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted, or
(2) a carbamoyl group optionally mono- or di-substituted by optionally substituted $C_{1-6}$ alkyl group(s), more preferably
(1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted by 1 to 3 substituents selected from (a) a $C_{1-6}$ alkyl group (preferably methyl, ethyl, propyl), and
(b) an amino group optionally mono- or di-substituted by $C_{1-6}$ alkyl group(s) (preferably methyl), or
(2) a carbamoyl group optionally mono- or di-substituted by $C_{1-6}$ alkyl group(s) (preferably methyl, ethyl, propyl, isopropyl, butyl, sec-butyl, isopentyl) optionally substituted by 1 to 3 substituents selected from
(a) a $C_{6-10}$ aryl group (preferably phenyl), and
(b) an aromatic heterocyclic group (preferably thienyl) optionally substituted by 1 to 3 halogen atoms (preferably a fluorine atom, a chlorine atom).

R is further more preferably an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) optionally substituted by 1 to 3 substituents selected from
(a) a $C_{1-6}$ alkyl group (preferably methyl, ethyl, propyl), and
(b) an amino group optionally mono- or di-substituted by $C_{1-6}$ alkyl group(s) (preferably methyl).

In another embodiment, R is preferably
(1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted,
(2) a carbamoyl group optionally mono- or di-substituted by substituent(s) selected from
  (A) an optionally substituted $C_{1-6}$ alkyl group (preferably methyl, ethyl, propyl, isopropyl, butyl, sec-butyl, isopentyl),
  (B) an optionally substituted $C_{3-10}$ cycloalkyl group (preferably cyclopropyl),
  (C) an optionally substituted $C_{6-14}$ aryl group (preferably phenyl),
  (D) an optionally substituted aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like), and
  (E) an optionally substituted non-aromatic heterocyclic group (preferably a 5- or 6-membered non-aromatic heterocyclic group such as pyrrolidinyl, piperidinyl and the like), or
(3) an optionally substituted nitrogen-containing heterocyclylcarbonyl group (preferably 1-pyrrolidinylcarbonyl, 1-piperidinocarbonyl, 1-piperazinylcarbonyl, morpholinocarbonyl),
more preferably
(1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted by 1 to 3 substituents selected from
  (a) a $C_{1-6}$ alkyl group (preferably methyl, ethyl, propyl), and
  (b) an amino group optionally mono- or di-substituted by $C_{1-6}$ alkyl group(s) (preferably methyl),
(2) a carbamoyl group optionally mono- or di-substituted by substituent(s) selected from
  (A) a $C_{1-6}$ alkyl group (preferably methyl, ethyl, propyl, isopropyl, butyl, sec-butyl, isopentyl) optionally substituted by 1 to 3 substituents selected from
    (a) a $C_{6-10}$ aryl group (preferably phenyl) optionally substituted by 1 to 3 substituents selected from
      (i) a $C_{1-6}$ alkyl group (preferably methyl) optionally substituted by 1 to 3 $C_{1-6}$ alkoxy groups (preferably methoxy),
      (ii) a $C_{1-6}$ alkylsulfonyl group (preferably methylsulfonyl), and
      (iii) a sulfamoyl group,
    (b) an aromatic heterocyclic group (preferably thienyl, thiazolyl, imidazolyl, triazolyl, isoxazolyl, pyridyl, indolyl) optionally substituted by 1 to 3 substituents selected from
      (i) a halogen atom (preferably a fluorine atom, a chlorine atom),
      (ii) a $C_{1-6}$ alkyl group (preferably methyl),
      (iii) a $C_{6-10}$ aryl group (preferably phenyl),
      (iv) an aromatic heterocyclic group (preferably thienyl), and
      (v) a non-aromatic heterocyclic group (preferably morpholinyl),
    (c) a non-aromatic heterocyclic group (preferably pyrrolidinyl, morpholinyl, thiazolidinyl, tetrahydropyranyl, tetrahydrofuryl) optionally substituted by 1 to 3 substituents selected from
      (i) a $C_{1-6}$ alkyl group (preferably methyl) optionally substituted by 1 to 3 $C_{6-10}$ aryl groups (preferably phenyl), and
      (ii) an oxo group,
    (d) a $C_{3-6}$ cycloalkyl group (preferably cyclopropyl, cyclohexyl),
    (e) a hydroxy group,
    (f) a $C_{1-6}$ alkoxy group (preferably ethoxy, isopropoxy),
    (g) a $C_{6-10}$ aryloxy group (preferably phenoxy),
    (h) a $C_{1-6}$ alkoxy-carbonyl group (preferably methoxycarbonyl),
    (i) a $C_{6-10}$ aryl-carbonyl group (preferably benzoyl),
    (j) a $C_{1-6}$ alkylsulfonyl group (preferably methylsulfonyl),
    (k) a $C_{6-10}$ arylsulfonyl group (preferably phenylsulfonyl),
    (l) an aromatic heterocyclesulfonyl group (preferably pyridylsulfonyl),
    (m) a $C_{1-6}$ alkylsulfonylamino group (preferably methylsulfonylamino) optionally substituted by 1 to 3 halogen atoms (preferably a fluorine atom),
    (n) a halogen atom (preferably a fluorine atom), and
    (o) a cyano group,
  (B) a $C_{3-10}$ cycloalkyl group (preferably cyclopropyl) optionally substituted by 1 to 3 $C_{6-10}$ aryl groups (preferably phenyl),
  (C) a $C_{6-14}$ aryl group (preferably phenyl) optionally substituted by 1 to 3 $C_{1-6}$ alkyl groups (preferably methyl) optionally substituted by 1 to 3 non-aromatic heterocyclic groups (preferably morpholinyl),
  (D) an aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like) optionally substituted by 1 to 3 substituents selected from
    (a) a $C_{1-6}$ alkyl group (preferably methyl) optionally substituted by 1 to 3 $C_{6-10}$ aryl groups (preferably phenyl) optionally substituted by 1 to 3 halogen atoms (preferably a fluorine atom), and
    (b) a $C_{1-6}$ alkoxy group (preferably methoxy), and
  (E) a non-aromatic heterocyclic group (preferably a 5- or 6-membered non-aromatic heterocyclic group such as pyrrolidinyl, piperidinyl and the like) optionally substituted from (a) a C$_{1-6}$ alkyl group (preferably methyl) optionally substituted by 1 to 3 C$_{6-10}$ aryl groups (preferably phenyl), and
(b) a C$_{1-6}$ alkyl-carbonyl group (preferably acetyl) optionally substituted by 1 to 3 halogen atoms (preferably a fluorine atom), or (3) a nitrogen-containing heterocyclylcarbonyl group (preferably 1-pyrrolidinylcarbonyl, 1-piperidinocarbonyl, 1-piperazinylcarbonyl, morpholinocarbonyl) optionally substituted by 1 to 3 substituents selected from
   (a) a C$_{1-6}$ alkyl group (preferably methyl, ethyl) optionally substituted by 1 to 3 substituents selected from
      (i) a halogen atom (preferably a fluorine atom),
      (ii) a C$_{6-10}$ aryl group (preferably phenyl),
      (iii) a C$_{1-6}$ alkylsulfonyl group (preferably methylsulfonyl), and
      (iv) an aromatic heterocyclic group (preferably pyridyl),
   (b) a C$_{6-10}$ aryl group (preferably phenyl),
   (c) a C$_{6-10}$ aryloxy group (preferably phenoxy),
   (d) a C$_{6-10}$ aryl-carbonyl group (preferably benzoyl),
   (e) a C$_{6-10}$ arylsulfonyl group (preferably phenylsulfonyl),
   (f) an aromatic heterocyclic group (preferably pyridyl, pyrazinyl),
   (g) an aromatic heterocyclyloxy group (preferably pyridyloxy), and
   (h) a non-aromatic heterocyclic group (preferably hexahydropyrimidinyl) optionally substituted by 1 to 3 oxo groups.

R is more preferably an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) optionally substituted by 1 to 3 C$_{1-6}$ alkyl groups (preferably methyl, ethyl, propyl).

Alternatively, in another embodiment, R is preferably
(1) a C$_{6-14}$ aryl group (preferably phenyl), an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) or a non-aromatic heterocyclic group (preferably oxazolinyl, thiazolinyl), each of which is optionally substituted,
(2) a carbamoyl group optionally mono- or di-substituted by substituent(s) selected from
   (A) an optionally substituted C$_{1-6}$ alkyl group (preferably methyl, ethyl, propyl, isopropyl, butyl, sec-butyl, isopentyl),
   (B) an optionally substituted C$_{3-10}$ cycloalkyl group (preferably cyclopropyl),
   (C) an optionally substituted C$_{6-14}$ aryl group (preferably phenyl),
   (D) an optionally substituted aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like), and
   (E) an optionally substituted non-aromatic heterocyclic group (preferably a 5- or 6-membered non-aromatic heterocyclic group such as pyrrolidinyl, piperidinyl and the like), or
(3) an optionally substituted nitrogen-containing heterocyclylcarbonyl group (preferably 1-pyrrolidinylcarbonyl, 1-piperidinocarbonyl, 1-piperazinylcarbonyl, morpholinocarbonyl),
more preferably
(1) a C$_{6-14}$ aryl group (preferably phenyl), an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) or a non-aromatic heterocyclic group (preferably oxazolinyl, thiazolinyl), each of which is optionally substituted by 1 to 3 substituents selected from
   (a) a C$_{1-6}$ alkyl group (preferably methyl, ethyl, propyl) optionally substituted by 1 to 3 substituents selected from
      (i) a hydroxy group,
      (ii) a C$_{1-6}$ alkoxy group (preferably methoxy),
      (iii) a C$_{1-6}$ alkyl-carbonyloxy group (preferably acetyloxy), and
      (iv) a carboxy group,
   (b) an amino group optionally mono- or di-substituted by C$_{1-6}$ alkyl group(s) (preferably methyl), and
   (c) a C$_{7-12}$ aralkyl group (preferably benzyl),
(2) a carbamoyl group optionally mono- or di-substituted by substituent(s) selected from
   (A) a C$_{1-6}$ alkyl group (preferably methyl, ethyl, propyl, isopropyl, butyl, sec-butyl, isopentyl) optionally substituted by 1 to 3 substituents selected from
      (a) a C$_{6-10}$ aryl group (preferably phenyl) optionally substituted by 1 to 3 substituents selected from
         (i) a C$_{1-6}$ alkyl group (preferably methyl) optionally substituted by 1 to 3 C$_{1-6}$ alkoxy groups (preferably methoxy),
         (ii) a C$_{1-6}$ alkylsulfonyl group (preferably methylsulfonyl), and
         (iii) a sulfamoyl group,
      (b) an aromatic heterocyclic group (preferably thienyl, thiazolyl, imidazolyl, triazolyl, isoxazolyl, pyridyl, indolyl) optionally substituted by 1 to 3 substituents selected from
         (i) a halogen atom (preferably a fluorine atom, a chlorine atom),
         (ii) a C$_{1-6}$ alkyl group (preferably methyl),
         (iii) a C$_{6-10}$ aryl group (preferably phenyl),
         (iv) an aromatic heterocyclic group (preferably thienyl), and
         (v) a non-aromatic heterocyclic group (preferably morpholinyl),
      (c) a non-aromatic heterocyclic group (preferably pyrrolidinyl, morpholinyl, thiazolidinyl, tetrahydropyranyl, tetrahydrofuryl) optionally substituted by 1 to 3 substituents selected from
         (i) a C$_{1-6}$ alkyl group (preferably methyl) optionally substituted by 1 to 3 C$_{6-10}$ aryl groups (preferably phenyl), and
         (ii) an oxo group,
      (d) a C$_{3-6}$ cycloalkyl group (preferably cyclopropyl, cyclohexyl),
      (e) a hydroxy group,
      (f) a C$_{1-6}$ alkoxy group (preferably ethoxy, isopropoxy),
      (g) a C$_{6-10}$ aryloxy group (preferably phenoxy),
      (h) a C$_{1-6}$ alkoxy-carbonyl group (preferably methoxycarbonyl),
      (i) a C$_{6-10}$ aryl-carbonyl group (preferably benzoyl),
      (j) a C$_{1-6}$ alkylsulfonyl group (preferably methylsulfonyl),
      (k) a C$_{6-10}$ arylsulfonyl group (preferably phenylsulfonyl),
      (l) an aromatic heterocyclesulfonyl group (preferably pyridylsulfonyl),
      (m) a C$_{1-6}$ alkylsulfonylamino group (preferably methylsulfonylamino) optionally substituted by 1 to 3 halogen atoms (preferably a fluorine atom),
      (n) a halogen atom (preferably a fluorine atom), and
      (o) a cyano group, (B) a $C_{3-10}$ cycloalkyl group (preferably cyclopropyl) optionally substituted by 1 to 3 $C_{6-10}$ aryl groups (preferably phenyl), (C) a $C_{6-14}$ aryl group (preferably phenyl) optionally substituted by 1 to 3 $C_{1-6}$ alkyl groups (preferably methyl) optionally substituted by 1 to 3 non-aromatic heterocyclic groups (preferably morpholinyl), (D) an aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like) optionally substituted by 1 to 3 substituents selected from
  (a) a $C_{1-6}$ alkyl group (preferably methyl) optionally substituted by 1 to 3 $C_{6-10}$ aryl groups (preferably phenyl) optionally substituted by 1 to 3 halogen atoms (preferably a fluorine atom), and
  (b) a $C_{1-6}$ alkoxy group (preferably methoxy), and (E) a non-aromatic heterocyclic group (preferably a 5- or 6-membered non-aromatic heterocyclic group such as pyrrolidinyl, piperidinyl and the like) optionally substituted by 1 to 3 substituents selected from
  (a) a $C_{1-6}$ alkyl group (preferably methyl) optionally substituted by 1 to 3 $C_{6-10}$ aryl groups (preferably phenyl), and
  (b) a $C_{1-6}$ alkyl-carbonyl group (preferably acetyl) optionally substituted by 1 to 3 halogen atoms (preferably a fluorine atom), or (3) a nitrogen-containing heterocyclylcarbonyl group (preferably 1-pyrrolidinylcarbonyl, 1-piperidinocarbonyl, 1-piperazinylcarbonyl, morpholinocarbonyl) optionally substituted by 1 to 3 substituents selected from
  (a) a $C_{1-6}$ alkyl group (preferably methyl, ethyl) optionally substituted by 1 to 3 substituents selected from
    (i) a halogen atom (preferably a fluorine atom),
    (ii) a $C_{6-10}$ aryl group (preferably phenyl),
    (iii) a $C_{1-6}$ alkylsulfonyl group (preferably methylsulfonyl), and
    (iv) an aromatic heterocyclic group (preferably pyridyl),
  (b) a $C_{6-10}$ aryl group (preferably phenyl),
  (c) a $C_{6-10}$ aryloxy group (preferably phenoxy),
  (d) a $C_{6-10}$ aryl-carbonyl group (preferably benzoyl),
  (e) a $C_{6-10}$ arylsulfonyl group (preferably phenylsulfonyl),
  (f) an aromatic heterocyclic group (preferably pyridyl, pyrazinyl),
  (g) an aromatic heterocyclyloxy group (preferably pyridyloxy), and
  (h) a non-aromatic heterocyclic group (preferably hexahydropyrimidinyl) optionally substituted by 1 to 3 oxo groups.

Ring A is an optionally further substituted pyridazine ring.

Ring A optionally further has substituent(s), besides group R and the cyclic amino group. Examples of the "substituent" of the "optionally substituted pyridazine ring" for ring A include substituents selected from the above-mentioned Substituent Group (a).

The "pyridazine ring" of the "optionally substituted pyridazine ring" optionally has 1 or 2 of the above-mentioned substituents at substitutable positions. When the number of the substituents is not less than 2, the respective substituents may be the same or different. These substituents are optionally further substituted by substituent(s) selected from Substituent Group (a).

Ring A is preferably a pyridazine ring.

$R_1$, $R_2$, $R_3$, $R_4$, $R_{11}$, $R_{12}$, $R_{13}$ and $R_{14}$ are each independently a hydrogen atom or a substituent, or $R_1$ and $R_{11}$ in combination, $R_2$ and $R_{12}$ in combination, $R_3$ and $R_{13}$ in combination, or $R_4$ and $R_{14}$ in combination optionally form an oxo group, or $R_2$ and $R_4$ in combination optionally form a bond or an alkylene cross-linkage.

Examples of the "substituent" for $R_1$, $R_2$, $R_3$, $R_4$, $R_{11}$, $R_{12}$, $R_{13}$ or $R_{14}$ include an optionally substituted hydrocarbon group, an optionally substituted heterocyclic group, an optionally substituted hydroxyl group, an optionally substituted amino group, an optionally substituted mercapto group, a cyano group, nitro group, an acyl group, halogen atom and the like.

Examples of the "optionally substituted hydrocarbon group" and "optionally substituted heterocyclic group" include those similar to the "optionally substituted hydrocarbon group" and "optionally substituted heterocyclic group", which are exemplified as "substituent" of the "optionally substituted carbamoyl group" for R.

The "optionally substituted hydroxyl group" is a hydroxyl group optionally substituted by a substituent selected from an "optionally substituted hydrocarbon group", an "optionally substituted heterocyclic group", an "acyl group" and the like. The "optionally substituted mercapto group" is a mercapto group optionally substituted by a substituent selected from an "optionally substituted hydrocarbon group", an "optionally substituted heterocyclic group", an "acyl group" and the like. The "optionally substituted amino group" is an amino group optionally mono- or di-substituted by substituent(s) selected from an "optionally substituted hydrocarbon group", an "optionally substituted heterocyclic group", an "acyl group" and the like. When the amino group is di-substituted, the respective substituents may be the same or different.

Examples of the "optionally substituted hydrocarbon group" and "optionally substituted heterocyclic group" include those similar to the "optionally substituted hydrocarbon group" and "optionally substituted heterocyclic group", which are exemplified as "substituent" of the "optionally substituted carbamoyl group" for R.

Examples of the "acyl group" exemplified as "substituent" for $R_1$, $R_2$, $R_3$, $R_4$, $R_{11}$, $R_{12}$, $R_{13}$ or $R_{14}$, and the "acyl group" exemplified as the substituent of the above-mentioned "optionally substituted hydroxyl group", "optionally substituted mercapto group" and "optionally substituted amino group" include a group represented by formula: —$COR^A$, —CO—$OR^A$, —$SO_3R^A$, —$SO_2R^A$, —$SOR^A$, —CO—$NR^{A\prime}R^{B\prime}$, —CS—$NR^{A\prime}R^{B\prime}$ or —$SO_2NR^{A\prime}R^{B\prime}$ wherein $R^A$ is a hydrogen atom, an optionally substituted hydrocarbon group or an optionally substituted heterocyclic group, and $R^{A\prime}$ and $R^{B\prime}$ are the same or different and each is a hydrogen atom, an optionally substituted hydrocarbon group or an optionally substituted heterocyclic group, or $R^{A\prime}$ and $R^{B\prime}$ optionally form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A\prime}$ or $R^{B\prime}$ include those similar to the "optionally substituted hydrocarbon group" and "optionally substituted heterocyclic group", which are exemplified as "substituent" of the "optionally substituted carbamoyl group" for R.

Examples of the "nitrogen-containing heterocycle" of the "optionally substituted nitrogen-containing heterocycle" formed by $R^{A\prime}$ and $R^{B\prime}$ together with the adjacent nitrogen atom include a 5- to 7-membered nitrogen-containing heterocycle containing, as a ring-constituting atom besides carbon atom, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

Examples of the "substituent" of the above-mentioned "optionally substituted nitrogen-containing heterocycle" include those exemplified in the above-mentioned Substituent Group (a).

The "nitrogen-containing heterocycle" of the "optionally substituted nitrogen-containing heterocycle" optionally has 1 or 2 of the above-mentioned substituents at substitutable positions. When the number of the substituents is not less than 2, the respective substituents may be the same or different. These substituents are optionally further substituted by substituent(s) selected from Substituent Group (a).

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by $C_{1-6}$ alkyl group(s) optionally substituted by 1 to 3 halogen atoms;
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl) optionally substituted by 1 to 3 substituents selected from a $C_{1-6}$ alkyl group optionally substituted by 1 to 3 halogen atoms;
and the like.

Examples of the "alkylene" of the "alkylene cross-linkage" formed by $R_2$ and $R_4$ in combination include a $C_{1-6}$ alkylene, specifically, —$CH_2$—, —$(CH_2)_2$—, —$(CH_2)_3$—, —$(CH_2)_4$—, —$(CH_2)_5$—, —$(CH_2)_6$—, —$CH(CH_3)$—, —$CH(C_2H_5)$—, —$CH(C_3H_7)$—, —$CH(i$-$C_3H_7)$—, —$CH(CH_3)$—$CH_2$—, —$CH_2$—$CH(CH_3)$—, —$CH(CH_3)$—$(CH_2)_2$—, —$(CH_2)_2$—$CH(CH_3)$—, —$CH_2$—$CH(CH_3)$—$CH_2$—, —$C(CH_3)_2$—, —$(CH(CH_3))_2$—, —$(CH_2)_2$—$C(CH_3)_2$—, —$(CH_2)_3$—$C(CH_3)_2$—, —$CH_2$—$CH(CH_3)$—, —$CH_2$—$C(CH_3)_2$—) and the like. Of these, a $C_{1-3}$ alkylene (—$CH_2$—, —$(CH_2)_2$—, —$(CH_2)_3$—) is preferable.

$R_1$, $R_2$, $R_3$, $R_4$, $R_{11}$, $R_{12}$, $R_{13}$ and $R_{14}$ are preferably all hydrogen atoms.

m and n are each independently an integer of 0 to 2.

m and n is each preferably independently 0 or 1, more preferably the one is 0 or 1, and the other is 1, further more preferably, the one is 0, and the other is 1.

Ring B is an optionally substituted ring, provided that the two atoms constituting ring B, which are adjacent to the spiro carbon atom, are not oxygen atoms at the same time.

The "ring" of the "optionally substituted ring" for ring B only needs to be a ring wherein the one of the carbon atoms constituting the "ring" is a spiro carbon atom, and the two atoms adjacent to the spiro carbon atom are not oxygen atoms at the same time. Examples of the ring include a non-aromatic cyclic hydrocarbon, a non-aromatic heterocycle, non-aromatic fused ring and the like.

Examples of the "non-aromatic cyclic hydrocarbon" include a cycloalkane, a cycloalkene, a cycloalkadiene and the like, each of which is optionally condensed with a benzene ring. Specific examples thereof include a monocyclic non-aromatic cyclic hydrocarbon such as a $C_{3-10}$ cycloalkane (e.g., cyclopropane, cyclobutane, cyclopentane, cyclohexane, cycloheptane, cyclooctane, cyclononane, cyclodecane), a $C_{3-10}$ cycloalkene (e.g., cyclopropene, cyclobutene, cyclopentene, cyclohexene, cycloheptene, cyclooctene, cyclononene, cyclodecene), a $C_{4-10}$ cycloalkadiene (e.g., cyclobutadiene, cyclopentadiene, cyclohexadiene, cycloheptadiene, cyclooctadiene, cyclononadiene, cyclodecadiene) and the like.

Examples of the "non-aromatic heterocycle" include a 3- to 8-membered (preferably 5- or 6-membered) saturated or unsaturated (preferably saturated) non-aromatic heterocycle and the like. Specific examples thereof include a 3- to 8-membered (preferably 5- or 6-membered) saturated or unsaturated (preferably saturated) monocyclic non-aromatic heterocycle such as oxirane, azetidine, oxetane, thietane, pyrroline, pyrrolidine, dihydrofuran, tetrahydrofuran, thiolane, imidazolidine, oxazolidine, isoxazoline, piperidine, dihydropyran, tetrahydropyran, thiane, morpholine, thiomorpholine, piperazine, dihydrooxazine, tetrahydrooxazine, dihydropyrimidine, tetrahydropyrimidine, azepane, oxepane, thiepane, oxazepane, thiazepane, azocane, oxocane, thiocane, oxazocane, thiazocane, dioxine and the like, and the like.

Examples of the "non-aromatic fused ring" include a non-aromatic ring (the above-mentioned non-aromatic cyclic hydrocarbon or non-aromatic heterocycle, preferably a 5- or 6-membered non-aromatic ring) condensed with a benzene ring or a 5- or 6-membered aromatic heterocycle. Specific examples thereof include the above-mentioned monocyclic non-aromatic cyclic hydrocarbon (preferably a $C_{5-6}$ non-aromatic cyclic hydrocarbon) condensed with a benzene ring (e.g., indane, indene, dihydronaphthalene (e.g., 3,4-dihydronaphthalene), tetrahydronaphthalene (e.g., 1,2,3,4-tetrahydronaphthalene), fluorene etc.); the above-mentioned monocyclic non-aromatic heterocycle (preferably a 5- or 6-membered monocyclic non-aromatic heterocycle) condensed with a benzene ring or a 5- or 6-membered aromatic heterocycle (e.g., pyridine) (e.g., dihydrobenzoxazine, dihydrobenzofuran, chromane, chromene, tetrahydroquinazoline, dihydrofuropyridine, indoline etc.), and the like.

The "ring" of the "optionally substituted ring" for ring B is preferably a monocyclic non-aromatic heterocycle (e.g., oxazolidine, imidazolidine, tetrahydrooxazine, isoxazoline, pyrrolidine) or a non-aromatic fused ring (e.g., indane, indene, dihydrobenzoxazine, dihydrobenzofuran, chromane, chromene, tetrahydroquinazoline, dihydrofuropyridine, indoline), more preferably a non-aromatic fused ring, further more preferably a non-aromatic ring condensed with a benzene ring or a 5- or 6-membered aromatic heterocycle (e.g., pyridine), still more preferably a 5- or 6-membered non-aromatic ring condensed with a benzene ring, i.e., a ring represented by the formula (II):

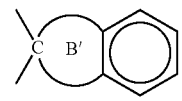

wherein ring B' is a 5- or 6-membered non-aromatic ring.

Examples of the "5- or 6-membered non-aromatic ring" for ring B' include a 5- or 6-membered monocyclic ring, from among the "non-aromatic cyclic hydrocarbon" and "non-aromatic heterocycle" exemplified as the "ring" of the "optionally substituted ring" for ring B. In the "5- or 6-membered non-aromatic ring", the one of the ring-constituting carbon atoms is a spiro carbon atom, and ring B' is condensed with a benzene ring. However, the two atoms constituting ring B', which are adjacent to the spiro carbon atom, are not oxygen atoms at the same time.

The ring represented by the formula (II) is preferably indane, indene, dihydrobenzoxazine, dihydrobenzofuran, chromane, chromene, tetrahydroquinazoline, dihydrofuropyridine or indoline, more preferably dihydrobenzofuran.

Examples of the "substituent" for the "ring" of the "optionally substituted ring" for ring B include those exemplified in the above-mentioned Substituent Group (a).

The "ring" of the "optionally substituted ring" optionally has 1 to 5, preferably 1 to 3 of the above-mentioned substituents at substitutable positions. When the number of the substituents is not less than 2, the respective substituents may be the same or different. These substituents are optionally further substituted by substituent(s) selected from Substituent Group (a). When the "ring" of the "optionally substituted ring" is a non-aromatic fused ring, the ring optionally has substituent(s) at any substitutable position on the ring. For example, when the ring is a 5- or 6-membered non-aromatic ring condensed with a benzene ring, the 5- or 6-membered non-aromatic ring optionally has substituent(s), or the benzene ring optionally has substituent(s), or the both ring optionally have substituent(s).

Preferable examples of the substituent for the "ring" of the "optionally substituted ring" for ring B include
(a) an oxo group,
(b) a $C_{1-6}$ alkyl group (preferably methyl, propyl) optionally substituted by $C_{3-6}$ cycloalkyl group(s) (preferably cyclopropyl),
(c) a $C_{3-6}$ cycloalkyl group (preferably cyclohexyl),
(d) a $C_{6-10}$ aryl group (preferably phenyl) optionally substituted by 1 to 3 halogen atoms (preferably a fluorine atom),
(e) a halogen atom (preferably a chlorine atom) and the like.

In another embodiment, preferable examples of the substituent for the "ring" of the "optionally substituted ring" for ring B include
(a) an oxo group,
(b) a $C_{1-6}$ alkyl group (preferably methyl, propyl) optionally substituted by 1 to 3 substituents selected from
 (i) a $C_{3-6}$ cycloalkyl group (preferably cyclopropyl), and
 (ii) a halogen atom (preferably a fluorine atom),
(c) a $C_{3-6}$ cycloalkyl group (preferably cyclohexyl),
(d) a $C_{6-10}$ aryl group (preferably phenyl) optionally substituted by 1 to 3 halogen atoms (preferably a fluorine atom),
(e) a halogen atom (preferably a chlorine atom) and the like.

In one embodiment, ring B is preferably
a monocyclic non-aromatic heterocycle (preferably oxazolidine, imidazolidine, tetrahydrooxazine, isoxazoline, pyrrolidine); or
a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran);
each of which is optionally substituted, more preferably a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted by 1 to 3 substituents selected from the group consisting of
(a) an oxo group,
(b) a $C_{1-6}$ alkyl group (preferably methyl, propyl) optionally substituted by $C_{3-6}$ cycloalkyl group(s) (preferably cyclopropyl),
(c) a $C_{3-6}$ cycloalkyl group (preferably cyclohexyl),
(d) a $C_{6-10}$ aryl group (preferably phenyl) optionally substituted by 1 to 3 halogen atoms (preferably a fluorine atom), and
(e) a halogen atom (preferably a chlorine atom)
(in the present specification, to be referred to as Substituent Group (b1)).

In another embodiment, ring B is preferably a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted,
more preferably a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted by 1 to 3 substituents selected from the group consisting of
(a) an oxo group,
(b) a $C_{1-6}$ alkyl group (preferably methyl, propyl) optionally substituted by 1 to 3 substituents selected from
 (i) a $C_{3-6}$ cycloalkyl group (preferably cyclopropyl), and
 (ii) a halogen atom (preferably a fluorine atom),
(c) a $C_{3-6}$ cycloalkyl group (preferably cyclohexyl),
(d) a $C_{6-10}$ aryl group (preferably phenyl) optionally substituted by 1 to 3 halogen atoms (preferably a fluorine atom), and
(e) a halogen atom (preferably a chlorine atom)
(in the present specification, to be referred to as Substituent Group (b2)).

Ring B is more preferably a non-aromatic fused ring optionally substituted by 1 to 3 of the above-mentioned Substituent Group (b1) or (b2),
further more preferably a non-aromatic ring condensed with a benzene ring or a 5- or 6-membered aromatic heterocycle (preferably pyridine), which is optionally substituted by 1 to 3 of the above-mentioned Substituent Group (b1) or (b2),
particularly preferably a 5- or 6-membered non-aromatic ring (preferably indane, indene, dihydrobenzoxazine, dihydrobenzofuran, chromane, chromene, tetrahydroquinazoline, indoline, more preferably dihydrobenzofuran) condensed with a benzene ring, which is optionally substituted by 1 to 3 of the above-mentioned Substituent Group (b1) or (b2).

Preferable examples of compound (I) include the following compound or a salt thereof.

[Compound A]

Compound (I) wherein

R is an optionally substituted 5-membered nitrogen-containing aromatic heterocyclic group (preferably thiadiazolyl, pyrazolyl, oxadiazolyl, imidazolyl, more preferably oxadiazolyl);

m and n are each independently 0 or 1 (preferably the one of m and n is 0 or 1, and the other is 1, more preferably the one of m and n is 1, and the other is 0);

ring B is an optionally substituted non-aromatic fused ring (preferably a 5- or 6-membered non-aromatic ring condensed with a benzene ring or a 5- or 6-membered aromatic heterocycle (preferably pyridine) (preferably indane, indene, dihydrobenzoxazine, dihydrobenzofuran, chromane, chromene, tetrahydroquinazoline, dihydrofuropyridine, indoline), which is optionally substituted), or a optionally substituted monocyclic non-aromatic heterocycle (preferably oxazolidine, imidazolidine, tetrahydrooxazine, isoxazoline, pyrrolidine); and $R_1$, $R_2$, $R_3$, $R_4$, $R_{11}$, $R_{12}$, $R_{13}$ and $R_{14}$ are all hydrogen atoms.

[Compound A-1]

Compound (I) wherein

R is (1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted, or (2) a carbamoyl group optionally mono- or di-substituted by optionally substituted $C_{1-6}$ alkyl group(s);

ring A is an optionally further substituted pyridazine ring;

$R_1$, $R_2$, $R_3$, $R_4$, $R_{11}$, $R_{12}$, $R_{13}$ and $R_{14}$ are all hydrogen atoms;

m and n are each independently 0 or 1 (preferably the one of m and n is 0 or 1, and the other is 1, more preferably the one of m and n is 1, and the other is 0); and ring B is a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted.

[Compound B-1]

Compound (I) wherein

R is (1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted by 1 to 3 substituents selected from (a) a $C_{1-6}$ alkyl group (preferably methyl, ethyl, propyl), and (b) an amino group optionally mono- or di-substituted by $C_{1-6}$ alkyl group(s) (preferably methyl), or (2) a carbamoyl group optionally mono- or di-substituted by $C_{1-6}$ alkyl group(s) (preferably methyl, ethyl, propyl, isopropyl, butyl, sec-butyl, isopentyl) optionally substituted by 1 to 3 substituents selected from (a) a $C_{6-10}$ aryl group (preferably phenyl), and (b) an aromatic heterocyclic group (preferably thienyl) optionally substituted by 1 to 3 halogen atoms (preferably a fluorine atom, a chlorine atom);

ring A is a pyridazine ring;

$R_1$, $R_2$, $R_3$, $R_4$, $R_{11}$, $R_{12}$, $R_{13}$ and $R_{14}$ are all hydrogen atoms;

m and n are each independently 0 or 1 (preferably the one of m and n is 0 or 1, and the other is 1, more preferably the one of m and n is 1, and the other is 0); and ring B is a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted by 1 to 3 substituents selected from (a) an oxo group, (b) a $C_{1-6}$ alkyl group (preferably methyl, propyl) optionally substituted by $C_{3-6}$ cycloalkyl group(s) (preferably cyclopropyl), (c) a $C_{3-6}$ cycloalkyl group (preferably cyclohexyl), (d) a $C_{6-10}$ aryl group (preferably phenyl) optionally substituted by 1 to 3 halogen atoms (preferably a fluorine atom), and (e) a halogen atom (preferably a chlorine atom).

[Compound C-1]

Compound (I) wherein

R is an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) optionally substituted by 1 to 3 substituents selected from (a) a $C_{1-6}$ alkyl group (preferably methyl, ethyl, propyl), and (b) an amino group optionally mono- or di-substituted by $C_{1-6}$ alkyl group(s) (preferably methyl);

ring A is a pyridazine ring;

$R_1$, $R_2$, $R_3$, $R_4$, $R_{11}$, $R_{12}$, $R_{13}$ and $R_{14}$ are all hydrogen atoms;

m and n are each independently 0 or 1 (preferably the one of m and n is 0 or 1, and the other is 1, more preferably the one of m and n is 1, and the other is 0); and ring B is a non-aromatic fused ring (preferably a non-aromatic ring condensed with a benzene ring or a 5- or 6-membered aromatic heterocycle (e.g., pyridine), more preferably a 5- or 6-membered non-aromatic ring condensed with a benzene ring (preferably a 5- or 6-membered non-aromatic ring condensed with a benzene ring, such as indane, indene, dihydrobenzoxazine, dihydrobenzofuran, chromane, chromene, tetrahydroquinazoline, indoline and the like, more preferably dihydrobenzofuran)) optionally substituted by 1 to 3 substituents selected from (a) an oxo group, (b) a $C_{1-6}$ alkyl group (preferably methyl, propyl) optionally substituted by $C_{3-6}$ cycloalkyl group(s) (preferably cyclopropyl), (c) a $C_{3-6}$ cycloalkyl group (preferably cyclohexyl), (d) a $C_{6-10}$ aryl group (preferably phenyl) optionally substituted by 1 to 3 halogen atoms (preferably a fluorine atom), and (e) a halogen atom (preferably a chlorine atom).

[Compound A-2]
Compound (I) wherein
R is
(1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted,
(2) a carbamoyl group optionally mono- or di-substituted by substituent(s) selected from
    (A) an optionally substituted $C_{1-6}$ alkyl group (preferably methyl, ethyl, propyl, isopropyl, butyl, sec-butyl, isopentyl),
    (B) an optionally substituted $C_{3-10}$ cycloalkyl group (preferably cyclopropyl),
    (C) an optionally substituted $C_{6-14}$ aryl group (preferably phenyl),
    (D) an optionally substituted aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like), and
    (E) an optionally substituted non-aromatic heterocyclic group (preferably a 5- or 6-membered non-aromatic heterocyclic group such as pyrrolidinyl, piperidinyl and the like), or
(3) an optionally substituted nitrogen-containing heterocyclylcarbonyl group (preferably 1-pyrrolidinylcarbonyl, 1-piperidinocarbonyl, 1-piperazinylcarbonyl, morpholinocarbonyl);
ring A is an optionally further substituted pyridazine ring; $R_1$, $R_2$, $R_3$, $R_4$, $R_{11}$, $R_{12}$, $R_{13}$ and $R_{14}$ are all hydrogen atoms; m and n are each independently 0 or 1 (preferably the one of m and n is 0 or 1, and the other is 1, more preferably the one of m and n is 1, and the other is 0); and
ring B is a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted.

[Compound B-2]
Compound (I) wherein
R is
(1) a $C_{6-14}$ aryl group (preferably phenyl) or an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl), each of which is optionally substituted by 1 to 3 substituents selected from
    (a) a $C_{1-6}$ alkyl group (preferably methyl, ethyl, propyl), and
    (b) an amino group optionally mono- or di-substituted by $C_{1-6}$ alkyl group(s) (preferably methyl),
(2) a carbamoyl group optionally mono- or di-substituted by substituent(s) selected from
    (A) a $C_{1-6}$ alkyl group (preferably methyl, ethyl, propyl, isopropyl, butyl, sec-butyl, isopentyl) optionally substituted by 1 to 3 substituents selected from
        (a) a $C_{6-10}$ aryl group (preferably phenyl) optionally substituted by 1 to 3 substituents selected from
            (i) a $C_{1-6}$ alkyl group (preferably methyl) optionally substituted by 1 to 3 $C_{1-6}$ alkoxy groups (preferably methoxy),
            (ii) a $C_{1-6}$ alkylsulfonyl group (preferably methylsulfonyl), and
            (iii) a sulfamoyl group,
        (b) an aromatic heterocyclic group (preferably thienyl, thiazolyl, imidazolyl, triazolyl, isoxazolyl, pyridyl, indolyl) optionally substituted by 1 to 3 substituents selected from
            (i) a halogen atom (preferably a fluorine atom, a chlorine atom),
            (ii) a $C_{1-6}$ alkyl group (preferably methyl),
            (iii) a $C_{6-10}$ aryl group (preferably phenyl),
            (iv) an aromatic heterocyclic group (preferably thienyl), and
            (v) a non-aromatic heterocyclic group (preferably morpholinyl),
        (c) a non-aromatic heterocyclic group (preferably pyrrolidinyl, morpholinyl, thiazolidinyl, tetrahydropyranyl, tetrahydrofuryl) optionally substituted by 1 to 3 substituents selected from
            (i) a $C_{1-6}$ alkyl group (preferably methyl) optionally substituted by 1 to 3 $C_{6-10}$ aryl groups (preferably phenyl), and
            (ii) an oxo group,
        (d) a $C_{3-6}$ cycloalkyl group (preferably cyclopropyl, cyclohexyl),
        (e) a hydroxy group,
        (f) a $C_{1-6}$ alkoxy group (preferably ethoxy, isopropoxy),
        (g) a $C_{6-10}$ aryloxy group (preferably phenoxy),
        (h) a $C_{1-6}$ alkoxy-carbonyl group (preferably methoxycarbonyl),
        (i) a $C_{6-10}$ aryl-carbonyl group (preferably benzoyl),
        (j) a $C_{1-6}$ alkylsulfonyl group (preferably methylsulfonyl),
        (k) a $C_{6-10}$ arylsulfonyl group (preferably phenylsulfonyl),
        (l) an aromatic heterocyclesulfonyl group (preferably pyridylsulfonyl),
        (m) a $C_{1-6}$ alkylsulfonylamino group (preferably methylsulfonylamino) optionally substituted by 1 to 3 halogen atoms (preferably a fluorine atom),
        (n) a halogen atom (preferably a fluorine atom), and
        (o) a cyano group,
    (B) a $C_{3-10}$ cycloalkyl group (preferably cyclopropyl) optionally substituted by 1 to 3 $C_{6-10}$ aryl groups (preferably phenyl),
    (C) a $C_{6-14}$ aryl group (preferably phenyl) optionally substituted by 1 to 3 $C_{1-6}$ alkyl groups (preferably methyl) optionally substituted by 1 to 3 non-aromatic heterocyclic groups (preferably morpholinyl),
    (D) an aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like) optionally substituted by 1 to 3 substituents selected from
        (a) a $C_{1-6}$ alkyl group (preferably methyl) optionally substituted by 1 to 3 $C_{6-10}$ aryl groups (preferably phenyl) optionally substituted by 1 to 3 halogen atoms (preferably a fluorine atom), and
        (b) a $C_{1-6}$ alkoxy group (preferably methoxy), and
    (E) a non-aromatic heterocyclic group (preferably a 5- or 6-membered non-aromatic heterocyclic group such as pyrrolidinyl, piperidinyl and the like) optionally substituted by 1 to 3 substituents selected from
        (a) a $C_{1-6}$ alkyl group (preferably methyl) optionally substituted by 1 to 3 $C_{6-10}$ aryl groups (preferably phenyl), and (b) a $C_{1-6}$ alkyl-carbonyl group (preferably acetyl) optionally substituted by 1 to 3 halogen atoms (preferably a fluorine atom), or (3) a nitrogen-containing heterocyclylcarbonyl group (preferably 1-pyrrolidinylcarbonyl, 1-piperidinocarbonyl, 1-piperazinylcarbonyl, morpholinocarbonyl) optionally substituted by 1 to 3 substituents selected from (a) a $C_{1-6}$ alkyl group (preferably methyl, ethyl) optionally substituted by 1 to 3 substituents selected from
  (i) a halogen atom (preferably a fluorine atom),
  (ii) a $C_{6-10}$ aryl group (preferably phenyl),
  (iii) a $C_{1-6}$ alkylsulfonyl group (preferably methylsulfonyl), and
  (iv) an aromatic heterocyclic group (preferably pyridyl),
(b) a $C_{6-10}$ aryl group (preferably phenyl),
(c) a $C_{6-10}$ aryloxy group (preferably phenoxy),
(d) a $C_{6-10}$ aryl-carbonyl group (preferably benzoyl),
(e) a $C_{6-10}$ arylsulfonyl group (preferably phenylsulfonyl),
(f) an aromatic heterocyclic group (preferably pyridyl, pyrazinyl),
(g) an aromatic heterocyclyloxy group (preferably pyridyloxy), and
(h) a non-aromatic heterocyclic group (preferably hexahydropyrimidinyl) optionally substituted by 1 to 3 oxo groups;

ring A is a pyridazine ring;
$R_1$, $R_2$, $R_3$, $R_4$, $R_{11}$, $R_{12}$, $R_{13}$ and $R_{14}$ are all hydrogen atoms;
m and n are each independently 0 or 1 (preferably the one of m and n is 0 or 1, and the other is 1, more preferably the one of m and n is 1, and the other is 0); and
ring B is a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted by 1 to 3 substituents selected from (a) an oxo group,
(b) a $C_{1-6}$ alkyl group (preferably methyl, propyl) optionally substituted by $C_{3-6}$ cycloalkyl group(s) (preferably cyclopropyl),
(c) a $C_{3-6}$ cycloalkyl group (preferably cyclohexyl),
(d) a $C_{6-10}$ aryl group (preferably phenyl) optionally substituted by 1 to 3 halogen atoms (preferably a fluorine atom), and
(e) a halogen atom (preferably a chlorine atom).

[Compound D-2]
Compound (I) wherein
R is an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) optionally substituted by 1 to 3 $C_{1-6}$ alkyl groups (preferably methyl, ethyl, propyl); ring A is a pyridazine ring;
$R_1$, $R_2$, $R_3$, $R_4$, $R_{11}$, $R_{12}$, $R_{13}$ and $R_{14}$ are all hydrogen atoms;
m and n are each independently 0 or 1 (preferably the one of m and n is 0 or 1, and the other is 1, more preferably the one of m and n is 1, and the other is 0); and
ring B is a 5- or 6-membered non-aromatic ring condensed with a benzene ring (preferably a 5- or 6-membered non-aromatic ring condensed with a benzene ring, such as indane, indene, dihydrobenzoxazine, dihydrobenzofuran, chromane, chromene, tetrahydroquinazoline, indoline and the like, more preferably dihydrobenzofuran).

[Compound A-3]
Compound (I) wherein
R is
(1) a $C_{6-14}$ aryl group (preferably phenyl), an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) or a non-aromatic heterocyclic group (preferably oxazolinyl, thiazolinyl), each of which is optionally substituted,
(2) a carbamoyl group optionally mono- or di-substituted by substituent(s) selected from
  (A) an optionally substituted $C_{1-6}$ alkyl group (preferably methyl, ethyl, propyl, isopropyl, butyl, sec-butyl, isopentyl),
  (B) an optionally substituted $C_{3-10}$ cycloalkyl group (preferably cyclopropyl),
  (C) an optionally substituted $C_{6-14}$ aryl group (preferably phenyl),
  (D) an optionally substituted aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like), and
  (E) an optionally substituted non-aromatic heterocyclic group (preferably a 5- or 6-membered non-aromatic heterocyclic group such as pyrrolidinyl, piperidinyl and the like), or
(3) an optionally substituted nitrogen-containing heterocyclylcarbonyl group (preferably 1-pyrrolidinylcarbonyl, 1-piperidinocarbonyl, 1-piperazinylcarbonyl, morpholinocarbonyl);
ring A is an optionally further substituted pyridazine ring;
$R_1$, $R_2$, $R_3$, $R_4$, $R_{11}$, $R_{12}$, $R_{13}$ and $R_{14}$ are all hydrogen atoms;
m and n are each independently 0 or 1 (preferably the one of m and n is 0 or 1, and the other is 1, more preferably the one of m and n is 1, and the other is 0); and
ring B is a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted.

[Compound B-3]
Compound (I) wherein
R is
(1) a $C_{6-14}$ aryl group (preferably phenyl), an aromatic heterocyclic group (preferably a 5-membered nitrogen-containing aromatic heterocyclic group such as thiadiazolyl, pyrazolyl, oxadiazolyl, imidazolyl and the like, more preferably oxadiazolyl) or a non-aromatic heterocyclic group (preferably oxazolinyl, thiazolinyl), each of which is optionally substituted by 1 to 3 substituents selected from (a) a $C_{1-6}$ alkyl group (preferably methyl, ethyl, propyl) optionally substituted by 1 to 3 substituents selected from
  (i) a hydroxy group,
  (ii) a $C_{1-6}$ alkoxy group (preferably methoxy),
  (iii) a $C_{1-6}$ alkyl-carbonyloxy group (preferably acetyloxy), and
  (iv) a carboxy group,
(b) an amino group optionally mono- or di-substituted by $C_{1-6}$ alkyl group(s) (preferably methyl), and
(c) a $C_{7-12}$ aralkyl group (preferably benzyl), (2) a carbamoyl group optionally mono- or di-substituted by substituent(s) selected from
  (A) a $C_{1-6}$ alkyl group (preferably methyl, ethyl, propyl, isopropyl, butyl, sec-butyl, isopentyl) optionally substituted by 1 to 3 substituents selected from
    (a) a $C_{6-10}$ aryl group (preferably phenyl) optionally substituted by 1 to 3 substituents selected from
      (i) a $C_{1-6}$ alkyl group (preferably methyl) optionally substituted by 1 to 3 $C_{1-6}$ alkoxy groups (preferably methoxy),
      (ii) a $C_{1-6}$ alkylsulfonyl group (preferably methylsulfonyl), and
      (iii) a sulfamoyl group,
    (b) an aromatic heterocyclic group (preferably thienyl, thiazolyl, imidazolyl, triazolyl, isoxazolyl, pyridyl, indolyl) optionally substituted by 1 to 3 substituents selected from
      (i) a halogen atom (preferably a fluorine atom, a chlorine atom),
      (ii) a $C_{1-6}$ alkyl group (preferably methyl),
      (iii) a $C_{6-10}$ aryl group (preferably phenyl),
      (iv) an aromatic heterocyclic group (preferably thienyl), and
      (v) a non-aromatic heterocyclic group (preferably morpholinyl),
    (c) a non-aromatic heterocyclic group (preferably pyrrolidinyl, morpholinyl, thiazolidinyl, tetrahydropyranyl, tetrahydrofuryl) optionally substituted by 1 to 3 substituents selected from
      (i) a $C_{1-6}$ alkyl group (preferably methyl) optionally substituted by 1 to 3 $C_{6-10}$ aryl groups (preferably phenyl), and
      (ii) an oxo group,
    (d) a $C_{3-6}$ cycloalkyl group (preferably cyclopropyl, cyclohexyl),
    (e) a hydroxy group,
    (f) a $C_{1-6}$ alkoxy group (preferably ethoxy, isopropoxy),
    (g) a $C_{6-10}$ aryloxy group (preferably phenoxy),
    (h) a $C_{1-6}$ alkoxy-carbonyl group (preferably methoxycarbonyl),
    (i) a $C_{6-10}$ aryl-carbonyl group (preferably benzoyl),
    (j) a $C_{1-6}$ alkylsulfonyl group (preferably methylsulfonyl),
    (k) a $C_{6-10}$ arylsulfonyl group (preferably phenylsulfonyl),
    (l) an aromatic heterocyclesulfonyl group (preferably pyridylsulfonyl),
    (m) a $C_{1-6}$ alkylsulfonylamino group (preferably methylsulfonylamino) optionally substituted by 1 to 3 halogen atoms (preferably a fluorine atom),
    (n) a halogen atom (preferably a fluorine atom), and
    (o) a cyano group,
  (B) a $C_{3-10}$ cycloalkyl group (preferably cyclopropyl) optionally substituted by 1 to 3 $C_{6-10}$ aryl groups (preferably phenyl),
  (C) a $C_{6-14}$ aryl group (preferably phenyl) optionally substituted by 1 to 3 $C_{1-6}$ alkyl groups (preferably methyl) optionally substituted by 1 to 3 non-aromatic heterocyclic groups (preferably morpholinyl),
  (D) an aromatic heterocyclic group (preferably a 5- or 6-membered aromatic heterocyclic group such as pyrazolyl, triazolyl, tetrazolyl, thiazolyl, isothiazolyl, thiadiazolyl, oxadiazolyl, pyridyl, pyridazinyl and the like) optionally substituted by 1 to 3 substituents selected from
    (a) a $C_{1-6}$ alkyl group (preferably methyl) optionally substituted by 1 to 3 $C_{6-10}$ aryl groups (preferably phenyl) optionally substituted by 1 to 3 halogen atoms (preferably a fluorine atom), and
    (b) a $C_{1-6}$ alkoxy group (preferably methoxy), and
  (E) a non-aromatic heterocyclic group (preferably a 5- or 6-membered non-aromatic heterocyclic group such as pyrrolidinyl, piperidinyl and the like) optionally substituted by 1 to 3 substituents selected from
    (a) a $C_{1-6}$ alkyl group (preferably methyl) optionally substituted by 1 to 3 $C_{6-10}$ aryl groups (preferably phenyl), and
    (b) a $C_{1-6}$ alkyl-carbonyl group (preferably acetyl) optionally substituted by 1 to 3 halogen atoms (preferably a fluorine atom), or
(3) a nitrogen-containing heterocyclylcarbonyl group (preferably 1-pyrrolidinylcarbonyl, 1-piperidinocarbonyl, 1-piperazinylcarbonyl, morpholinocarbonyl) optionally substituted by 1 to 3 substituents selected from
  (a) a $C_{1-6}$ alkyl group (preferably methyl, ethyl) optionally substituted by 1 to 3 substituents selected from
    (i) a halogen atom (preferably a fluorine atom),
    (ii) a $C_{6-10}$ aryl group (preferably phenyl),
    (iii) a $C_{1-6}$ alkylsulfonyl group (preferably methylsulfonyl), and
    (iv) an aromatic heterocyclic group (preferably pyridyl),
  (b) a $C_{6-10}$ aryl group (preferably phenyl),
  (c) a $C_{6-10}$ aryloxy group (preferably phenoxy),
  (d) a $C_{6-10}$ aryl-carbonyl group (preferably benzoyl),
  (e) a $C_{6-10}$ arylsulfonyl group (preferably phenylsulfonyl),
  (f) an aromatic heterocyclic group (preferably pyridyl, pyrazinyl),
  (g) an aromatic heterocyclyloxy group (preferably pyridyloxy), and
  (h) a non-aromatic heterocyclic group (preferably hexahydropyrimidinyl) optionally substituted by 1 to 3 oxo groups;

ring A is a pyridazine ring;
$R_1$, $R_2$, $R_3$, $R_4$, $R_{11}$, $R_{12}$, $R_{13}$ and $R_{14}$ are all hydrogen atoms;
m and n are each independently 0 or 1 (preferably the one of m and n is 0 or 1, and the other is 1, more preferably the one of m and n is 1, and the other is 0); and
ring B is a monocyclic non-aromatic heterocycle (preferably oxazolidine, imidazolidine, tetrahydrooxazine, isoxazoline, pyrrolidine) or a non-aromatic fused ring (preferably a 5- or 6-membered non-aromatic ring condensed with a benzene ring or a 5- or 6-membered aromatic heterocycle (preferably pyridine), such as indane, indene, dihydrobenzoxazine, dihydrobenzofuran, chromane, chromene, tetrahydroquinazoline, dihydrofuropyridine, indoline and the like, more preferably dihydrobenzofuran), each of which is optionally substituted by 1 to 3 substituents selected from
  (a) an oxo group,
  (b) a $C_{1-6}$ alkyl group (preferably methyl, propyl) optionally substituted by 1 to 3 substituents selected from
    (i) a $C_{3-6}$ cycloalkyl group (preferably cyclopropyl), and
    (ii) a halogen atom (preferably a fluorine atom),
  (c) a $C_{3-6}$ cycloalkyl group (preferably cyclohexyl),
  (d) a $C_{6-10}$ aryl group (preferably phenyl) optionally substituted by 1 to 3 halogen atoms (preferably a fluorine atom), and
  (e) a halogen atom (preferably a chlorine atom).

[Compound E]
1'-[6-(3-methyl-1,2,4-thiadiazol-5-yl)pyridazin-3-yl]spiro[1-benzofuran-3,4'-piperidine] (Example 17),
1'-[6-(3-methyl-1,2,4-oxadiazol-5-yl)pyridazin-3-yl]-3H-spiro[2-benzofuran-1,3'-pyrrolidine] (Example 43, 177, 178), 1'-[6-(3-methyl-1,2,4-oxadiazol-5-yl)pyridazin-3-yl]spiro[1-benzofuran-3,3'-pyrrolidine] (Example 51, 179), {5-[6-(1'H-spiro[1-benzofuran-3,4'-piperidin]-1'-yl)pyridazin-3-yl]-1,2,4-oxadiazol-3-yl}methanol (Example 143), 1'-[6-(4-methyl-4,5-dihydro-1,3-thiazol-2-yl)pyridazin-3-yl]spiro[1-benzofuran-3,4'-piperidine] (Example 146), {3-[6-(1'H-spiro[1-benzofuran-3,4'-piperidin]-1'-yl)pyridazin-3-yl]-1,2,4-oxadiazol-5-yl}methanol (Example 148), 1'-[6-(5-methyl-1,2,4-oxadiazol-3-yl)pyridazin-3-yl]-3H-spiro[2-benzofuran-1,3'-pyrrolidine] (Example 150), {5-[6-(1'H,3H-spiro[2-benzofuran-1,3'-pyrrolidin]-1'-yl)pyridazin-3-yl]-1,2,4-oxadiazol-3-yl}methanol (Example 156), {5-[6-(1'H-spiro[1-bensofuran-3,3'-pyrrolidin]-1'-yl)pyridazin-3-yl]-1,2,4-oxadiazol-3-yl}methanol (Example 157), 1-methyl-1'-[6-(3-methyl-1,2,4-oxadiazol-5-yl)pyridazin-3-yl]spiro[indole-3,3'-pyrrolidin]-2(1H)-one (Example 159), or 1'-[6-(3-methyl-1,2,4-oxadiazol-5-yl)pyridazin-3-yl]-3H-spiro[1-benzofuran-2,3'-pyrrolidine] (Example 170)

or a salt thereof.

The compound represented by the formula (I) may be used in the form of a salt.

The "salts" of these compounds are preferably acceptable salts as pharmaceutical products or physiologically acceptable acid addition salts. Examples of such salt include salts with inorganic acid (e.g., hydrochloric acid, phosphoric acid, hydrobromic acid, sulfuric acid etc.) or organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like. When these compounds have an acidic group such as carboxylic acid and the like, for example, they may form salts with inorganic base (e.g., alkali metal or alkaline earth metal such as sodium, potassium, calcium, magnesium and the like, or ammonia etc.) or organic base (e.g., tri-$C_{1-3}$ alkylamine such as triethylamine and the like etc.).

Compound (I) may be used as a prodrug.

A "prodrug" of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc. Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any of these compounds can be produced from compound (I) by a method known per se.

In addition, the prodrug of compound (I) may be a compound, which is converted to compound (I) under the physiological conditions, as described in "Pharmaceutical Research and Development", Vol. 7 (Drug Design), pp. 163-198 (1990), published by Hirokawa Publishing Co. In addition, compound (I) may be a hydrate.

When compound (I) contains an optical isomer (an optically active form), a stereoisomer, a regioisomer or a rotamer, either one of the isomer and a mixture thereof are also encompassed in compound (I). For example, when compound (I) contains an optical isomer, an optical isomer resolved from a racemate is also encompassed in compound (I). These isomers can be each obtained as a single product according to synthesis and separation methods known per se (concentration, solvent extraction, column chromatography, recrystallization etc.).

Compound (I) may be a crystal, and a single crystal and a mixture of crystals are encompassed in compound (I). The crystal can be produced by crystallization by applying a crystallization method known per se.

Compound (I) may be a solvate (e.g., hydrate etc.) or a non-solvate, both of which are encompassed in compound (I).

Compounds labeled with isotope (e.g., $^3H$, $^{14}C$, $^{35}S$, $^{125}I$ etc.) and the like are encompassed in compound (I).

The production methods of compound (I) are explained in the following.

Each symbol of the compounds in the following reaction schemes is as defined above, unless otherwise specified.

The starting material compounds used for the following synthesis methods may used in the form of the salt. Examples thereof include those exemplified as the salt of the compound represented by the above-mentioned the formula (I).

When specific production methods of the starting compounds are not described, commercially available compounds may be easily available, or they can be produced by a method known per se or a method analogous thereto.

The compound obtained in each step can be used as a crude product (as reaction mixture) in the next reaction. In addition, the compound can be isolated from a reaction mixture according to a conventional method, and can be easily purified by a separation means such as recrystallization, distillation, chromatography and the like.

Compound (I) can be synthesized, for example, according to Production Method A-1, Production Method A-2, Production Method B-1, Production Method B-2, Production Method B-3, Production Method C-1 or Production Method C-2, which are explained below, and the like.

[Production Method A-1]

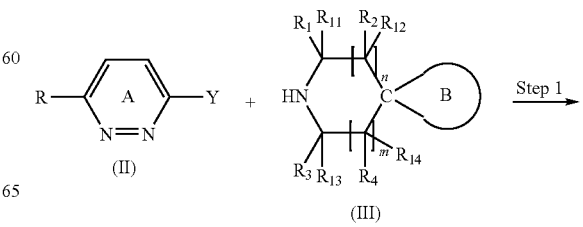

-continued
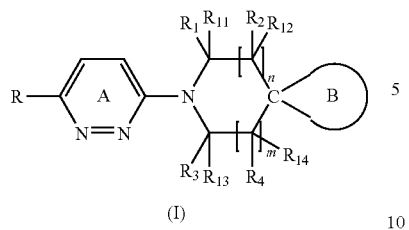
(I)
-continued
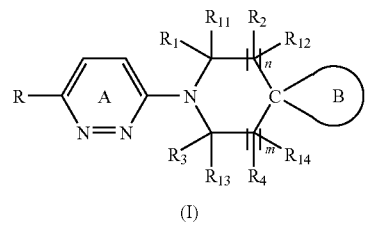
(I)
[Production Method A-2]
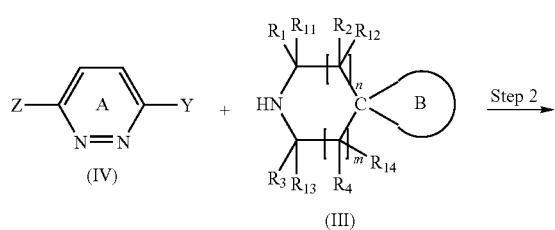
[Production Method B-2]
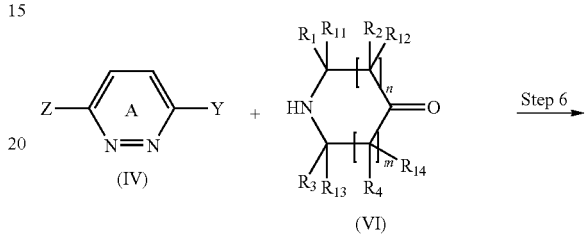
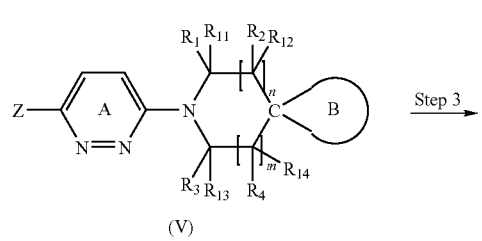
(V)
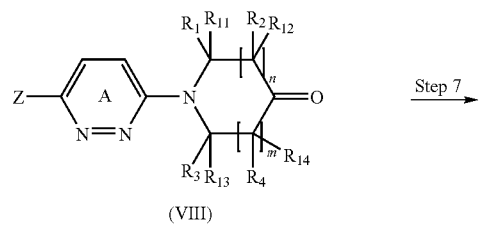
(VIII)
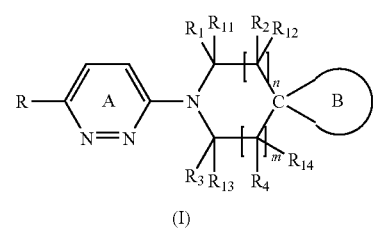
(I)
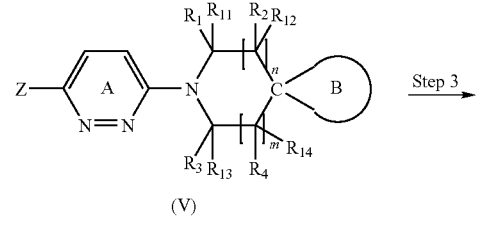
(V)
[Production Method B-1]
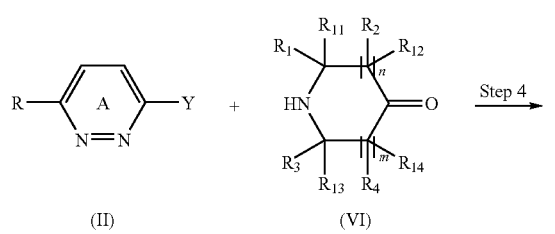
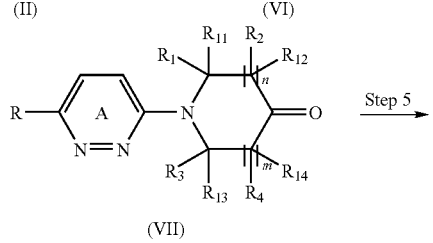
(VII)
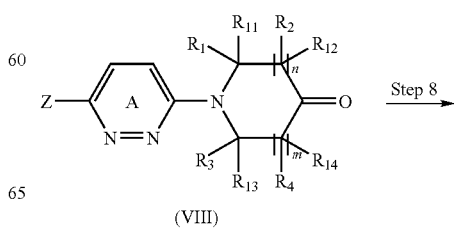
(I)
[Production Method B-3]
(VIII)

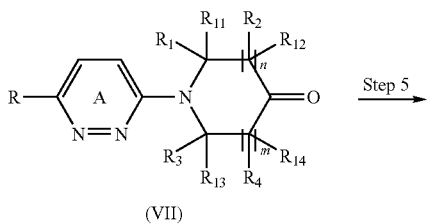
(VII)

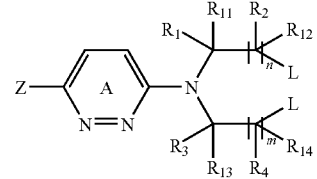
(XI)

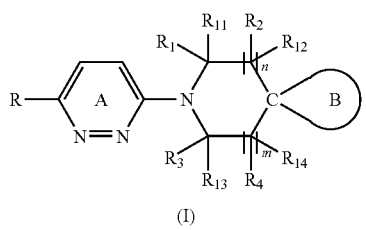
(I)

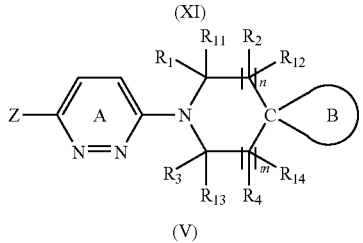
(V)

[Production Method C-1]

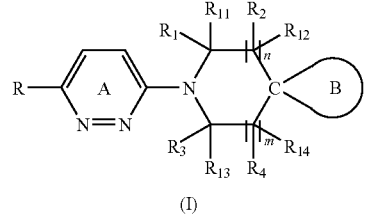
(I)

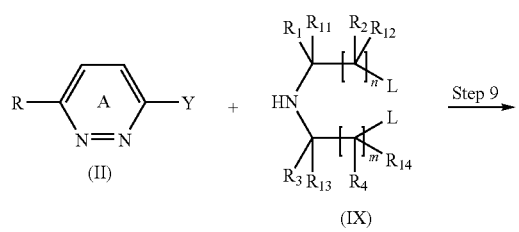
(II)   (IX)

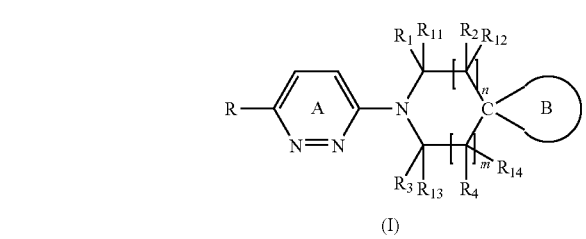
(X)

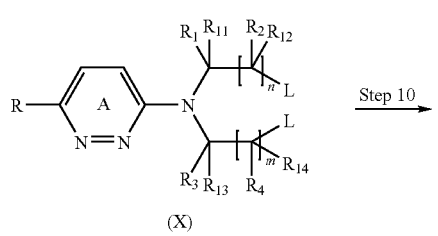
(I)

[Production Method C-2]

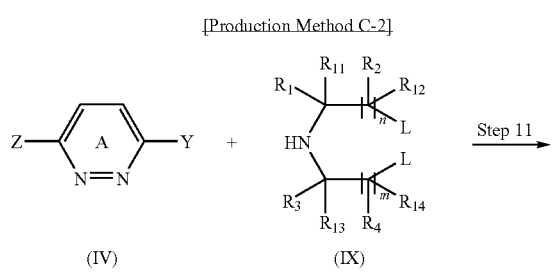
(IV)   (IX)

wherein

Y is a leaving group such as a halogen atom, an alkoxy group, a trifluoromethanesulfonyl group, a p-toluenesulfonyl group, a methanesulfonyl group, a diazonio group; or a sulfanyl group, a sulfinyl group, a sulfonyl group, an amino group, a phosphano group or a phosphono group, each of which is optionally substituted, or the like, Z is a methyl group, a halogen atom, a diazonio group, an acyl group (e.g., an alkoxycarbonyl group, a carboxy group, a trifluoromethanesulfonyl group, a thiocarbamoyl group), a cyano group; or an amino group, a boryl group, a stanyl group or a carbamimido group, each of which is optionally substituted, or the like, and L is a leaving group such as a halogen atom, a p-toluenesulfonyl group, a methanesulfonyl group or the like.

Examples of the "substituent" that the "sulfanyl group, sulfinyl group, sulfonyl group, amino group, phosphano group or phosphono group" of the "sulfanyl group, sulfinyl group, sulfonyl group, amino group, phosphano group or phosphono group, each of which is optionally substituted" for Y optionally has, and the "substituent" that the "amino group, boryl group, stanyl group or carbamimido group" of the "amino group, boryl group, stanyl group or carbamimido group, each of which is optionally substituted" for Z optionally has include those exemplified in the above-mentioned Substituent Group (a).

Step 1 is a production method of compound (I) by heating compound (II) with compound (III).

In this step, the heating is carried out in the presence of a base (e.g., triethylamine, pyridine, potassium carbonate etc.) or an activator (e.g., hydrochloric acid, pyridine hydrochloride, p-toluenesulfonic acid, quaternary ammonium salt etc.). Alternatively, this step may be performed in the presence of a metal catalyst such as palladium, copper and the like.

The amount of compound (III) to be used is generally 0.5 to 10 mol, preferably 1 to 5 mol, per 1 mol of compound (II).

The amount of the base or activator to be used is generally 1 to 10 mol, preferably 1 to 5 mol, per 1 mol of compound (II), respectively.

The amount of the metal catalyst to be used is generally 0.01 to 2 mol, preferably 0.1 to 0.5 mol, per 1 mol of compound (II).

The reaction temperature is generally 50 to 200° C.

The reaction time is generally 1 to 24 hr.

Step 2 is a production method of compound (V) by heating compound (IV) with compound (III).

This step can be performed in the same manner and under similar conditions as in Step 1.

Step 4 is a production method of compound (VII) by heating compound (II) with compound (VI).

This step can be performed in the same manner and under similar conditions as in Step 1.

Step 6 is a production method of compound (VIII) by heating compound (IV) with compound (VI).

This step can be performed in the same manner and under similar conditions as in Step 1.

Step 9 is a production method of compound (X) by heating compound (II) with compound (IX).

This step can be performed in the same manner and under similar conditions as in Step 1.

Step 11 is a production method of compound (XI) by heating compound (IV) with compound (IX).

This step can be performed in the same manner and under similar conditions as in Step 1.

Step 3 is a production method of compound (I) from compound (V).

A compound wherein Z in the formula (V) is an alkoxycarbonyl group or a carboxy group is hereinafter referred to as "compound (Va)". Compound (I) wherein R in the formula (I) is an optionally substituted carbamoyl group can be produced, for example, by any of the following reaction:

(1) a method of heating compound (Va) with an amine derivative corresponding to R in the formula (I), (2) a method of condensing compound (Va) with the amine derivative using a dehydration-condensation agent, or (3) a method of activating the carboxylic acid of compound (Va) according to a conventional activation method, and reacting the resulting compound with the amine derivative.

The amount of the amine derivative to be used for the above-mentioned method (1) is generally 1 to 10 mol, preferably 1 to 5 mol, per 1 mol of compound (Va).

The reaction temperature for this method is generally 10 to 200° C., and the reaction time for this method is generally 1 to 24 hr.

Examples of the dehydration-condensation agent used for the above-mentioned method (2) include N,N'-dicyclohexylcarbodiimide, 1-ethyl-3-(3-dimethylaminopropyl)carbodiimide, carbonyldiimidazole, N,N'-disuccinimidylcarbonate, 1H-benzotriazol-1-yloxytris(dimethylamino)phosphonium hexafluorophosphate, O-(benzotriazol-1-yl)-N,N,N',N'-tetramethyluronium tetrafluoroborate and the like.

The amount of the dehydration-condensation agent to be used is generally 1 to 10 mol, preferably 1 to 5 mol, per 1 mol of compound (Va).

The amount of the amine derivative to be used for this method is generally 1 to 10 mol, preferably 1 to 5 mol, per 1 mol of compound (Va).

The reaction temperature for this method is generally 0 to 200° C., and the reaction time for this method is generally 1 to 24 hr.

Examples of the activation method of the carboxylic acid for the above-mentioned (3) include the following methods:

(a) a method of converting the carboxylic acid moiety of compound (Va) to a mixed acid anhydride with a chloroformate, pivaloyl chloride and the like, and reacting the mixed acid anhydride with the above-mentioned amine derivative, (b) a method of converting the carboxylic acid moiety of compound (Va) to an acid chloride with oxalyl chloride, thionyl chloride and the like, and reacting the acid chloride with the above-mentioned amine derivative, or (c) a method of converting the carboxylic acid moiety of compound (Va) to an ester with 1-hydroxylbenzotriazole (HOBt) and a dehydration-condensation agent and the like, and reacting the ester with the above-mentioned amine derivative.

The amount of the chloroformate, pivaloyl chloride and the like to be used for the above-mentioned method (a) is generally 1 to 10 mol, preferably 1 to 5 mol, per 1 mol of compound (Va).

The amount of the amine derivative to be used for this method is generally 1 to 10 mol, preferably 1 to 5 mol, per 1 mol of compound (Va).

The reaction temperature for this method is generally 0 to 200° C., and the reaction time for this method is generally 1% to 24 hr.

The amount of the oxalyl chloride, thionyl chloride and the like to be used for the above-mentioned method (b) is generally 1 to 10 mol, preferably 1 to 5 mol, per 1 mol of compound (Va).

The amount of the amine derivative to be used for this method is generally 1 to 10 mol, preferably 1 to 5 mol, per 1 mol of compound (Va).

The reaction temperature for this method is generally 0 to 200° C., and the reaction time for this method is generally 0.5 to 24 hr.

The amount of the 1-hydroxylbenzotriazole to be used for the above-mentioned method (c) is generally 1 to 10 mol, preferably 1 to 5 mol, per 1 mol of compound (Va).

Examples of the dehydration-condensation agent for this method include those exemplified in the above-mentioned method (2).

The amount of the dehydration-condensation agent to be used is generally 1 to 10 mol, preferably 1 to 5 mol, per 1 mol of compound (Va).

The amount of the amine derivative to be used for this method is generally 1 to 10 mol, preferably 1 to 5 mol, per 1 mol of compound (Va).

The reaction temperature for this method is generally 0 to 200° C., and the reaction time for this method is generally 1 to 24 hr.

The amine derivative used for this method can be produced according to a method known per se or a method analogous thereto.

A compound wherein Z in the formula (V) is a methyl group is hereinafter referred to as "compound (Vb)". Compound (I) wherein R in the formula (I) is an optionally substituted carbamoyl group can be produced by a method of converting the methyl group to a carboxy group with an oxidant such as potassium permanganate, selenium dioxide and the like, and condensing the resulting compound with an amine derivative corresponding to R in the formula (I) in the presence of a dehydration-condensation agent, in the same manner and under similar conditions as in the above-mentioned method (2), and the like.

The amount of the oxidant to be used for the conversion reaction of the methyl group of compound (Vb) to a carboxy group is generally 1 to 30 mol, preferably 1 to 10 mol, per 1 mol of compound (Vb).

The reaction temperature for this reaction is generally 0 to 200° C., and the reaction time for this reaction is generally 1 to 24 hr.

Compound (I) wherein R in the formula (I) is an optionally substituted thiadiazolyl group can be produced by subjecting compound (Vb) to a cyclization with thionyl chloride and an optionally substituted amidine derivative corresponding to the optionally substituted thiadiazolyl group.

The amount of the thionyl chloride to be used for this reaction is generally 1 to 10 mol, preferably 1 to 5 mol, per 1 mol of compound (Vb).

The amount of the optionally substituted amidine derivative to be used for this reaction is generally 1 to 10 mol, preferably 1 to 5 mol, per 1 mol of compound (Vb).

The reaction temperature for this reaction is generally 0 to 200° C., and the reaction time for this reaction is generally 1 to 24 hr.

The above-mentioned optionally substituted amidine derivative used for this method can be produced according to a method known per se or a method analogous thereto.

A compound wherein Z in the formula (V) is a halogen atom, a trifluoromethanesulfonyl group, a diazonio group; or an amino group, a boryl group or a stanyl group, each of which is optionally substituted is hereinafter referred to as "compound (Vc)". Compound (I) wherein R in the formula (I) is an optionally substituted cyclic group can be produced by reacting compound (Vc) with a boron acid derivative, halide, stanyl derivative, alkene derivative, amine derivative, amide derivative, urea derivative or the like, each of which corresponds to R in the formula (I) (optionally substituted cyclic group), in the presence of a metal catalyst generally known (e.g., palladium, nickel, zinc, magnesium).

For example, compound (I) wherein R in the formula (I) is an optionally substituted cyclic group can be produced as follows:
(i) when Z is a halogen atom, compound (Vc) is reacted with a boron acid derivative, stanyl derivative, alkene derivative, amine derivative, amide derivative, urea derivative or the like, each of which corresponds to R in the formula (I) (optionally substituted cyclic group), in the presence of a metal catalyst,
(ii) when Z is a trifluoromethanesulfonyl group, compound (Vc) is reacted with a boron acid derivative, stanyl derivative, alkene derivative, amine derivative, amide derivative, urea derivative or the like, each of which corresponds to R in the formula (I) (optionally substituted cyclic group), in the presence of a metal catalyst,
(iii) when Z is a diazonio group, compound (Vc) is reacted with a boron acid derivative, stanyl derivative, alkene derivative, amine derivative, amide derivative, urea derivative or the like, each of which corresponds to R in the formula (I) (optionally substituted cyclic group), in the presence of a metal catalyst,
(iv) when Z is an optionally substituted amino group, the optionally substituted amino group is converted to a diazonio group, and the compound (Vc) is reacted with a boron acid derivative, stanyl derivative, alkene derivative, amine derivative, amide derivative, urea derivative or the like, each of which corresponds to R in the formula (I) (optionally substituted cyclic group), in the presence of a metal catalyst,
(v) when Z is an optionally substituted boryl group, compound (Vc) is reacted with a halide, alkene derivative or the like, each of which corresponds to R in the formula (I) (optionally substituted cyclic group), in the presence of a metal catalyst, and
(vi) when Z is an optionally substituted stanyl group, compound (Vc) is reacted with a halide, alkene derivative or the like, each of which corresponds to R in the formula (I) (optionally substituted cyclic group), in the presence of a metal catalyst.

The amount of the boron acid derivative, halide, stanyl derivative, alkene derivative, amine derivative, amide derivative, urea derivative or the like to be used for this reaction is generally 1 to 10 mol, preferably 1 to 5 mol, per 1 mol of compound (Vc).

The amount of the metal catalyst to be used for this reaction is generally 0.01 to 2 mol, preferably 0.1 to 0.5 mol, per 1 mol of compound (Vc).

The reaction temperature for this reaction is generally 0 to 200° C., and the reaction time for this reaction is generally 1 to 24 hr.

The above-mentioned boron acid derivative, halide, stanyl derivative, alkene derivative, amine derivative, amide derivative, urea derivative or the like used for this method can be produced according to a method known per se or a method analogous thereto.

A compound wherein Z in the formula (V) is an acyl group is hereinafter referred to as "compound (Vd)". Compound (I) wherein R in the formula (I) is an optionally substituted cyclic group (e.g., an oxadiazolyl group, a thiadiazolyl group, an oxazolyl group, a pyrazole group or the like) can be produced by subjecting compound (Vd) to a cyclization with an amidine derivative, hydrazide derivative, amine derivative or the like, each of which corresponds to the optionally substituted cyclic group, under heating or in the presence of a reagent.

The amount of the amidine derivative, hydrazide derivative, amine derivative or the like to be used for this method is generally 1 to 10 mol, preferably 1 to 5 mol, per 1 mol of compound (Vd).

Examples of the reagent include Lawesson's reagents, p-toluenesulfonyl chloride, phosphorus oxychloride, mixed acid anhydrides, hydrazine and the like. When the reagent is used, the amount thereof to be used is generally 1 to 10 mol, preferably 1 to 5 mol, per 1 mol of compound (Vd).

The reaction temperature is generally 0 to 200° C., and the reaction time is generally 1 to 24 hr.

The above-mentioned amidine derivative, hydrazide derivative, amine derivative or the like used for this method can be produced according to a method known per se or a method analogous thereto.

A compound wherein Z in the formula (V) is a thiocarbamoyl group is hereinafter referred to as "compound (Ve)". Compound (I) wherein R in the formula (I) is an optionally substituted thiadiazolyl group can be produced by dehydrating compound (Ve) with an optionally substituted amidacetal derivative corresponding to the optionally substituted thiadiazolyl group and (aminooxy)(hydroxy)sulfane dioxide and the like, under heating or in the presence of a condensation agent, an acid, a base or the like.

The amount of the optionally substituted amidacetal derivative to be used for this method is generally 1 to 10 mol, preferably 1 to 5 mol, per 1 mol of compound (Ve).

The amount of the (aminooxy)(hydroxy)sulfane dioxide to be used for this method is generally 1 to 10 mol, preferably 1 to 5 mol, per 1 mol of compound (Ve).

Examples of the condensation agent include those exemplified as the dehydration-condensation agent in the above-mentioned (2). When the condensation agent is used, the amount thereof to be used is generally 1 to 10 mol, preferably 1 to 5 mol, per 1 mol of compound (Ve).

Examples of the acid include p-toluenesulfonic acid, polyphosphoric acid, phosphoryl chloride and the like. Examples of the base include 1,8-diazabicyclo[5.4.0]undec-7-ene, sodium hydride, sodium methoxide and the like. When the acid or base is used, the amount thereof to be used is generally 1 to 50 mol, preferably 1 to 10 mol, per 1 mol of compound (Ve).

The reaction temperature for this method is generally 0 to 200° C., and the reaction time for this method is generally 1 to 24 hr.

The optionally substituted amidacetal derivative used for this method can be produced according to a method known per se or a method analogous thereto.

A compound wherein Z in the formula (V) is a cyano group is hereinafter referred to as "compound (Vf)". Compound (I) wherein R in the formula (I) is an optionally substituted tetrazolyl group can be produced by reacting compound (Vf) with an optionally substituted azido derivative corresponding to the optionally substituted tetrazolyl group, under heating or in the presence of a metal catalyst (palladium, copper etc.).

The amount of the optionally substituted azido derivative to be used for this method is generally 1 to 10 mol, preferably 1 to 5 mol, per 1 mol of compound (Vf).

When the metal catalyst is used, the amount thereof to be used is generally 0.01 to 2 mol, preferably 0.1 to 0.5 mol, per 1 mol of compound (Vf).

The reaction temperature for this method is generally 0 to 200° C., and the reaction time for this method is generally 1 to 24 hr.

The optionally substituted azido derivative used for this method can be produced according to a method known per se or a method analogous thereto.

A compound wherein Z in the formula (V) is an optionally substituted carbamimdoyl group is hereinafter referred to as "compound (Vg)". Compound (I) wherein R in the formula (I) is an optionally substituted cyclic group (e.g., an imidazolyl group, an oxadiazolyl group or the like) can be produced by reacting compound (Vg) with an acid chloride derivative, mixed acid anhydrides derivative, orthoester derivative, carboxylic acid derivative or the like, each of which corresponds to the optionally substituted cyclic group, under heating or in the presence of a reagent.

The amount of the acid chloride derivative, mixed acid anhydrides derivative, orthoester derivative, carboxylic acid derivative or the like to be used for this method is generally 1 to 10 mol, preferably 1 to 5 mol, per 1 mol of compound (Vg).

Examples of the reagent include phosphorus oxychloride, p-toluenesulfonyl chloride and the like. When the reagent is used, the amount thereof to be used is generally 0.1 to 50 mol, preferably 0.1 to 10 mol, per 1 mol of, compound (Vg).

The reaction temperature for this method is generally 0 to 200° C., and the reaction time for this method is generally 0.5 to 24 hr.

The acid chloride derivative, mixed acid anhydrides derivative, orthoester derivative, carboxylic acid derivative or the like used for this method can be produced according to a method known per se or a method analogous thereto.

Step 8, which is a production method of compound (VII) from compound (VIII), can be performed in the same manner and under similar conditions as in Step 3.

Step 5, which is a production method of compound (I) from compound (VII), and Step 7, which is a production method of compound (V) from compound (VIII), can be performed according to a method known per se, for example, the method described in WO2006/092731, US2006/0009471, J. Med. Chem. 1992; 35: 2033-2039, J. Med. Chem. 1983; 26: 657-661, J. Heterocyclic Chem. 1981; 18: 811-814, Chem. Pharm. Bull. 2006; 54(5): 611-622, Bioorg. Med. Chem. Lett. 1999; 9: 875-880, Tetrahedron Lett. 2005; 46: 6991-6993, J. Org. Chem. 1976; 41(15): 2628-2633, J. Med. Chem. 1981; 24: 1320-1328, J. Labelled. Compd. Radiopharm. 1998; 41(5): 363-376, Bioorg. Med. Chem. Lett. 1998; 8: 107-112, J. Med. Chem. 1983; 26: 855-861, Bioorg. Med. Chem. Lett. 1997; 7: 663-668 or the like, or a method analogous thereto.

Step 10, which is a production method of compound (I) from compound (X), and Step 12, which is a production method of compound (V) from compound (XI), can be performed by condensing with a dianion derivative corresponding to ring B moiety in the formula (I), according to a method known per se, for example, the method described in J. Med. Chem. 1992; 35:2033-2039 or a method analogous thereto.

The above-mentioned dianion derivative can be produced according to a method known per se or a method analogous thereto.

Compound (II) and compound (IV) can be produced according to a method known per se, for example, the method described in EP 1091956 A, U.S. Pat. No. 5,340,808, Bioorg. Med. Chem. Lett. 2002; 12: 589-591, Chem. Pharm. Bull. 1994; 42(2):371-372 or the like, or a method analogous thereto.

Compound (III) can be produced according to a method known per se, for example, the method described in WO2006/092731, US2006/0009471, J. Med. Chem. 1992; 35: 2033-2039, J. Med. Chem. 1983; 26: 657-661, J. Heterocyclic Chem. 1981; 18: 811-814, Chem. Pharm. Bull. 2006; 54(5): 611-622, Bioorg. Med. Chem. Lett. 1999; 9: 875-880, Tetrahedron Lett. 2005; 46: 6991-6993, J. Org. Chem. 1976; 41(15): 2628-2633, J. Med. Chem. 1981; 24: 1320-1328, J. Labelled. Compd. Radiopharm. 1998; 41(5): 363-376, Bioorg. Med. Chem. Lett. 1998; 8: 107-112, J. Med. Chem. 1983; 26: 855-861, Bioorg. Med. Chem. Lett. 1997; 7: 663-668 or the like, or a method analogous thereto.

Compound (VI) may be commercially available compound, or can be produced according to a method known per se, for example, the method described in Helv. Chim. Acta. 1988; 71: 1035-1041, J. Heterocycl. Chem. 1994; 31: 271-276, J. Heterocycl. Chem. 1965; 2: 308-309, Angew. Chem. 1957; 69: 60, Chem. Ber. 1915; 48: 961, J. Org. Chem. 1949; 14: 530, 534, Bull. Chem. Soc. Jpn 1956; 29: 631, J. Med. Chem. 1980; 23: 895-899 or the like, or a method analogous thereto.

Compound (IX) may be commercially available compound, or can be produced according to a method known per se, for example, the method described in J. Chem. Soc. 1934; 464, Chem. Pharm. Bull. 1962; 10: 390-398 or the like, or a method analogous thereto.

In each reaction of the production method of the above-mentioned compound (I) or a salt thereof and each reaction for the synthesis of the starting material compounds, when the starting material compound has an amino group, a carboxy group or a hydroxy group as a substituent, these groups may have a protecting group introduced thereinto, which is generally used in the peptide chemistry and the like, and the object compound can be obtained by removing, where necessary, the protecting group after the reaction.

Examples of the amino-protecting group include formyl; $C_{1-6}$ alkyl-carbonyl (e.g., acetyl, ethylcarbonyl etc.), phenylcarbonyl, $C_{1-6}$ alkoxy-carbonyl (e.g., methoxycarbonyl, ethoxycarbonyl etc.), phenyloxycarbonyl, $C_{7-10}$ aralkyl-carbonyl (e.g., benzylcarbonyl etc.), trityl, phthaloyl, N,N-dimethylaminomethylene and the like, each of which optionally has substituents(s). Examples of these substituents include a halogen atom (e.g., fluorine, chlorine, bromine, iodine etc.), $C_{1-6}$ alkyl-carbonyl (e.g., methylcarbonyl, ethylcarbonyl, butylcarbonyl etc.), nitro and the like, and the number of the substituent is 1 to 3.

Examples of the carboxy-protecting group include $C_{1-6}$ alkyl (e.g., methyl, ethyl, n-propyl, i-propyl, n-butyl, tert-butyl etc.), phenyl, trityl, silyl and the like, each of which optionally has substituents(s). Examples of these substituents include a halogen atom (e.g., fluorine, chlorine, bromine, iodine etc.), formyl, $C_{1-6}$ alkyl-carbonyl (e.g., acetyl, ethylcarbonyl, butylcarbonyl etc.), nitro and the like, and the number of the substituent is 1 to 3.

Examples of the hydroxy-protecting group include $C_{1-6}$ alkyl (e.g., methyl, ethyl, n-propyl, i-propyl, n-butyl, tert-butyl etc.), phenyl, $C_{7-10}$ aralkyl (e.g., benzyl etc.), formyl, $C_{1-6}$ alkyl-carbonyl (e.g., acetyl, ethylcarbonyl etc.), phenyloxycarbonyl, benzoyl, $C_{7-10}$ aralkyl-carbonyl (e.g., benzylcarbonyl etc.), pyranyl, furanyl, silyl and the like, each of which optionally has substituents(s). Examples of these substituents include a halogen atom (e.g., fluorine, chlorine, bromine, iodine etc.), $C_{1-6}$ alkyl (e.g., methyl, ethyl, n-propyl etc.), phenyl, $C_{7-10}$ aralkyl (e.g., benzyl etc.), nitro and the like and the number of the substituent is 1 to 4.

Elimination of the above-mentioned protecting group can be carried out according to a method known per se or a method analogous thereto, for example, a method of treating with an acid, a base, ultraviolet rays, hydrazine, phenylhydrazine, sodium N-methyldithiocarbamate, tetrabutylammonium fluoride, palladium acetate or the like, reduction or the like.

In addition, in each reaction of the above-mentioned production method of compound (I) or a salt thereof, and each reaction for the synthesis of the starting material compounds, a generally-known solvent may be used during the reaction.

Examples of the solvent generally known include ethers such as tetrahydrofuran, diethyl ether, 1,2-dimethoxyethane, 1,4-dioxane and the like; esters such as ethyl acetate, butyl acetate and the like; aromatic hydrocarbons such as benzene, toluene and the like; aromatic heterocycles such as pyridine, lutidine and the like; amides such as N,N-dimethylformamide, N-methylpyrrolidone and the like; halides such as chloroform, methylene chloride and the like; alcohols such as methanol, ethanol, 2-propanol, 2,2-dimethylethanol and the like; aliphatic hydrocarbon compounds such as hexane, heptane, petroleum ether and the like; carboxylic acids such as formic acid, acetic acid and the like; water and the like.

The solvent to be used during the reaction may be a single solvent or a mixture of 2 to 6 kinds of solvents.

The reaction may be carried out in the presence of, for example, an amine such as triethylamine, N,N-diisopropylamine, pyridine, N-methylmorpholine and the like, or a base such as sodium hydroxide, potassium carbonate and the like. Alternatively, the reaction may be carried out in the presence of, for example, an acid such as hydrochloric acid, sulfuric acid, acetic acid and the like.

Compound (I) obtained by the above method can be isolated and purified by general separation means such as recrystallization, distillation, chromatography and the like. When the thus-obtained compound (I) of the present invention is in a free form, it can be converted to a salt by a method known per se or a method according thereto (e.g., neutralization etc.). Conversely, when it is obtained as a salt, it can be converted to a free form or other salt by a method known per se or a method according thereto. When the obtained compound is a racemate, it can be separated into a d-form and an l-form by a general optical resolution means.

Compound (I) or a prodrug thereof (hereinafter to be also referred to as "the compound of the present invention") shows low toxicity (e.g., more superior as a medicament from the aspects of acute toxicity, chronic toxicity, genetic toxicity, reproductive toxicity, cardiotoxicity, drug interaction, carcinogenicity and the like), and can be safely administered as it is or a pharmaceutical composition containing pharmaceutically acceptable carrier etc. known per se to a mammal (e.g., human, monkey, bovine, horse, swine, mouse, rat, hamster, rabbit, cat, dog, sheep, goat etc.).

Since the compound of the present invention shows an SCD inhibitory action (particularly, SCD-1 inhibitory action), it is useful as an SCD inhibitor.

In addition, the compound of the present invention can show a fatty acid desaturation inhibitory action, an insulin signal enhancing action, suppression of body weight gain and a visceral fat-decreasing action based on a promoted energy consumption, plasma and liver triglyceride lowering action, cholesterol ester and lipoprotein synthesis inhibitory action, and cholesterol efflux improving effect via ATP-binding cassette transporter A1 (ABCA1), which are afforded by an SCD inhibitory action (particularly, SCD-1 inhibitory action). Accordingly, the compound of the present invention is also useful as a medicament based on the above-mentioned action.

Specifically, the compound of the present invention is highly useful as a prophylactic or therapeutic agent for hyperlipidemia (including hypercholesterolemia, high LDL-cholesterolemia, low HDL-cholesterolemia and hypertriglycerid (TG)emia and the like, particularly hypertriglyceridemia), diabetes (including type 1 diabetes, type 2 diabetes, gestational diabetes, obese diabetes and the like, particularly type 2 diabetes), diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, lipid metabolism abnormality, fatty liver, metabolic syndrome, hypertension, cardiac failure, arteriosclerosis (e.g., atherosclerosis), arteriosclerosis-associated disease, fatal myocardial infarction, sudden cardiac death, nonfatal myocardial infarction, angina pectoris decubitus, effort angina pectoris, destabilized angina pectoris, cardiovascular disorders (cardiovascular diseases including cerebral thrombus, cerebral embolism, cerebral hemorrhage, subarachnoid hemorrhage, TIA (transient ischemic attack)) and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can also prevent progress of borderline type, impaired glucose tolerance, IFG (Impaired Fasting Glucose) or IFG (Impaired Fasting Glycemia) into diabetes.

In the present specification, SCD inhibitors and medicaments containing the compound of the present invention are sometimes collectively referred to as "the SCD inhibitor of the present invention".

When the SCD inhibitor of the present invention is administered, compound (I) or a prodrug thereof, which is an active ingredient, may be used as bulk powder. However, it is generally administered in the form of a pharmaceutical preparation produced according to a conventional method using appropriate amounts of carrier for preparation, for example, excipient (e.g., calcium carbonate, kaolin, sodium hydrogen carbonate, lactose, starches, crystalline cellulose, talc, granulated sugar, porous substance etc.), binder (e.g., dextrin, rubbers, alcohol starch, gelatin, hydroxypropylcellulose, hydroxypropylmethylcellulose, pullulan etc.), disintegrant (e.g., calcium carboxymethylcellulose, croscarmellose sodium, crospovidone, low-substituted hydroxypropylcellulose, partly pregelatinized starch etc.), lubricant (e.g., magnesium stearate, calcium stearate, talc, starch, sodium benzoate etc.), colorant (e.g., tar pigment, caramel, diiron trioxide, titanium oxide, riboflavins etc.), corrigent (e.g., sweeteners, flavor etc.), stabilizer (e.g., sodium sulfite etc.), preservative (e.g., parabens, sorbic acid etc.) and the like.

The SCD inhibitor of the present invention appropriately contains the compound of the present invention in an amount effective for the prophylaxis or treatment of a disease. The content of the compound of the present invention in the SCD inhibitor is generally 0.1 to 100 wt % of the whole preparation. The SCD inhibitor of the present invention may contain pharmaceutical components other than the compound of the present invention as an active ingredient. Such component is not particularly limited as long as the object of the present invention can be achieved, and can be appropriately used at a suitable blending ratio.

Specific examples of the dosage form include tablet (including sugar-coated tablet, film-coated tablet, orally disintegrating tablet), film (including orally disintegrable film), pill, capsule, granule, fine granules, powder, syrup, emulsion, suspension, injection, sustained-release injection, inhalant, ointment and the like. These preparations are prepared according to a conventional method (e.g., the method described in the Japanese Pharmacopoeia etc.).

Specifically, as a production method of a tablet, the compound of the present invention as it is, or a homogeneous blend of the compound and an excipient, a binder, a disintegrant or any other suitable additive is granulated by a suitable method, a lubricant and the like are added, and the mixture is compression formed; the compound of the present invention as it is, or a homogeneous blend of the compound and an excipient, a binder, a disintegrant or any other suitable additive is directly compression formed; or granules produced in advance, or a homogeneous blend of the granules and a suitable additive, are(is) compression formed. In addition, the agent can contain a colorant, a corrigent and the like as necessary. Moreover, the agent can be coated with a suitable coating agent.

As a production method of an injection, a given amount of the compound of the present invention is dissolved, suspended or emulsified in water for injection, saline, Ringer's solution and the like to give an aqueous agent, a given amount of the compound of the present invention is generally dissolved, suspended or emulsified in vegetable oil and the like to give a nonaqueous agent, or a given amount of the compound of the present invention is tightly sealed in a container for injection.

As a carrier for oral preparation, a substance conventionally used in the pharmaceutical field such as starch, mannitol, crystalline cellulose, carboxymethylcellulose sodium and the like is used. Examples of the injectable carrier include distilled water, saline, glucose solution, transfusion and the like. In addition, additives generally used for preparations can also be added as appropriate.

Moreover, the SCD inhibitor of the present invention can also be used as a sustained-release preparation. The sustained-release preparation can be produced by directly using a microcapsule (e.g., microsphere•microcapsule, microparticle etc.) produced, for example, by in-water drying method (o/w method, w/o/w method etc.), phase separation method, spray drying method or a method analogous thereto and administered as it is, or said microcapsule, or a pharmaceutical composition in the form of sphere, needle, pellet, film or a cream as a starting material may be formulated into various dosage forms and administered. Examples of the dosage form include parenteral agents (e.g., intramuscular, subcutaneous, intravenous, intraperitoneal or organ injection or implant and the like; transmucosal agent for nasal cavity, rectum, uterus and the like, etc.), oral preparation (e.g., hard capsule, soft capsule, granule, powder, suspension etc.) and the like.

When the sustained-release preparation is an injection, the microcapsule is processed with a dispersing agent (e.g., surfactant such as Tween 80, HCO-60 and the like; polysaccharides such as carboxymethylcellulose, sodium alginate, sodium hyaluronate and the like; protamine sulfate, polyethylene glycol etc.), a preservative (e.g., methylparaben, propylparaben etc.), an isotonicity agent (e.g., sodium chloride, mannitol, sorbitol, glucose etc.), a topical anesthetic (e.g., xylocalne hydrochloride, chlorobutanol etc.) and the like to give an aqueous suspension, or dispersed in a vegetable oil (e.g., sesame oil, corn oil etc.) or a mixture thereof with phospholipid (e.g., lecithin etc.), or medium-chain triglyceride (e.g., miglyol 812 etc.) to give an oil suspension as a sustained-release injection.

When the sustained-release preparation is a microcapsule, its average particle size is about 0.1 to about 300 μm, preferably about 1 to about 150 μm, more preferably about 2 to about 100 μm. To formulate an aseptic microcapsule preparation, a method comprising sterilizing the whole production steps, a method comprising sterilization with γ rays, a method comprising addition of a preservative and the like can be nonlimitatively mentioned.

While the dose of the SCD inhibitor of the present invention varies depending on the administration route, symptom, age or body weight of patients and the like, it is, for example, 0.1-500 mg/day, preferably 1-100 mg/day, as the compound of the present invention for oral administration to an adult patient as an agent for the prophylaxis or treatment of hyperlipidemia, diabetes, obesity, abnormal lipid metabolism, fatty liver, metabolic syndrome, arteriosclerosis-associated disease, cardiovascular disease and the like, which is desirably administered in one to several portions a day. The administration route may be any of oral and parenteral.

Moreover, while the dose of a sustained-release preparation as an example of the SCD inhibitor of the present invention also varies depending on the administration route, symptom, age or body weight of patients and the like, as well as duration of release and the like, it is not particularly limited as long as the effective concentration of the active ingredient can be maintained in the body. The administration frequency is once a day to 3 days or once a week to 3 months and the like, which can be appropriately determined according to the situation.

The SCD inhibitor of the present invention can be used concurrently with other drug treatment, hormone replacement therapy or surgical method. Accordingly, the present invention also provides a combination drug using an SCD inhibitor and other drug or various treatment methods in combination.

Examples of the drug that can be used concurrently with an SCD inhibitor in the combination drug of the present invention (hereinafter sometimes to be abbreviated as a concomitant drug) include a drug having a blood lipid improving effect other than SCD inhibitors, a drug showing a prophylactic or therapeutic effect on any of various diseases that promote arteriosclerosis or ischemic cardiac diseases, and the like.

Examples of the drug other than SCD inhibitors, which has a blood lipid improving effect include HMG-CoA reductase inhibitors, fibrate compounds, squalene synthase inhibitors, ACAT (Acyl-CoA: cholesterol acyltransferase) inhibitors, cholesterol absorption suppressive drug ezetimibe and the like.

Examples of the HMG-CoA reductase inhibitor include pravastatin, simvastatin, lovastatin, atorvastatin, fluvastatin, pitavastatin, rosuvastatin or a salt thereof (e.g., sodium salt etc.) and the like.

Examples of the fibrate compound include bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate and the like.

Examples of the squalene synthase inhibitors include Lapaquistat acetate and the like.

Examples of the ACAT inhibitor include Avasimibe, Eflucimibe, pactimibe and the like.

Examples of the drug other than the above-mentioned, which has a blood lipid improving effect, include, but are not limited to, anion exchange resins (e.g., colestyramine etc.), probucol, nicotinic acid drugs (e.g., nicomol, niceritrol etc.), preparations containing ω-3 polyvalent unsaturated fatty acid or an ester thereof (e.g., ethyl icosapentate, ethyl docosahexaenoate, or a mixture thereof), phytosterol (e.g., soysterol, gamma oryzanol etc.) and the like.

Examples of the hormone replacement therapy include thyroid hormone or estrogen replacement therapy and the like.

Examples of the surgical method include, but are not limited to, intervention treatments such as LDL apheresis, percutaneous transluminal coronary angioplasty, percutaneous coronary recanalization, stenting and the like, and the like.

As various diseases, pathologies and factors that promote arteriosclerosis or ischemic cardiac diseases, hypertension, diabetes, obesity, thrombophilia, autoimmune hyperlipidemia, inflammatory disease, infections and the like are known. Examples of a drug showing a prophylactic or therapeutic effect therefor include, but are not limited to, therapeutic drugs for diabetes, therapeutic drugs for diabetic complications, therapeutic drugs for hyperlipidemia, anti-obesity drugs, anorectic drug, therapeutic drugs for hypertension, antithrombotic, anti-inflammatory drugs, anti-rheumatic drugs, antibacterial agents, antifungal agents, antivirus drugs, antiallergic agents, anti-angiopathic drugs and the like.

Examples of the therapeutic drug for diabetes include insulin preparations (e.g., animal insulin preparation extracted from the pancreas of bovine or swine; human insulin preparation genetically synthesized using $Escherichia\ coli$ or yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors (e.g., Alogliptin or a salt thereof (preferably benzoate), Vildagliptin, Sitagliptin, Saxagliptin, T-6666, TS-021), β3 agonists (e.g., AJ-9677), GPR40 agonists, GLP-1 receptor agonists [e.g., GLP-1, GLP-1MR, NN-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonist), SGLUT (sodium-glucose cotransporter) inhibitors (e.g., T-1095), 11β-hydroxysteroid dehydrogenase inhibitors (e.g., BVT-3498), adiponectins or agonists thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic drug for diabetic complications include aldose reductase inhibitors (e.g., tolrestat, epalrestat, zenarestat, zopolrestat, minalrestat, fidarestat, CT-112, ranireatat (AS-3201)), neurotrophic factor and increasing drugs thereof (e.g., NGF, NT-3, BDNF, neurotrophin production/secretion promoting agents described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavengers (e.g., thioctic acid), cerebral vasodilators (e.g., tiapuride, mexiletine), somatostatin receptor agonists (e.g., BIM23190) and apoptosis signal regulating kinase-1 (ASK-1) inhibitors.

Examples of the therapeutic drug for hyperlipidemia include HMG-CoA reductase inhibitors (e.g., cerivastatin, pravastatin, simvastatin, lovastatin, atorvastatin, fluvastatin, itavastatin, rosuvastatin, pitavastatin or a salt thereof (e.g., sodium salt, calcium salt)), squalene synthase inhibitors (e.g., lapaquistat or a salt thereof (preferably acetate)), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like.

Examples of the anti-obesity drug include lipase inhibitors, a melanin coagulation hormone receptor antagonist and a cannabinoid receptor antagonist as anorectic drugs, and the like.

Examples of the lipase inhibitor include orlistat, ATL-962 and the like.

Examples of the anorectic drug include dexfenfluramin, fluoxetine, sibutramine, biamine, rimonabant and the like.

Examples of the therapeutic drug for hypertension include angiotensin converting enzyme inhibitor, calcium antagonist, potassium channel opener, rennin inhibitor, angiotensin II antagonist, diuretic and the like.

Examples of the angiotensin converting enzyme inhibitor include captopril, enalapril, alacepril, delapril, ramipril, lisinopril, imidapril, benazepril, ceronapril, cilazapril, enalaprilat, fosinopril, moveltopril, perindopril, quinapril, sprapril, temocapril, trandolapril, manidipine and the like.

Examples of the calcium antagonist include nifedipine, amlodipine, efonidipine, nicardipine and the like.

Examples of the rennin inhibitor include aliskiren and the like.

Examples of the potassium channel opener include levcromakalim, L-27152, AL 0671, NIP-121 and the like.

Examples of the angiotensin II antagonist include losartan, candesartan cilexetil, valsartan, irbesartan, (5-methyl-2-oxo-1,3-dioxolen-4-yl)methyl 4-(1-hydroxy-1-methylethyl)-2-propyl-1-[2'-(1H-tetrazol-5-yl)biphenyl-4-ylmethyl]imidazole-5-carboxylate (CS-866), E4177 and the like.

Examples of the diuretic include xanthine derivative preparation, thiazide preparation, antialdosterone preparation, carbonic anhydrase inhibitor, chlorobenzenesulfonamide agent and the like.

Examples of the xanthine derivative preparation include theobromine sodium salicylate, theobromine calcium salicylate and the like.

Examples of the thiazide preparation include ethiazide, cyclopenthiazide, trichloromethiazide, hydrochlorothiazide, hydroflumethiazide, benzylhydrochlorothiazide, penflutizide, polythiazide, methyclothiazide and the like.

Examples of the antialdosterone preparation include spironolactone, triamterene and the like.

Examples of the carbonic anhydrase inhibitor include acetazolamide and the like.

Examples of the chlorobenzenesulfonamide agent include chlortalidone, mefruside, indapamide and the like.

Besides the above, examples of the diuretic include azosemide, isosorbide, ethacrynic acid, piretanide, bumetanide, furosemide and the like.

Examples of the antithrombotic include heparin, warfarin, anti-thrombin drug, thrombolytic agent, platelet aggregation inhibitor and the like.

Examples of the heparin include heparin sodium, heparin calcium, dalteparin sodium and the like.

Examples of the warfarin include warfarin potassium and the like.

Examples of the anti-thrombin drug include aragatroban and the like.

Examples of the thrombolytic agent include urokinase, tisokinase, alteplase, nateplase, monteplase, pamiteplase and the like.

Examples of the platelet aggregation inhibitor include ticlopidine hydrochloride, cilostazol, ethyl icosapentate, beraprost sodium, sarpogrelate hydrochloride and the like.

Examples of the anti-inflammatory drug include non-steroidal antiphlogistic analgetics which are cyclooxygenase (COX) inhibitors (e.g., salicylic acid drug such as various aspirins and the like, anthranilic drug such as mefenamic acid, flufenamic acid and the like, indoleacetic acid drug such as indomethacin, sulindac, acemetacin and the like, phenylacetic acid drug such as diclofenac, fenbufen and the like, propionic drug such as ibuprofen, ketoprofen, loxoprofen, naproxen, tiaprofen and the like, oxicam drug such as piroxicam, tenoxicam, ampiroxicam and the like, pyrazolone drug such as ketophenylbutazone and the like etc.), anti-cytokine drugs (e.g., anti-cytokine antibody such as anti-TNF-α antibody, anti-IL-6 antibody and the like, antisense oligonucleotide of cytokine gene, cytokine binding protein etc.), and the like.

Examples of the anti-rheumatic drug include gold preparation such as gold sodium thiomalate, auranofin and the like, penicillamine drug such as bucillamine, penicillamine and the like, lobenzarit drug such as lobenzarit disodium and the like, acritat, salazosulfapyridine, methotrexate, mizoribine, cyclosporine, azathiopurine, cyclophosphamide, prednisolone farnesylate and the like.

Examples of the antibacterial agents include penicillin antibiotics (e.g., sawacillin, pasetocin, yamacillin, bacacil, viccillin, pentrex etc.), cephem antibiotics (e.g., keflex, kefral, cefzon, tomiron, cefspan, pansporin etc.), macrolide antibiotics (e.g., erythrosine, clarith, klaricid, rulid, josamycin etc.), tetracycline antibiotics (e.g., minomycin, vibramycin, hydramycin, ledermycin etc.), fosfomycin antibiotics (e.g., fosmicin, eukocin etc.), aminoglycoside antibiotics (e.g., kanamycin etc.), new quinolone antibacterial agents (e.g., cravat, tarivid, baccidal, tosuxacin, ozex etc.) and the like.

Examples of the antifungal agent include polyene antifungal agents (e.g., trichomycin, amphotericin B, nystatin etc.), imidazole antifungal agents (e.g., econazole, miconazole, clotrimazole etc.), triazole antifungal agents (e.g., fluconazole, itraconazole, fluconazole etc.), allylamine antifungal agents (e.g., butenafine, terbinafine hydrochloride etc.), flucytosine(5-FC) antifungal agents (e.g., flucytosine etc.) and the like.

Examples of the antivirus drug include nucleic acid synthesis inhibiting antivirus drugs (e.g., acyclovir, gancyclovir, vidarabine, foscarnet, zidovudine, lamivudine, didanosine etc.), intracellular entry suppressing antivirus drugs (e.g., amantadine, zanamivir, oseltamivir etc.), host infection defending ability enhancing antivirus drugs (e.g., interferon, isoprinosine etc.) and the like.

Examples of the antiallergic agent include anti-histamic antiallergic agents (e.g., ketotifen, azelastine, oxatomide, mequitazine, epinastine hydrochloride, terfenadine etc.), non-anti-histamic antiallergic agents (e.g., ozagrel hydrochloride, sodium cromoglycate, tranilast, repirinast, amlexanox etc.) and the like.

Examples of the anti-angiopathic drug include cilostazol, abciximab and the like.

The administration mode of an SCD inhibitor and a concomitant drug to be used in the present invention is not particularly limited, and the SCD inhibitor and the concomitant drug may be combined on administration. Examples of such administration mode include the following: (1) administration of a single preparation obtained by simultaneously processing the SCD inhibitor and the concomitant drug (so-called combination agent), (2) simultaneous administration of two kinds of preparations of the SCD inhibitor and the concomitant drug, which have been separately produced, by the same administration route, (3) administration of two kinds of preparations of the SCD inhibitor and the concomitant drug, which have been separately produced, by the same administration route in a staggered manner, (4) simultaneous administration of two kinds of preparations of the SCD inhibitor and the concomitant drug, which have been separately produced, by different administration routes, (5) administration of two kinds of preparations of the SCD inhibitor and the concomitant drug, which have been separately produced, by different administration routes in a staggered manner (e.g., administration in the order of the SCD inhibitor and the concomitant drug, or in the reverse order) and the like.

The "concurrent use of an SCD inhibitor and a concomitant drug" in the present invention means, for example, concurrent use of the both drugs in any of the above-mentioned administration modes, and an "agent obtained by combining an SCD inhibitor with a concomitant drug" means any agent formulated for a concurrent use of the both drugs in any of the above-mentioned administration modes.

The dose of the concomitant drug can be appropriately determined based on the dose employed clinically. The mixing ratio of the SCD inhibitor and the concomitant drug can be appropriately determined according to the kind of the concomitant drug, subject of administration, administration route, target disease, symptom, combination and the like. For example, for administration of a HMG-CoA reductase inhibitor as a concomitant drug to human, 0.01 to 100 parts by weight of the SCD inhibitor is used per 1 part by weight of the HMG-CoA reductase inhibitor.

EXAMPLES

The present invention is explained in detail in the following by referring to Reference Examples, Examples, Experimental Examples and Formulation Examples, which are mere exemplifications and do not limit the present invention. In addition, the present invention may be modified without departing from the scope of the invention.

The $^1$H-NMR spectrum was measured by Varian Gemini 300 (300 MHz) or BRUKER AVANCE300 (300 MHz) spectrometer using tetramethylsilane as the internal standard, and all δ values are shown in ppm. Unless otherwise specified, the numerical value shown for mixed solvent is a volume mixing ratio of each solvent. Unless otherwise specified, % means wt %. Unless otherwise specified, the ratio of elution solvents used for silica gel chromatography is a volume ratio. In the Examples, room temperature (ambient temperature) means a temperature of from about 20° C. to about 30° C.

Each symbol in the Examples means the following. DMSO: dimethyl sulfoxide, CDCl$_3$: deuterated chloroform, s: singlet, d: doublet, t: triplet, q: quartet, dd: double doublet, dt: double triplet, m: multiplet, brs: broad singlet, J: coupling constant In the Examples, LC/MS analysis was performed under the following conditions.
measurement device: Waters LC/MS system
HPLC part: Agilent HP1100
MS part: Micromass ZMD
column: CAPCELL PAK c18UG120 S-3 μm, 1.5×35 mm (manufactured by Shiseido Co., Ltd.)
solvent: SOLUTION A; 0.05% aqueous trifluoroacetic acid solution, SOLUTION B; 0.04% trifluoroacetic acid acetonitrile solution
gradient cycle: 0 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)
injection volume: 2 μL, flow rate: 0.5 mL/min, detection method: UV 220 nm
MS conditions ionization method: ESI In the Examples, purification by preparative HPLC was performed under the following conditions.
apparatus: high-throughput purification system, Gilson Inc.
column: YMC CombiPrep ODS-A S-5 μm, 50×20 mm, or CombiPrep Hydrosphere C18 S-5 μm, 50×20 mm
solvent: SOLUTION A; 0.1% aqueous trifluoroacetic acid solution, SOLUTION B; 0.1% trifluoroacetic acid acetonitrile solution
gradient cycle: 0 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5), or 0 min (SOLUTION A/SOLUTION B=98/2), 1.00 min (SOLUTION A/SOLUTION B=98/2), 5.00 min (SOLUTION A/SOLUTION B=0/100), 6.40 min (SOLUTION A/SOLUTION B=0/100), 6.50 min (SOLUTION A/SOLUTION B=98/2), 6.60 min (SOLUTION A/SOLUTION B=98/2)
flow rate: 20 mL/min, detection method: UV 220 nm

Example 1

1'-[6-(3-methyl-1,2,4-thiadiazol-5-yl)pyridazin-3-yl]-2,3-dihydrospiro[indene-1,4'-piperidine]

3-Chloro-6-(3-methyl-1,2,4-thiadiazol-5-yl)pyridazine (51 mg), 2,3-dihydrospiro[indene-1,4'-piperidine] hydrochloride (78 mg) and potassium carbonate (70 mg) were suspended in N,N-dimethylformamide (3 mL), and the suspension was stirred at 80° C. overnight. The mixture was cooled to room temperature, diluted with ethyl acetate, and washed twice with aqueous sodium hydrogen carbonate solution. The organic layer was dried over sodium sulfate and the solvent was evaporated under reduced pressure. The residue was purified by silica gel column chromatography (15% ethyl acetate/hexane to 50% ethyl acetate/hexane) and recrystallized from hexane/ethyl acetate to give the object product (53 mg, 60%).

$^1$H NMR (300 MHz, DMSO-d$_6$) δ ppm 1.62 (d, J=13.63 Hz, 2H) 1.77-1.91 (m, 2H) 2.16 (t, J=7.38 Hz, 2H) 2.65 (s, 3H) 2.92 (t, J=7.38 Hz, 2H) 3.18-3.30 (m, 2H) 4.56 (d, J=14.01 Hz, 2H) 7.08-7.26 (m, 4H) 7.48 (d, J=9.47 Hz, 1H) 7.97 (d, J=9.47 Hz, 1H)

Example 2

1'-[6-(3-methyl-1,2,4-thiadiazol-5-yl)pyridazin-3-yl] spiro[indene-1,4'-piperidine]

The object product (22 mg, 25%) was obtained in the same manner as in Example 1 and using 3-chloro-6-(3-methyl-1,2, 4-thiadiazol-5-yl)pyridazine (51 mg), spiro[indene-1,4'-piperidine] trifluoroacetate (105 mg) and potassium carbonate (70 mg).

$^1$H NMR (300 MHz, DMSO-d$_6$) δ ppm 1.28-1.40 (m, 2H) 2.06-2.20 (m, 2H) 2.66 (s, 3H) 3.44-3.57 (m, 2H) 4.57-4.70 (m, 2H) 6.88 (d, J=5.65 Hz, 1H) 7.11-7.29 (m, 3H) 7.36 (d, J=7.16 Hz, 1H) 7.44 (d, J=7.35 Hz, 1H) 7.52 (d, J=9.61 Hz, 1H) 8.01 (d, J=9.61 Hz, 1H)

Example 3

1'-[6-(3-methyl-1,2,4-thiadiazol-5-yl)pyridazin-3-yl] spiro[3,1-benzoxazine-4,4'-piperidin]-2(1H)-one The object product (72 mg, 76%) was obtained in the same manner as in Example 1 and using 3-chloro-6-(3-methyl-1,2, 4-thiadiazol-5-yl)pyridazine (51 mg), spiro[3,1-benzoxazine-4,4'-piperidin]-2(1H)-one hydrochloride (89 mg) and potassium carbonate (70 mg).

$^1$H NMR (300 MHz, DMSO-$d_6$) δ ppm 2.04-2.22 (m, 4H) 2.65 (s, 3H) 3.36-3.50 (m, 2H) 4.58 (d, J=13.63 Hz, 2H) 6.92 (d, J=7.57 Hz, 1H) 7.01 (t, J=7.19 Hz, 1H) 7.22-7.33 (m, 2H) 7.51 (d, J=9.84 Hz, 1H) 8.00 (d, J=9.47 Hz, 1H) 10.32 (s, 1H)

Example 4

1'-[6-(3-methyl-1,2,4-thiadiazol-5-yl)pyridazin-3-yl]-3H-spiro[1-benzofuran-2,4'-piperidine]

The object product (49 mg, 56%) was obtained in the same manner as in Example 1 and using 3-chloro-6-(3-methyl-1,2,4-thiadiazol-5-yl)pyridazine (50 mg), 3H-spiro[1-benzofuran-2,4'-piperidine] (50 mg) and potassium carbonate (50 mg).

$^1$H NMR (300 MHz, DMSO-$d_6$) δ ppm 1.80-1.98 (m, 4H) 2.65 (s, 3H) 3.08 (s, 2H) 3.73-3.85 (m, 2H) 4.03-4.14 (m, 2H) 6.75-6.87 (m, 2H) 7.07-7.15 (m, 1H) 7.21 (d, J=7.35 Hz, 1H) 7.51 (d, J=9.61 Hz, 1H) 7.99 (d, J=9.61 Hz, 1H)

Example 5

1'-[6-(3-methyl-1,2,4-thiadiazol-5-yl)pyridazin-3-yl]spiro[chromene-2,4'-piperidin]-4(3H)-one The object product (29 mg, 31%) was obtained in the same manner as in Example 1 and using 3-chloro-6-(3-methyl-1,2,4-thiadiazol-5-yl)pyridazine (50 mg), spiro[chromene-2,4'-piperidin]-4(3H)-one hydrochloride (60 mg) and potassium carbonate (50 mg).

$^1$H NMR (300 MHz, DMSO-$d_6$) δ ppm 1.74-1.88 (m, 2H) 1.99-2.08 (m, 2H) 2.65 (s, 3H) 2.89 (s, 2H) 3.44-3.56 (m, 2H) 4.23-4.40 (m, 2H) 7.04-7.17 (m, 2H) 7.47 (d, J=9.61 Hz, 1H) 7.58-7.65 (m, 1H) 7.76 (dd, J=7.82, 1.60 Hz, 1H) 7.99 (d, J=9.61 Hz, 1H)

Example 6

1-[6-(3-methyl-1,2,4-thiadiazol-5-yl)pyridazin-3-yl]-1'H-spiro[piperidine-4,2'-quinazolin]-4'(3'H)-one (1) 1'H-spiro[piperidine-4,2'-quinazolin]-4'(3'H)-one 1-Benzyl-1'H-spiro[piperidine-4,2'-quinazolin]-4' (3'H)-one (5.0 g) and 10% palladium-carbon (500 mg) were suspended in methanol (200 mL), and the suspension was stirred at room temperature for 2 days under a hydrogen atmosphere. The catalyst was removed by filtration through celite. The solvent was evaporated under reduced pressure and the residue was crystallized from ethanol/ether to give the object product (2.34 g, 41%).

$^1$H NMR (300 MHz, CDCl$_3$) δ ppm 1.81-2.03 (m, 5H) 2.84-2.99 (m, 4H) 4.47 (s, 1H) 4.47 (s, 1H) 6.62-6.85 (m, 2H) 7.24-7.32 (m, 1H) 7.84-7.88 (m, 1H)

(2) 1-[6-(3-methyl-1,2,4-thiadiazol-5-yl)pyridazin-3-yl]-1'H-spiro[piperidine-4,2'-quinazolin]-4'(3'H)-one The object product (39 mg, 41%) was obtained in the same manner as in Example 1 and using 1'H-spiro[piperidine-4,2'-quinazolin]-4'(3'H)-one (60 mg) obtained by the above-mentioned reaction, 3-chloro-6-(3-methyl-1,2,4-thiadiazol-5-yl)pyridazine (50 mg) and potassium carbonate (50 mg).

$^1$H NMR (300 MHz, DMSO-$d_6$) δ ppm 1.89 (t, J=5.46 Hz, 4H) 2.65 (s, 3H) 3.73-3.89 (m, 2H) 3.97-4.12 (m, 2H) 6.64-6.73 (m, 1H) 6.79 (d, J=7.72 Hz, 1H) 6.91 (s, 1H) 7.22-7.33 (m, 1H) 7.48 (d, J=9.61 Hz, 1H) 7.61 (dd, J=7.72, 1.51 Hz, 1H) 8.00 (d, J=9.61 Hz, 1H) 8.21 (s, 1H)

Example 7

8-[6-(3-methyl-1,2,4-thiadiazol-5-yl)pyridazin-3-yl]-3-phenyl-1-oxa-3,8-diazaspiro[4.5]decan-2-one The object product (72 mg, 29%) was obtained in the same manner as in Example 1 and using 3-chloro-6-(3-methyl-1,2,4-thiadiazol-5-yl)pyridazine (130 mg), 3-phenyl-1-oxa-3,8-diazaspiro[4.5]decan-2-one (142 mg) and potassium carbonate (127 mg).

$^1$H NMR (300 MHz, DMSO-$d_6$) δ ppm 1.97-2.01 (m, 4H) 2.65 (s, 3H) 3.70-3.78 (m, 2H) 3.95 (s, 2H) 4.12-4.16 (m, 2H) 7.13 (t, J=7.2 Hz, 1H) 7.37-7.42 (m, 2H) 7.51-7.59 (m, 3H) 7.99 (d, J=9.6 Hz, 1H)

Example 8

1'-[6-(3-methyl-1,2,4-thiadiazol-5-yl)pyridazin-3-yl]-3H-spiro[2-benzofuran-1,4'-piperidine]

The object product (66 mg, 26%) was obtained in the same manner as in Example 1 and using 3-chloro-6-(3-methyl-1,2,4-thiadiazol-5-yl)pyridazine (150 mg), 3H-spiro[2-benzofuran-1,4'-piperidine] hydrochloride (159 mg) and potassium carbonate (244 mg).

$^1$H NMR (300 MHz, CDCl$_3$) δ ppm 1.88-2.04 (m, 2H) 2.72 (s, 3, H) 3.51-3.61 (m, 2H) 4.53-4.58 (m, 2H) 5.14 (s, 2H) 7.03-7.07 (m, 2H) 7.25-7.30 (m, 3H) 7.97 (d, J=9.6 Hz, 1H)

Example 9

3-methyl-8-[6-(3-methyl-1,2,4-thiadiazol-5-yl)pyridazin-3-yl]-1-phenyl-1,3,8-triazaspiro[4.5]decan-4-one The object product (85 mg, 33%) was obtained in the same manner as in Example 1 and using 3-chloro-6-(3-methyl-1,2,4-thiadiazol-5-yl)pyridazine (130 mg), 3-methyl-1-phenyl-1,3,8-triazaspiro[4.5]decan-4-one dihydrochloride (223 mg) and potassium carbonate (130 mg).

$^1$H NMR (300 MHz, DMSO-$d_6$) δ ppm 1.79 (d, J=14.01 Hz, 2H) 2.42-2.59 (m, 2H) 2.66 (s, 3H) 2.93 (s, 3H) 3.74-3.92 (m, 2H) 4.44 (brs, 2H) 4.69 (s, 2H) 6.62 (d, J=7.95 Hz, 2H) 6.71 (t, J=7.38 Hz, 1H) 7.11 (t, J=8.14 Hz, 2H) 7.49 (d, J=9.84 Hz, 1H) 8.02 (d, J=9.47 Hz, 1H)

Example 10

1'-(6-phenylpyridazin-3-yl)spiro[indene-1,4'-piperidine]

The object product (54 mg, 27%) was obtained in the same manner as in Example 1 and using 3-chloro-6-phenylpyridazine (114 mg), spiro[indene-1,4'-piperidine] trifluoroacetate (210 mg) and potassium carbonate (130 mg).

$^1$H NMR (300 MHz, DMSO-$d_6$) δ ppm 1.27-1.39 (m, 2H) 2.06-2.20 (m, 2H) 3.35-3.47 (m, 2H). 4.46-4.60 (m, 2H) 6.87 (d, J=5.65 Hz, 1H) 7.11-7.29 (m, 3H) 7.31-7.56 (m, 6H) 7.97 (d, J=9.80 Hz, 1H) 8.02-8.09 (m, 2H)

Example 11

1'-[6-(1,2,4-thiadiazol-5-yl)pyridazin-3-yl]spiro[indene-1,4'-piperidine]

The object product (177 mg, 51%) was obtained in the same manner as in Example 1 and using 3-chloro-6-(1,2,4-thiadiazol-5-yl)pyridazine (200 mg), spiro[indene-1,4'-piperidine]trifluoroacetate (300 mg) and potassium carbonate (300 mg).

$^1$H NMR (300 MHz, CDCl$_3$) δ ppm 2.09-2.32 (m, 2H) 3.37-3.61 (m, 2H) 4.66 (d, J=13.56 Hz, 2H) 6.84-6.89 (m, 1H) 6.92-6.97 (m, 1H) 7.10 (d, J=9.61 Hz, 1H) 7.17-7.40 (m, 6H) 8.05 (d, J=9.61 Hz, 1H) 8.72 (s, 1H)

Example 12

N,N-dimethyl-5-[6-(1'H-spiro[indene-1,4'-piperidin]-1'-yl)pyridazin-3-yl]-1,2,4-thiadiazol-3-amine The object product (124 mg, 64%) was obtained in the same manner as in Example 1 and using 5-(6-chloropyridazin-3-yl)-N,N-dimethyl-1,2,4-thiadiazol-3-amine (120 mg), spiro[indene-1,4'-piperidine] trifluoroacetate (150 mg) and potassium carbonate (150 mg).

$^1$H NMR (300 MHz, CDCl$_3$) δ ppm 1.52 (brs, 1H) 2.04 (s, 1H) 2.11-2.28 (m, 2H) 3.25 (s, 6H) 3.41-3.56 (m, 2H) 4.55-4.70 (m, 2H) 6.85 (d, J=5.68 Hz, 1H) 6.94 (d, J=5.68 Hz, 1H) 7.05 (d, J=9.47 Hz, 1H) 7.17-7.40 (m, 4H) 7.98 (d, J=9.84 Hz, 1H)

Example 13

1'-[6-(3-propyl-1,2,4-thiadiazol-5-yl)pyridazin-3-yl]spiro[indene-1,4'-piperidine]

(1) 3-chloro-6-(3-propyl-1,2,4-thiadiazol-5-yl)pyridazine

3-Chloro-6-methylpyridazine (2.06 g) was dissolved in thionyl chloride (11.5 mL). The mixed solution was stirred under reflux overnight. Thionyl chloride was evaporated under reduced pressure, and the residue was azeotroped with toluene. The residue was dissolved in tetrahydrofuran solution, and the solution was cooled to 0° C. Butylamidine hydrochloride (1.97 g) was added and the mixture was stirred for 30 min. 50% Aqueous sodium hydroxide solution was added, and the mixture was warmed from 0° C. to room temperature and stirred overnight. To the reaction solution was added water, and the mixture was extracted with ethyl acetate. The organic layer was washed with saturated brine, and dried over magnesium sulfate. The desiccant was filtered off, and the filtrate was concentrated. The residue was purified by silica gel column chromatography (50% ethyl acetate/hexane), and further recrystallized from ethyl acetate/hexane to give the object product (157 mg, 4%).

$^1$H NMR (300 MHz, CDCl$_3$) δ ppm 1.03 (t, J=7.38 Hz, 3H) 1.83-2.00 (m, 2H) 3.05 (t, J=7.38 Hz, 2H) 7.70 (d, J=9.09 Hz, 1H) 8.28 (d, J=9.09 Hz, 1H)

(2) 1'-[6-(3-propyl-1,2,4-thiadiazol-5-yl)pyridazin-3-yl]spiro[indene-1,4'-piperidine]

The object product (82 mg, 42%) was obtained in the same manner as in Example 1 and using 3-chloro-6-(3-propyl-1,2,4-thiadiazol-5-yl)pyridazine (120 mg) obtained by the above-mentioned reaction, spiro[indene-1,4'-piperidine]trifluoroacetate (150 mg) and potassium carbonate (150 mg).

$^1$H NMR (300 MHz, CDCl$_3$) δ ppm 1.04 (t, J=7.38 Hz, 3H) 1.53 (brs, 1H) 1.84-1.99 (m, 2H) 2.04 (s, 1H) 2.12-2.26 (m, 2H) 2.96-3.06 (m, 2H) 3.39-3.57 (m, 2H) 4.57-4.70 (m, 2H) 6.82-6.89 (m, 1H) 6.91-6.97 (m, 1H) 7.07 (d, J=9.84 Hz, 1H) 7.16-7.40 (m, 4H) 8.03 (d, J=9.47 Hz, 1H)

Example 14

1-[6-(3-methyl-1,2,4-thiadiazol-5-yl)pyridazin-3-yl]-3'H-spiro[azetidine-3,1'-[2]benzofuran]

(1) tert-butyl 3-hydroxy-3-[2-(hydroxymethyl)phenyl]azetidine-1-carboxylate

To a solution of (2-bromophenyl)methanol (4.4 g) in dry tetrahydrofuran (90 mL) was added n-butyllithium (1.6 M hexane solution, 31 mL) at −78° C., and the mixture was warmed to room temperature over 2 hr. A solution of tert-butyl 3-oxoazetidine-1-carboxylate (4.0 g) in dry tetrahydrofuran (30 mL) was added at −78° C., and the mixture was stirred at room temperature for 18 hr. The reaction solution was poured into water, and the mixture was extracted with ethyl acetate. The organic layer was washed with saturated brine, dried over sodium sulfate and concentrated. The residue was purified by silica gel column chromatography (50% ethyl acetate/hexane to 60% ethyl acetate/hexane) to give the object product (4.0 g, 61%).

$^1$H NMR (300 MHz, CDCl$_3$) δ ppm 1.44 (s, 9H) 3.85 (brs, 1H) 4.17 (d, J=9.0 Hz, 2H) 4.39 (d, J=9.0 Hz, 2H) 4.62 (brs, 2H) 5.25 (brs, 1H) 7.25-7.34 (m, 4H)

(2) tert-butyl 1H,3'H-spiro[azetidine-3,1'-[2]benzofuran]-1-carboxylate

To a solution of tert-butyl 3-hydroxy-3-[2-(hydroxymethyl)phenyl]azetidine-1-carboxylate (4.0 g) obtained by the above-mentioned reaction in ethyl acetate (100 mL) were added triethylamine (5.0 mL) and methanesulfonyl chloride (1.2 mL) under ice-cooling, and the mixture was stirred at room temperature for 24 hr. To the reaction solution was added water, and the mixture was extracted with ethyl acetate. The organic layer was washed with saturated brine, dried over sodium sulfate and concentrated. The residue was purified by silica gel column chromatography (25% ethyl acetate/hexane to 30% ethyl acetate/hexane) to give the object product (1.5 g, 40%).

$^1$H NMR (300 MHz, CDCl$_3$) δ ppm 1.48 (s, 9H) 4.14 (d, J=9.6 Hz, 2H) 4.30 (d, J=9.6 Hz, 2H) 5.12 (s, 2H) 7.20 (d, J=7.2 Hz, 1H) 7.25-7.39 (m, 2H) 7.46 (d, J=7.5 Hz, 1H)

(3) 3'H-spiro[azetidine-3,1'-[2]benzofuran] hydrochloride

To a solution of tert-butyl 1H,3'H-spiro[azetidine-3,1'-[2]benzofuran]-1-carboxylate (1.5 g) obtained by the above-mentioned reaction in ethyl acetate (20 mL) was added hydrochloric acid (4N ethyl acetate solution, 15 mL), and the mixture was stirred at room temperature for 8 hr. The reaction solution was evaporated under reduced pressure, and the obtained residue was washed with diisopropyl ether to give the object product (520 mg, 46%).

$^1$H NMR (300 MHz, CDCl$_3$) δ ppm 4.46 (d, J=11.1 Hz, 2H) 4.59 (d, J=11.1 Hz, 2H) 5.12 (s, 2H) 7.19 (d, J=6.3 Hz, 1H) 7.38-7.53 (m, 2H) 8.11 (d, J=7.5 Hz, 1H) 9.75 (brs, 1H) 10.10 (brs, 1H)

(4) 1-[6-(3-methyl-1,2,4-thiadiazol-5-yl)pyridazin-3-yl]-3'H-spiro[azetidine-3,1'-[2]benzofuran]

The object product (93 mg, 39%) was obtained in the same manner as in Example 1 and using 3-chloro-6-(3-methyl-1,2,4-thiadiazol-5-yl)pyridazine (150 mg), 3'H-spiro[azetidine-3,1'-[2]benzofuran] hydrochloride (140 mg) obtained by the above-mentioned reaction and potassium carbonate (290 mg).
$^1$H NMR (300 MHz, CDCl$_3$) δ ppm 2.72 (s, 3H) 4.49 (d, J=10.2 Hz, 2H) 4.61 (d, J=10.2 Hz, 2H) 5.21 (s, 2H) 6.71 (d, J=9.3 Hz, 2H) 7.26 (m, 1H) 7.37-7.40 (m, 2H) 7.50 (m, 1H) 8.01 (d, J=9.6 Hz, 1H)

Example 15

1'-[6-(3-methyl-1,2,4-thiadiazol-5-yl)pyridazin-3-yl]-3H-spiro[2-benzofuran-1,3'-pyrrolidine]

The object product (82 mg, 41%) was obtained in the same manner as in Example 1 and using 3-chloro-6-(3-methyl-1,2,4-thiadiazol-5-yl)pyridazine (120 mg), 3H-spiro[2-benzofuran-1,3'-pyrrolidine] (100 mg) and potassium carbonate (138 mg).
$^1$H NMR (300 MHz, DMSO-d$_6$) δ ppm 2.30 (dd, J=12.87, 6.44 Hz, 1H) 2.39-2.48 (m, 1H) 2.65 (s, 3H) 3.59-4.24 (m, 4H) 5.07 (s, 2H) 7.10 (d, J=9.09 Hz, 1H) 7.32-7.39 (m, 3H) 7.46-7.52 (m, 1H) 8.00 (d, J=9.47 Hz, 1H)

Example 16

1'-[6-(3,5-dimethyl-1H-pyrazol-1-yl)pyridazin-3-yl]spiro[indene-1,4'-piperidine]

The object product (67 mg, 19%) was obtained in the same manner as in Example 1 and using 3-chloro-6-(3,5-dimethyl-1H-pyrazol-1-yl)pyridazine (209 mg), spiro[indene-1,4'-piperidine] trifluoroacetate (300 mg) and potassium carbonate (275 mg).
$^1$H NMR (300 MHz, DMSO-d$_6$) δppm 1.33 (d, J=13.25 Hz, 2H) 2.08-2.19 (m, 2H) 2.21 (s, 3H) 2.52 (s, 3H) 3.34-3.45 (m, 2H) 4.47 (d, J=13.63 Hz, 2H) 6.12 (s, 1H) 6.87 (d, J=5.68 Hz, 1H) 7.14-7.26 (m, 3H) 7.36 (d, J=7.19 Hz, 1H) 7.44 (d, J=7.19 Hz, 1H) 7.57 (d, J=9.84 Hz, 1H) 7.78 (d, J=9.84 Hz, 1H)

Example 17

1'-[6-(3-methyl-1,2,4-thiadiazol-5-yl)pyridazin-3-yl]spiro[1-benzofuran-3,4'-piperidine]

A solution (4 ml) of 3-Chloro-6-(3-methyl-1,2,4-thiadiazol-5-yl)pyridazine (69 mg), spiro[1-benzofuran-3,4'-piperidine] (62 mg) and potassium carbonate (54 mg) in N,N-dimethylformamide was stirred at 70° C. overnight. After cooling to room temperature, water was added, and the mixture was extracted with ethyl acetate. The organic layer was washed with saturated brine and dried over magnesium sulfate. The desiccant was filtered off, and the filtrate was concentrated. The residue was purified by silica gel chromatography (33% ethyl acetate/hexane) to give the object product (42 mg, 35%).
$^1$H NMR (300 MHz, DMSO-d$_6$) δ ppm 1.73-1.84 (m, 2H) 1.86-1.99 (m, 2H) 2.65 (s, 3H) 3.18-3.31 (m, 3H) 4.55 (s, 3H) 6.76-6.89 (m, 2H) 7.13 (t, J=7.57 Hz, 1H) 7.25 (d, J=6.44 Hz, 1H) 7.50 (d, J=9.84 Hz, 1H) 7.99 (d, J=9.84 Hz, 1H)

Example 18

7-[6-(3-methyl-1,2,4-thiadiazol-5-yl)pyridazin-3-yl]-3-phenyl-1-oxa-3,7-diazaspiro[4.5]decan-2-one (1) benzyl 1-oxa-5-azaspiro[2.5]octane-5-carboxylate To a solution of trimethylsulfoxonium iodide (3.1 g) in dimethyl sulfoxide (40 mL) was added sodium hydride (570 mg), and the mixture was stirred at room temperature for 1 hr. A solution of benzyl 3-oxopiperidine-1-carboxylate (3.0 g) in dimethyl sulfoxide (10 mL) was added under ice-cooling, and the mixture was stirred at room temperature for 16 hr. To the reaction solution was added water, and the mixture was extracted with ethyl acetate. The organic layer was washed with saturated brine, dried over sodium sulfate and concentrated. The residue was purified by silica gel column chromatography (30% ethyl acetate/hexane to 50% ethyl acetate/hexane) to give the object product (1.9 g, 60%).
$^1$H NMR (300 MHz, CDCl$_3$) δ ppm 1.64-1.88 (m, 4H) 2.65-2.71 (m, 2H) 3.42-3.54 (m, 4H) 5.13 (s, 2H) 7.25-7.37 (m, 5H)

(2) benzyl 3-(anilinomethyl)-3-hydroxypiperidine-1-carboxylate

To a solution of benzyl 1-oxa-5-azaspiro[2.5]octane-5-carboxylate (1.9 g) obtained by the above-mentioned reaction in acetonitrile (30 mL) were added aniline (785 mg) and lithium perchlorate (980 mg), and the mixture was stirred at 80° C. for 15 hr. The reaction solution was poured into water, and the mixture was extracted with ethyl acetate. The organic layer was washed with aqueous sodium hydrogen carbonate solution and saturated brine, dried over sodium sulfate and concentrated. The residue was purified by silica gel column chromatography (25% ethyl acetate/hexane to 30% ethyl acetate/hexane) to give the object product (2.2 g, 84%).
$^1$H NMR (300 MHz, CDCl$_3$) δ ppm 1.60-1.82 (m, 4H) 3.10 (d, J=13.2 Hz, 1H) 3.16 (d, J=13.2 Hz, 1H) 3.22-3.39 (m, 2H) 3.53-3.73 (m, 2H) 5.13 (s, 2H) 6.63 (brs, 1H) 6.72 (t, J=6.9 Hz, 1H) 7.31-7.33 (m, 6H)

(3) 3-phenyl-1-oxa-3,7-diazaspiro[4.5]decan-2-one

N,N'-Carbonyldiimidazole (1.5 g) and 1,8-diazabicyclo[5.4.0]undec-7-ene (2.5 g) were added to benzyl 3-(anilinomethyl)-3-hydroxypiperidine-1-carboxylate (2.2 g) obtained by the above-mentioned reaction in acetonitrile (35 mL), and the mixture was stirred at 80° C. for 20 hr. The reaction solution was poured into water, and the mixture was extracted with ethyl acetate. The organic layer was washed with saturated brine, dried over sodium sulfate and concentrated. The residue was purified by silica gel column chromatography (25% ethyl acetate/hexane to 50% ethyl acetate/hexane) to give crude benzyl 2-oxo-3-phenyl-1-oxa-3,7-diazaspiro[4.5]decane-7-carboxylate (2.0 g).

To a solution of the above-mentioned crude benzyl 2-oxo-3-phenyl-1-oxa-3,7-diazaspiro[4.5]decane-7-carboxylate (2.0 g) in ethyl acetate (50 mL) was added 20% palladium hydroxide-carbon (200 mg), and the mixture was stirred at room temperature for 20 hr under a hydrogen atmosphere. The catalyst was filtered through celite, and the filtrate was evaporated under reduced pressure. The residue was washed with diisopropyl ether to give the object product (800 mg, 53%).

¹H NMR (300 MHz, DMSO-d₆) δ ppm 1.47 (m, 1H) 1.65 (m, 1H) 1.81 (m, 1H) 1.90 (m, 1H) 2.39 (brs, 1H) 2.51 (m, 1H) 2.68-2.72 (m, 2H) 2.85 (d, J=11.1 Hz, 1H) 3.79 (d, J=9.0 Hz, 1H) 3.94 (d, J=9.0 Hz, 1H) 7.11 (t, J=6.3 Hz, 1H) 7.35-7.40 (m, 2H) 7.56 (d, J=7.8 Hz, 2H)

(4) 7-[6-(3-methyl-1,2,4-thiadiazol-5-yl)pyridazin-3-yl]-3-phenyl-1-oxa-3,7-diazaspiro[4.5]decan-2-one The object product (70 mg, 24%) was obtained in the same manner as in Example 1 and using 3-chloro-6-(3-methyl-1,2,4-thiadiazol-5-yl)pyridazine (150 mg) and 3-phenyl-1-oxa-3,7-diazaspiro[4.5]decan-2-one (165 mg) obtained by the above-mentioned reaction and potassium carbonate (195 mg).
¹H NMR (300 MHz, CDCl₃) δ ppm 2.04-2.27 (m, 4H) 2.71 (s, 3H) 3.78 (d, J=9.0 Hz, 2H) 3.90 (d, J=9.0 Hz, 2H) 4.04 (d, J=13.5 Hz, 1H) 4.12 (d, J=13.5 Hz, 1H) 7.04 (d, J=9.6 Hz, 1H) 7.14 (t, J=7.5 Hz, 1H) 7.34-7.39 (m, 2H) 7.50-7.54 (m, 2H) 8.00 (d, J=9.6 Hz, 1H)

Example 19

7-[6-(3-methyl-1,2,4-thiadiazol-5-yl)pyridazin-3-yl]-3-phenyl-1-oxa-3,7-diazaspiro[4.4]nonan-2-one (1) 3-(anilinomethyl)-1-benzylpyrrolidin-3-ol 5-Benzyl-1-oxa-5-azaspiro[2.4]heptane (946 mg) was dissolved in acetonitrile (30 mL), and aniline (0.55 mL) and lithium perchlorate (640 mg) were added. After stirring at 80° C. overnight, the solvent was evaporated under reduced pressure. The residue was dissolved in ethyl acetate, and the solution was washed twice with aqueous sodium hydrogen carbonate solution. The organic layer was dried over sodium sulfate, and the solvent was evaporated under reduced pressure. The residue was purified by silica gel column chromatography using basic silica gel (20% ethyl acetate/hexane to 60% ethyl acetate/hexane) to give the object product (768 mg, 54%).
¹H NMR (300 MHz, DMSO-d₆) δ ppm 1.67-1.78 (m, 1H) 1.79-1.93 (m, 1H) 2.38 (d, J=9.47 Hz, 1H) 2.52-2.67 (m, 3H) 2.97-3.10 (m, 2H) 3.49-3.61 (m, 2H) 4.82 (s, 1H) 5.24 (t, J=5.49 Hz, 1H) 6.51 (t, J=7.19 Hz, 1H) 6.60 (d, J=7.57 Hz, 2H) 7.04 (t, J=7.95 Hz, 2H) 7.18-7.27 (m, 1H) 7.27-7.34 (m, 4H)

(2) 7-benzyl-3-phenyl-1-oxa-3,7-diazaspiro[4.4]nonan-2-one 3-(Anilinomethyl)-1-benzylpyrrolidin-3-ol (400 mg) obtained by the above-mentioned reaction was dissolved in acetonitrile (20 mL), and N,N'-carbonyldiimidazole (324 mg) and 1,8-diazabicyclo[5.4.0]undec-7-ene (0.53 mL) were added. After stirring at 80° C. overnight, the solvent was evaporated under reduced pressure. The residue was dissolved in ethyl acetate, and the solution was washed twice with aqueous sodium hydrogen carbonate solution. The organic layer was dried over sodium sulfate, and the solvent was evaporated under reduced pressure. The residue was purified by silica gel column chromatography using basic silica gel (15% ethyl acetate/hexane to 40% ethyl acetate/hexane) to give the object product (400 mg, 91%).
¹H NMR (300 MHz, DMSO-d₆) δ ppm 2.14-2.25 (m, 2H) 2.52-2.61 (m, 1H) 2.68-2.80 (m, 2H) 2.90 (d, J=10.55 Hz, 1H) 3.57-3.70 (m, 2H) 4.06-4.13 (m, 2H) 7.07-7.15 (m, 1H) 7.22-7.30 (m, 1H) 7.30-7.42 (m, 6H) 7.50-7.56 (m, 2H)

(3) 3-phenyl-1-oxa-3,7-diazaspiro[4.4]nonan-2-one

7-Benzyl-3-phenyl-1-oxa-3,7-diazaspiro[4.4]nonan-2-one (353 mg) obtained by the above-mentioned reaction and 20% palladium hydroxide-carbon (80 mg) were suspended in methanol (10 mL), and the suspension was stirred at room temperature overnight under a hydrogen atmosphere. The catalyst was filtered through celite, and the solvent was evaporated under reduced pressure to give the object product (170 mg, 68%).
¹H NMR (300 MHz, DMSO-d₆) δ ppm 1.89-2.04 (m, 1H) 2.06-2.19 (m, 1H) 2.81-3.01 (m, 3H) 3.08 (d, J=12.24 Hz, 1H) 4.02-4.15 (m, 2H) 7.12 (t, J=7.35 Hz, 1H) 7.33-7.43 (m, 2H) 7.51-7.59 (m, 2H)

(4) 7-[6-(3-methyl-1,2,4-thiadiazol-5-yl)pyridazin-3-yl]-3-phenyl-1-oxa-3,7-diazaspiro[4.4]nonan-2-one The object product (73 mg, 31%) was obtained in the same manner as in Example 1 and using 3-phenyl-1-oxa-3,7-diazaspiro[4.4]nonan-2-one (170 mg) obtained by the above-mentioned reaction, 3-chloro-6-(3-methyl-1,2,4-thiadiazol-5-yl)pyridazine (130 mg) and potassium carbonate (138 mg).
¹H NMR (300 MHz, DMSO-d₆) δ ppm 2.33-2.59 (m, 2H) 2.65 (s, 3% H) 3.60-3.75 (m, 1H) 3.85 (d, J=12.49 Hz, 2H) 4.07-4.19 (m, 1H) 4.19-4.36 (m, 2H) 7.07-7.20 (m, 2H) 7.42 (t, J=7.95 Hz, 2H) 7.60 (d, J=7.95 Hz, 2H) 8.04 (d, J=9.09 Hz, 1H)

Example 20

1'-[6-(3-methyl-1,2,4-thiadiazol-5-yl)pyridazin-3-yl]spiro[chromene-2,4'-piperidine]

(1) spiro[chromene-2,4'-piperidine] hydrochloride tert-Butyl 4-oxo-3,4-dihydro-1'H-spiro[chromene-2,4'-piperidine]-1'-carboxylate (5.0 g) was dissolved in tetrahydrofuran (150 mL), and borane-tetrahydrofuran complex (1M tetrahydrofuran solution, 150 mL) was added dropwise at room temperature. The reaction mixture was refluxed overnight, and cooled to room temperature. Hydrochloric acid (6N aqueous solution, 400 mL) was slowly added, and the reaction mixture was refluxed for 3 hr. The solvent was evaporated under reduced pressure, and the reaction mixture was basified with sodium hydroxide (4N aqueous solution). The mixture was extracted 3 times with ethyl acetate, and the organic layer was dried over sodium sulfate. The solvent was evaporated under reduced pressure. The residue was purified by silica gel column chromatography using basic silica gel (5% ethyl acetate/hexane to 60% ethyl acetate/hexane), and the crude product was dissolved in ethyl acetate-diisopropyl ether (3:1 v/v, 100 mL). Hydrochloric acid (4N ethyl acetate solution, 10 mL) was added, and the resulting precipitate was collected by filtration to give the object product (340 mg, 9%).
¹H NMR (300 MHz, DMSO-d₆) δ ppm 1.85-2.08 (m, 4H) 3.07-3.22 (m, 4H) 5.81 (d, J=9.80 Hz, 1H) 6.55 (d, J=9.80 Hz, 1H) 6.87-6.95 (m, 2H) 7.09-7.21 (m, 2H) 9.16 (brs, 2H)

(2) 1'-[6-(3-methyl-1,2,4-thiadiazol-5-yl)pyridazin-3-yl]spiro[chromene-2,4'-piperidine]

The object product (111 mg, 41%) was obtained in the same manner as in Example 1 and using 3-chloro-6-(3-methyl-1,2,4-thiadiazol-5-yl)pyridazine (150 mg), spiro [chromene-2,4'-piperidine] hydrochloride (190 mg) and potassium carbonate (274 mg).

$^1$H NMR (300 MHz, DMSO-d$_6$) δ ppm 1.70-1.87 (m, 2H) 1.90-2.04 (m, 2H) 2.65 (s, 3H) 3.52-3.65 (m, 2H) 4.21-4.35 (m, 2H) 5.79 (d, J=9.80 Hz, 1H) 6.51 (d, J=9.80 Hz, 1H) 6.80-6.95 (m, 2H) 7.04-7.24 (m, 2H) 7.48 (d, J=9.80 Hz, 1H) 7.98 (d, J=9.61 Hz, 1H)

Example 21

1'-[6-(3-methyl-1,2,4-thiadiazol-5-yl)pyridazin-3-yl] spiro[chromene-2,3'-pyrrolidin]-4(3H)-one (1) tert-butyl 4-oxo-3,4-dihydro-1'H-spiro [chromene-2,3'-pyrrolidine]-1'-carboxylate 1-(2-Hydroxyphenyl)ethanone (7.35 g) and pyrrolidine (4.6 ml) were dissolved in methanol (60 mL), and the solution was stirred at room temperature for 30 min. tert-Butyl 3-oxopyrrolidine-1-carboxylate (10 g) was slowly added to the reaction mixture, and the mixture was stirred at room temperature overnight. The solvent was evaporated under reduced pressure, and the residue was dissolved in ethyl acetate, and the solution was washed twice with aqueous sodium hydrogen carbonate solution. The organic layer was dried over sodium sulfate, and the solvent was evaporated under reduced pressure. The residue was purified by silica gel column chromatography to give the object product (11.5 g, 70%).

$^1$H NMR (300 MHz, DMSO-d$_6$) δ ppm 1.34-1.46 (m, 9H) 1.91-2.08 (m, 1H) 2.09-2.22 (m, 1H) 2.94 (d, J=16.95 Hz, 1H) 3.11 (d, J=16.95 Hz, 1H) 3.31-3.42 (m, 2H) 3.43-3.53 (m, 1H) 3.59 (dd, J=12.06, 1.70 Hz, 1H) 6.98-7.14 (m, 2H) 7.51-7.65 (m, 1H) 7.76 (dd, J=7.82, 1.60 Hz, 1H)

(2) spiro[chromene-2,3'-pyrrolidin]-4(3H)-one hydrochloride tert-Butyl 4-oxo-3,4-dihydro-1'H-spiro[chromene-2,3'-pyrrolidine]-1'-carboxylate (1.0 g) obtained by the above-mentioned reaction was dissolved in ethyl acetate (20 mL), and hydrochloric acid (4N ethyl acetate solution, 5 mL) was added. The mixture was stirred at room temperature overnight, and the resulting precipitate was collected by filtration to give the object product (364 mg, 46%).

$^1$H NMR (300 MHz, DMSO-d$_6$) δ ppm 2.00-2.13 (m, 1H) 2.24-2.35 (m, 1H) 3.06 (d, J=16.95 Hz, 1H) 3.18 (d, J=16.95 Hz, 1H) 3.22-3.58 (m, 4H) 7.05 (d, J=8.29 Hz, 1H) 7.09-7.17 (m, 1H) 7.59-7.67 (m, 1H) 7.78 (dd, J=7.91, 1.51 Hz, 1H) 9.64 (brs, 1H) 9.78 (brs, 1H)

(3) 1'-[6-(3-methyl-1,2,4-thiadiazol-5-yl)pyridazin-3-yl]spiro[chromene-2,3'-pyrrolidin]-4(3H)-one The object product (35 mg, 13%) was obtained in the same manner as in Example 1 and using spiro[chromene-2,3'-pyrrolidin]-4(3H)-one hydrochloride (192 mg) obtained by the above-mentioned reaction, 3-chloro-6-(3-methyl-1,2,4-thiadiazol-5-yl)pyridazine (150 mg) and potassium carbonate (274 mg).

$^1$H NMR (300 MHz, DMSO-d$_6$) δ ppm 2.14-2.32 (m, 1H) 2.41 (d, J=6.40 Hz, 1H) 2.64 (s, 3H) 3.11 (d, J=16.58 Hz, 1H) 3.24 (d, J=16.95 Hz, 1H) 3.65-4.12 (m, 4H) 7.00-7.16 (m, 3H) 7.54-7.63 (m, 1H) 7.81 (dd, J=7.91, 1.51 Hz, 1H) 8.00 (d, J=9.42 Hz, 1H)

Example 22

1'-[6-(3-methyl-1,2,4-thiadiazol-5-yl)pyridazin-3-yl]-5H-spiro[furo[3,4-b]pyridine-7,4'-piperidine]

The object product (72 mg, 28%) was obtained in the same manner as in Example 1 and using 3-chloro-6-(3-methyl-1,2,4-thiadiazol-5-yl)pyridazine (150 mg), 5H-spiro[furo[3,4-b]pyridine-7,4'-piperidine] dihydrochloride (86 mg) and potassium carbonate (290 mg).

$^1$H NMR (300 MHz, CDCl$_3$) δ ppm 1.83-1.87 (m, 2H) 2.13-2.19 (m, 2H) 2.73 (s, 3H) 3.59-3.68 (m, 2H) 4.54-4.58 (m, 2H) 5.14 (s, 2H) 7.04 (d, J=9.0 Hz, 1H) 7.19 (dd, J=7.8, 5.1 Hz, 1H) 7.57 (brd, J=7.8 Hz, 1H) 7.96 (d, J=9.0 Hz, 1H) 8.44 (d, J=5.1 Hz, 1H)

Example 23

1'-[6-(3-methyl-1,2,4-thiadiazol-5-yl)pyridazin-3-yl]-3H-spiro[2-benzofuran-1,3'-piperidine]

(1) tert-butyl 3-hydroxy-3-[2-(hydroxymethyl)phenyl]piperidine-1-carboxylate

The object product (1.6 g, 30%) was obtained in the same manner as in Example 14(1) and using (2-bromophenyl)methanol (3.3 g), tert-butyl 3-oxopiperidine-1-carboxylate (3.5 g) and n-butyllithium (1.6 M hexane solution, 23 mL).

$^1$H NMR (300 MHz, CDCl$_3$) δ ppm 1.46 (s, 9H) 1.88-2.31 (m, 4H) 2.60 (m, 1H) 3.50-3.71 (m, 2H) 4.21-4.61 (m, 3H) 4.72 (s, 2H) 7.51-7.82 (m, 4H)

(2) tert-butyl 1'H,3H-spiro[2-benzofuran-1,3'-piperidine]-1'-carboxylate

The object product (700 mg, 46%) was obtained in the same manner as in Example 14(2) and using tert-butyl 3-hydroxy-3-[2-(hydroxymethyl)phenyl]piperidine-1-carboxylate (1.6 g) obtained by the above-mentioned reaction, triethylamine (1.8 mL) and methanesulfonyl chloride (0.4 mL).

$^1$H NMR (300 MHz, CDCl$_3$) δ ppm 1.47 (s, 9H) 1.76-2.02 (m, 4H) 2.93-3.20 (m, 2H) 3.64-4.06 (m, 2H) 5.07 (s, 2H) 6.99-7.47 (m, 4H)

(3) 3H-spiro[2-benzofuran-1,3'-piperidine] hydrochloride

The object product (550 mg, 100%) was obtained in the same manner as in Example 14(3) and using tert-butyl 1'H,3H-spiro[2-benzofuran-1,3'-piperidine]-1'-carboxylate (700 mg) obtained by the above-mentioned reaction and hydrochloric acid (4N ethyl acetate solution, 5 mL).

$^1$H NMR (300 MHz, DMSO-d$_6$) δ ppm 1.72-1.83 (m, 2H) 1.95-2.09 (m, 2H) 2.93-3.38 (m, 4H) 5.09 (s, 2H) 7.31-7.40 (m, 4H) 8.45 (brs, 1H) 9.86 (brs, 1H)

(4) 1'-[6-(3-methyl-1,2,4-thiadiazol-5-yl)pyridazin-3-yl]-3H-spiro[2-benzofuran-1,3'-piperidine]

The object product (100 mg, 39%) was obtained in the same manner as in Example 1 and using 3-chloro-6-(3-methyl-1,2,4-thiadiazol-5-yl)pyridazine (150 mg), 3H-spiro[2-benzofuran-1,3'-piperidine] hydrochloride (160 mg) obtained by the above-mentioned reaction and potassium carbonate (245 mg).

¹H NMR (300 MHz, CDCl₃) δ ppm 1.85-2.12 (m, 4H) 2.71 (s, 3H) 3.29-3.37 (m, 2H) 4.29 (m, 1H) 4.63 (m, 1H) 5.05 (s, 2H) 6.96 (d, J=9.6 Hz, 1H) 7.17-7.35 (m, 4H) 7.90 (d, J=9.3 Hz, 1H)

Example 24

3-cyclohexyl-8-[6-(3-methyl-1,2,4-thiadiazol-5-yl)pyridazin-3-yl]-1-oxa-3,8-diazaspiro[4.5]decan-2-one (1) benzyl 4-[(cyclohexylamino)methyl]-4-hydroxypiperidine-1-carboxylate Benzyl 1-oxa-6-azaspiro[2.5]octane-6-carboxylate (1.98 g) was dissolved in acetonitrile (80 mL), and cyclohexylamine (800 mg) and lithium perchlorate (960 mg) were added. The mixture was stirred at 80° C. overnight, and cooled to room temperature. The solvent was evaporated under reduced pressure, and the residue was purified by silica gel column chromatography using basic silica gel (15% ethyl acetate/hexane to 80% ethyl acetate/hexane) to give the object product (2.39 g, 96%).
¹H NMR (300 MHz, DMSO-d₆) δ ppm 0.91-1.06 (m, 2H) 1.06-1.27 (m, 3H) 1.31-1.48 (m, 5H) 1.49-1.58 (m, 1H) 1.63 (brs, 2H) 1.76 (brs, 2H) 2.21-2.33 (m, 1H) 2.44 (s, 2H) 3.15 (brs, 2H) 3.63-3.76 (m, 2H) 4.27 (brs, 1H) 5.05 (s, 2H) 7.26-7.42 (m, 5H)

(2) benzyl 3-cyclohexyl-2-oxo-1-oxa-3,8-diazaspiro[4.5]decane-8-carboxylate

Benzyl 4-[(cyclohexylamino)methyl]-4-hydroxypiperidine-1-carboxylate (2.6 g) obtained by the above-mentioned reaction was dissolved in acetonitrile (100 mL), and N,N'-carbonyldiimidazole (1.95 g) and 1,8-diazabicyclo[5.4.0]undec-7-ene (3.05 mL) were added. The mixture was stirred at 80° C. overnight, and the solvent was evaporated under reduced pressure. The residue was purified by silica gel column chromatography to give the object product (2.67 g, 96%).
¹H NMR (300 MHz, DMSO-d₆) δ ppm 0.96-1.16 (m, 1H) 1.18-1.44 (m, 4H) 1.52-1.79 (m, 9H) 3.20-3.37 (m, 4H) 3.37-3.51 (m, 1H) 3.58-3.70 (m, 2H) 5.08 (s, 2H) 7.26-7.42 (m, 5H)

(3) 3-cyclohexyl-1-oxa-3,8-diazaspiro[4.5]decan-2-one

Benzyl 3-cyclohexyl-2-oxo-1-oxa-3,8-diazaspiro[4.5]decane-8-carboxylate (2.6 g) obtained by the above-mentioned reaction and 5% palladium-carbon (500 mg) were suspended in methanol (50 mL), and the suspension was stirred at room temperature overnight under a hydrogen atmosphere. The catalyst was filtered off through celite. The solvent was evaporated under reduced pressure. Hexane-ethyl acetate was added, and the resulting precipitate was collected by filtration to give the object product (1.49 g, 88%).
¹H NMR (300 MHz, DMSO-d₆) δ ppm 0.97-1.14 (m, 1H) 1.17-1.47 (m, 4H) 1.51-1.68 (m, 7H) 1.74 (d, J=12.06 Hz, 2H) 2.56-2.68 (m, 2H) 2.72-2.84 (m, 2H) 3.05-3.33 (m, 2H) 3.35-3.50 (m, 1H)

(4) 3-cyclohexyl-8-[6-(3-methyl-1,2,4-thiadiazol-5-yl)pyridazin-3-yl]-1-oxa-3,8-diazaspiro[4.5]decan-2-one The object product (75 mg, 25%) was obtained in the same manner as in Example 1 and using 3-cyclohexyl-1-oxa-3,8-diazaspiro[4.5]decan-2-one (190 mg) obtained by the above-mentioned reaction, 3-chloro-6-(3-methyl-1,2,4-thiadiazol-5-yl)pyridazine (150 mg) and potassium carbonate (138 mg).
¹H NMR (300 MHz, DMSO-d₆) δ ppm 0.96-1.15 (m, 1H) 1.20-1.49 (m, 4H) 1.53-1.95 (m, 9H) 2.65 (s, 3H) 3.34 (s, 2H) 3.41-3.54 (m, 1H) 3.56-3.72 (m, 2H) 4.04-4.15 (m, 2H) 7.50 (d, J=9.80 Hz, 1H) 7.98 (d, J=9.61 Hz, 1H)

Example 25

8-[6-(3-methyl-1,2,4-thiadiazol-5-yl)pyridazin-3-yl]-3-propyl-1-oxa-3,8-diazaspiro[4.5]decan-2-one (1) benzyl 2-oxo-3-propyl-1-oxa-3,8-diazaspiro[4.5]decane-8-carboxylate The object product (2.52 g, 98%) was obtained in the same manner as in Example 24(2) and using benzyl 4-hydroxy-4-[(propylamino)methyl]piperidine-1-carboxylate (2.38 g), N,N'-carbonyldiimidazole (1.95 g) and 1,8-diazabicyclo[5.4.0]undec-7-ene (3.0 mL).
¹H NMR (300 MHz, DMSO-d₆) δ ppm 0.83 (t, J=7.38 Hz, 3H) 1.39-1.57 (m, 2H) 1.64-1.82 (m, 4H) 3.10 (t, J=7.00 Hz, 2H) 3.21-3.38 (m, 4H) 3.58-3.74 (m, 2H) 5.08 (s, 2H) 7.20-7.47 (m, 5H)

(2) 3-propyl-1-oxa-3,8-diazaspiro[4.5]decan-2-one hydrochloride

3-Propyl-1-oxa-3,8-diazaspiro[4.5]decan-2-one was obtained in the same manner as in Example 24(3) and using benzyl 2-oxo-3-propyl-1-oxa-3,8-diazaspiro[4.5]decane-8-carboxylate (2.5 g) obtained by the above-mentioned reaction and 5% palladium-carbon (400 mg). This was dissolved in ethyl acetate (50 mL), hydrochloric acid (4N ethyl acetate solution, 5 mL) was added, and the resulting precipitate was collected by filtration to give the object product (1.55 g, 87%).
¹H NMR (300 MHz, DMSO-d₆) δ ppm 0.84 (t, J=7.38 Hz, 3H) 1.43-1.56 (m, 2H) 1.99 (t, J=5.68 Hz, 4H) 2.98-3.23 (m, 6H) 3.39 (s, 2H) 9.16 (brs, 2H)

(3) 8-[6-(3-methyl-1,2,4-thiadiazol-5-yl)pyridazin-3-yl]-3-propyl-1-oxa-3,8-diazaspiro[4.5]decan-2-one The object product (72 mg, 34%) was obtained in the same manner as in Example 1 and using 3-propyl-1-oxa-3,8-diazaspiro[4.5]decan-2-one hydrochloride (140 mg) obtained by the above-mentioned reaction, 3-chloro-6-(3-methyl-1,2,4-thiadiazol-5-yl)pyridazine (120 mg) and potassium carbonate (138 mg).
¹H NMR (300 MHz, DMSO-d₆) δ ppm 0.86 (t, J=7.35 Hz, 3H) 1.43-1.59 (m, 2H) 1.79-1.93 (m, 4H) 2.65 (s, 3H) 3.13 (t, J=7.06 Hz, 2H) 3.37 (s, 2H) 3.56-3.73 (m, 2H) 4.04-4.17 (m, 2H) 7.50 (d, J=9.61 Hz, 1H) 7.99 (d, J=9.61 Hz, 1H)

Example 26

3-(cyclopropylmethyl)-8-[6-(3-methyl-1,2,4-thiadiazol-5-yl)pyridazin-3-yl]-1-oxa-3,8-diazaspiro[4.5]decan-2-one (1) benzyl 4-{[(cyclopropylmethyl)amino]methyl}-4-hydroxypiperidine-1-carboxylate The object product (2.53 g, 99%) was obtained in the same manner as in Example 24(1) and using benzyl 1-oxa-6-azaspiro[2.5]octane-6-carboxylate (1.98 g), 1-cyclopropylmethanamine (570 mg) and lithium perchlorate (960 mg).

$^1$H NMR (300 MHz, DMSO-d$_6$) δ ppm 0.02-0.12 (m, 2H) 0.33-0.44 (m, 2H) 0.78-0.95 (m, 1H) 1.31-1.66 (m, 5H) 2.37 (d, J=6.78 Hz, 2H) 2.45 (s, 2H) 3.15 (brs, 2H) 3.62-3.79 (m, 2H) 4.32 (brs, 1H) 5.06 (s, 2H) 7.26-7.42 (m, 5H)

(2) benzyl 3-(cyclopropylmethyl)-2-oxo-1-oxa-3,8-diazaspiro[4.5]decane-8-carboxylate The object product (2.4 g, 88%) was obtained in the same manner as in Example 24(2) and using benzyl 4-{[(cyclopropylmethyl)amino]methyl}-4-hydroxypiperidine-1-carboxylate (2.5 g) obtained by the above-mentioned reaction, N,N'-carbonyldiimidazole (1.95 g) and 1,8-diazabicyclo[5.4.0]undec-7-ene (3.0 mL).

$^1$H NMR (300 MHz, DMSO-d$_6$) δ ppm 0.14-0.23 (m, 2H) 0.41-0.54 (m, 2H) 0.82-0.99 (m, 1H) 1.65-1.84 (m, 4H) 3.02 (d, J=6.97 Hz, 2H) 3.22-3.36 (m, 2H) 3.40 (s, 2H) 3.62-3.74 (m, 2H) 5.09 (s, 2H) 7.27-7.43 (m, 5H)

(3) 3-(cyclopropylmethyl)-1-oxa-3,8-diazaspiro[4.5]decan-2-one hydrochloride The object product (1.39 g, 80%) was obtained in the same manner as in Example 24(3) and using benzyl 3-(cyclopropylmethyl)-2-oxo-1-oxa-3,8-diazaspiro[4.5]decane-8-carboxylate (2.4 g) obtained by the above-mentioned reaction and 5% palladium-carbon (500 mg).

$^1$H NMR (300 MHz, DMSO-d$_6$) δ ppm 0.14-0.24 (m, 2H) 0.42-0.53 (m, 2H) 0.84-1.04 (m, 1H) 1.95-2.11 (m, 4H) 2.96-3.14 (m, 4H) 3.13-3.25 (m, 2H) 3.48 (s, 2H) 9.14 (brs, 1H) 9.29 (brs, 1H)

(4) 3-(cyclopropylmethyl)-8-[6-(3-methyl-1,2,4-thiadiazol-5-yl)pyridazin-3-yl]-1-oxa-3,8-diazaspiro[4.5]decan-2-one The object product (115 mg, 42%) was obtained in the same manner as in Example 1 and using 3-(cyclopropylmethyl)-1-oxa-3,8-diazaspiro[4.5]decan-2-one hydrochloride (200 mg) obtained by the above-mentioned reaction, 3-chloro-6-(3-methyl-1,2,4-thiadiazol-5-yl)pyridazine (150 mg) and potassium carbonate (280 mg).

$^1$H NMR (300 MHz, DMSO-d$_6$) δ ppm 0.14-0.26 (m, 2H) 0.43-0.54 (m, 2H) 0.83-1.02 (m, 1H) 1.80-1.96 (m, 4H) 2.65 (s, 3H) 3.05 (d, J=7.16 Hz, 2H) 3.47 (s, 2H) 3.57-3.69 (m, 2H) 4.08-4.22 (m, 2H) 7.50 (d, J=9.61 Hz, 1H) 7.98 (d, J=9.80 Hz, 1H)

Example 27

1'-[6-(3-methyl-1,2,4-thiadiazol-5-yl)pyridazin-3-yl]-3,4-dihydrospiro[chromene-2,4'-piperidine]

The object product (74 mg, 44%) was obtained in the same manner as in Example 1 and using 3-chloro-6-(3-methyl-1,2,4-thiadiazol-5-yl)pyridazine (95 mg), 3,4-dihydrospiro[chromene-2,4'-piperidine] hydrochloride (105 mg) and potassium carbonate (138 mg).

$^1$H NMR (300 MHz, DMSO-d$_6$) δ ppm 1.63-1.77 (m, 2H) 1.83 (t, J=6.69 Hz, 4H) 2.65 (s, 3H) 2.76 (t, J=6.69 Hz, 2H) 3.44-3.56 (m, 2H) 4.24-4.36 (m, 2H) 6.78-6.88 (m, 2H) 7.05-7.13 (m, 2H) 7.47 (d, J=9.61 Hz, 1H) 7.97 (d, J=9.61 Hz, 1H)

Example 28

1'-[6-(3-methyl-1,2,4-thiadiazol-5-yl)pyridazin-3-yl]spiro[indene-1,4'-piperidin]-3(2H)-one The object product (106 mg, 40%) was obtained in the same manner as in Example 1 and using spiro[indene-1,4'-piperidin]-3(2H)-one (190 mg), 3-chloro-6-(3-methyl-1,2,4-thiadiazol-5-yl)pyridazine (150 mg) and potassium carbonate (150 mg).

$^1$H NMR (300 MHz, DMSO-d$_6$) δ ppm 1.65 (d, J=13.19 Hz, 2H) 2.00-2.14 (m, 2H) 2.66 (s, 3H) 2.83 (s, 2H) 3.13-3.27 (m, 2H) 4.61-4.73 (m, 2H) 7.43-7.49 (m, 1H) 7.52 (d, J=9.61 Hz, 1H) 7.64 (d, J=7.72 Hz, 1H) 7.67-7.75 (m, 2H) 7.99 (d, J=9.61 Hz, 1H)

Example 29

3-(3-fluorophenyl)-8-[6-(3-methyl-1,2,4-thiadiazol-5-yl)pyridazin-3-yl]-1-oxa-3,8-diazaspiro[4.5]decan-2-one

(1) benzyl 4-{[(3-fluorophenyl)amino]methyl}-4-hydroxypiperidine-1-carboxylate The object product (2.53 g, 94%) was obtained in the same manner as in Example 24(1) and using benzyl 1-oxa-6-azaspiro[2.5]octane-6-carboxylate (1.98 g), 3-fluoroaniline (889 mg) and lithium perchlorate (960 mg).

$^1$H NMR (300 MHz, DMSO-d$_6$) δ ppm 1.42-1.57 (m, 4H) 2.99 (d, J=5.84 Hz, 2H) 3.15 (brs, 2H) 3.73-3.82 (m, 2H) 4.59 (s, 1H) 5.06 (s, 2H) 5.74 (t, J=5.65 Hz, 1H) 6.16-6.31 (m, 1H) 6.37-6.50 (m, 2H) 6.95-7.08 (m, 1H) 7.25-7.43 (m, 5H)

(2) benzyl 3-(3-fluorophenyl)-2-oxo-1-oxa-3,8-diazaspiro[4.5]decane-8-carboxylate The object product (944 mg, 88%) was obtained in the same manner as in Example 24(2) and using benzyl 4-{[(3-fluorophenyl)amino]methyl}-4-hydroxypiperidine-1-carboxylate (1.0 g) obtained by the above-mentioned reaction, N,N'-carbonyldiimidazole (635 mg) and 1,8-diazabicyclo[5.4.0]undec-7-ene (1.0 mL).

$^1$H NMR (300 MHz, DMSO-d$_6$) δ ppm 1.74-1.96 (m, 4H) 3.28-3.47 (m, 2H) 3.60-3.74 (m, 2H) 3.90 (s, 2H) 5.10 (s, 2H) 6.90-7.02 (m, 1H) 7.28-7.54 (m, 8H)

(3) 3-(3-fluorophenyl)-1-oxa-3,8-diazaspiro[4.5]decan-2-one

The object product (550 mg, 90%) was obtained in the same manner as in Example 24(3) and using benzyl 3-(3-fluorophenyl)-2-oxo-1-oxa-3,8-diazaspiro[4.5]decane-8-carboxylate (944 mg) obtained by the above-mentioned reaction and 5% palladium-carbon (100 mg).

$^1$H NMR (300 MHz, DMSO-d$_6$) δ ppm 1.76 (t, J=5.49 Hz, 4H) 2.64-2.79 (m, 2H) 2.78-2.92 (m, 2H) 3.17 (brs, 1H) 3.87 (s, 2H) 6.89-7.01 (m, 1H) 7.33-7.57 (m, 3H)

(4) 3-(3-fluorophenyl)-8-[6-(3-methyl-1,2,4-thiadiazol-5-yl)pyridazin-3-yl]-1-oxa-3,8-diazaspiro[4.5]decan-2-one The object product (125 mg, 41%) was obtained in the same manner as in Example 1 and using 3-(3-fluorophenyl)-

1-oxa-3,8-diazaspiro[4.5]decan-2-one (200 mg) obtained by the above-mentioned reaction, 3-chloro-6-(3-methyl-1,2,4-thiadiazol-5-yl)pyridazine (150 mg) and potassium carbonate (140 mg).

$^1$H NMR (300 MHz, DMSO-d$_6$) δ ppm 1.91-2.11 (m, 4H) 2.65 (s, 3H) 3.69-3.81 (m, 2H) 3.97 (s, 2H) 4.07-4.20 (m, 2H) 6.93-7.02 (m, 1H) 7.32-7.38 (m, 1H) 7.40-7.58 (m, 3H) 8.00 (d, J=9.61 Hz, 1H)

Example 30

3-(4-fluorophenyl)-8-[6-(3-methyl-1,2,4-thiadiazol-5-yl)pyridazin-3-yl]-1-oxa-3,8-diazaspiro[4.5]decan-2-one (1) benzyl 4-{[(4-fluorophenyl)amino]methyl}-4-hydroxypiperidine-1-carboxylate The object product (2.8 g, 98%) was obtained in the same manner as in Example 24(1) and using benzyl 1-oxa-6-azaspiro[2.5]octane-6-carboxylate (1.98 g), 4-fluoroaniline (889 mg) and lithium perchlorate (960 mg).

$^1$H NMR (300 MHz, DMSO-d$_6$) δ ppm 1.44-1.58 (m, 4H) 2.95 (d, J=6.03 Hz, 2H) 3.15 (brs, 2H) 3.71-3.83 (m, 2H) 4.57 (s, 1H) 5.06 (s, 2H) 5.28 (t, J=5.93 Hz, 1H) 6.56-6.66 (m, 2H) 6.82-6.94 (m, 2H) 7.24-7.44 (m, 5H)

(2) benzyl 3-(4-fluorophenyl)-2-oxo-1-oxa-3,8-diazaspiro[4.5]decane-8-carboxylate The object product (976 mg, 91%) was obtained in the same manner as in Example 24(2) and using benzyl 4-{[(4-fluorophenyl)amino]methyl}-4-hydroxypiperidine-1-carboxylate (1.0 g) obtained by the above-mentioned reaction, N,N'-carbonyldiimidazole (635 mg) and 1,8-diazabicyclo[5.4.0]undec-7-ene (1.0 mL).

$^1$H NMR (300 MHz, DMSO-d$_6$) δ ppm 1.76-1.97 (m, 4H) 3.41 (brs, 2H) 3.61-3.75 (m, 2H) 3.88 (s, 2H) 5.10 (s, 2H) 7.16-7.45 (m, 7H) 7.53-7.62 (m, 2H)

(3) 3-(4-fluorophenyl)-1-oxa-3,8-diazaspiro[4.5]decan-2-one

The object product (450 mg, 72%) was obtained in the same manner as in Example 24(3) and using benzyl 3-(4-fluorophenyl)-2-oxo-1-oxa-3,8-diazaspiro[4.5]decane-8-carboxylate (976 mg) obtained by the above-mentioned reaction and 5% palladium-carbon (100 mg).

$^1$H NMR (300 MHz, DMSO-d$_6$) δ ppm 1.76 (t, J=5.68 Hz, 4H) 2.61-2.78 (m, 2H) 2.78-2.92 (m, 2H) 3.01 (brs, 1H) 3.85 (s, 2H) 7.13-7.30 (m, 2H) 7.52-7.65 (m, 2H)

(4) 3-(4-fluorophenyl)-8-[6-(3-methyl-1,2,4-thiadiazol-5-yl)pyridazin-3-yl]-1-oxa-3,8-diazaspiro[4.5]decan-2-one The object product (144 mg, 48%) was obtained in the same manner as in Example 1 and using 3-(4-fluorophenyl)-1-oxa-3,8-diazaspiro[4.5]decan-2-one (200 mg) obtained by the above-mentioned reaction, 3-chloro-6-(3-methyl-1,2,4-thiadiazol-5-yl)pyridazine (150 mg) and potassium carbonate (140 mg).

$^1$H NMR (300 MHz, DMSO-d$_6$) δ ppm 1.89-2.10 (m, 4H) 2.65 (s, 3H) 3.66-3.81 (m, 2H) 3.95 (s, 2H) 4.07-4.21 (m, 2H) 7.20-7.31 (m, 2H) 7.49-7.65 (m, 3H) 8.00 (d, J=9.61 Hz, 1H)

Example 31

1'-[6-(3-methyl-1,2,4-thiadiazol-5-yl)pyridazin-3-yl]spiro[1,3-benzoxazine-2,4'-piperidin]-4(3H)-one (1) spiro[1,3-benzoxazine-2,4'-piperidin]-4(3H)-one Salicylamide (7.24 g), 1-benzylpiperidin-4-one (10.0 g) and p-toluenesulfonic acid hydrate (500 mg) were suspended in toluene (200 mL), and the suspension was stirred under reflux overnight while removing the water in the reaction system using a Dean-Stark tube. The mixture was cooled to room temperature, and the resulting precipitate was collected by filtration and washed with water, ethanol and diethyl ether to give 1'-benzylspiro[1,3-benzoxazine-2,4'-piperidin]-4(3H)-one as a crude product (9.7 g). The obtained crude 1'-benzylspiro[1,3-benzoxazine-2,4'-piperidin]-4(3H)-one (5.0 g) and 10% palladium-carbon (1.0 g) were suspended in ethanol (50 mL), and the suspension was stirred at 50° C. for 5 hr under a hydrogen atmosphere. The catalyst was removed by filtration through celite and the solvent was evaporated under reduced pressure. The resulting precipitate was collected by filtration, and washed with ethanol and diethyl ether to give the object product (2.7 g, 77%).

$^1$H NMR (300 MHz, DMSO-d$_6$) δ ppm 1.58-1.74 (m, 2H) 1.82-1.95 (m, 2H) 2.01 (brs, 1H) 2.67-2.84 (m, 4H) 6.84-7.15 (m, 2H) 7.41-7.56 (m, 1H) 7.73 (dd, J=7.63, 1.60 Hz, 1H) 8.68 (s, 1H)

(2) 1'-[6-(3-methyl-1,2,4-thiadiazol-5-yl)pyridazin-3-yl]spiro[1,3-benzoxazine-2,4'-piperidin]-4(3H)-one The object product (82 mg, 29%) was obtained in the same manner as in Example 1 and using spiro[1,3-benzoxazine-2,4'-piperidin]-4(3H)-one (175 mg) obtained by the above-mentioned reaction, 3-chloro-6-(3-methyl-1,2,4-thiadiazol-5-yl)pyridazine (150 mg) and potassium carbonate (140 mg).

$^1$H NMR (300 MHz, DMSO-d$_6$) δ ppm 1.78-1.95 (m, 2H) 2.15 (d, J=13.75 Hz, 2H) 2.65 (s, 3H) 3.51 (t, J=11.30 Hz, 2H) 4.35 (d, J=13.56 Hz, 2H) 7.05-7.21 (m, 2H) 7.41-7.65 (m, 2H) 7.78 (dd, J=7.63, 1.41 Hz, 1H) 8.01 (d, J=9.61 Hz, 1H) 8.77 (s, 1H)

Example 32

9-[6-(3-methyl-1,2,4-thiadiazol-5-yl)pyridazin-3-yl]-4-phenyl-1-oxa-4,9-diazaspiro[5.5]undecan-3-one The object product (147 mg, 49%) was obtained in the same manner as in Example 1 and using 4-phenyl-1-oxa-4,9-diazaspiro[5.5]undecan-3-one (230 mg), 3-chloro-6-(3-methyl-1,2,4-thiadiazol-5-yl)pyridazine (150 mg) and potassium carbonate (140 mg).

$^1$H NMR (300 MHz, DMSO-d$_6$) δ ppm 1.71-1.87 (m, 2H) 1.95-2.09 (m, 2H) 2.64 (s, 3H) 3.34-3.48 (m, 2H) 3.71 (s, 2H) 4.25-4.36 (m, 4H) 7.23-7.31 (m, 1H) 7.32-7.50 (m, 5H) 7.97 (d, J=9.80 Hz, 1H)

Example 33

1'-[6-(3-methyl-1,2,4-thiadiazol-5-yl)pyridazin-3-yl]spiro[chromene-2,3'-pyrrolidine]

(1) spiro[chromene-2,3'-pyrrolidine] hydrochloride

The object product (327 mg, 15%) was obtained in the same manner as in Example 20(1) and using tert-butyl 4-oxo- 3,4-dihydro-1'H-spiro[chromene-2,3'-pyrrolidine]-1'-carboxylate (3.0 g) synthesized in Example 21(1), borane-tetrahydrofuran complex (1M tetrahydrofuran solution, 80 mL) and hydrochloric acid (6N aqueous solution, 250 mL).

$^1$H NMR (300 MHz, DMSO-d$_6$) δ ppm 1.96-2.10 (m, 1H) 2.26-2.39 (m, 1H) 3.18 (d, J=12.62 Hz, 1H) 3.28-3.54 (m, 3H) 5.88 (d, J=9.80 Hz, 1H) 6.67 (d, J=9.80 Hz, 1H) 6.82 (d, J=8.10 Hz, 1H) 6.89-6.99 (m, 1H) 7.09-7.25 (m, 2H) 9.74 (brs, 2H)

(2) 1'-[6-(3-methyl-1,2,4-thiadiazol-5-yl)pyridazin-3-yl]spiro[chromene-2,3'-pyrrolidine]

The object product (82 mg, 35%) was obtained in the same manner as in Example 1 and using spiro[chromene-2,3'-pyrrolidine] hydrochloride (150 mg) obtained by the above-mentioned reaction, 3-chloro-6-(3-methyl-1,2,4-thiadiazol-5-yl)pyridazine (140 mg) and potassium carbonate (140 mg).

$^1$H NMR (300 MHz, DMSO-d$_6$) δ ppm 2.11-2.30 (m, 1H) 2.41-2.49 (m, 1H) 2.64 (s, 3H) 3.53-4.32 (m, 4H) 5.97 (d, J=9.84 Hz, 1H) 6.67 (d, J=9.84 Hz, 1H) 6.78 (d, J=7.95 Hz, 1H) 6.91 (t, J=7.00 Hz, 1H) 7.13 (t, J=8.33 Hz, 3H) 7.99 (d, J=9.47 Hz, 1H)

Example 34

1'-[6-(3-methyl-1,2,4-thiadiazol-5-yl)pyridazin-3-yl]-3,4-dihydrospiro[chromene-2,3'-pyrrolidine]

(1) 3,4-dihydrospiro[chromene-2,3'-pyrrolidine] hydrochloride

Spiro[chromene-2,3'-pyrrolidine] hydrochloride (150 mg) synthesized in Example 33(1) and 5% palladium-carbon (30 mg) were suspended in methanol (10 mL), and the suspension was stirred overnight under a hydrogen atmosphere at room temperature. The catalyst was removed by filtration through celite, and the solvent was evaporated under reduced pressure to give the object product (130 mg, 86%).

$^1$H NMR (300 MHz, DMSO-d$_6$) δ ppm 1.83-2.18 (m, 4H) 2.79 (t, J=6.59 Hz, 2H) 3.13-3.44 (m, 2H) 6.63-6.96 (m, 2H) 7.00-7.23 (m, 2H) 9.54 (brs, 1H)

(2) 1'-[6-(3-methyl-1,2,4-thiadiazol-5-yl)pyridazin-3-yl]-3,4-dihydrospiro[chromene-2,3'-pyrrolidine]

The object product (45 mg, 27%) was obtained in the same manner as in Example 1 and using 3,4-dihydrospiro[chromene-2,3'-pyrrolidine] hydrochloride (110 mg) obtained by the above-mentioned reaction, 3-chloro-6-(3-methyl-1,2,4-thiadiazol-5-yl)pyridazine (96 mg) and potassium carbonate (140 mg).

$^1$H NMR (300 MHz, DMSO-d$_6$) δ ppm 1.97-2.33 (m, 4H) 2.64 (s, 3H) 2.86 (t, J=6.63 Hz, 2H) 3.55-4.17 (m, 4H) 6.68-6.76 (m, 1H) 6.79-6.91 (m, 1H) 6.99-7.19 (m, 3H) 7.98 (d, J=9.47 Hz, 1H)

Example 35

6'-chloro-1-[6-(3-methyl-1,2,4-thiadiazol-5-yl)pyridazin-3-yl]-1'H-spiro[piperidine-4,2'-quinazolin]-4'(3'H)-one (1) benzyl 6'-chloro-4'-oxo-3',4'-dihydro-1H,1'H-spiro[piperidine-4,2'-quinazoline]-1-carboxylate The object product (2.65 g, 61%) was obtained in the same manner as in Example 31(1) and using 2-amino-5-chlorobenzamide (1.9 g), benzyl 4-oxopiperidine-1-carboxylate (2.6 g) and p-toluenesulfonic acid hydrate (120 mg).

$^1$H NMR (300 MHz, DMSO-d$_6$) δppm 1.67-1.85 (m, 4H) 3.34-3.52 (m, 2H) 3.58-3.72 (m, 2H) 5.09 (s, 2H) 6.81 (d, J=8.71 Hz, 1H) 7.04 (s, 1H) 7.25-7.42 (m, 6H) 7.52 (d, J=2.65 Hz, 1H) 8.32 (s, 1H)

(2) 6'-chloro-1-[6-(3-methyl-1,2,4-thiadiazol-5-yl)pyridazin-3-yl]-1'H-spiro[piperidine-4,2'-quinazolin]-4'(3'H)-one Benzyl 6'-chloro-4'-oxo-3',4'-dihydro-1H,1'H-spiro[piperidine-4,2'-quinazoline]-1-carboxylate (1.0 g) obtained by the above-mentioned reaction was suspended in potassium hydroxide solution (40% v/w, methanol-water (1:1), 30 mL) and the suspension was stirred at 100° C. overnight. The mixture was cooled to room temperature, and the solvent was concentrated to a half amount under reduced pressure. The residue was diluted with saturated brine, and the mixture was extracted with ethyl acetate. The organic layer was dried over sodium sulfate and the solvent was evaporated under reduced pressure. The residue was dissolved in ethyl acetate, and hydrochloric acid (4N ethyl acetate solution, 5 mL) was added. After stirring at room temperature for 30 min, the resulting precipitate was collected by filtration to give 6'-chloro-1'H-spiro[piperidine-4,2'-quinazolin]-4'(3'H)-one hydrochloride as a crude product (320 mg). The object product (42 mg, 14%) was obtained in the same manner as in Example 1 and using the obtained crude 6'-chloro-1'H-spiro[piperidine-4,2'-quinazolin]-4'(3'H)-one hydrochloride (300 mg), 3-chloro-6-(3-methyl-1,2,4-thiadiazol-5-yl)pyridazine (150 mg) and potassium carbonate (140 mg).

$^1$H NMR (300 MHz, DMSO-d$_6$) δ ppm 1.82-1.95 (m, 4H) 2.65 (s, 3 H) 3.82 (s, 2H) 3.98-4.14 (m, 2H) 6.83 (d, J=8.67 Hz, 1H) 7.14 (s, 1H) 7.31 (dd, J=8.67, 2.64 Hz, 1H) 7.42-7.59 (m, 2H) 8.00 (d, J=9.61 Hz, 1H) 8.39 (s, 1H)

Example 36

N-(3-methylbutyl)-6-(1'H-spiro[indene-1,4'-piperidin]-1'-yl)pyridazine-3-carboxamide (1) ethyl 6-(1'H-spiro[indene-1,4'-piperidin]-1'-yl)pyridazine-3-carboxylate Ethyl 6-chloropyridazine-3-carboxylate (1.0 g), spiro[indene-1,4'-piperidine] trifluoroacetate (1.0 g), potassium carbonate (2.1 g) and tetrabutylammonium bromide (18 mg) were suspended in 1,4-dioxane (50 mL), and the suspension was refluxed overnight. The mixture was cooled to room temperature, the solvent was evaporated under reduced pressure, and the residue was suspended in ethyl acetate. The suspension was washed 3 times with aqueous sodium hydrogen carbonate solution, the organic layer was dried over sodium sulfate and the solvent was evaporated under reduced pressure. Ethyl acetate-hexane was added to the residue and the resulting precipitate was collected by filtration to give the object product (1.0 g, 57%).

$^1$H NMR (300 MHz, DMSO-d$_6$) δ ppm 1.34 (t, J=7.00 Hz, 5H) 2.02-2.20 (m, 2H) 3.41-3.54 (m, 2H) 4.35 (q, J=7.07 Hz, 2H) 4.57-4.68 (m, 2H) 6.88 (d, J=5.68 Hz, 1H) 7.12-7.27 (m, 3H) 7.33-7.47 (m, 3H) 7.86 (d, J=9.47 Hz, 1H)

(2) 6-(1'H-spiro[indene-1,4'-piperidin]-1'-yl)pyridazine-3-carboxylic acid

Ethyl 6-(1'H-spiro[indene-1,4'-piperidin]-1'-yl)pyridazine-3-carboxylate (500 mg) obtained by the above-mentioned reaction was dissolved in methanol-tetrahydrofuran (1:1, 20 mL), and sodium hydroxide (1N aqueous solution, 10 mL) was added. After stirring at room temperature overnight, hydrochloric acid (1N aqueous solution, 10 mL) was added, and the mixture was further stirred at room temperature for 1 hr. The resulting precipitate was collected by filtration to give the object product (440 mg, 96%).

$^1$H NMR (300 MHz, DMSO-$d_6$) δ ppm 1.34 (d, J=13.25 Hz, 2H) 2.04-2.20 (m, 2H) 3.40-3.55 (m, 2H) 4.63 (d, J=13.63 Hz, 2H) 6.88 (d, J=5.30 Hz, 1H) 7.11-7.30 (m, 3H) 7.31-7.48 (m, 3H) 7.86 (d, J=9.47 Hz, 1H) 12.60 (brs, 1H)

(3) N-(3-methylbutyl)-6-(1'H-spiro[indene-1,4'-piperidin]-1'-yl)pyridazine-3-carboxamide A solution of 6-(1'H-spiro[indene-1,4'-piperidin]-1'-yl)pyridazine-3-carboxylic acid (92 mg) obtained by the abovementioned reaction, 3-methylbutan-1-amine (35 mg), 1-ethyl-3-(3-dimethylaminopropyl)carbodiimide hydrochloride (95 mg) and hydroxybenzotriazole hydrate (75 mg) in N,N-dimethylformamide (3 mL) was stirred at room temperature overnight. Ethyl acetate was added, the mixture was washed 3 times with aqueous sodium hydrogen carbonate solution, and the organic layer was dried over sodium sulfate. The solvent was evaporated under reduced pressure, ethyl acetate-hexane was added and the resulting precipitate was collected by filtration to give the object product (66 mg, 59%).

$^1$H NMR (300 MHz, DMSO-$d_6$) δ ppm 0.90 (s, 3H) 0.92 (s, 3H) 1.33 (d, J=13.19 Hz, 2H) 1.44 (q, J=6.91 Hz, 2H) 1.51-1.70 (m, 1H) 2.05-2.19 (m, 2H) 3.27-3.37 (m, 2H) 3.38-3.52 (m, 2H) 4.52-4.66 (m, 2H) 6.87 (d, J=5.65 Hz, 1H) 7.12-7.28 (m, 3H) 7.36 (d, J=7.16 Hz, 1H) 7.38-7.47 (m, 2H) 7.85 (d, J=9.42 Hz, 1H) 8.79 (t, J=6.03 Hz, 1H)

Example 37

N-(3-phenylpropyl)-6-(1'H-spiro[indene-1,4'-piperidin]-1'-yl)pyridazine-3-carboxamide The object product (55 mg, 43%) was obtained in the same manner as in Example 36(3) and using 6-(1'H-spiro[indene-1,4'-piperidin]-1'-yl)pyridazine-3-carboxylic acid (92 mg) synthesized in Example 32(2), 3-phenylpropan-1-amine (54 mg), 1-ethyl-3-(3-dimethylaminopropyl)carbodiimide hydrochloride (77 mg) and hydroxybenzotriazole hydrate (61 mg).

$^1$H NMR (300 MHz, DMSO-$d_6$) δ ppm 1.33 (d, J=13.37 Hz, 2H) 1.79-1.91 (m, 2H) 2.05-2.19 (m, 2H) 2.58-2.67 (m, 2H) 3.28-3.38 (m, 2H) 3.38-3.52 (m, 2H) 4.53-4.66 (m, 2H) 6.87 (d, J=5.65 Hz, 1H) 7.11-7.38 (m, 9H) 7.39-7.47 (m, 2H) 7.86 (d, J=9.61 Hz, 1H) 8.91 (t, J=5.84 Hz, 1H)

Example 38

N-[2-(5-chloro-2-thienyl)ethyl]-6-(1'H-spiro[indene-1,4'-piperidin]-1'-yl)pyridazine-3-carboxamide The object product (55 mg, 64%) was obtained in the same manner as in Example 36(3) and using 6-(1'H-spiro[indene-1,4'-piperidin]-1'-yl)pyridazine-3-carboxylic acid (92 mg) synthesized in Example 36(2), 2-(5-chloro-2-thienyl)ethanamine hydrochloride (79 mg), 1-ethyl-3-(3-dimethylaminopropyl)carbodiimide hydrochloride (77 mg), hydroxybenzotriazole hydrate (61 mg) and triethylamine (0.056 mL).

$^1$H NMR (300 MHz, DMSO-$d_6$) δ ppm 1.34 (d, J=13.38 Hz, 2H) 2.04-2.19 (m, 2H) 3.04 (t, J=6.78 Hz, 2H) 3.38-3.60 (m, 4H) 4.53-4.65 (m, 2H) 6.79 (d, J=3.77 Hz, 1H) 6.87 (d, J=5.65 Hz, 1H) 6.94 (d, J=3.77 Hz, 1H) 7.10-7.27 (m, 3H) 7.31-7.48 (m, 3H) 7.86 (d, J=9.61 Hz, 1H) 8.99 (t, J=5.93 Hz, 1H)

Example 39

1'-[6-(3-methyl-1,2,4-oxadiazol-5-yl)pyridazin-3-yl]spiro[indene-1,4'-piperidine]

To a suspension (5 mL) of ethyl 6-(1'H-spiro[indene-1,4'-piperidin]-1'-yl)pyridazine-3-carboxylate (150 mg) synthesized in Example 36(1), N'-hydroxyethanimidamide (60 mg) and molecular sieves 4A (300 mg) in tetrahydrofuran was added sodium hydride (40 mg). The mixture was stirred at 80° C. for 3 hr. Ethyl acetate was added, the mixture was washed twice with saturated aqueous sodium hydrogen carbonate solution, and the organic layer was dried over sodium sulfate. The solvent was evaporated under reduced pressure, and the residue was purified by silica gel column chromatography (15% ethyl acetate/hexane to 60% ethyl acetate/hexane) to give the object product (29.4 mg, 19%).

$^1$H NMR (300 MHz, DMSO-$d_6$) δ ppm 1.36 (d, J=13.19 Hz, 2H) 2.05-2.20 (m, 2H) 2.45 (s, 3H) 3.45-3.58 (m, 2H) 4.67 (d, J=13.56 Hz, 2H) 6.88 (d, J=5.65 Hz, 1H) 7.12-7.27 (m, 3H) 7.36 (d, J=6.97 Hz, 1H) 7.44 (d, J=7.16 Hz, 1H) 7.50 (d, J=9.80 Hz, 1H) 8.02 (d, J=9.80 Hz, 1H)

Example 40

8-[6-(3-methyl-1,2,4-thiadiazol-5-yl)pyridazin-3-yl]-3-phenyl-1-oxa-2,8-diazaspiro[4.5]dec-2-ene The object product (95 mg, 35%) was obtained in the same manner as in Example 1 and using 3-chloro-6-(3-methyl-1,2,4-thiadiazol-5-yl)pyridazine (150 mg), 3-phenyl-1-oxa-2,8-diazaspiro[4.5]dec-2-ene hydrochloride (200 mg) and potassium carbonate (140 mg).

$^1$H NMR (300 MHz, DMSO-$d_6$) δ ppm 1.36 (d, J=13.19 Hz, 2H) 2.05-2.20 (m, 2H) 2.45 (s, 3H) 3.45-3.58 (m, 2H) 4.67 (d, J=13.56 Hz, 2H) 6.88 (d, J=5.65 Hz, 1H) 7.12-7.27 (m, 3H) 7.36 (d, J=6.97 Hz, 1H) 7.44 (d, J=7.16 Hz, 1H) 7.50 (d, J=9.80 Hz, 1H) 8.02 (d, J=9.80 Hz, 1H)

Example 41

1'-[6-(3-methyl-1,2,4-oxadiazol-5-yl)pyridazin-3-yl]spiro[indene-1,4'-piperidine]

To a suspension (5 mL) of ethyl 6-(1'H-spiro[indene-1,4'-piperidin]-1'-yl)pyridazine-3-carboxylate (150 mg) obtained in Example 36(1), N'-hydroxyethanimidamide (60 mg) and molecular sieves 4A (300 mg) in tetrahydrofuran was added sodium hydride (40 mg). The mixture was stirred at 70° C. for 1 hr, and cooled to room temperature. The insoluble material was filtered off, and the filtrate was diluted with ethyl acetate (10 mL). The mixture was washed with saturated aqueous sodium hydrogen carbonate solution, and the organic layer was dried over sodium sulfate, and the solvent was evaporated under reduced pressure. The residue was purified by silica gel column chromatography (20% to 50% ethyl acetate/hexane) to give the object product (29 mg, 19%).

$^1$H NMR (300 MHz, DMSO-$d_6$) δ ppm 1.36 (d, J=13.19 Hz, 2H) 2.05-2.20 (m, 2H) 2.45 (s, 3H) 3.45-3.58 (m, 2H) 4.67 (d, J=13.56 Hz, 2H) 6.88 (d, J=5.65 Hz, 1H) 7.12-7.27

(m, 3H) 7.36 (d, J=6.97 Hz, 1H) 7.44 (d, J=7.16 Hz, 1H) 7.50 (d, J=9.80 Hz, 1H) 8.02 (d, J=9.80 Hz, 1H)

Example 42

2-[6-(3-methyl-1,2,4-thiadiazol-5-yl)pyridazin-3-yl]-7-phenyl-5-oxa-2,7-diazaspiro[3.4]octan-6-one (1) 1-(diphenylmethyl)azetidin-3-one 1-(Diphenylmethyl)azetidin-3-ol (2.0 g) was dissolved in N,N-dimethyl sulfoxide (60 mL), and triethylamine (11.7 mL) was added. The reaction solution was cooled to 10° C., a solution of pyridine sulfur trioxide complex (10.6 g) in N,N-dimethyl sulfoxide (20 mL) was added, and the mixture was stirred for 1 hr. The mixture was warmed to room temperature and further stirred for 3 hr. The reaction solution was poured into cold water, and the mixture was extracted with ethyl acetate. The organic layer was washed with saturated brine, and dried over sodium sulfate. The desiccant was filtered off, and the filtrate was concentrated. The residue was purified by silica gel column chromatography (30% to 50% ethyl acetate/hexane) to give the object product as a white solid (1.83 g, 92.4%).
$^1$H NMR (300 MHz, CDCl$_3$) δ ppm 4.00 (s, 4H) 4.59 (s, 1H) 7.17-7.35 (m, 6H) 7.44-7.52 (m, 4H)

(2) 5-(diphenylmethyl)-1-oxa-5-azaspiro[2.3]hexane

A solution of sodium hydride (60% in oil, 170 mg) in N,N-dimethylformamide (30 mL) was cooled to 0° C., trimethylsulfonium iodide (930 mg) and N,N-dimethyl sulfoxide (0.3 mL) were added, and the mixture was stirred for 1 hr. The solution was cooled to −70° C., a solution of 1-(diphenylmethyl)azetidin-3-one (1.0 g) obtained by the above-mentioned reaction in N,N-dimethylformamide (10 mL) was added dropwise over 30 min or longer, and the mixture was further stirred for 3 hr. The to mixture was warmed to 0° C. and further stirred for 1 hr. The reaction solution was poured into ice water, and the mixture was extracted with ethyl acetate. The organic layer was washed with saturated brine, and dried over magnesium sulfate. The desiccant was filtered off, the filtrate was concentrated, and the residue was purified by silica gel column chromatography (25% to 50% ethyl acetate/hexane) to give the object product as a white solid (0.52 g, 49%).
$^1$H NMR (300 MHz, DMSO-d$_6$) δ ppm 2.79 (s, 2H) 3.27 (d, J=10.22 Hz, 2H) 3.46 (d, J=9.84 Hz, 2H) 4.60 (s, 1H) 7.11-7.23 (m, 2H) 7.23-7.33 (m, 4H) 7.42-7.52 (m, 4H)

(3) 3-(anilinomethyl)-1-(diphenylmethyl)azetidin-3-ol 5-(Diphenylmethyl)-1-oxa-5-azaspiro[2.3]hexane (500 mg) obtained by the above-mentioned reaction, aniline (0.14 mL) and lithium perchlorate (250 mg) were dissolved in acetonitrile (20 mL). The mixed solution was stirred under reflux overnight. The mixture was cooled to room temperature, and acetonitrile was evaporated under reduced pressure. The residue was dissolved in ethyl acetate, and the solution was washed with saturated brine. The organic layer was dried over magnesium sulfate. The desiccant was filtered off, and the filtrate was concentrated. The residue was purified by basic silica gel column chromatography (40% to 50% ethyl acetate/hexane) to give the object product as a colorless oil (0.41 g, 60%).
$^1$H NMR (300 MHz, DMSO-d$_6$) δ ppm 2.30 (s, 1H) 2.80 (d, J=8.10 Hz, 2H) 3.20 (d, J=8.10 Hz, 2H) 3.30 (d, J=5.84 Hz, 2H) 4.42 (s, 1H) 5.40 (t, J=5.65 Hz, 1H) 6.52 (t, J=7.25 Hz, 1H) 6.68 (d, J=7.54 Hz, 2H) 7.07 (dd, J=8.38, 7.25 Hz, 2H) 7.12-7.20 (m, 2H) 7.21-7.32 (m, 4H) 7.38-7.47 (m, 4H)

(4) 2-(diphenylmethyl)-7-phenyl-5-oxa-2,7-diazaspiro[3.4]octan-6-one 3-(Ailinomethyl)-1-(diphenylmethyl)azetidin-3-ol (410 mg) obtained by the above-mentioned reaction, 1,1'-carbonylbis(1H-imidazole) (270 mg) and 2,3,4,6,7,8,9,10-octahydropyrimido[1,2-a]azepine (450 mg) were dissolved in acetonitrile (10 mL). The mixed solution was stirred at 80° C. overnight. The mixture was cooled to room temperature, poured into water, and extracted with ethyl acetate. The organic layer was washed with saturated brine, and dried over sodium sulfate. The desiccant was filtered off, and the filtrate was concentrated. The residue was purified by silica gel column chromatography (25% to 50% ethyl acetate/hexane) to give the object product as a white solid (0.37 g, 84%).
$^1$H NMR (300 MHz, DMSO-d$_6$) δ ppm 3.27-3.46 (m, 4H) 4.33 (s, 2H) 4.54 (s, 1H) 7.06-7.62 (m, 15H)

(5) 7-phenyl-5-oxa-2,7-diazaspiro[3.4]octan-6-one

To a solution of 2-(diphenylmethyl)-7-phenyl-5-oxa-2,7-diazaspiro[3.4]octan-6-one (370 mg) obtained by the above-mentioned reaction in methanol (2 mL) was added 5% palladium-carbon (40 mg). The mixed solution was stirred under a hydrogen atmosphere at room temperature overnight. Tetrahydrofuran (2 mL) was added, and the mixture was further stirred for 5 days. The catalyst was removed using celite, and the filtrate was concentrated. The residue was purified by basic silica gel column chromatography (ethyl acetate to 5% methanol/ethyl acetate) to give the object product (144 mg, 71%).
$^1$H NMR (300 MHz, DMSO-d$_6$) δ ppm 3.61 (d, J=9.98 Hz, 2H) 3.74-3.83 (m, 2H) 4.29 (s, 2H) 7.13 (t, J=7.35 Hz, 1H) 7.32-7.45 (m, 2H) 7.51-7.60 (m, 2H)

(6) 2-[6-(3-methyl-1,2,4-thiadiazol-5-yl)pyridazin-3-yl]-7-phenyl-5-oxa-2,7-diazaspiro[3.4]octan-6-one 7-Phenyl-5-oxa-2,7-diazaspiro[3.4]octan-6-one (94 mg) obtained by the above-mentioned reaction, 3-chloro-6-(3-methyl-1,2,4-thiadiazol-5-yl)pyridazine (98 mg) and potassium carbonate (77 mg) were dissolved in N,N-dimethylformamide (2 mL), the mixed solution was stirred at 80° C. for 3 days. The reaction solution was poured into water, and the mixture was extracted with ethyl acetate. The organic layer was dried over sodium sulfate, the desiccant was filtered off, and the filtrate was concentrated. The residue was purified by silica gel column chromatography (50% ethyl acetate/hexane to ethyl acetate), and the obtained crude product was recrystallized from ethyl acetate to give the object product (4.9 mg, 2.8%).
$^1$H NMR (300 MHz, DMSO-d$_6$) δ ppm 2.66 (s, 3H) 4.19-4.65 (m, 6H) 7.08 (d, J=9.47 Hz, 1H) 7.16 (t, J=7.19 Hz, 1H) 7.36-7.46 (m, 2H) 7.56 (d, J=8.71 Hz, 2H) 8.06 (d, J=9.09 Hz, 1H)

Example 43

1'-[6-(3-methyl-1,2,4-oxadiazol-5-yl)pyridazin-3-yl]-3H-spiro[2-benzofuran-1,3'-pyrrolidine]

(1) 6-(3-methyl-1,2,4-oxadiazol-5-yl)pyridazin-3(2H)-one

A solution of 6-oxo-1,6-dihydropyridazine-3-carboxylic acid (1.4 g) and 1,1'-carbonylbis(1H-imidazole) (2.1 g) in N,N-dimethylformamide (80 mL) was stirred at 60° C. for 1 hr. The mixture was cooled to room temperature, and N'-hydroxyethanimidamide (963 mg) was added. Sodium hydride (520 mg) was slowly added, and the mixture was stirred at 100° C. for 8 hr. The mixture was cooled to room temperature, diluted with saturated aqueous ammonium chloride solution (100 mL) and saturated aqueous sodium chloride solution (100 mL), and the mixture was extracted 3 times with ethyl acetate-tetrahydrofuran (1:1, v/v, 100 mL). The organic layers were combined, and dried over sodium sulfate, and the solvent was evaporated under reduced pressure. The residue was suspended in diethyl ether and diisopropyl ether and the precipitate was collected by filtration to give the object product (1.1 g, 60%).

$^1$H NMR (300 MHz, DMSO-$d_6$) δ ppm 2.43 (s, 3H) 7.08 (d, J=9.98 Hz, 1H) 7.98 (d, J=9.98 Hz, 1H) 13.81 (brs, 1H)

(2) 3-chloro-6-(3-methyl-1,2,4-oxadiazol-5-yl)pyridazine 6-(3-Methyl-1,2,4-oxadiazol-5-yl)pyridazin-3(2H)-one (640 mg) obtained by the above-mentioned reaction was dissolved in phosphoryl chloride (8 mL), and the solution was refluxed for 3 hr. The solvent was evaporated under reduced pressure, and the residue was diluted with distilled water (10 mL). The mixture was neutralized with 1N aqueous sodium hydroxide solution, and diluted with distilled water (50 mL). The resulting precipitate was collected by filtration, and recrystallized from diisopropyl alcohol to give the object product (360 mg, 51%).

$^1$H NMR (300 MHz, DMSO-$d_6$) δ ppm 2.51 (s, 3H) 8.23 (d, J=8.85 Hz, 1H) 8.47 (d, J=8.85 Hz, 1H)

(3) tert-butyl 3-hydroxy-3-[2-(hydroxymethyl)phenyl]pyrrolidine-1-carboxylate A solution of (2-bromophenyl)methanol (56 g) in tetrahydrofuran (300 mL) was cooled to −78° C., n-butyllithium (1.6 M, hexane solution, 390 mL) was slowly added dropwise. After stirring at −78° C. for 1 hr, a solution of tert-butyl 3-oxopyrrolidine-1-carboxylate (60 g) in tetrahydrofuran (200 mL) was added dropwise. The reaction mixture was warmed to room temperature, and the mixture was stirred at room temperature overnight. The reaction was quenched with water and stirring at room temperature for 30 min. The reaction mixture was diluted with ethyl acetate, and washed with aqueous sodium chloride solution. The organic layer was dried over sodium sulfate and the solvent was evaporated under reduced pressure. The residue was purified by silica gel column chromatography (hexane-ethyl acetate, 40%-80%) and crystallized from ethyl acetate-hexane to give the object product (35 g).

$^1$H NMR (300 MHz, DMSO-$d_6$) δ ppm 1.37-1.45 (m, 9H) 2.09-2.25 (m, 1H) 2.25-2.42 (m, 1H) 3.34-3.48 (m, 3H) 3.63-3.77 (m, 1H) 4.64-4.86 (m, 2H) 5.17-5.27 (m, 1H) 5.42-5.49 (m, 1H) 7.15-7.35 (m, 3H) 7.55 (d, J=7.35 Hz, 1H)

(4) tert-butyl 1'H,3H-spiro[2-benzofuran-1,3'-pyrrolidine]-1'-carboxylate tert-Butyl 3-hydroxy-3-[2-(hydroxymethyl)phenyl]pyrrolidine-1-carboxylate (33 g) obtained by the above-mentioned reaction and triethylamine (40 mL) were dissolved in ethyl acetate (900 mL), and methanesulfonyl chloride (9.7 mL) was added dropwise under ice-cooling. The mixture was stirred at room temperature overnight, and the reaction was quenched with water. The reaction mixture was washed with aqueous sodium hydrogen carbonate solution, and the organic layer was dried over sodium sulfate. The solvent was evaporated under reduced pressure and purified by silica gel column chromatography (hexane-ethyl acetate, 5%-20%) to give the object product (29 g, 94%).

$^1$H NMR (300 MHz, CDCl$_3$) δ ppm 1.37-1.60 (m, 9H) 2.10-2.23 (m, 2H) 3.44-3.81 (m, 4H) 5.10 (s, 2H) 7.09-7.40 (m, 4H)

(5) 3H-spiro[2-benzofuran-1,3'-pyrrolidine] hydrochloride tert-Butyl 1'H,3H-spiro[2-benzofuran-1,3'-pyrrolidine]-1'-carboxylate (29 g) obtained by the above-mentioned reaction was dissolved in ethyl acetate (400 mL), and hydrochloric acid (4N, ethyl acetate solution, 100 mL) was added. The mixture was stirred at room temperature overnight and the solvent was evaporated under reduced pressure to give the object product (22 g, 99%).

$^1$H NMR (300 MHz, DMSO-$d_6$) δ ppm 2.13-2.34 (m, 2H) 3.22-3.61 (m, 4H) 4.98-5.14 (m, 2H) 7.26-7.43 (m, 3H) 7.44-7.54 (m, 1H) 9.62 (brs, 1H) 10.06 (brs, 1H)

(6) 1'-[6-(3-methyl-1,2,4-oxadiazol-5-yl)pyridazin-3-yl]-3H-spiro[2-benzofuran-1,3'-pyrrolidine]

3-Chloro-6-(3-methyl-1,2,4-oxadiazol-5-yl)pyridazine (150 mg) obtained by the above-mentioned reaction, 3H-spiro[2-benzofuran-1,3'-pyrrolidine] hydrochloride (169 mg) and potassium carbonate (138 mg) were suspended in N,N-dimethylformamide (10 mL), and the suspension was stirred at 80° C. overnight. The reaction mixture was diluted with ethyl acetate, washed with saturated aqueous sodium hydrogen carbonate solution, and the organic layer was dried over sodium sulfate. The solvent was evaporated under reduced pressure, ethyl acetate-hexane was added and the resulting precipitate was collected by filtration to give the object product (174 mg, 68%).

$^1$H NMR (300 MHz, DMSO-$d_6$) δ ppm 2.24-2.35 (m, 1H) 2.43 (s, 3H) 2.46-2.58 (m, 1H) 3.63-4.32 (m, 4H) 5.07 (s, 2H) 6.99-7.18 (m, 1H) 7.31-7.41 (m, 3H) 7.46-7.53 (m, 1H) 8.02 (d, J=9.42 Hz, 1H)

Example 44 methyl N-{[6-(1'H-spiro[indene-1,4'-piperidin]-1'-yl)pyridazin-3-yl]carbonyl}phenylalaninate A solution of 6-(1'H-spiro[indene-1,4'-piperidin]-1'-yl)pyridazine-3-carboxylic acid (460 mg) obtained in Example 36(2), methyl phenylalaninate hydrochloride (650 mg), 1-ethyl-3-(3-dimethylaminopropyl)carbodiimide hydrochloride (450 mg) and hydroxybenzotriazole hydrate (380 mg) in N,N-dimethylformamide (15 mL) was stirred at room temperature overnight. Ethyl acetate was added, and the mixture was washed 3 times with aqueous sodium hydrogen carbonate solution, and the organic layer was dried over sodium sulfate. The solvent was evaporated under reduced pressure, and the residue was purified by silica gel column chromatography (40% to 80% ethyl acetate/hexane) to give the object product (570 mg, 81%).

$^1$H NMR (300 MHz, DMSO-$d_6$) δ ppm 1.33 (d, J=13.19 Hz, 2H) 2.03-2.19 (m, 2H) 3.16-3.26 (m, 2H) 3.46 (t, J=11.96 Hz, 2H) 3.67 (s, 3H) 4.50-4.66 (m, 2H) 4.74-4.86 (m, 1H) 6.87 (d, J=5.65 Hz, 1H) 7.11-7.32 (m, 8H) 7.36 (d, J=6.97 Hz, 1H) 7.39-7.47 (m, 2H) 7.80 (d, J=9.61 Hz, 1H) 8.95 (d, J=8.10 Hz, 1H)

Example 45

1'-[6-(5-methyl-1,3,4-oxadiazol-2-yl)pyridazin-3-yl]spiro[indene-1,4'-piperidine]

(1) N'-acetyl-6-(1'H-spiro[indene-1,4'-piperidin]-1'-yl)pyridazine-3-carbohydrazide A solution of 6-(1'H-spiro[indene-1,4'-piperidin]-1'-yl)pyridazine-3-carboxylic acid (310 mg) obtained in Example 36(2), acetohydrazide (89 mg), 1-ethyl-3-(3-dimethylaminopropyl)carbodiimide hydrochloride (290 mg) and hydroxybenzotriazole hydrate (230 mg) in N,N-dimethylformamide (10 mL) was stirred at room temperature overnight. Ethyl acetate was added, the mixture was washed 3 times with aqueous sodium hydrogen carbonate solution, and the organic layer was dried over sodium sulfate. The solvent was evaporated under reduced pressure, ethyl acetate-hexane was added and the resulting precipitate was collected by filtration to give the object product (290 mg, 80%).

$^1$H NMR (300 MHz, DMSO-$d_6$) δ ppm 1.33 (d, J=13.19 Hz, 2H) 1.91 (s, 3H) 2.05-2.20 (m, 2H) 3.41-3.53 (m, 2H) 4.62 (d, J=13.56 Hz, 2H) 6.87 (d, J=5.65 Hz, 1H) 7.10-7.28 (m, 3H) 7.36 (d, J=6.97 Hz, 1H) 7.40-7.51 (m, 2H) 7.85 (d, J=9.61 Hz, 1H) 9.89 (brs, 1H) 10.44 (brs, 1H)

(2) 1'-[6-(5-methyl-1,3,4-oxadiazol-2-yl)pyridazin-3-yl]spiro[indene-1,4'-piperidine]

N'-Acetyl-6-(1'H-spiro[indene-1,4'-piperidin]-1'-yl)pyridazine-3-carbohydrazide (200 mg) obtained by the above-mentioned reaction was dissolved in phosphoryl chloride (5 mL) and the solution was refluxed for 6 hr. The solvent was evaporated under reduced pressure, and the residue was diluted with ethyl acetate. The mixture was washed with saturated brine and saturated aqueous sodium hydrogen carbonate solution, and the organic layer was dried over sodium sulfate. The solvent was evaporated under reduced pressure and the residue was purified by silica gel column chromatography (50% to 80% ethyl acetate/hexane) to give the object product (60 mg. 32%).

$^1$H NMR (300 MHz, DMSO-$d_6$) δ ppm 1.35 (d, J=13.37 Hz, 2H) 2.05-2.20 (m, 2H) 2.62 (s, 3H) 3.40-3.57 (m, 2H) 4.63 (d, J=13.75 Hz, 2H) 6.88 (d, J=5.65 Hz, 1H) 7.11-7.28 (m, 3H) 7.36 (d, J=6.97 Hz, 1H) 7.44 (d, J=7.35 Hz, 1H) 7.51 (d, J=9.80 Hz, 1H) 8.00 (d, J=9.61 Hz, 1H)

Example 46

1'-[6-(3-methyl-1,2,4-oxadiazol-5-yl)pyridazin-3-yl]-2,3-dihydrospiro[indene-1,4'-piperidine]

The object product (175 mg, 76%) was obtained in the same manner as in Example 1 and using 3-chloro-6-(3-methyl-1,2,4-oxadiazol-5-yl)pyridazine (130 mg) obtained in Example 43(2), 2,3-dihydrospiro[indene-1,4'-piperidine] hydrochloride (180 mg) and potassium carbonate (110 mg).

$^1$H NMR (300 MHz, DMSO-$d_6$) δ ppm 1.62 (d, J=13.19 Hz, 2H) 1.78-1.91 (m, 2H) 2.16 (t, J=7.25 Hz, 2H) 2.44 (s, 3H) 2.93 (t, J=7.25 Hz, 2H) 3.20-3.32 (m, 2H) 4.59 (d, J=13.38 Hz, 2H) 7.09-7.27 (m, 4H) 7.46 (d, J=9.80 Hz, 1H) 7.99 (d, J=9.80 Hz, 1H)

Example 47

3-(4-fluorophenyl)-8-[6-(3-methyl-1,2,4-oxadiazol-5-yl)pyridazin-3-yl]-1-oxa-3,8-diazaspiro[4.5]decan-2-one The object product (24 mg, 58%) was obtained in the same manner as in Example 1 and using 3-chloro-6-(3-methyl-1,2,4-oxadiazol-5-yl)pyridazine (20 mg) obtained in Example 43(2), 3-(4-fluorophenyl)-1-oxa-3,8-diazaspiro[4.5]decan-2-one (25 mg) obtained in Example 30(3) and potassium carbonate (15 mg).

$^1$H NMR (300 MHz, DMSO-$d_6$) δ ppm 1.88-2.12 (m, 4H) 2.44 (s, 3H) 3.66-3.81 (m, 2H) 3.95 (s, 2H) 4.09-4.23 (m, 2H) 7.19-7.34 (m, 2H) 7.47-7.65 (m, 3H) 8.02 (d, J=9.80 Hz, 1H)

Example 48

3-(3-fluorophenyl)-8-[6-(3-methyl-1,2,4-oxadiazol-5-yl)pyridazin-3-yl]-1-oxa-3,8-diazaspiro[4.5]decan-2-one The object product (82 mg, 57%) was obtained in the same manner as in Example 1 and using 3-chloro-6-(3-methyl-1,2,4-oxadiazol-5-yl)pyridazine (70 mg) obtained in Example 43(2), 3-(3-fluorophenyl)-1-oxa-3,8-diazaspiro[4.5]decan-2-one (80 mg) obtained in Example 29(3) and potassium carbonate (50 mg).

$^1$H NMR (300 MHz, DMSO-$d_6$) δ ppm 1.90-2.12 (m, 4H) 2.44 (s, 3H) 3.68-3.85 (m, 2H) 3.97 (s, 2H) 4.07-4.25 (m, 2H) 6.91-7.05 (m, 1H) 7.28-7.61 (m, 4H) 8.03 (d, J=9.61 Hz, 1H)

Example 49

1'-[6-(3-methyl-1,2,4-oxadiazol-5-yl)pyridazin-3-yl]spiro[chromene-2,3'-pyrrolidin]-4(3H)-one The object product (148 mg, 62%) was obtained in the same manner as in Example 1 and using 3-chloro-6-(3-methyl-1,2,4-oxadiazol-5-yl)pyridazine (130 mg) obtained in Example 43(2), spiro[chromene-2,3'-pyrrolidin]-4(3H)-one hydrochloride (160 mg) obtained in Example 21(2) and potassium carbonate (110 mg).

$^1$H NMR (300 MHz, DMSO-$d_6$) δ ppm 2.15-2.34 (m, 1H) 2.36-2.48 (m, 4H) 3.05-3.16 (m, 1H) 3.18-3.29 (m, 1H) 3.60-3.79 (m, 2H) 3.85 (brs, 1H) 4.06 (brs, 1H) 7.01-7.16 (m, 3H) 7.52-7.64 (m, 1H) 7.81 (dd, J=7.82, 1.60 Hz, 1H) 8.02 (d, J=9.42 Hz, 1H)

Example 50

1'-[6-(3-methyl-1,2,4-thiadiazol-5-yl)pyridazin-3-yl]spiro[1-benzofuran-3,3'-pyrrolidine]

(1) ethyl 1-benzyl-2,5-dihydro-1H-pyrrole-3-carboxylate

N-Benzyl-1-methoxy-N-[(trimethylsilyl)methyl]methanamine (4.7 mL) was dissolved in dichloromethane (75 mL), and the solution was cooled to 0° C. To this solution was added dropwise a solution (10 mL) of ethyl propiolate (1.55 mL) in dichloromethane, and acetic acid (0.1 mL) was further added. The mixed solution was stirred for 4 hr while gradually warming to room temperature. The reaction solution was added to saturated aqueous sodium hydrogen carbonate solution, and the mixture was extracted with ethyl acetate. The organic layer was washed with saturated brine, and dried over sodium sulfate. The desiccant was filtered off, and the filtrate was concentrated. The residue was purified by silica gel column chromatography (20% ethyl acetate/hexane) to give the object product as a pale-yellow oil (1.37 g). The obtained compound was used for the next reaction without purification.

(2) (1-benzyl-2,5-dihydro-1H-pyrrol-3-yl)methanol

Ethyl 1-benzyl-2,5-dihydro-1H-pyrrole-3-carboxylate (1.37 g) obtained by the above-mentioned reaction was dissolved in tetrahydrofuran (50 mL), and the solution was cooled to −78° C. To this solution was slowly added dropwise DIBAL-H (1.5 M toluene solution, 13 mL). The reaction solution was stirred for 3 days while gradually warming to room temperature. The solution was cooled to 0° C., and saturated aqueous ammonium chloride solution (6 mL) and 6N sulfuric acid were added dropwise. The aqueous layer was separated, and neutralized with 8N aqueous sodium hydroxide solution. The precipitated solid was filtered off and washed with ether. The filtrate was extracted with ether, and the organic layer was dried over sodium sulfate. The desiccant was filtered off, and the filtrate was concentrated to give the object product as a pale-yellow oil (1.0 g). The obtained compound was used for the next reaction without purification.

(3) 1-benzyl-3-[(2-bromophenoxy)methyl]-2,5-dihydro-1H-pyrrole (1-Benzyl-2,5-dihydro-1H-pyrrol-3-yl)methanol (1.0 g) obtained by the above-mentioned reaction, 2-bromophenol (680 μL), DEAD (40% toluene solution, 1.2 mL) and triphenylphosphine (1.66 g) were dissolved in tetrahydrofuran (50 mL). The reaction solution was stirred at 50° C. overnight, DEAD (40% toluene solution, 1.2 mL) was added, and the mixture was stirred at 60° C. for 1 day. Tetrahydrofuran was evaporated under reduced pressure, and the residue was purified by silica gel column chromatography (50% ethyl acetate/hexane to ethyl acetate) to give the object product as a white solid (1.44 g).
$^1$H NMR (300 MHz, DMSO-d$_6$) δ ppm 3.46 (s, 4H) 3.76 (s, 2H) 4.71 (s, 2H) 5.84 (s, 1H) 6.84-6.93 (m, 1H) 7.12 (d, J=7.19 Hz, 1H) 7.17-7.37 (m, 6H) 7.57 (dd, J=7.95, 1.51 Hz, 1H)

(4) 1'-benzylspiro[1-benzofuran-3,3'-pyrrolidine]

1-Benzyl-3-[(2-bromophenoxy)methyl]-2,5-dihydro-1H-pyrrole (1.44 g) obtained by the above-mentioned reaction, AIBN (170 mg) and tributyltin hydride (4.5 ml) were dissolved in toluene (50 mL), and the solution was stirred under reflux overnight. Toluene was evaporated under reduced pressure, ether and saturated aqueous potassium fluoride solution was added to the residue and the mixture was stirred at room temperature for 4 hr. The aqueous layer was separated and extracted with ether. The organic layer was dried over sodium sulfate. The desiccant was filtered off, and the filtrate was concentrated. The residue was purified by silica gel column chromatography (20% ethyl acetate/hexane) to give the object product as a colorless oil (0.49 g, 44%).
$^1$H NMR (300 MHz, DMSO-d$_6$) δ ppm 1.93-2.18 (m, 2H) 2.45-2.81 (m, 4H) 3.63 (s, 2H) 4.28-4.46 (m, 2H) 6.74 (d, J=7.95 Hz, 1H) 6.83-6.92 (m, 1H) 7.05-7.15 (m, 1H) 7.18-7.38 (m, 6H)

(5) spiro[1-benzofuran-3,3'-pyrrolidine]

A solution of 1'-benzylspiro[1-benzofuran-3,3'-pyrrolidine] (490 mg) obtained by the above-mentioned reaction, ammonium formate (600 mg) and 5% palladium carbon (100 mg) in ethanol (50 mL) was stirred under reflux overnight. The catalyst was removed using celite, and the filtrate was concentrated. The residue was purified by basic silica gel column chromatography (5% to 10% methanol/ethyl acetate) to give the object product as a yellow oil (170 mg, 53%).
$^1$H NMR (300 MHz, DMSO-d$_6$) δ ppm 1.83-2.08 (m, 2H) 2.68-3.04 (m, 5H) 4.21-4.44 (m, 2H) 6.75 (d, J=7.91 Hz, 1H) 6.80-6.90 (m, 1H) 7.04-7.15 (m, 1H) 7.23 (dd, J=7.44, 1.22 Hz, 1H)

(6) 1'-[6-(3-methyl-1,2,4-thiadiazol-5-yl)pyridazin-3-yl]spiro[1-benzofuran-3,3'-pyrrolidine]

Spiro[1-benzofuran-3,3'-pyrrolidine] (45 mg) obtained by the above-mentioned reaction, 3-chloro-6-(3-methyl-1,2,4-thiadiazol-5-yl)pyridazine (55 mg) and potassium carbonate (70 mg) were dissolved in N,N-dimethylformamide (3 ml), and the solution was stirred at 95° C. for 3 days. The reaction solution was poured into water, and the mixture was extracted with ethyl acetate. The organic layer was washed with saturated brine, and dried over sodium sulfate. The desiccant was filtered off, and the filtrate was concentrated. The residue was purified by recrystallization using ethyl acetate to give the object product (29.8 mg, 33%).
$^1$H NMR (300 MHz, DMSO-d$_6$) δ ppm 2.24-2.39 (m, 2H) 2.65 (s, 3H) 3.57-4.04 (m, 4H) 4.51 (d, J=1.13 Hz, 2H) 6.85 (d, J=8.10 Hz, 1H) 6.88-6.96 (m, 1H) 7.11 (d, J=9.61 Hz, 1H) 7.15-7.23 (m, 1H) 7.29-7.37 (m, 1H) 8.00 (d, J=9.42 Hz, 1H)

Example 51

1'-[6-(3-methyl-1,2,4-oxadiazol-5-yl)pyridazin-3-yl]spiro[1-benzofuran-3,3'-pyrrolidine]

A solution (5 ml) of spiro[1-benzofuran-3,3'-pyrrolidine] (50 mg) obtained in Example 50-(5) and 3-chloro-6-(3-methyl-1,2,4-oxadiazol-5-yl)pyridazine (56 mg) obtained in Example 43-(2) and potassium carbonate (79 mg) in N,N-dimethylformamide was stirred at 95° C. for 3 days. To the reaction solution was added water, and the mixture was extracted with ethyl acetate. The organic layer was washed with saturated brine, and dried over sodium sulfate. The desiccant was filtered off, and the filtrate was concentrated. The residue was recrystallized from ethyl acetate to give the object product (45.1 mg, 47%).
$^1$H NMR (300 MHz, DMSO-d$_6$) δ ppm 2.19-2.40 (m, 2H) 2.43 (s, 3H) 3.55-4.11 (m, 4H) 4.51 (s, 2H) 6.85 (d, J=7.95 Hz, 1H) 6.91 (t, J=7.57 Hz, 1H) 7.10 (d, J=9.47 Hz, 1H) 7.15-7.24 (m, 1H) 7.33 (d, J=7.19 Hz, 1H) 8.03 (d, J=9.47 Hz, 1H)

Example 52

1'-[6-(3-methyl-1,2,4-oxadiazol-5-yl)pyridazin-3-yl]spiro[1-benzofuran-3,4'-piperidine]

The object product (185 mg, 53%) was obtained in the same manner as in Example 1 and using 3-chloro-6-(3-methyl-1,2,4-oxadiazol-5-yl)pyridazine (200 mg) obtained in Example 43(2), spiro[1-benzofuran-3,4'-piperidine] (210 mg) and potassium carbonate (150 mg).
$^1$H NMR (300 MHz, DMSO-d$_6$) δ ppm 1.75-2.01 (m, 4H) 2.44 (s, 3 H) 3.19-3.32 (m, 2H) 4.47-4.64 (m, 4H) 6.71-6.90 (m, 2H) 7.03-7.19 (m, 1H) 7.25 (dd, J=7.35, 0.94 Hz, 1H) 7.48 (d, J=9.80 Hz, 1H) 8.00 (d, J=9.80 Hz, 1H)

Example 53

1'-[6-(3-methyl-1,2,4-oxadiazol-5-yl)pyridazin-3-yl]-3H-spiro[1-benzofuran-2,4'-piperidine]

The object product (201 mg, 87%) was obtained in the same manner as in Example 1 and using 3-chloro-6-(3-methyl-1,2,4-oxadiazol-5-yl)pyridazine (130 mg) obtained in Example 43(2), 3H-spiro[1-benzofuran-2,4'-piperidine] (150 mg) and potassium carbonate (110 mg).

¹H NMR (300 MHz, DMSO-d₆) δ ppm 1.74-2.00 (m, 4H) 2.44 (s, 3H) 3.08 (s, 2H) 3.73-3.87 (m, 2H) 4.05-4.17 (m, 2H) 6.73-6.88 (m, 2H) 7.06-7.15 (m, 1H) 7.22 (d, J=7.35 Hz, 1H) 7.49 (d, J=9.80 Hz, 1H) 8.01 (d, J=9.61 Hz, 1H)

Example 54

N-[(4-methyl-2-phenyl-1,3-thiazol-5-yl)methyl]-6-(1'H-spiro[indene-1,4'-piperidin]-1'-yl)pyridazine-3-carboxamide The object product (90 mg, 61%) was obtained in the same manner as in Example 36(3) and using 6-(1'H-spiro[indene-1,4'-piperidin]-1'-yl)pyridazine-3-carboxylic acid (92 mg) obtained in Example 36(2), 1-(4-methyl-2-phenyl-1,3-thiazol-5-yl)methanamine (82 mg), 1-ethyl-3-(3-dimethylaminopropyl)carbodiimide hydrochloride (95 mg) and hydroxybenzotriazole hydrate (75 mg).

¹H NMR (300 MHz, DMSO-d₆) δ ppm 1.33 (d, J=13.19 Hz, 2H) 2.04-2.19 (m, 2H) 2.47 (s, 3H) 3.45 (t, J=11.77 Hz, 2H) 4.51-4.71 (m, 4H) 6.87 (d, J=5.65 Hz, 1H) 7.09-7.28 (m, 3H) 7.31-7.52 (m, 6H) 7.81-7.93 (m, 3H) 9.61 (t, J=6.12 Hz, 1H)

Example 55

N-(2-oxo-2-phenylethyl)-6-(1'H-spiro[indene-1,4'-piperidin]-1'-yl)pyridazine-3-carboxamide The object product (130 mg, 63%) was obtained in the same manner as in Example 36(3) and using 6-(1'H-spiro [indene-1,4'-piperidin]-1'-yl)pyridazine-3-carboxylic acid (154 mg) obtained in Example 36(2), 2-amino-1-phenylethanone (104 mg), 1-ethyl-3-(3-dimethylaminopropyl)carbodiimide hydrochloride (153 mg) and hydroxybenzotriazole hydrate (120 mg).

¹H NMR (300 MHz, DMSO-d₆) δ ppm 1.35 (d, J=13.37 Hz, 2H) 2.06-2.22 (m, 2H) 3.39-3.57 (m, 2H) 4.63 (d, J=13.56 Hz, 2H) 4.86 (d, J=5.65 Hz, 2H) 6.88 (d, J=5.65 Hz, 1H) 7.13-7.28 (m, 3H) 7.36 (d, J=6.97 Hz, 1H) 7.40-7.50 (m, 2H) 7.52-7.63 (m, 2H) 7.65-7.74 (m, 1H) 7.89 (d, J=9.61 Hz, 1H) 8.01-8.10 (m, 2H) 9.07 (t, J=5.65 Hz, 1H)

Examples 56-135

To a solution (0.50 mL) of 6-(1'H-spiro[indene-1,4'-piperidin]-1'-yl)pyridazine-3-carboxylic acid (18.4 mg) obtained in Example 36(2) in dimethylformamide was added a solution (0.50 mL) of an amine reagent (0.072 mmol) and triethylamine (7.3 mg) in dimethylformamide, and then a solution (0.50 mL) of 2-(1H-benzotriazol-1-yl)-1,1,3,3-tetramethyluroniume trafluoroborate (23.0 mg) in dimethylformamide, and the mixture was stirred at room temperature overnight. The mixture was extracted with ethyl acetate (3.0 mL) and water (1.0 mL) and the ethyl acetate layer was separated and concentrated. The residue was dissolved in dimethyl sulfoxide/methanol=1/1 solution (1.0 mL) and purified by reversed-phase preparative HPLC. The object fraction was concentrated by drying under a stream of nitrogen apparatus to give the object product at a purity of 80% or above (LCMS analysis).

Example 56

N-(3-hydroxypropyl)-6-(1'H-spiro[indene-1,4'-piperidin]-1'-yl)pyridazine-3-carboxamide ESI(pos) 365 [M+H]⁺

Example 57

N-(2-isopropoxyethyl)-6-(1'H-spiro[indene-1,4'-piperidin]-1'-yl)pyridazine-3-carboxamide ESI(pos) 393 [M+H]⁺

Example 58

N-benzyl-6-(1'H-spiro[indene-1,4'-piperidin]-1'-yl)pyridazine-3-carboxamide

ESI(pos) 397 [M+H]⁺

Example 59

N-(2-phenylethyl)-6-(1'H-spiro[indene-1,4'-piperidin]-1'-yl)pyridazine-3-carboxamide ESI(pos) 411 [M+H]⁺

Example 60

N-(2-hydroxy-2-phenylethyl)-6-(1'H-spiro[indene-1,4'-piperidin]-1'-yl)pyridazine-3-carboxamide Example 61

N-(2-phenoxyethyl)-6-(1'H-spiro[indene-1,4'-piperidin]-1'-yl)pyridazine-3-carboxamide ESI(pos) 427 [M+H]⁺

Example 62

N-[3-(2-oxopyrrolidin-1-yl)propyl]-6-(1'H-spiro[indene-1,4'-piperidin]-1'-yl)pyridazine-3-carboxamide ESI(pos) 432 [M+H]⁺

Example 63

N-[2-(1H-indol-3-yl)ethyl]-6-(1'H-spiro[indene-1,4'-piperidin]-1'-yl)pyridazine-3-carboxamide ESI(pos) 450 [M+H]⁺

Example 64

N-[4-(methylsulfonyl)benzyl]-6-(1'H-spiro[indene-1,4'-piperidin]-1'-yl)pyridazine-3-carboxamide ESI(pos) 475 [M+H]⁺

Example 65

N-[4-(aminosulfonyl)benzyl]-6-(1'H-spiro[indene-1,4'-piperidin]-1'-yl)pyridazine-3-carboxamide ESI(pos) 476 [M+H]⁺

Example 66

N-(2-hydroxyethyl)-6-(1'H-spiro[indene-1,4'-piperidin]-1'-yl)pyridazine-3-carboxamide ESI(pos) 351 [M+H]+

Example 67

N-(3-ethoxypropyl)-6-(1'H-spiro[indene-1,4'-piperidin]-1'-yl)pyridazine-3-carboxamide ESI(pos) 393 [M+H]+

Example 68

N-(4-phenylbutyl)-6-(1'H-spiro[indene-1,4'-piperidin]-1'-yl)pyridazine-3-carboxamide ESI(pos) 439 [M+H]+

Example 69

N-(3,3-diphenylpropyl)-6-(1'H-spiro[indene-1,4'-piperidin]-1'-yl)pyridazine-3-carboxamide ESI(pos) 501 [M+H]+

Example 70

1'-{6-[(4-benzylpiperidin-1-yl)carbonyl]pyridazin-3-yl}spiro[indene-1,4'-piperidine]

ESI(pos) 465 [M+H]+

Example 71

N-(pyridin-3-ylmethyl)-6-(1'H-spiro[indene-1,4'-piperidin]-1'-yl)pyridazine-3-carboxamide ESI(pos) 398 [M+H]+

Example 72

N-(pyridin-2-ylmethyl)-6-(1'H-spiro[indene-1,4'-piperidin]-1'-yl)pyridazine-3-carboxamide ESI(pos) 398 [M+H]+

Example 73

N-(2-(pyridin-2-yl)ethyl)-6-(1'H-spiro[indene-1,4'-piperidin]-1'-yl)pyridazine-3-carboxamide ESI(pos) 412 [M+H]+

Example 74

N-(2-(pyridin-3-yl)ethyl)-6-(1'H-spiro[indene-1,4'-piperidin]-1'-yl)pyridazine-3-carboxamide ESI(pos) 412 [M+H]+

Example 75

N-[3-(1H-imidazol-1-yl)propyl]-6-(1'H-spiro[indene-1,4'-piperidin]-1'-yl)pyridazine-3-carboxamide ESI(pos) 415 [M+H]+

Example 76

N-(2-morpholinoethyl)-6-(1'H-spiro[indene-1,4'-piperidin]-1'-yl)pyridazine-3-carboxamide ESI(pos) 420 [M+H]+

Example 77

N-(3-morpholinopropyl)-6-(1'H-spiro[indene-1,4'-piperidin]-1'-yl)pyridazine-3-carboxamide ESI(pos) 434 [M+H]+

Example 78

N-(1-benzylpyrrolidin-3-yl)-6-(1'H-spiro[indene-1,4'-piperidin]-1'-yl)pyridazine-3-carboxamide ESI(pos) 466 [M+H]+

Example 79

N-[2-(1H-imidazol-4-yl)ethyl]-6-(1'H-spiro[indene-1,4'-piperidin]-1'-yl)pyridazine-3-carboxamide ESI(pos) 401 [M+H]+

Example 80

1'-{6-[(4-(pyridin-2-yl)piperazin-1-yl)carbonyl]pyridazin-3-yl}spiro[indene-1,4'-piperidine]

ESI(pos) 453 [M+H]+

Example 81

N-phenyl-6-(1'H-spiro[indene-1,4'-piperidin]-1'-yl)pyridazine-3-carboxamide

ESI(pos) 383 [M+H]+

Example 82

N-(pyridin-2-yl)-6-(1'H-spiro[indene-1,4'-piperidin]-1'-yl)pyridazine-3-carboxamide ESI(pos) 384 [M+H]+

Example 83

N-(pyridin-3-yl)-6-(1'H-spiro[indene-1,4'-piperidin]-1'-yl)pyridazine-3-carboxamide ESI(pos) 384 [M+H]+

Example 84

N-(pyridin-4-yl)-6-(1'H-spiro[indene-1,4'-piperidin]-1'-yl)pyridazine-3-carboxamide ESI(pos) 384 [M+H]$^+$

Example 85

6-(1'H-spiro[indene-1,4'-piperidin]-1'-yl)-N-(1,3-thiazol-2-yl)pyridazine-3-carboxamide ESI(pos) 390 [M+H]$^+$

Example 86

N-(2-hydroxy-3-phenylpropyl)-6-(1'H-spiro[indene-1,4'-piperidin]-1'-yl)pyridazine-3-carboxamide ESI(pos) 441 [M+H]$^+$

Example 87

N-(3-cyclohexylpropyl)-6-(1'H-spiro[indene-1,4'-piperidin]-1'-yl)pyridazine-3-carboxamide ESI(pos) 431 [M+H]$^+$

Example 88

N-(4-benzyl-4H-1,2,4-triazol-3-yl)-6-(1'H-spiro[indene-1,4'-piperidin]-1'-yl)pyridazine-3-carboxamide ESI(pos) 464 [M+H]$^+$

Example 89

1'-{6-[(4-phenoxypiperidin-1-yl)carbonyl]pyridazin-3-yl}spiro[indene-1,4'-piperidine]

ESI(pos) 467 [M+H]$^+$

Example 90

1'-{6-[(4-benzoylpiperazin-1-yl)carbonyl]pyridazin-3-yl}spiro[indene-1,4'-piperidine]

ESI(pos) 480 [M+H]$^+$

Example 91

1'-{6-[(2-phenylmorpholin-4-yl)carbonyl]pyridazin-3-yl}spiro[indene-1,4'-piperidine]

ESI(pos) 453 [M+H]$^+$

Example 92

N-[2-(pyridin-2-ylsulfonyl)ethyl]-6-(1'H-spiro[indene-1,4'-piperidin]-1'-yl)pyridazine-3-carboxamide ESI(pos) 476 [M+H]$^+$

Example 93

N-[2-(phenylsulfonyl)ethyl]-6-(1'H-spiro[indene-1,4'-piperidin]-1'-yl)pyridazine-3-carboxamide ESI(pos) 475 [M+H]$^+$

Example 94

6-(1'H-spiro[indene-1,4'-piperidin]-1'-yl)-N-[1-(trifluoroacetyl)piperidin-4-yl]pyridazine-3-carboxamide ESI(pos) 486 [M+H]$^+$

Example 95

N-(2-morpholino-2-phenylethyl)-6-(1'H-spiro[indene-1,4'-piperidin]-1'-yl)pyridazine-3-carboxamide ESI(pos) 496 [M+H]$^+$

Example 96

N-methyl-N-(3-phenylpropyl)-6-(1'H-spiro[indene-1,4'-piperidin]-1'-yl)pyridazine-3-carboxamide ESI(pos) 439 [M+H]$^+$

Example 97

6-(1'H-spiro[indene-1,4'-piperidin]-1'-yl)-N-[2-(1H-1,2,4-triazol-1-yl)ethyl]pyridazine-3-carboxamide ESI(pos) 402 [M+H]$^+$

Example 98

6-(1'H-spiro[indene-1,4'-piperidin]-1'-yl)-N-{[5-(2-thienyl)isoxazol-3-yl]methyl}pyridazine-3-carboxamide ESI(pos) 470 [M+H]$^+$

Example 99

N-[(4-benzylmorpholin-2-yl)methyl]-6-(1'H-spiro[indene-1,4'-piperidin]-1'-yl)pyridazine-3-carboxamide ESI(pos) 496 [M+H]$^+$

Example 100

N-[2-(methylsulfonyl)ethyl]-6-(1'H-spiro[indene-1,4'-piperidin]-1'-yl)pyridazine-3-carboxamide ESI(pos) 413 [M+H]$^+$

Example 101

6-(1'H-spiro[indene-1,4'-piperidin]-1'-yl)-N-(tetrahydro-2H-pyran-4-ylmethyl)pyridazine-3-carboxamide ESI(pos) 405 [M+H]$^+$

Example 102

6-(1'H-spiro[indene-1,4'-piperidin]-1'-yl)-N-(3,3,3-trifluoropropyl)pyridazine-3-carboxamide ESI(pos) 403 [M+H]$^+$

Example 103

6-(1'H-spiro[indene-1,4'-piperidin]-1'-yl)-N-(2-{[(trifluoromethyl)sulfonyl]amino}ethyl)pyridazine-3-carboxamide ESI(pos) 482 [M+H]$^+$

Example 104

N-[(6-morpholinopyridin-2-yl)methyl]-6-(1'H-spiro[indene-1,4'-piperidin]-1'-yl)pyridazine-3-carboxamide ESI(pos) 483 [M+H]$^+$

Example 105

N-[2-(2,4-dioxo-1,3-thiazolidin-3-yl)methyl]-6-(1'H-spiro[indene-1,4'-piperidin]-1'-yl)pyridazine-3-carboxamide ESI(pos) 450 [M+H]$^+$

Example 106

N-[(5-methyl-2-phenyl-2H-1,2,3-triazol-4-yl)methyl]-6-(1'H-spiro[indene-1,4'-piperidin]-1'-yl)pyridazine-3-carboxamide ESI(pos) 478 [M+H]$^+$

Example 107

1'-{6-[(3-phenylpyrrolidin-1-yl)carbonyl]pyridazin-3-yl}spiro[indene-1,4'-piperidine]

ESI(pos) 437 [M+H]$^+$

Example 108

1'-(6-{[2-(2-phenylethyl)pyrrolidin-1-yl]carbonyl}pyridazin-3-yl)spiro[indene-1,4'-piperidine]

ESI(pos) 465 [M+H]$^+$

Example 109

1'-(6-{[3-(phenylsulfonyl)pyrrolidin-1-yl]carbonyl}pyridazin-3-yl)spiro[indene-1,4'-piperidine]

ESI(pos) 501 [M+H]$^+$

Example 110

1'-{6-[(3-(pyrazin-2-yl)pyrrolidin-1-yl)carbonyl]pyridazin-3-yl}spiro[indene-1,4'-piperidine]

ESI(pos) 439 [M+H]$^+$

Example 111

1'-(6-{[3-(trifluoromethyl)pyrrolidin-1-yl]carbonyl}pyridazin-3-yl)spiro[indene-1,4'-piperidine]

ESI(pos) 429 [M+H]$^+$

Example 112

1'-(6-{[4-(pyridin-2-yloxy)piperidin-1-yl]carbonyl}pyridazin-3-yl)spiro[indene-1,4'-piperidine]

ESI(pos) 468 [M+H]$^+$

Example 113

1'-[6-({4-[2-(methylsulfonyl)ethyl]piperazin-1-yl}carbonyl)pyridazin-3-yl]spiro[indene-1,4'-piperidine]

ESI(pos) 482 [M+H]$^+$

Example 114

1'-(6-{[4-(pyridin-2-ylmethyl)piperazin-1-yl]carbonyl}pyridazin-3-yl)spiro[indene-1,4'-piperidine]

ESI(pos) 467 [M+H]$^+$

Example 115

1'-(6-{[4-(2-phenylethyl)piperazin-1-yl]carbonyl}pyridazin-3-yl)spiro[indene-1,4'-piperidine]

ESI(pos) 480 [M+H]$^+$

Example 116

1-(1-{[6-(1'H-spiro[indene-1,4'-piperidin]-1'-yl)pyridazin-3-yl]carbonyl}piperidin-4-yl)tetrahydropyrimidin-2(1H)-one ESI(pos) 473 [M+H]$^+$

Example 117

N-[4-(morpholinomethyl)phenyl]-6-(1'H-spiro[indene-1,4'-piperidin]-1'-yl)pyridazine-3-carboxamide ESI(pos) 482 [M+H]$^+$

Example 118

N-[(5-methyl-3-phenylisoxazol-4-yl)methyl]-6-(1'H-spiro[indene-1,4'-piperidin]-1'-yl)pyridazine-3-carboxamide ESI(pos) 478 [M+H]$^+$

Example 119

1'-(6-{[4-(phenylsulfonyl)piperazin-1-yl]carbonyl}pyridazin-3-yl)spiro[indene-1,4'-piperidine]

ESI(pos) 516 [M+H]$^+$

Example 120

N-[3-(methoxymethyl)benzyl]-6-(1'H-spiro[indene-1,4'-piperidin]-1'-yl)pyridazine-3-carboxamide ESI(pos) 441 [M+H]$^+$

Example 121

6-(1'H-spiro[indene-1,4'-piperidin]-1'-yl)-N-(tetrahydrofuran-2-ylmethyl)pyridazine-3-carboxamide ESI(pos) 391 [M+H]$^+$

Example 122

N-(6-methoxypyridazin-3-yl)-6-(1'H-spiro[indene-1,4'-piperidin]-1'-yl)pyridazine-3-carboxamide ESI(pos) 415 [M+H]$^+$

Example 123

N-(cyclopropylmethyl)-6-(1'H-spiro[indene-1,4'-piperidin]-1'-yl)pyridazine-3-carboxamide ESI(pos) 361 [M+H]$^+$

Example 124

N-(2-cyanoethyl)-6-(1'H-spiro[indene-1,4'-piperidin]-1'-yl)pyridazine-3-carboxamide ESI(pos) 360 [M+H]$^+$

Example 125

N-(1-methyl-3-phenylpropyl)-6-(1'H-spiro[indene-1,4'-piperidin]-1'-yl)pyridazine-3-carboxamide ESI(pos) 439 [M+H]$^+$

Example 126

N-[(1S,2R)-2-phenylcyclopropyl]-6-(1'H-spiro[indene-1,4'-piperidin]-1'-yl)pyridazine-3-carboxamide ESI(pos) 423 [M+H]$^+$

Example 127

1'-{6-[(4-phenylpiperidin-1-yl)carbonyl]pyridazin-3-yl}spiro[indene-1,4'-piperidine]

ESI(pos) 451 [M+H]$^+$

Example 128

N-(4,6-dimethylpyridin-2-yl)-6-(1'H-spiro[indene-1,4'-piperidin]-1'-yl)pyridazine-3-carboxamide ESI(pos) 412 [M+H]$^+$

Example 129

N-[1-(2-fluorobenzyl)-1H-pyrazol-3-yl]-6-(1'H-spiro[indene-1,4'-piperidin]-1'-yl)pyridazine-3-carboxamide ESI(pos) 481 [M+H]$^+$

Example 130

6-(1'H-spiro[indene-1,4'-piperidin]-1'-yl)-N-(1H-tetrazol-5-yl)pyridazine-3-carboxamide ESI(pos) 375 [M+H]$^+$

Example 131

N-(3-methylisothiazol-5-yl)-6-(1'H-spiro[indene-1,4'-piperidin]-1'-yl)pyridazine-3-carboxamide ESI(pos) 404 [M+H]$^+$

Example 132

N-(3-methyl-1,2,4-thiadiazol-5-yl)-6-(1'H-spiro[indene-1,4'-piperidin]-1'-yl)pyridazine-3-carboxamide ESI(pos) 405 [M+H]$^+$

Example 133

N-(5-methyl-1H-pyrazol-3-yl)-6-(1'H-spiro[indene-1,4'-piperidin]-1'-yl)pyridazine-3-carboxamide ESI(pos) 387 [M+H]$^+$

Example 134

N-(5-methyl-1,3,4-thiadiazol-2-yl)-6-(1'H-spiro[indene-1,4'-piperidin]-1'-yl)pyridazine-3-carboxamide ESI(pos) 405 [M+H]$^+$

Example 135

N-(5-methyl-1,3,4-oxadiazol-2-yl)-6-(1'H-spiro[indene-1,4'-piperidin]-1'-yl)pyridazine-3-carboxamide ESI(pos) 389 [M+H]$^+$

Example 136

N-(2-hydroxy-3-phenylpropyl)-6-(1'H-spiro[indene-1,4'-piperidin]-1'-yl)pyridazine-3-carboxamide The object product (160 mg, 73%) was obtained in the same manner as in Example 36(3) and using 6-(1'H-spiro

[indene-1,4'-piperidin]-1'-yl)pyridazine-3-carboxylic acid (150 mg) obtained in Example 36(2), 1-amino-3-phenylpropan-2-ol (91 mg), 1-ethyl-3-(3-dimethylaminopropyl)carbodiimide hydrochloride (150 mg) and hydroxybenzotriazole hydrate (120 mg).

$^1$H NMR (300 MHz, DMSO-d$_6$) δ ppm 1.33 (d, J=13.37 Hz, 2H) 2.01-2.20 (m, 2H) 2.59-2.81 (m, 2H) 3.17-3.29 (m, 1H) 3.37-3.54 (m, 3H) 3.79-3.96 (m, 1H) 4.60 (d, J=13.56 Hz, 2H) 5.05 (d, J=5.65 Hz, 1H) 6.87 (d, J=5.65 Hz, 1H) 7.11-7.48 (m, 11H) 7.87 (d, J=9.42 Hz, 1H) 8.67 (t, J=5.75 Hz, 1H)

Example 137

N-(2-hydroxy-2-phenylethyl)-6-(1'H-spiro[indene-1,4'-piperidin]-1'-yl)pyridazine-3-carboxamide The object product (140 mg, 63%) was obtained in the same manner as in Example 36(3) and using 6-(1'H-spiro [indene-1,4'-piperidin]-1'-yl)pyridazine-3-carboxylic acid (150 mg) obtained in Example 36(2), 2-amino-1-phenylethanol (82 mg), 1-ethyl-3-(3-dimethylaminopropyl)carbodiimide hydrochloride (150 mg) and hydroxybenzotriazole hydrate (120 mg).

$^1$H NMR (300 MHz, DMSO-d$_6$) δ ppm 1.33 (d, J=13.19 Hz, 2H) 2.04-2.20 (m, 2H) 3.36-3.52 (m, 3H) 3.52-3.67 (m, 1H) 4.59 (d, J=13.37 Hz, 2H) 4.76-4.89 (m, 1H) 5.63 (d, J=4.33 Hz, 1H) 6.87 (d, J=5.65 Hz, 1H) 7.12-7.29 (m, 4H) 7.29-7.48 (m, 7H) 7.85 (d, J=9.42 Hz, 1H) 8.63 (t, J=5.75 Hz, 1H)

Example 138

N-(2-oxo-2-phenylethyl)-6-(1'H-spiro[indene-1,4'-piperidin]-1'-yl)pyridazine-3-carboxamide The object product (130 mg, 63%) was obtained in the same manner as in Example 36(3) and using 6-(1'H-spiro [indene-1,4'-piperidin]-1'-yl)pyridazine-3-carboxylic acid (150 mg) obtained in Example 36(2), 2-amino-1-phenylethanone (100 mg), 1-ethyl-3-(3-dimethylaminopropyl)carbodiimide hydrochloride (150 mg) and hydroxybenzotriazole hydrate (120 mg).

$^1$H NMR (300 MHz, DMSO-d$_6$) δ ppm 1.35 (d, J=13.37 Hz, 2H) 2.06-2.22 (m, 2H) 3.39-3.57 (m, 2H) 4.63 (d, J=13.56 Hz, 2H) 4.86 (d, J=5.65 Hz, 2H) 6.88 (d, J=5.65 Hz, 1H) 7.13-7.28 (m, 3H) 7.36 (d, J=6.97 Hz, 1H) 7.40-7.50 (m, 2H) 7.52-7.63 (m, 2H) 7.65-7.74 (m, 1H) 7.89 (d, J=9.61 Hz, 2H) 8.01-8.10 (m, 2H) 9.07 (t, J=5.65 Hz, 1H)

Example 139

1'-[6-(5-methyl-1,3,4-oxadiazol-2-yl)pyridazin-3-yl] spiro[indene-1,4'-piperidine]

(1) N'-acetyl-6-(1'H-spiro[indene-1,4'-piperidin]-1'-yl)pyridazine-3-carbohydrazide The object product (290 mg, 80%) was obtained in the same manner as in Example 36(3) and using 6-(1'H-spiro [indene-1,4'-piperidin]-1'-yl)pyridazine-3-carboxylic acid (310 mg) obtained in Example 36(2), acetohydrazide (89 mg), 1-ethyl-3-(3-dimethylaminopropyl)carbodiimide hydrochloride (290 mg) and hydroxybenzotriazole hydrate (230 mg).

$^1$H NMR (300 MHz, DMSO-d$_6$) δ ppm 1.33 (d, J=13.19 Hz, 2H) 1.91 (s, 3H) 2.05-2.20 (m, 2H) 3.41-3.53 (m, 2H) 4.62 (d, J=13.56 Hz, 2H) 6.87 (d, J=5.65 Hz, 1H) 7.10-7.28 (m, 3H) 7.36 (d, J=6.97 Hz, 1H) 7.40-7.51 (m, 2H) 7.85 (d, J=9.61 Hz, 1H) 9.89 (brs, 1H) 10.44 (brs, 1H)

(2) 1'-[6-(5-methyl-1,3,4-oxadiazol-2-yl)pyridazin-3-yl]spiro[indene-1,4'-piperidine]

The object product (60 mg, 32%) was obtained in the same manner as in Example 45(2) and using N'-acetyl-6-(1'H-spiro[indene-1,4'-piperidin]-1'-yl)pyridazine-3-carbohydrazide (200 mg) obtained by the above-mentioned reaction and phosphorus oxychloride (5 mL).

$^1$H NMR (300 MHz, DMSO-d$_6$) δ ppm 1.35 (d, J=13.37 Hz, 2H) 2.05-2.20 (m, 2H) 2.62 (s, 3H) 3.40-3.57 (m, 2H) 4.63 (d, J=13.75 Hz, 2H) 6.88 (d, J=5.65 Hz, 1H) 7.11-7.28 (m, 3H) 7.36 (d, J=6.97 Hz, 1H) 7.44 (d, J=7.35 Hz, 1H) 7.51 (d, J=9.80 Hz, 1H) 8.00 (d, J=9.61 Hz, 1H)

Example 140

1'-[6-(3-methyl-1,2,4-oxadiazol-5-yl)pyridazin-3-yl]-2,3-dihydrospiro[indene-1,4'-piperidine]

The object product (175 mg, 76%) was obtained in the same manner as in Example 1 and using 3-chloro-6-(3-methyl-1,2,4-oxadiazol-5-yl)pyridazine (130 mg) obtained in Example 43(2), 2,3-dihydrospiro[indene-1,4'-piperidine] hydrochloride (180 mg) and potassium carbonate (110 mg).

$^1$H NMR (300 MHz, DMSO-d$_6$) δ ppm 1.62 (d, J=13.19 Hz, 2H) 1.78-1.91 (m, 2H) 2.16 (t, J=7.25 Hz, 2H) 2.44 (s, 3H) 2.93 (t, J=7.25 Hz, 2H) 3.20-3.32 (m, 2H) 4.59 (d, J=13.38 Hz, 2H) 7.09-7.27 (m, 4H) 7.46 (d, J=9.80 Hz, 1H) 7.99 (d, J=9.80 Hz, 1H)

Example 141

1'-[6-(3-methyl-1,2,4-oxadiazol-5-yl)pyridazin-3-yl]-3H-spiro[1-benzofuran-2,4'-piperidine]

The object product (200 mg, 87%) was obtained in the same manner as in Example 1 and using 3-chloro-6-(3-methyl-1,2,4-oxadiazol-5-yl)pyridazine (130 mg) obtained in Example 43(2), 3H-spiro[1-benzofuran-2,4'-piperidine] (150 mg) and potassium carbonate (110 mg).

$^1$H NMR (300 MHz, DMSO-d$_6$) δ ppm 1.74-2.00 (m, 4H) 2.44 (s, 3H) 3.08 (s, 2H) 3.73-3.87 (m, 2H) 4.05-4.17 (m, 2H) 6.73-6.88 (m, 2H) 7.06-7.15 (m, 1H) 7.22 (d, J=7.35 Hz, 1H) 7.49 (d, J=9.80 Hz, 1H) 8.01 (d, J=9.61 Hz, 1H)

Example 142

1'-[6-(3-methyl-1,2,4-oxadiazol-5-yl)pyridazin-3-yl]spiro[1-benzofuran-3,4'-piperidine]

The object product (185 mg, 53%) was obtained in the same manner as in Example 1 and using 3-chloro-6-(3-methyl-1,2,4-oxadiazol-5-yl)pyridazine (200 mg) obtained in Example 43(2), spiro[1-benzofuran-3,4'-piperidine] (210 mg) and potassium carbonate (150 mg).

$^1$H NMR (300 MHz, DMSO-d$_6$) δ ppm 1.75-2.01 (m, 4H) 2.44 (s, 3H) 3.19-3.32 (m, 2H) 4.47-4.64 (m, 4H) 6.71-6.90

(m, 2H) 7.03-7.19 (m, 1H) 7.25 (dd, J=0.94, 7.35 Hz, 1H) 7.48 (d, J=9.80 Hz, 1H) 8.00 (d, J=9.80 Hz, 1H)

Example 143

{5-[6-(1'H-spiro[1-benzofuran-3,4'-piperidin]-1'-yl)pyridazin-3-yl]-1,2,4-oxadiazol-3-yl}methanol (1) methyl 6-(1'H-spiro[1-benzofuran-3,4'-piperidin]-1'-yl)pyridazine-3-carboxylate Methyl 6-chloropyridazine-3-carboxylate (4.5 g), spiro[1-benzofuran-3,4'-piperidine] (5.0 g), potassium carbonate (3.6 g) and tetrabutylammonium iodide (1 g) were suspended in tetrahydrofuran (260 mL), and the suspension was refluxed overnight. The mixture was cooled to room temperature, the reaction mixture was diluted with ethyl acetate and partitioned with aqueous sodium hydrogen carbonate solution. The resulting precipitate was collected by filtration to give the object product (3.8 g). The filtrate was washed 3 times with aqueous sodium hydrogen carbonate solution, the organic layer was dried over sodium sulfate and the solvent was evaporated under reduced pressure. Ethyl acetate-hexane was added to the residue and the resulting precipitate was collected by filtration to give the object product (2.6 g) (total 6.4 g, 76%).

$^1$H NMR (300 MHz, DMSO-$d_6$) δ ppm 1.68-2.00 (m, 4H) 3.10-3.30 (m, 2H) 3.88 (s, 3H) 4.35-4.67 (m, 4H) 6.69-6.89 (m, 2H) 7.04-7.19 (m, 1H) 7.19-7.31 (m, 1H) 7.37 (d, J=9.80 Hz, 1H) 7.85 (d, J=9.61 Hz, 1H)

(2) 6-(1'H-spiro[1-benzofuran-3,4'-piperidin]-1'-yl)pyridazine-3-carboxylic acid To a solution of methyl 6-(1'H-spiro[1-benzofuran-3,4'-piperidin]-1'-yl)pyridazine-3-carboxylate (6.4 g) obtained by the above-mentioned reaction in tetrahydrofuran-methanol (1:1, 160 mL) was added aqueous sodium hydroxide solution (1N, 80 mL), and the mixture was stirred at room temperature overnight. Hydrochloric acid (1N, 80 mL) and water (150 mL) were added and the resulting precipitate was collected by filtration to give the object product (5.6 g, 91%).

$^1$H NMR (300 MHz, DMSO-$d_6$) δ ppm 1.72-1.97 (m, 4H) 3.17-3.28 (m, 2H) 4.45-4.59 (m, 4H) 6.75-6.88 (m, 2H) 7.08-7.16 (m, 1H) 7.21-7.27 (m, 1H) 7.37 (d, J=9.61 Hz, 1H) 7.84 (d, J=9.61 Hz, 1H)

(3) ethyl 5-[6-(1'H-spiro[1-benzofuran-3,4'-piperidin]-1'-yl)pyridazin-3-yl]-1,2,4-oxadiazole-3-carboxylate 6-(1'H-Spiro[1-benzofuran-3,4'-piperidin]-1'-yl)pyridazine-3-carboxylic acid (930 mg) obtained by the above-mentioned reaction and 1,1'-carbonylbis(1H-imidazole) (570 mg) were dissolved in N,N-dimethylformamide (20 mL), and the solution was stirred at 60° C. for 1 hr. After cooling to room temperature, pyridine (40 mL) and ethyl amino(hydroxyimino)acetate (460 mg) were added and the mixture was stirred at 120° C. for 2 hr. After cooling to room temperature, the reaction system was diluted with ethyl acetate, and washed with saturated aqueous sodium hydrogen carbonate solution. After drying over sodium sulfate, hexane/ethyl acetate was added and the resulting precipitate was collected by filtration to give the object product (670 mg, 55%).

$^1$H NMR (300 MHz, DMSO-$d_6$) δ ppm 1.37 (t, J=7.16 Hz, 3H) 1.74-2.01 (m, 3H) 3.21-3.37 (m, 3H) 4.46 (q, J=7.03 Hz, 2H) 4.56 (s, 4H) 6.74-6.90 (m, 2H) 7.12 (dd, J=1.32, 7.54 Hz, 1H) 7.25 (d, J=7.35 Hz, 1H) 7.50 (d, J=9.80 Hz, 1H) 8.09 (d, J=9.80 Hz, 1H)

(4) {5-[6-(1'H-spiro[1-benzofuran-3,4'-piperidin]-1'-yl)pyridazin-3-yl]-1,2,4-oxadiazol-3-yl}methanol Ethyl 5-[6-(1'H-spiro[1-benzofuran-3,4'-piperidin]-1'-yl)pyridazin-3-yl]-1,2,4-oxadiazole-3-carboxylate (200 mg) obtained by the above-mentioned reaction was dissolved in tetrahydrofuran (5 mL), and lithium tetrahydroborate (22 mg) was added under ice-cooling. After stirring at room temperature for 3 hr, the mixture was diluted with ethyl acetate-methanol-water, and washed with saturated aqueous sodium hydrogen carbonate solution, and the organic layer was dried over sodium sulfate. Hexane/ethyl acetate was added and the resulting precipitate was collected by filtration to give the object product (115 mg, 63%).

$^1$H NMR (300 MHz, DMSO-$d_6$) δ ppm 1.83 (brs, 2H) 1.86-2.01 (m, 2H) 3.18-3.31 (m, 2H) 4.56 (s, 4H) 4.64 (d, J=6.22 Hz, 2H) 5.77 (t, J=6.12 Hz, 1H) 6.76-6.89 (m, 2H) 7.09-7.17 (m, 1H) 7.25 (dd, J=0.94, 7.35 Hz, 1H) 7.49 (d, J=9.80 Hz, 1H) 8.02 (d, J=9.61 Hz, 1H)

Example 144

N-(2-hydroxy-1-methylethyl)-6-(1'H-spiro[1-benzofuran-3,4'-piperidin]-1'-yl)pyridazine-3-carboxamide 6-(1'H-Spiro[1-benzofuran-3,4'-piperidin]-1'-yl)pyridazine-3-carboxylic acid (930 mg) obtained in Example 143(2), 2-aminopropan-1-ol (0.26 mL), 1-ethyl-3-(3-dimethylaminopropyl)carbodiimide hydrochloride (770 mg) and hydroxybenzotriazole hydrate (610 mg) were dissolved in N,N-dimethylformamide (30 mL) and the solution was stirred overnight. The reaction mixture was diluted with ethyl acetate, and washed with aqueous sodium hydrogen carbonate solution. The organic layer was dried over sodium sulfate and the solvent was evaporated under reduced pressure. Diethyl ether-diisopropyl ether was added and the resulting precipitate was collected by filtration to give the object product (910 mg, 82%).

$^1$H NMR (300 MHz, DMSO-$d_6$) δ ppm 1.16 (d, J=6.59 Hz, 3H) 1.72-1.82 (m, 2H) 1.89-1.92 (m, 2H) 3.11-3.26 (m, 2H) 3.36-3.53 (m, 2H) 3.94-4.11 (m, 1H) 4.40-4.59 (m, 4H) 4.83 (t, J=5.56 Hz, 1H) 6.74-6.89 (m, 2H) 7.12 (td, J=7.72, 1.32 Hz, 1H) 7.23 (dd, J=0.94, 7.35 Hz, 1H) 7.43 (d, J=9.61 Hz, 1H) 7.85 (d, J=9.61 Hz, 1H) 8.44 (d, J=8.48 Hz, 1H)

Example 145

1'-[6-(4-methyl-4,5-dihydro-1,3-oxazol-2-yl)pyridazin-3-yl]spiro[1-benzofuran-3,4'-piperidine]

N-(2-Hydroxy-1-methylethyl)-6-(1'H-spiro[1-benzofuran-3,4'-piperidin]-1'-yl)pyridazine-3-carboxamide (400 mg) obtained in Example 144 was dissolved in tetrahydrofuran (10 mL), and triethylamine (0.2 mL) and methanesulfonyl chloride (0.11 mL) were added. After stirring at room temperature for 3 hr, the mixture was diluted with ethyl acetate, and washed with saturated aqueous sodium hydrogen carbonate solution, and the organic layer was dried over sodium sulfate. The residue was dissolved in methanol (10 mL), and aqueous sodium hydroxide solution (1N, 3 mL) was added. After stirring at room temperature overnight, tetrahydrofuran (5 mL) was added, and the mixture was stirred at 50° C. for 3 hr. After cooling to room temperature, the solvent was evaporated to a half amount under reduced pressure, and the residue was diluted with ethyl acetate. The mixture was washed with saturated aqueous sodium hydrogen carbonate solution, and the organic layer was dried over sodium sulfate. The solvent was evaporated under reduced pressure. Ethyl acetate was added, and the resulting precipitate was collected by filtration to give the object product (210 mg, 55%).

$^1$H NMR (300 MHz, DMSO-d$_6$) δ ppm 1.26 (d, J=6.44 Hz, 3H) 1.72-1.82 (m, 2H) 1.88-1.91 (m, 2H) 3.17-3.20 (m, 2H) 3.97 (t, J=7.95 Hz, 1H) 4.25-4.39 (m, 1H) 4.40-4.59 (m, 5H) 6.75-6.89 (m, 2H) 7.06-7.17 (m, 1H) 7.22 (d, J=7.57 Hz, 1H) 7.36 (d, J=9.47 Hz, 1H) 7.82 (d, J=9.47 Hz, 1H)

Example 146

1'-[6-(4-methyl-4,5-dihydro-1,3-thiazol-2-yl)pyridazin-3-yl]spiro[1-benzofuran-3,4'-piperidine]

N-(2-Hydroxy-1-methylethyl)-6-(1'H-spiro[1-benzofuran-3,4'-piperidin]-1'-yl)pyridazine-3-carboxamide (400 mg) obtained in Example 144 was dissolved in pyridine (10 mL), diphosphorus pentasulfide (1 g) was added. The mixture was stirred at 110° C. for 6 hr, and cooled to room temperature. Aqueous sodium hydroxide solution (1N, 30 mL) was added, and the mixture was extracted twice with ethyl acetate, and the organic layer was dried over sodium sulfate. The solvent was evaporated under reduced pressure, and the residue was purified by silica gel column chromatography (hexane-ethyl acetate, 30% to 80%), and crystallized from ethyl acetate-hexane to give the object product (110 mg, 27%).

$^1$H NMR (300 MHz, DMSO-d$_6$) δ ppm 1.36 (d, J=6.44 Hz, 3H) 1.71-1.82 (m, 2H) 1.87-1.90 (m, 2H) 2.95 (dd, J=7.19, 10.98 Hz, 1H) 3.12-3.27 (m, 2H) 3.49 (dd, J=8.33, 10.98 Hz, 1H) 4.41-4.56 (m, 4H) 4.64-4.83 (m, 1H) 6.74-6.88 (m, 2H) 7.11-7.18 (m, 1H) 7.23 (d, J=7.19 Hz, 1H) 7.39 (d, J=9.84 Hz, 1H) 7.85 (d, J=9.47 Hz, 1H)

Example 147

1'-[6-(5-methyl-1,2,4-oxadiazol-3-yl)pyridazin-3-yl]spiro[1-benzofuran-3,4'-piperidine]

(1) 6-(1'H-spiro[1-benzofuran-3,4'-piperidin]-1'-yl)pyridazine-3-carbonitrile

6-Chloropyridazine-3-carbonitrile (3.0 g), spiro[1-benzofuran-3,4'-piperidine] (4.7 g), potassium carbonate (4.2 g) and tetrabutylammonium iodide (510 mg) were suspended in tetrahydrofuran (300 mL), and the suspension was stirred under reflux overnight. The reaction mixture was diluted with ethyl acetate, and washed with sodium hydrogen carbonate solution. The organic layer was dried over sodium sulfate and the solvent was evaporated under reduced pressure. Ethyl acetate-hexane was added and the resulting precipitate was collected by filtration to give the object product (6.1 g, 98%).

$^1$H NMR (300 MHz, DMSO-d$_6$) δ ppm 1.73-1.83 (m, 2H) 1.83-1.96 (m, 2H) 3.18-3.31 (m, 2H) 4.44-4.58 (m, 4H) 6.76-6.88 (m, 2H) 7.08-7.16 (m, 1H) 7.24 (dd, J=1.04, 7.44 Hz, 1H) 7.43 (d, J=9.80 Hz, 1H) 7.87 (d, J=9.80 Hz, 1H)

(2) N'-hydroxy-6-(1'H-spiro[1-benzofuran-3,4'-piperidin]-1'-yl)pyridazine-3-carboximdamide 6-(1'H-Spiro[1-benzofuran-3,4'-piperidin]-1'-yl)pyridazine-3-carbonitrile (2.0 g) obtained by the above-mentioned reaction was dissolved in ethanol (70 mL), and hydroxylamine hydrochloride (2.4 g) and potassium carbonate (4.8 g) were added. After stirring at 50° C. overnight, water (200 mL) was added, and the resulting precipitate was collected by filtration to give the object product (1.9 g, 86%).

$^1$H NMR (300 MHz, DMSO-d$_6$) δ ppm 1.70-1.82 (m, 2H) 1.83-1.98 (m, 2H) 3.05-3.21 (m, 2H) 4.40 (d, J=13.75 Hz, 2H) 4.47-4.58 (m, 2H) 5.89 (brs, 2H) 6.73-6.90 (m, 2H) 7.06-7.16 (m, 1H) 7.18-7.28 (m, 1H) 7.35 (d, J=9.61 Hz, 1H) 7.72 (d, J=9.80 Hz, 1H) 9.88 (s, 1H)

(3) 1'-[6-(5-methyl-1,2,4-oxadiazol-3-yl)pyridazin-3-yl]spiro[1-benzofuran-3,4'-piperidine]

N'-Hydroxy-6-(1'H-spiro[1-benzofuran-3,4'-piperidin]-1'-yl)pyridazine-3-carboximdamide (330 mg) obtained by the above-mentioned reaction was dissolved in pyridine (5 mL). Acetic anhydride (0.15 mL) was added, and the mixture was stirred under reflux overnight. The mixture was cooled to room temperature, diluted with ethyl acetate, and washed with saturated sodium hydrogen carbonate, and the organic layer was dried over sodium sulfate. The solvent was evaporated under reduced pressure, ethyl acetate-hexane was added and the resulting precipitate was collected by filtration to give the object product (190 mg, 54%).

$^1$H NMR (300 MHz, DMSO-d$_6$) δ ppm 1.74-1.84 (m, 2H) 1.85-1.98 (m, 2H) 2.69 (s, 3H) 3.16-3.27 (m, 2H) 4.44-4.58 (m, 4H) 6.77-6.88 (m, 2H) 7.13 (td, J=7.72, 1.32 Hz, 1H) 7.24 (dd, J=1.04, 7.44 Hz, 1H) 7.46 (d, J=9.80 Hz, 1H) 7.88 (d, J=9.61 Hz, 1H)

Example 148

{3-[6-(1'H-spiro[1-benzofuran-3,4'-piperidin]-1'-yl)pyridazin-3-yl]-1,2,4-oxadiazol-5-yl}methanol N'-Hydroxy-6-(1'H-spiro[1-benzofuran-3,4'-piperidin]-1'-yl)pyridazine-3-carboximdamide (1.3 g) obtained in Example 147(2) was dissolved in pyridine (40 mL). 2-Chloro-2-oxoethyl acetate (0.65 mL) was added, and the mixture was stirred under reflux overnight. The mixture was cooled to room temperature, diluted with ethyl acetate, and washed with saturated sodium hydrogen carbonate, and the organic layer was dried over sodium sulfate. The solvent was evaporated under reduced pressure, and the residue was dissolved in methanol-tetrahydrofuran (1:1, v/v, 40 mL), and aqueous sodium hydroxide solution (1N, 30 mL) was added. After stirring at room temperature overnight, the solvent was evaporated to a half amount under reduced pressure. The residue was diluted with ethyl acetate, the mixture was washed with saturated sodium hydrogen carbonate solution, and the organic layer was dried over sodium sulfate. The solvent was evaporated under reduced pressure. The residue was purified by silica gel column chromatography, ethyl acetate-hexane was added and the resulting precipitate was collected by filtration to give the object product (290 mg, 20%).

$^1$H NMR (300 MHz, DMSO-d$_6$) δ ppm 1.73-1.85 (m, 2H) 1.85-2.01 (m, 2H) 3.15-3.30 (m, 2H) 4.50 (d, J=14.01 Hz, 4H) 4.82 (s, 2H) 6.23 (brs, 1H) 6.76-6.89 (m, 2H) 7.13 (t, J=7.76 Hz, 1H) 7.24 (d, J=7.19 Hz, 1H) 7.47 (d, J=9.47 Hz, 1H) 7.90 (d, J=9.47 Hz, 1H)

Example 149

1'-[6-(5-ethyl-1,2,4-oxadiazol-3-yl)pyridazin-3-yl]spiro[1-benzofuran-3,4'-piperidine]

The object product (78 mg, 43%) was obtained in the same manner as in Example 149 and using N'-hydroxy-6-(1'H- spiro[1-benzofuran-3,4'-piperidin]-1'-yl)pyridazine-3-carboximdamide (165 mg) obtained in Example 147(2) and propionic anhydride (110 mg).

$^1$H NMR (300 MHz, DMSO-d$_6$) δ ppm 1.36 (t, J=7.38 Hz, 3H) 1.73-1.84 (m, 2H) 1.92-1.95 (m, 2H) 3.04 (q, J=7.57 Hz, 2H) 3.14-3.28 (m, 2H) 4.50 (d, J=14.01 Hz, 4H) 6.71-6.92 (m, 2H) 7.12 (t, J=7.76 Hz, 1H) 7.24 (d, J=7.19 Hz, 1H) 7.46 (d, J=9.84 Hz, 1H) 7.89 (d, J=9.84 Hz, 1H)

Example 150

1'-[6-(5-methyl-1,2,4-oxadiazol-3-yl)pyridazin-3-yl]-3H-spiro[2-benzofuran-1,3'-pyrrolidine]

(1) 6-(1'H,3H-spiro[2-benzofuran-1,3'-pyrrolidin]-1'-yl)pyridazine-3-carbonitrile 6-Chloropyridazine-3-carbonitrile (1.3 g), 3H-spiro[2-benzofuran-1,3'-pyrrolidine] hydrochloride (2.1 g) obtained in Example 43(5), potassium carbonate (1.4 g) and tetrabutylammonium iodide (370 mg) were suspended in tetrahydrofuran (100 mL), and the suspension was stirred under reflux for 2 days. The reaction mixture was diluted with ethyl acetate, and washed with sodium hydrogen carbonate solution. The organic layer was dried over sodium sulfate and the solvent was evaporated under reduced pressure. Ethyl acetate-hexane was added and the resulting precipitate was collected by filtration to give the object product (1.1 g, 44%).

$^1$H NMR (300 MHz, DMSO-d$_6$) δ ppm 2.22-2.34 (m, 1H) 2.39-2.48 (m, 1H) 3.52-4.29 (m, 4H) 5.06 (s, 2H) 6.91-7.17 (m, 1H) 7.31-7.41 (m, 3H) 7.42-7.52 (m, 1H) 7.88 (d, J=9.47 Hz, 1H)

(2) N'-hydroxy-6-(1'H,3H-spiro[2-benzofuran-1,3'-pyrrolidin]-1'-yl)pyridazine-3-carboximdamide 6-(1'H,3H-Spiro[2-benzofuran-1,3'-pyrrolidin]-1'-yl)pyridazine-3-carbonitrile (800 mg) obtained by the above-mentioned reaction, hydroxylamine hydrochloride (1.1 g) and potassium carbonate (2.1 g) were suspended in ethanol (50 mL), and the suspension was stirred under reflux for 3 hr. The reaction mixture was ice-cooled, and water (100 mL) was added. The resulting precipitate was collected by filtration to give the object product (690 mg, 76%).

$^1$H NMR (300 MHz, DMSO-d$_6$) δ ppm 2.19-2.33 (m, 1H) 2.41-2.43 (m, 1H) 3.57-3.77 (m, 2H) 3.83 (d, J=12.24 Hz, 2H) 5.06 (s, 2H) 5.86 (brs, 2H) 6.95 (d, J=9.61 Hz, 1H) 7.29-7.41 (m, 3H) 7.43-7.50 (m, 2H) 7.71 (d, J=9.42 Hz, 1H) 9.84 (s, 1H)

(3) 1'-[6-(5-methyl-1,2,4-oxadiazol-3-yl)pyridazin-3-yl]-3H-spiro[2-benzofuran-1,3'-pyrrolidine]

N'-Hydroxy-6-(1'H,3H-spiro[2-benzofuran-1,3'-pyrrolidin]-1'-yl)pyridazine-3-carboximdamide (155 mg) obtained by the above-mentioned reaction was dissolved in N-methylpyrrolidone-ethanol (1:1, v/v, 10 mL), and sodium ethoxide (200 mg) and ethyl acetate (2 mL) were added. The mixture was stirred at 100° C. overnight, cooled to room temperature, diluted with ethyl acetate, and washed with saturated aqueous sodium hydrogen carbonate solution, and the organic layer was dried over sodium sulfate. The solvent was evaporated under reduced pressure. Hexane-ethyl acetate was added, and the resulting precipitate was collected by filtration to give the object product (120 mg, 72%).

$^1$H NMR (300 MHz, DMSO-d$_6$) δ ppm 2.23-2.34 (m, 1H) 2.38-2.48 (m, 1H) 2.68 (s, 3H) 3.61-4.11 (m, 4H) 5.07 (s, 2H) 7.05 (d, J=9.47 Hz, 1H) 7.32-7.39 (m, 3H) 7.46-7.48 (m, 1H) 7.89 (d, J=9.47 Hz, 1H)

Example 151

1'-{6-[5-(methoxymethyl)-1,2,4-oxadiazol-3-yl]pyridazin-3-yl}spiro[1-benzofuran-3,4'-piperidine]

The object product (42 mg, 22%) was obtained in the same manner as in Example 150 and using N'-hydroxy-6-(1'H-spiro[1-benzofuran-3,4'-piperidin]-1'-yl)pyridazine-3-carboximdamide (165 mg) obtained in Example 147(2), sodium ethoxide (260 mg) and methyl methoxyacetate (170 mg).

$^1$H NMR (300 MHz, DMSO-d$_6$) δ ppm 1.74-1.83 (m, 2H) 1.90 (dd, J=3.79, 12.12 Hz, 2H) 3.17-3.29 (m, 2H) 3.45 (s, 3H) 4.51 (d, J=13.25 Hz, 4H) 4.85 (s, 2H) 6.76-6.89 (m, 2H) 7.13 (t, J=7.57 Hz, 1H) 7.24 (d, J=7.19 Hz, 1H) 7.47 (d, J=9.84 Hz, 1H) 7.92 (d, J=9.47 Hz, 1H)

Example 152

1'-[6-(5-benzyl-4,5-dihydro-1,3-thiazol-2-yl)pyridazin-3-yl]spiro[1-benzofuran-3,4'-piperidine]

(1) N-(2-hydroxy-3-phenylpropyl)-6-(1'H-spiro[1-benzofuran-3,4'-piperidin]-1'-yl)pyridazine-3-carboxamide The object product (840 mg, 95%) was obtained in the same manner as in Example 36(3) and using 6-(1'H-spiro[1-benzofuran-3,4'-piperidin]-1'-yl)pyridazine-3-carboxylic acid (620 mg) obtained in Example 143(2), 1-amino-3-phenylpropan-2-ol (380 mg), 1-ethyl-3-(3-dimethylaminopropyl)carbodiimide hydrochloride (480 mg) and hydroxybenzotriazole hydrate (380 mg).

$^1$H NMR (300 MHz, DMSO-d$_6$) δ ppm 1.71-1.96 (m, 4H) 2.59-2.80 (m, 2H) 3.14-3.28 (m, 3H) 3.40-3.42 (m, 1H) 3.81-3.93 (m, 1H) 4.41-4.56 (m, 4H) 5.03 (d, J=5.65 Hz, 1H) 6.76-6.87 (m, 2H) 7.08-7.31 (m, 7H) 7.43 (d, J=9.61 Hz, 1H) 7.85 (d, J=9.42 Hz, 1H) 8.65 (t, J=5.84 Hz, 1H)

(2) 1'-[6-(5-benzyl-4,5-dihydro-1,3-thiazol-2-yl)pyridazin-3-yl]spiro[1-benzofuran-3,4'-piperidine]

The object product (182 mg, 41%) was obtained in the same manner as in Example 146 and using N-(2-hydroxy-3-phenylpropyl)-6-(1'H-spiro[1-benzofuran-3,4'-piperidin]-1'-yl)pyridazine-3-carboxamide (450 mg) obtained by the above-mentioned reaction and diphosphorus pentasulfide (890 mg).

$^1$H NMR (300 MHz, DMSO-d$_6$) δ ppm 1.71-1.82 (m, 2H) 1.82-1.96 (m, 2H) 2.78-2.90 (m, 1H) 2.91-3.01 (m, 1H) 3.13-3.26 (m, 2H) 4.17-4.29 (m, 1H) 4.29-4.35 (m, 2H) 4.47 (d, J=13.63 Hz, 2H) 4.54 (s, 2H) 6.71-6.90 (m, 2H) 7.04-7.16 (m, 1H) 7.20-7.36 (m, 6H) 7.40 (d, J=9.47 Hz, 1H) 7.86 (d, J=9.47 Hz, 1H).

Example 153

1'-[6-(4,4-dimethyl-4,5-dihydro-1,3-thiazol-2-yl)pyridazin-3-yl]spiro[1-benzofuran-3,4'-piperidine]

(1) N-(2-hydroxy-1,1-dimethylethyl)-6-(1'H-spiro[1-benzofuran-3,4'-piperidin]-1'-yl)pyridazine-3-carboxamide The object product (610 mg, 80%) was obtained in the same manner as in Example 36(3) and using 6-(1'H-spiro[1- benzofuran-3,4'-piperidin]-1'-yl)pyridazine-3-carboxylic acid (620 mg) obtained in Example 143(2), 2-amino-2-methylpropan-1-ol (220 mg), 1-ethyl-3-(3-dimethylaminopropyl)carbodiimide hydrochloride (480 mg) and hydroxybenzotriazole hydrate (380 mg).

$^1$H NMR (300 MHz, DMSO-d$_6$) δ ppm 1.35 (s, 6H) 1.71-1.94 (m, 4H) 3.20 (t, J=11.30 Hz, 2H) 3.45 (d, J=5.46 Hz, 2H) 4.47 (d, J=13.75 Hz, 4H) 5.15 (t, J=5.56 Hz, 1H) 6.81 (t, J=8.48 Hz, 2H) 7.09-7.13 (m, 1H) 7.19-7.22 (m, 1H) 7.43 (d, J=9.61 Hz, 1H) 7.84 (d, J=9.61 Hz, 1H) 8.14 (s, 1H)

(2) 1'-[6-(4,4-dimethyl-4,5-dihydro-1,3-thiazol-2-yl)pyridazin-3-yl]spiro[1-benzofuran-3,4'-piperidine]

The object product (220 mg, 651%) was obtained in the same manner as in Example 146 and using N-(2-hydroxy-1,1-dimethylethyl)-6-(1'H-spiro[1-benzofuran-3,4'-piperidin]-1'-yl)pyridazine-3-carboxamide (340 mg) obtained by the above-mentioned reaction and diphosphorus pentasulfide (780 mg).

$^1$H NMR (300 MHz, DMSO-d$_6$) δ ppm 1.39 (s, 6H) 1.72-1.81 (m, 2H) 1.83-1.95 (m, 2H) 3.14-3.27 (m, 4H) 4.40-4.52 (m, 2H) 4.54 (s, 2H) 6.76-6.88 (m, 2H) 7.12 (t, J=7.76 Hz, 1H) 7.22 (d, J=7.19 Hz, 1H) 7.38 (d, J=9.47 Hz, 1H) 7.83 (d, J=9.84 Hz, 1H)

Example 154

1'-[6-(3-methyl-1,2,4-oxadiazol-5-yl)pyridazin-3-yl]-3H-spiro[2-benzofuran-1,3'-pyrrolidin]-3-one The object product (10 mg, 6%) was obtained in the same manner as in Example 1 and using 3-chloro-6-(3-methyl-1,2,4-oxadiazol-5-yl)pyridazine (100 mg) obtained in Example 43(2), 3H-spiro[2-benzofuran-1,3'-pyrrolidin]-3-one (110 mg) and potassium carbonate (150 mg).

$^1$H NMR (300 MHz, DMSO-d$_6$) δ ppm 2.37-2.47 (m, 4H) 2.76-2.92 (m, 1H) 3.76-4.27 (m, 4H) 7.07-7.20 (m, 1H) 7.69-7.71 (t, J=7.35 Hz, 1H) 7.91-7.93 (m, 3H) 8.08 (d, J=9.42 Hz, 1H)

Example 155

1'-[6-(3-methyl-1,2,4-oxadiazol-5-yl)pyridazin-3-yl]-3H-spiro[2-benzofuran-1,4'-piperidin]-3-one The object product (187 mg, 52%) was obtained in the same manner as in Example 1 and using 3-chloro-6-(3-methyl-1,2,4-oxadiazol-5-yl)pyridazine (200 mg) obtained in Example 43(2), 3H-spiro[2-benzofuran-1,4'-piperidin]-3-one (240 mg) and potassium carbonate (140 mg).

$^1$H NMR (300 MHz, DMSO-d$_6$) δ ppm 1.75-1.85 (m, 2H) 2.26-2.41 (m, 2H) 2.45 (s, 3H) 3.37-3.50 (m, 2H) 4.68-4.80 (m, 2H) 7.55 (d, J=9.80 Hz, 1H) 7.59-7.67 (m, 1H) 7.78 (d, J=4.33 Hz, 2H) 7.87 (d, J=7.72 Hz, 1H) 8.05 (d, J=9.80 Hz, 1H)

Example 156

{5-[6-(1'H,3H-spiro[2-benzofuran-1,3'-pyrrolidin]-1'-yl)pyridazin-3-yl]-1,2,4-oxadiazol-3-yl}methanol (1) methyl 6-(1'H,3H-spiro[2-benzofuran-1,3'-pyrrolidin]-1'-yl)pyridazine-3-carboxylate Methyl 6-chloropyridazine-3-carboxylate (2.4 g), 3H-spiro[2-benzofuran-1,3'-pyrrolidine] hydrochloride (3.0 g) obtained in Example 43(5), potassium carbonate (2.0 g) and tetrabutylammonium iodide (520 mg) were suspended in tetrahydrofuran (150 mL), and the suspension was stirred under reflux overnight. The reaction mixture was diluted with ethyl acetate, and washed with aqueous sodium carbonate solution. The organic layer was dried over sodium sulfate and the solvent was evaporated under reduced pressure. Ethyl acetate-hexane was added and the resulting precipitate was collected by filtration to give the object product (1.8 g, 41%).

$^1$H NMR (300 MHz, DMSO-d$_6$) δ ppm 2.23-2.34 (m, 1H) 2.39-2.48 (m, 1H) 3.58-4.08 (m, 7H) 5.06 (s, 2H) 6.97 (d, J=9.42 Hz, 1H) 7.29-7.41 (m, 3H) 7.44-7.52 (m, 1H) 7.86 (d, J=9.42 Hz, 1H)

(2) 6-(1'H,3H-spiro[2-benzofuran-1,3'-pyrrolidin]-1'-yl)pyridazine-3-carboxylic acid Methyl 6-(1'H,3H-spiro[2-benzofuran-1,3'-pyrrolidin]-1'-yl)pyridazine-3-carboxylate (1.8 g) obtained by the above-mentioned reaction was dissolved in tetrahydrofuran-methanol (1:1, v/v, 80 mL), and aqueous sodium hydroxide solution (1N, 40 mL) was added. After stirring at room temperature overnight, hydrochloric acid (1N, 40 mL) was added, and the reaction mixture was concentrated to a half amount under reduced pressure and extracted with ethyl acetate, and the organic layer was dried over sodium sulfate. The solvent was evaporated under reduced pressure, ethyl acetate-hexane was added, and the resulting precipitate was collected by filtration to give the object product (1.0 g, 58%).

$^1$H NMR (300 MHz, DMSO-d$_6$) δ ppm 2.23-2.46 (m, 2H) 3.58-4.32 (m, 4H) 5.06 (s, 2H) 6.99 (s, 1H) 7.35-7.39 (m, 3H) 7.44-7.53 (m, 1H) 7.85 (d, J=9.42 Hz, 1H) 13.03 (brs, 1H)

(3) ethyl 5-[6-(1'H,3H-spiro[2-benzofuran-1,3'-pyrrolidin]-1'-yl)pyridazin-3-yl]-1,2,4-oxadiazole-3-carboxylate A solution of 6-(1'H,3H-spiro[2-benzofuran-1,3'-pyrrolidin]-1'-yl)pyridazine-3-carboxylic acid (450 mg) obtained by the above-mentioned reaction and 1,1'-carbonylbis(1H-imidazole) (300 mg) in N,N-dimethylformamide (5 mL) was stirred at 60° C. for 3 hr, and cooled to room temperature. Pyridine (10 mL) and ethyl amino(hydroxyimino)acetate (240 mg) were added and the mixture was stirred at 130° C. for 3 hr and cooled to room temperature. The reaction mixture was diluted with ethyl acetate, and washed with aqueous sodium hydrogen carbonate solution, and the organic layer was dried over sodium sulfate. The residue was purified by silica gel column chromatography to give the object product (350 mg, 59%) as a crude product.

(4) {5-[6-(1'H,3H-spiro[2-benzofuran-1,3'-pyrrolidin]-1'-yl)pyridazin-3-yl]-1,2,4-oxadiazol-3-yl}methanol To a solution of ethyl 5-[6-(1'H,3H-spiro[2-benzofuran-1,3'-pyrrolidin]-1'-yl)pyridazin-3-yl]-1,2,4-oxadiazole-3-carboxylate (200 mg) obtained by the above-mentioned reaction in tetrahydrofuran (5 mL) was added lithium tetrahydroborate (22 mg) under ice-cooling. After stirring at room temperature for 3 hr, the reaction was quenched with methanol-water (1:1, 5 mL), and the reaction mixture was diluted with ethyl acetate and washed with aqueous sodium hydrogen carbonate solution. The organic layer was dried over sodium sulfate and the solvent was evaporated under reduced pressure. Ethyl acetate-hexane was added, and the resulting precipitate was collected by filtration to give the object product (40 mg, 23%).

$^1$H NMR (300 MHz, DMSO-d$_6$) δ ppm 2.30 (dd, J=6.63, 12.68 Hz, 1H) 2.41-2.49 (m, 1H) 3.57-4.39 (m, 4H) 4.64 (d, J=4.92 Hz, 2H) 5.07 (s, 2H) 5.71-5.80 (m, 1H) 7.10 (d, J=9.09 Hz, 1H) 7.33-7.41 (m, 3H) 7.46-7.52 (m, 1H) 8.04 (d, J=9.84 Hz, 1H)

Example 157

{5-[(6-(1'H-spiro[1-benzofuran-3,3'-pyrrolidin]-1'-yl)pyridazin-3-yl]-1,2,4-oxadiazol-3-yl}methanol (1) methyl 6-(1'H-spiro[1-benzofuran-3,3'-pyrrolidin]-1'-yl)pyridazine-3-carboxylate Methyl 6-chloropyridazine-3-carboxylate (1.4 g), spiro[1-benzofuran-3,3'-pyrrolidine] (1.5 g), potassium carbonate (1.4 g) and tetrabutylammonium iodide (370 mg) were suspended in tetrahydrofuran (80 mL), and the suspension was stirred under reflux overnight. The reaction mixture was diluted with ethyl acetate, and washed with aqueous sodium carbonate solution. The organic layer was dried over sodium sulfate and the solvent was evaporated under reduced pressure. Ethyl acetate-hexane was added and the resulting precipitate was collected by filtration to give the object product (2.2 g, 88%).

$^1$H NMR (300 MHz, DMSO-d$_6$) δ ppm 2.21-2.41 (m, 2H) 3.52-4.04 (m, 7H) 4.43-4.54 (m, 2H) 6.80-7.02 (m, 3H) 7.13-7.25 (m, 1H) 7.32 (d, J=7.35 Hz, 1H) 7.87 (d, J=9.42 Hz, 1H)

(2) 6-(1'H-spiro[1-benzofuran-3,3'-pyrrolidin]-1'-yl)pyridazine-3-carboxylic acid Methyl 6-(1'H-spiro[1-benzofuran-3,3'-pyrrolidin]-1'-yl)pyridazine-3-carboxylate (2.2 g) obtained by the above-mentioned reaction was dissolved in tetrahydrofuran-methanol (1:1, v/v, 100 mL), and aqueous sodium hydroxide solution (1N, 50 mL) was added. After stirring at room temperature overnight, hydrochloric acid (1N, 50 mL) was added, and the reaction mixture was concentrated to a half amount under reduced pressure and extracted with ethyl acetate, and the organic layer was dried over sodium sulfate. The solvent was evaporated under reduced pressure, ethyl acetate-hexane was added, and the resulting precipitate was collected by filtration to give the object product (1.8 g, 86%).

$^1$H NMR (300 MHz, DMSO-d$_6$) δ ppm 2.33 (t, J=8.57 Hz, 2H) 3.86 (brs, 4H) 4.50 (d, J=1.13 Hz, 2H) 6.91 (t, J=7.44 Hz, 3H) 7.19 (t, J=7.72 Hz, 1H) 7.32 (d, J=7.35 Hz, 1H) 7.86 (d, J=9.42 Hz, 1H) 13.02 (brs, 1H)

(3) ethyl 5-[6-(1'H-spiro[1-benzofuran-3,3'-pyrrolidin]-1'-yl)pyridazin-3-yl]-1,2,4-oxadiazole-3-carboxylate A solution of 6-(1'H-spiro[1-benzofuran-3,3'-pyrrolidin]-1'-yl)pyridazine-3-carboxylic acid (450 mg) obtained by the above-mentioned reaction and 1,1'-carbonylbis(1H-imidazole) (300 mg) in N,N-dimethylformamide (5 mL) was stirred at 60° C. for 3 hr, and cooled to room temperature. Pyridine (10 mL) and ethyl amino(hydroxyimino)acetate (240 mg) were added and the mixture was stirred at 130° C. for 3 hr and cooled to room temperature. The reaction mixture was diluted with ethyl acetate, and washed with aqueous sodium hydrogen carbonate solution, and the organic layer was dried over sodium sulfate. The residue was purified by silica gel column chromatography to give the object product (380 mg, 64%) as a crude product.

$^1$H NMR (300 MHz, DMSO-d$_6$) δ ppm 1.36 (t, J=7.16 Hz, 3H) 2.22-2.45 (m, 2H) 3.51-4.30 (m, 4H) 4.45 (q, J=7.16 Hz, 2H) 4.52 (s, 2H) 6.85 (d, J=8.10 Hz, 1H) 6.92 (t, J=7.44 Hz, 1H) 7.12 (d, J=9.42 Hz, 1H) 7.16-7.23 (m, 1H) 7.34 (d, J=7.35 Hz, 1H) 8.11 (d, J=9.42 Hz, 1H)

(4) {5-[6-(1'H-spiro[1-benzofuran-3,3'-pyrrolidin]-1'-yl)pyridazin-3-yl]-1,2,4-oxadiazol-3-yl}methanol To a solution of ethyl 5-[6-(1'H-spiro[1-benzofuran-3,3'-pyrrolidin]-1'-yl)pyridazin-3-yl]-1,2,4-oxadiazole-3-carboxylate (200 mg) obtained by the above-mentioned reaction in tetrahydrofuran (5 mL) was added lithium tetrahydroborate (22 mg) under ice-cooling. After stirring at room temperature for 3 hr, the reaction was quenched with methanol-water (1:1, 5 mL), and the reaction mixture was diluted with ethyl acetate and washed with aqueous sodium hydrogen carbonate solution. The organic layer was dried over sodium sulfate and the solvent was evaporated under reduced pressure. Ethyl acetate-hexane was added, and the resulting precipitation was collected by filtration, and recrystallized from ethyl acetate-hexane to give the object product (25 mg, 14%).

$^1$H NMR (300 MHz, DMSO-d$_6$) δ ppm 2.23-2.44 (m, 2H) 3.61-4.09 (m, 4H) 4.52 (s, 2H) 4.64 (d, J=5.65 Hz, 2H) 5.73-5.81 (m, 1H) 6.81-6.96 (m, 2H) 7.11 (d, J=9.61 Hz, 1H) 7.20 (td, J=7.72, 1.32 Hz, 1H) 7.33 (d, J=1.13 Hz, 1H) 8.04 (d, J=9.61 Hz, 1H)

Example 158

1'-[6-(3-methyl-1,2,4-oxadiazol-5-yl)pyridazin-3-yl]spiro[indole-3,3'-pyrrolidin]-2(1H)-one 3-Chloro-6-(3-methyl-1,2,4-oxadiazol-5-yl)pyridazine (690 mg) obtained in Example 43(2), spiro[indole-3,3'-pyrrolidin]-2(1H)-one (800 mg), potassium carbonate (500 mg) and tetrabutylammonium iodide (130 mg) were suspended in N,N-dimethylformamide-tetrahydrofuran (1:1, v/v, 50 mL), and the suspension was stirred at 120° C. overnight. The mixture was cooled to room temperature, diluted with ethyl acetate, and washed with aqueous sodium carbonate solution. The organic layer was dried over sodium sulfate and the solvent was evaporated under reduced pressure. Ethyl acetate was added and the resulting precipitate was collected by filtration, and recrystallized from ethyl acetate to give the object product (750 mg, 62%).

$^1$H NMR (300 MHz, DMSO-d$_6$) δ ppm 2.24-2.48 (m, 6H) 3.72-4.12 (m, 4H) 6.90 (d, J=7.72 Hz, 1H) 6.98 (t, J=7.54 Hz, 1H) 7.14 (d, J=9.61 Hz, 1H) 7.24 (td, J=7.72, 1.13 Hz, 1H) 7.3.1 (d, J=7.16 Hz, 1H) 8.04 (d, J=9.42 Hz, 1H) 10.59 (brs, 1H)

Example 159

1-methyl-1'-[6-(3-methyl-1,2,4-oxadiazol-5-yl)pyridazin-3-yl]spiro[indole-3,3'-pyrrolidin]-2(1H)-one 1'-[6-(3-Methyl-1,2,4-oxadiazol-5-yl)pyridazin-3-yl]spiro[indole-3,3'-pyrrolidin]-2(1H)-one (300 mg) obtained in Example 158 was dissolved in N,N-dimethylformamide (10 mL), sodium hydride (60 w %, 35 mg) was added, and the mixture was stirred at room temperature for 30 min. Iodomethane (0.054 mL) was added, and the mixture was further stirred at room temperature for 3 hr. The reaction was quenched with saturated aqueous ammonium chloride solution, and water (20 mL) was added. The resulting precipitate was collected by filtration to give the object product (198 mg, 64%).

$^1$H NMR (300 MHz, DMSO-d$_6$) δ ppm 2.28-2.47 (m, 5H) 3.18 (s, 3H) 3.76-4.15 (m, 4H) 7.00-7.20 (m, 3H) 7.30-7.41 (m, 2H) 8.05 (d, J=9.42 Hz, 1H)

Example 160

{3-[6-(1'H,3H-spiro[2-benzofuran-1,3'-pyrrolidin]-1'-yl)pyridazin-3-yl]-1,2,4-oxadiazol-5-yl}methyl acetate N'-Hydroxy-6-(1'H,3H-spiro(2-benzofuran-1,3'-pyrrolidin)-1'-yl)pyridazine-3-carboximdamide (440 mg) obtained in Example 150(2) was dissolved in pyridine (10 mL), 2-chloro-2-oxoethyl acetate (0.23 ml) was added, and the mixture was stirred under reflux overnight. The mixture was cooled to room temperature, diluted with ethyl acetate, and washed with saturated aqueous sodium carbonate solution. The organic layer was dried over sodium sulfate and the solvent was evaporated under reduced pressure. The residue was purified by silica gel column chromatography to give the object product (335 mg, 60%).

$^1$H NMR (300 MHz, DMSO-d$_6$) δ ppm 2.18 (s, 3H) 2.24-2.35 (m, 1H) 2.39-2.47 (m, 1H) 3.61-4.21 (m, 4H) 5.07 (s, 2H) 5.48 (s, 2H) 7.06 (d, J=9.42 Hz, 1H) 7.37 (d, J=2.83 Hz, 3H) 7.45-7.52 (m, 1H) 7.91 (d, J=9.42 Hz, 1H)

Example 161

{3-[6-(1'H-spiro[1-benzofuran-3,3'-pyrrolidin]-1'-yl)pyridazin-3-yl]-1,2,4-oxadiazol-5-yl}methyl acetate (1) 6-(1'H-spiro[1-benzofuran-3,3'-pyrrolidin]-1'-yl)pyridazine-3-carbonitrile The object product (1.3 g, 88%) was obtained in the same manner as in Example 143(1) and using 6-chloropyridazine-3-carbonitrile (740 mg), spiro[1-benzofuran-3,3'-pyrrolidine] (1.0 g), potassium carbonate (830 mg) and tetrabutylammonium iodide (220 mg).

$^1$H NMR (300 MHz, DMSO-d$_6$) δ ppm 2.20-2.41 (m, 2H) 3.50-4.22 (m, 4H) 4.49 (s, 2H) 6.84 (d, J=7.95 Hz, 1H) 6.91 (t, J=7.38 Hz, 1H) 7.04 (d, J=9.84 Hz, 1H) 7.12-7.23 (m, 1H) 7.32 (d, J=7.57 Hz, 1H) 7.88 (d, J=9.47 Hz, 1H)

(2) N'-hydroxy-6-(1'H-spiro[1-benzofuran-3,3'-pyrrolidin]-1'-yl)pyridazine-3-carboximdamide 6-(1'H-Spiro[1-benzofuran-3,3'-pyrrolidin]-1'-yl)pyridazine-3-carbonitrile (1.3 g) obtained by the above-mentioned reaction was dissolved in ethanol-tetrahydrofuran (3:1, v/v, 40 mL), aqueous hydroxylamine solution (50%, 0.46 mL) was added, and the mixture was stirred at room temperature for 5 hr. Hexane (20 mL) was added, and the resulting precipitate was collected by filtration to give the object product (1.5 g) as a crude product.

(3) {3-[6-(1'H-spiro[1-benzofuran-3,3'-pyrrolidin]-1'-yl)pyridazin-3-yl]-1,2,4-oxadiazol-5-yl}methyl acetate The object product (330 mg, 84%) was obtained in the same manner as in Example 160 and using N'-hydroxy-6-(1'H-spiro[1-benzofuran-3,3'-pyrrolidin]-1'-yl)pyridazine-3-carboximdamide (310 mg) obtained by the above-mentioned reaction and 2-chloro-2-oxoethyl acetate (0.16 mL).

$^1$H NMR (300 MHz, DMSO-d$_6$) δ ppm 2.18 (s, 3H) 2.22-2.42 (m, 2H) 3.60-3.81 (m, 2H) 3.81-4.00 (m, 2H) 4.51 (s, 2H) 5.48 (s, 2H) 6.85 (d, J=8.10 Hz, 1H) 6.91 (t, J=7.44 Hz, 1H) 7.08 (d, J=9.61 Hz, 1H) 7.14-7.24 (m, 1H) 7.33 (d, J=7.54 Hz, 1H) 7.92 (d, J=9.42 Hz, 1H)

Example 162

{3-[6-(1'H,3H-spiro[2-benzofuran-1,3'-pyrrolidin]-1'-yl)pyridazin-3-yl]-1,2,4-oxadiazol-5-yl}methanol The object product (147 mg, 82%) was obtained in the same manner as in Example 36(2) and using {3-[6-(1'H,3H-spiro[2-benzofuran-1,3'-pyrrolidin]-1'-yl)pyridazin-3-yl]-1,2,4-oxadiazol-5-yl}methyl acetate (200 mg) obtained in Example 160 and aqueous sodium hydroxide solution (1N, 4 mL).

$^1$H NMR (300 MHz, DMSO-d$_6$) δ ppm 2.29 (dd, J=6.44, 12.87 Hz, 1H) 2.38-2.48 (m, 1H) 3.61-4.16 (m, 4H) 4.81 (d, J=4.16 Hz, 2H) 5.07 (s, 2H) 6.08 (s, 1H) 7.06 (d, J=9.47 Hz, 1H) 7.31-7.41 (m, 3H) 7.44-7.52 (m, 1H) 7.91 (d, J=9.47 Hz, 1H)

Example 163

{3-[6-(1'H-spiro[1-benzofuran-3,3'-pyrrolidin]-1'-yl)pyridazin-3-yl]-1,2,4-oxadiazol-5-yl}methanol The object product (178 mg, 99%) was obtained in the same manner as in Example 36(2) and using {3-[6-(1'H-spiro[1-benzofuran-3,3'-pyrrolidin]-1'-yl)pyridazin-3-yl]-1,2,4-oxadiazol-5-yl}methyl acetate (200 mg) obtained in Example 161 and aqueous sodium hydroxide solution (1N, 4 mL).

$^1$H NMR (300 MHz, DMSO-d$_6$) δ ppm 2.23-2.42 (m, 2H) 3.54-4.06 (m, 4H) 4.51 (s, 2H) 4.82 (s, 2H) 6.22 (brs, 1H) 6.85 (d, J=8.10 Hz, 1H) 6.91 (t, J=7.44 Hz, 1H) 7.08 (d, J=9.42 Hz, 1H) 7.14-7.23 (m, 1H) 7.30-7.35 (m, 1H) 7.92 (d, J=9.61 Hz, 1H)

Example 164

1'-[6-(5-methyl-1,2,4-oxadiazol-3-yl)pyridazin-3-yl]spiro[1-benzofuran-3,3'-pyrrolidine]

The object product (200 mg, 60%) was obtained in the same manner as in Example 160 and using N'-hydroxy-6-(1'H-spiro[1-benzofuran-3,3'-pyrrolidin]-1'-yl)pyridazine-3-carboximdamide (310 mg) obtained in Example 161(2) and acetyl chloride (0.11 mL).

$^1$H NMR (300 MHz, DMSO-d$_6$) δ ppm 2.21-2.42 (m, 2H) 2.68 (s, 3H) 3.60-3.96 (m, 4H) 4.51 (s, 2H) 6.85 (d, J=7.95 Hz, 1H) 6.91 (t, J=7.57 Hz, 1H) 7.06 (d, J=9.47 Hz, 1H) 7.19 (t, J=7.76 Hz, 1H) 7.33 (d, J=7.19 Hz, 1H) 7.89 (d, J=9.47 Hz, 1H)

Example 165

1'-[6-(1H-imidazol-1-yl)pyridazin-3-yl]spiro[1-benzofuran-3,4'-piperidine]

3-Chloro-6-(1H-imidazol-1-yl)pyridazine (180 mg), spiro[1-benzofuran-3,4'-piperidine] (200 mg) and triethylamine (0.42 mL) were dissolved in N,N-dimethylformamide (1 mL), and the solution was stirred at 160° C. under irradiation of microwave for 20 min. Water (10 mL) was added, and the resulting precipitate was collected by filtration, and recrystallized from ethyl acetate-hexane to give the object product (245 mg, 74%).

$^1$H NMR (300 MHz, DMSO-d$_6$) δ ppm 1.71-1.82 (m, 2H) 1.85-2.00 (m, 2H) 3.07-3.21 (m, 2H) 4.38 (d, J=13.63 Hz, 2H) 4.53 (s, 2H) 6.76-6.88 (m, 2H) 7.08-7.17 (m, 2H) 7.23 (d, J=7.57 Hz, 1H) 7.63 (d, J=9.47 Hz, 1H) 7.88-7.96 (m, 2H) 8.46 (s, 1H)

Example 166

1'-[6-(1H-imidazol-1-yl)pyridazin-3-yl]-3H-spiro[2-benzofuran-1,3'-pyrrolidine]

The object product (195 mg, 61%) was obtained in the same manner as in Example 165 and using 3-chloro-6-(1H-imidazol-1-yl)pyridazine (180 mg), 3H-spiro[2-benzofuran-1,3'-pyrrolidine] hydrochloride (200 mg) obtained in Example 43(5) and triethylamine (0.42 mL).

$^1$H NMR (300 MHz, DMSO-d$_6$) δ ppm 2.22-2.33 (m, 1H) 2.37-2.49 (m, 1H) 3.62-3.77 (m, 2H) 3.80-3.97 (m, 2H) 5.06 (s, 2H) 7.13 (s, 1H) 7.20 (d, J=9.84 Hz, 1H) 7.31-7.40 (m, 3H) 7.43-7.51 (m, 1H) 7.86-7.94 (m, 2H) 8.43 (s, 1H)

Example 167

9-{6-[3-(hydroxymethyl)-1,2,4-oxadiazol-5-yl]pyridazin-3-yl}-4-phenyl-1-oxa-4,9-diazaspiro[5.5]undecan-3-one (1) cyanomethyl benzoate Aqueous sodium hydroxide solution (4N, 60 mL) was added to aqueous hydroxyacetonitrile solution (52%, 25 g), and benzoyl chloride (25 mL) was slowly added dropwise under ice-cooling. After warming to room temperature, the mixture was stirred at room temperature overnight. Ethyl acetate was added to the solvent, and the mixture was washed with saturated aqueous sodium hydrogen carbonate solution. The organic layer was dried over sodium sulfate, and the residue was purified by silica gel column chromatography to give the object product (27.5 g, 75%).

$^1$H NMR (300 MHz, DMSO-d$_6$) δ ppm 4.64 (s, 2H) 5.68 (s, 2H) 7.50-7.58 (m, 2H) 7.63-7.71 (m, 1H) 7.96-8.03 (m, 2H) 9.36 (s, 1H)

(2) 2-amino-2-(hydroxyimino)ethyl benzoate

Cyanomethyl benzoate (24.1 g) obtained by the above-mentioned reaction was dissolved in ethanol (500 mL), aqueous hydroxylamine solution (50%, 12 mL) was added, and the mixture was stirred at room temperature for 5 hr. The solvent was evaporated under, reduced pressure, ethanol-hexane was added, and the resulting precipitate was collected by filtration to give the object product (14.5 g).

$^1$H NMR (300 MHz, DMSO-d$_6$) δ ppm 4.64 (s, 2H) 5.68 (s, 2H) 7.50-7.58 (m, 2H) 7.63-7.71 (m, 1H) 7.96-8.03 (m, 2H) 9.36 (s, 1H)

(3) [5-(6-oxo-1,6-dihydropyridazin-3-yl)-1,2,4-oxadiazol-3-yl]methyl benzoate

6-Oxo-1,6-dihydropyridazine-3-carboxylic acid (10.1 g) was dissolved in N,N-dimethylformamide (100 mL), and 1,1'-carbonylbis(1H-imidazole) (11.7 g) was added. After stirring at 60° C. for 1 hr, the mixture was cooled to room temperature. Pyridine (400 mL) and 2-amino-2-(hydroxyimino)ethyl benzoate (14 g) obtained by the above-mentioned reaction were added, and the mixture was stirred at 130° C. for 3 hr. The mixture was cooled to room temperature. The solvent was evaporated under reduced pressure, and the residue was purified by silica gel column chromatography to give the object product (10.2 g, 48%).

$^1$H NMR (300 MHz, DMSO-d$_6$) δ ppm 5.60 (s, 2H) 7.08 (d, J=9.98 Hz, 1H) 7.57 (t, J=7.63 Hz, 2H) 7.66-7.77 (m, 1H) 7.95-8.08 (m, 3H) 13.86 (brs, 1H)

(4) [5-(6-chloropyridazin-3-yl)-1,2,4-oxadiazol-3-yl]methyl benzoate

[5-(6-Oxo-1,6-dihydropyridazin-3-yl)-1,2,4-oxadiazol-3-yl]methyl benzoate (10 g) obtained by the above-mentioned reaction was dissolved in phosphorus oxychloride (100 mL), and the solution was stirred under reflux for 3 hr. The solvent was evaporated under reduced pressure, and the residue was diluted with ethyl acetate, and the mixture was washed with saturated aqueous sodium hydrogen carbonate solution. The organic layer was dried over sodium sulfate and the solvent was evaporated under reduced pressure. The residue was purified by silica gel column chromatography, and crystallized from ethanol-hexane to give the object product (8.6 g).

$^1$H NMR (300 MHz, DMSO-d$_6$) δ ppm 5.68 (s, 2H) 7.58 (t, J=7.72 Hz, 2H) 7.67-7.76 (m, 1H) 7.99-8.09 (m, 2H) 8.23 (d, J=9.04 Hz, 1H) 8.51 (d, J=9.04 Hz, 1H)

(5) 9-{6-[3-(hydroxymethyl)-1,2,4-oxadiazol-5-yl]pyridazin-3-yl}-4-phenyl-1-oxa-4,9-diazaspiro[5.5]undecan-3-one

[5-(6-Chloropyridazin-3-yl)-1,2,4-oxadiazol-3-yl]methyl benzoate (250 mg) obtained by the above-mentioned reaction, 4-phenyl-1-oxa-4,9-diazaspiro[5.5]undecan-3-one (255 mg) and potassium carbonate (125 mg) were suspended in N,N-dimethylformamide (5 mL), and the suspension was stirred at 100° C. under irradiation of microwave for 10 min. The mixture was cooled to room temperature, water (20 mL) was added and the resulting precipitate was collected by filtration. The obtained precipitate was dissolved in tetrahydrofuran-methanol (1:1, v/v, 8 mL), and aqueous sodium hydroxide solution (1N, 5 mL) was added. After stirring at room temperature overnight, the mixture was neutralized with hydrochloric acid and extracted with ethyl acetate. The organic layer was dried over sodium sulfate and the solvent was evaporated under reduced pressure. Ethyl acetate-hexane was added to the residue, and the resulting precipitate was collected by filtration to give the object product (58 mg, 17%).

$^1$H NMR (300 MHz, DMSO-d$_6$) δ ppm 1.71-1.86 (m, 2H) 2.04 (d, J=13.63 Hz, 2H) 3.36-3.49 (m, 2H) 3.71 (s, 2H) 4.24-4.42 (m, 4H) 4.63 (d, J=6.06 Hz, 2H) 5.71-5.80 (m, 1H) 7.22-7.31 (m, 1H) 7.33-7.50 (m, 5H) 8.01 (d, J=9.84 Hz, 1H)

Example 168

1'-[6-(3-methyl-1,2,4-oxadiazol-5-yl)pyridazin-3-yl]spiro[3,1-benzoxazine-4,4'-piperidin]-2(1H)-one 3-Chloro-6-(3-methyl-1,2,4-oxadiazol-5-yl)pyridazine (690 mg) obtained in Example 43(2), spiro[3,1-benzoxazine-4,4'-piperidin]-2(1H)-one (1 g) and triethylamine (1.4 mL) were suspended in N,N-dimethylformamide (20 mL), and the suspension was stirred at 160° C. under irradiation of microwave for 15 min. The mixture was cooled to room temperature, water (200 mL) was added and the resulting precipitate was collected by filtration. The precipitate was recrystallized from ethanol to give the object product (550 mg, 42%).

$^1$H NMR (300 MHz, DMSO-d$_6$) δ ppm 2.05-2.22 (m, 4H) 2.44 (s, 3H) 3.37-3.50 (m, 2H) 4.62 (d, J=13.75 Hz, 2H) 6.88-6.95 (m, 1H) 7.01 (t, J=7.54 Hz, 1H) 7.20-7.33 (m, 2H) 7.50 (d, J=9.80 Hz, 1H) 8.03 (d, J=9.80 Hz, 1H) 10.32 (s, 1H)

Example 169

{5-[6-(1'H-spiro[1-benzofuran-3,3'-pyrrolidin]-1'-yl)pyridazin-3-yl]-1,2,4-oxadiazol-3-yl}acetic acid (1) tert-butyl 3-amino-3-(hydroxyimino)propanoate tert-Butyl cyanoacetate (1.0 g) was dissolved in ethanol (10 mL), and aqueous hydroxyamine solution (50%, 0.5 mL) was added dropwise under ice-cooling. After stirring at room temperature for 5 hr, the mixture was diluted with ethyl acetate, and washed with brine, and the organic layer was dried over sodium sulfate. The solvent was evaporated under reduced pressure and ethyl acetate-hexane was added. The resulting precipitate was collected by filtration to give the object product (820 mg, 67%).

$^1$H NMR (300 MHz, DMSO-d$_6$) δ ppm 1.40 (s, 9H) 2.90 (s, 2H) 5.40 (brs, 2H) 8.97 (s, 1H)

(2) tert-butyl {5-[6-(1'H-spiro[1-benzofuran-3,3'-pyrrolidin]-1'-yl)pyridazin-3-yl]-1,2,4-oxadiazol-3-yl}acetate 6-(1'H-Spiro[1-benzofuran-3,3'-pyrrolidin]-1'-yl)pyridazine-3-carboxylic acid (600 mg) obtained in Example 157(2) was dissolved in N,N-dimethylformamide (5 mL) and 1,1'-carbonylbis(1H-imidazole) (360 mg) was added. After stirring at 60° C. for 30 min, the mixture was cooled to room temperature, and pyridine (25 mL), tert-butyl 3-amino-3-(hydroxyimino)propanoate (390 mg) obtained by the above-mentioned reaction and molecular sieves 4A (500 mg) were added. After stirring at 140° C. overnight, the mixture was cooled to room temperature, and the insoluble material was removed by filtration. The filtrate was diluted with ethyl acetate, and washed with saturated aqueous sodium hydrogen carbonate solution, and the organic layer was dried over sodium sulfate. The solvent was evaporated under reduced pressure, and purified by silica gel column chromatography to give the object product (230 mg, 26%).

$^1$H NMR (300 MHz, DMSO-d$_6$) δ ppm 1.43 (s, 9H) 2.22-2.43 (m, 2H) 3.62-4.20 (m, 6H) 4.52 (d, J=18.55 Hz, 2H) 6.85 (d, J=7.95 Hz, 1H) 6.91 (t, J=7.38 Hz, 1H) 7.10 (d, J=9.84 Hz, 1H) 7.15-7.24 (m, 1H) 7.34 (d, J=7.19 Hz, 1H) 8.04 (d, J=9.47 Hz, 1H)

(3) {5-[6-(1'H-spiro[1-benzofuran-3,3'-pyrrolidin]-1'-yl)pyridazin-3-yl]-1,2,4-oxadiazol-3-yl}acetic acid tert-Butyl {5-[6-(1'H-spiro[1-benzofuran-3,3'-pyrrolidin]-1'-yl)pyridazin-3-yl]-1,2,4-oxadiazol-3-yl}acetate (200 mg) obtained by the above-mentioned reaction was dissolved in ethyl acetate-acetic acid (1:1, v/v, 10 mL), and hydrochloric acid (4N, ethyl acetate solution, 2 mL) was added. After stirring at 60° C. for 3 hr, the reaction system was ice-cooled, and the resulting precipitate was collected by filtration to give the object product (170 mg, 98%).

$^1$H NMR (300 MHz, DMSO-d$_6$) δ ppm 2.22-2.44 (m, 2H) 3.63-4.12 (m, 6H) 4.52 (s, 2H) 6.85 (d, J=8.33 Hz, 1H) 6.92 (t, J=7.38 Hz, 1H) 7.13-7.25 (m, 2H) 7.35 (d, J=6.44 Hz, 1H) 8.08 (d, J=9.47 Hz, 1H)

Example 170

1'-[6-(3-methyl-1,2,4-oxadiazol-5-yl)pyridazin-3-yl]-3H-spiro[1-benzofuran-2,3'-pyrrolidine]

A mixture of 3-chloro-6-(3-methyl-1,2,4-oxadiazol-5-yl)pyridazine (39 mg) obtained in Example 43(2), 3H-spiro[1-benzofuran-2,3'-pyrrolidine] hydrochloride (42 mg) and potassium carbonate (55 mg) was stirred in DMF (5 mL) at 120° C. overnight. After cooling to room temperature, water was added, and the mixture was extracted with ethyl acetate. The organic layer was washed with saturated brine, and dried over magnesium sulfate. The desiccant was filtered off, and the filtrate was concentrated. The residue was washed with a small amount of acetic acid to give the object product (35 mg, 52%).

$^1$H NMR (300 MHz, DMSO-d$_6$) δ ppm 2.22-2.46 (m, 6H) 3.34-3.51 (m, 2H) 3.65-3.85 (m, 2H) 6.77 (d, J=8.0 Hz, 1H), 6.87 (t, J=7.2 Hz, 1H), 7.03-7.16 (m, 2H), 7.27 (d, J=7.2 Hz, 1H)

Example 171

1-methyl-1'-[6-(3-methyl-1,2,4-oxadiazol-5-yl)pyridazin-3-yl]spiro[indole-3,4'-piperidin]-2(1H)-one The object product (40 mg, 53%) was obtained in the same manner as in Example 1 and using 3-chloro-6-(3-methyl-1,2,4-oxadiazol-5-yl)pyridazine (39 mg) obtained in Example 43(2), 1-methylspiro[indole-3,4'-piperidin]-2(1H)-one hydrochloride (51 mg) and potassium carbonate (55 mg).

$^1$H NMR (300 MHz, DMSO-d$_6$) δ ppm 1.80-1.95 (m, 4H) 2.45 (s, 3H), 3.16 (s, 3H), 4.10-4.30 (m, 4H) 7.06 (d, J=7.5 Hz, 2H), 7.32 (t, J=7.3 Hz, 1H), 7.46-7.58 (m, 2H), 8.03 (d, J=9.4 Hz, 1H)

Example 172

8-[6-(3-methyl-1,2,4-oxadiazol-5-yl)pyridazin-3-yl]-2-phenyl-2,8-diazaspiro[4.5]decan-3-one The object product (142 mg, 64%) was obtained in the same manner as in Example 1 and using 3-chloro-6-(3-methyl-1,2,4-oxadiazol-5-yl)pyridazine (111 mg) obtained in Example 43(2), 2-phenyl-2,8-diazaspiro[4.5]decan-3-one hydrochloride (150 mg) and potassium carbonate (155 mg).

$^1$H NMR (300 MHz, CDCl$_3$) δ ppm 1.80-1.94 (m, 3H) 2.50 (s, 3H) 2.65 (s, 2H) 3.63-3.80 (m, 4H) 4.07 (dt, J=14.08, 5.20 Hz, 2H) 7.00 (d, J=9.80 Hz, 1H) 7.18 (t, J=7.35 Hz, 1H) 7.39 (t, J=8.01 Hz, 2H) 7.61 (dd, J=1.13, 8.67 Hz, 2H) 7.96 (d, J=9.61 Hz, 1H)

Example 173

1'-[6-(3-methyl-1,2,4-oxadiazol-5-yl)pyridazin-3-yl]-3H-spiro[1-benzofuran-2,4'-piperidin]-3-one The object product (163 mg, 72%) was obtained in the same manner as in Example 1 and using 3-chloro-6-(3-methyl-1,2,4-oxadiazol-5-yl)pyridazine (123 mg) obtained in Example 43(2), 3H-spiro[1-benzofuran-2,4'-piperidin]-3-one hydrochloride (150 mg) and potassium carbonate (173 mg).

$^1$H NMR (300 MHz, CDCl$_3$) δ ppm 1.79 (d, J=12.87 Hz, 2H) 2.12 (td, J=13.06, 4.92 Hz, 2H) 2.51 (s, 3H) 3.58-3.74 (m, 2H) 4.65 (d, J=13.63 Hz, 2H) 7.03 (d, J=9.47 Hz, 1H) 7.08-7.21 (m, 2H) 7.70 (d, J=7.57 Hz, 2H) 7.99 (d, J=9.47 Hz, 1H)

Example 174

1'-[6-(3-methyl-1,2,4-oxadiazol-5-yl)pyridazin-3-yl]spiro[indene-2,4'-piperidin]-1(3H)-one The object product (173 mg, 76%) was obtained in the same manner as in Example 1 and using 3-chloro-6-(3-methyl-1,2,4-oxadiazol-5-yl)pyridazine (124 mg) obtained in Example 43(2), spiro[indene-2,4'-piperidin]-1(3H)-one hydrochloride (150 mg) and potassium carbonate (174 mg).

$^1$H NMR (300 MHz, CDCl$_3$) δ ppm 1.62 (d, J=13.63 Hz, 2H) 2.06 (dd, J=3.98, 11.17 Hz, 2H) 2.50 (s, 3H) 3.19 (s, 2H) 3.49 (ddd, J=3.03, 10.89, 13.73 Hz, 2H) 4.57 (dt, J=13.63, 4.16 Hz, 2H) 7.00 (d, J=9.84 Hz, 1H) 7.42 (t, J=7.57 Hz, 1H) 7.50 (d, J=7.95 Hz, 1H) 7.65 (t, J=6.82 Hz, 1H) 7.80 (d, J=7.95 Hz, 1H) 7.96 (d, J=9.84 Hz, 1H)

Example 175

1'-[6-(3-methyl-1,2,4-oxadiazol-5-yl)pyridazin-3-yl]-5-(trifluoromethyl)spiro[1-benzofuran-3,3'-pyrrolidine]

(1) 1-benzyl-3-{[2-bromo-4-(trifluoromethyl)phenoxy]methyl}-2,5-dihydro-1H-pyrrole (1-Benzyl-2,5-dihydro-1H-pyrrol-3-yl)methanol (14.0 g) obtained in Example 50(2), 2-bromo-4-trifluoromethylphenol (19.0 g), DEAD (13.5 g) and triphenylphosphine (23.3 g) were dissolved in tetrahydrofuran (450 mL). The reaction solution was stirred under a nitrogen atmosphere at 50° C. overnight. Tetrahydrofuran was evaporated under reduced pressure, and the residue was purified by silica gel column (20% diethyl ether/petroleum ether to 33% diethyl ether/petroleum ether) to give the object product as a pale-yellow oil (10 g, 33%).

$^1$H NMR (300 MHz, CDCl$_3$): δ ppm 3.57-3.62 (m, 4H), 3.85 (s, 2H), 4.68 (s, 2H), 5.85-5.87 (m, 1H), 6.92 (d, J=8.1 Hz, 1H), 7.02-7.05 (m, 1H), 7.27-7.37 (m, 6H)

(2) 1'-benzyl-5-(trifluoromethyl)spiro[1-benzofuran-3,3'-pyrrolidine]

1-Benzyl-3-{[2-bromo-4-(trifluoromethyl)phenoxy]methyl}-2,5-dihydro-1H-pyrrole (10 g) obtained by the above-mentioned reaction and tributyltin hydride (28.3 g) were dissolved in toluene (600 mL), and the solution was stirred under reflux for 30 min, and cooled to room temperature. AIBN (797 mg) was added, and the mixture was heated under reflux under a nitrogen atmosphere overnight. Toluene was evaporated under reduced pressure, diethyl ether and aqueous saturated potassium fluoride solution were added to the residue and the mixture was stirred at room temperature for 4 hr. The aqueous layer was separated, and extracted with diethyl ether. The organic layer was dried over sodium sulfate. The desiccant was filtered off, and the filtrate was concentrated. The residue was purified by silica gel column (95% ethyl acetate/hexane) to give the object product as a pale-yellow oil (4.2 g, 51.8%).

$^1$H NMR (300 MHz, CDCl$_3$): δ ppm 2.04-2.12 (m, 1H), 2.21-2.30 (m, 1H), 2.56 (d, J=9.3 Hz, 1H), 2.60-2.75 (m, 1H), 2.79 (d, J=9.3 Hz, 1H), 2.84-2.92 (m, 1H), 3.63 (d, J=13.2 Hz, 1H), 3.70 (d, J=13.2 Hz, 1H), 4.41 (d, J=9 Hz, 1H), 4.57 (d, J=9 Hz, 1H), 6.79-6.85 (m, 1H), 7.24-7.41 (m, 6H), 7.47-7.50 (m, 1H)

(3) 5-(trifluoromethyl)spiro[1-benzofuran-3,3'-pyrrolidine]

A solution of 1'-benzyl-5-(trifluoromethyl)spiro[1-benzofuran-3,3'-pyrrolidine] (4.2 g) obtained by the above-mentioned reaction and 10% palladium carbon (1 g) in methanol (150 mL) was stirred under reflux overnight under a hydrogen atmosphere. The catalyst was removed using celite, and the filtrate was concentrated. The residue was added to 4N hydrochloric acid (ethyl acetate solution), and the precipitate was collected by filtration to give the object product as a white solid (2.46 g, 70%).

$^1$H NMR (300 MHz, DMSO-d$_6$): δ ppm 2.24-2.29 (m, 2H), 3.27-3.33 (m, 1H), 3.42-3.51 (m, 3H), 4.58 (d, J=9.3 Hz, 1H), 4.68 (d, J=9.3 Hz, 1H), 7.02 (d, J=8.7 Hz, 1H), 7.56-7.60 (m, 1H), 7.90-7.91 (m, 1H), 9.66 (brs, 2H)

(4) 1'-[6-(3-methyl-1,2,4-oxadiazol-5-yl)pyridazin-3-yl]-5-(trifluoromethyl)spiro[1-benzofuran-3,3'-pyrrolidine]

The object product (154 mg, 54%) was obtained in the same manner as in Example 1 and using 5-(trifluoromethyl)spiro[1-benzofuran-3,3'-pyrrolidine] (200 mg) obtained by the above-mentioned reaction, 3-chloro-6-(3-methyl-1,2,4-oxadiazol-5-yl)pyridazine (141 mg) obtained in Example 43(2) and potassium carbonate (198 mg).

$^1$H NMR (300 MHz, DMSO-d$_6$) δ ppm 2.34 (d, J=2.83 Hz, 5H) 3.55-4.14 (m, 4H) 4.65 (s, 2H) 7.08 (dd, J=9.04, 15.82 Hz, 2H) 7.59 (d, J=8.48 Hz, 1H) 7.79 (s, 1H) 8.04 (d, J=9.61 Hz, 1H)

Example 176

1'-[6-(3-methyl-1,2,4-oxadiazol-5-yl)pyridazin-3-yl]-6-(trifluoromethyl)spiro[1-benzofuran-3,3'-pyrrolidine]

(1) 1-benzyl-3-{[2-bromo-5-(trifluoromethyl)phenoxy]methyl}-2,5-dihydro-1H-pyrrole (1-Benzyl-2,5-dihydro-1H-pyrrol-3-yl)methanol (11.44 g) obtained in Example 50(2), 2-bromo-5-trifluoromethylphenol (16.04 g), DEAD (40% toluene solution, 11.06 mL) and triphenylphosphine (18.95 g) were dissolved in tetrahydrofuran (450 mL). The reaction solution was stirred at 50° C. overnight. Tetrahydrofuran was evaporated under reduced pressure, and the residue was purified by silica gel column (10% ethyl acetate/petroleum ether to 20% ethyl acetate/petroleum ether) to give the object product as a white solid (12.3 g, 49%).

$^1$H NMR (300 MHz, DMSO-d$_6$) δ ppm 3.46 (s, 4H) 3.76 (s, 2H) 4.71 (s, 2H) 5.84 (s, 1H) 6.84-6.93 (m, 1H) 7.12 (d, J=7.19 Hz, 1H) 7.17-7.37 (m, 6H) 7.57 (dd, J=1.51, 7.95 Hz, 1H)

(2) 1'-benzyl-6-(trifluoromethyl)spiro[1-benzofuran-3,3'-pyrrolidine]

1-Benzyl-3-{[2-bromo-5-(trifluoromethyl)phenoxy]methyl}-2,5-dihydro-1H-pyrrole (12.3 g) obtained by the abovementioned reaction, AIBN (980 mg) and tributyltin hydride (34.75 g) were dissolved in toluene (600 mL), and the solution was stirred under reflux overnight. Toluene was evaporated under reduced pressure, and ether and aqueous saturated potassium fluoride solution were added to the residue and the mixture was stirred at room temperature for 4 hr. The aqueous layer was separated, and extracted with ether. The organic layer was dried over sodium sulfate. The desiccant was filtered off, and the filtrate was concentrated. The residue was purified by silica gel column (20% ethyl acetate/hexane) to give the object product as a pale-yellow oil (5.18 g, 52%).

$^1$H NMR (300 MHz, CDCl$_3$) δ ppm 2.05-2.11 (m, 1H), 2.21-2.28 (m, 1H), 2.58 (d, J=9.3 Hz, 1H), 2.66-2.74 (m, 1H), 2.77 (d, J=9.3 Hz, 1H), 2.79-2.86 (m, 1H), 3.62 (d, J=6.9 Hz, 1H), 3.69 (d, J=6.9 Hz, 1H), 4.40 (d, J=9.0 Hz, 1H), 4.55 (d, J=9.0 Hz, 1H), 6.98 (s, 1H), 7.15-7.18 (m, 1H), 7.25-7.35 (m, 6H)

(3) 6-(trifluoromethyl)spiro[1-benzofuran-3,3'-pyrrolidine]hydrochloride

A solution of 1'-benzyl-6-(trifluoromethyl)spiro[1-benzofuran-3,3'-pyrrolidine] (5.18 g) obtained by the above-mentioned reaction, and 5% palladium carbon (1 g) in methanol (150 mL) was stirred under reflux overnight. The catalyst was removed using celite, and the filtrate was concentrated. The residue was added to 4N hydrochloric acid (ethyl acetate solution), and the precipitate was collected by filtration to give the object product as a white solid (1.62 g, 43%).

$^1$H NMR (300 MHz, DMSO-d$_6$) δ ppm 2.21-2.28 (m, 2H), 3.27-3.52 (m, 4H), 4.57 (d, J=6.3 Hz, 1H), 4.65 (d, J=6.3 Hz, 1H), 7.19 (m, 1H), 7.32 (d, J=7.8 Hz, 1H), 7.68 (d, J=7.8 Hz, 1H), 9.62 (brs, 2H)

(4) 1'-[6-(3-methyl-1,2,4-oxadiazol-5-yl)pyridazin-3-yl]-6-(trifluoromethyl)spiro[1-benzofuran-3,3'-pyrrolidine]

The object product (184 mg, 64%) was obtained in the same manner as in Example 1 and using 6-(trifluoromethyl)spiro[1-benzofuran-3,3'-pyrrolidine] hydrochloride (200 mg) obtained by the above-mentioned reaction, 3-chloro-6-(3-methyl-1,2,4-oxadiazol-5-yl)pyridazine (141 mg) obtained in Example 43(2) and potassium carbonate (198 mg).

$^1$H NMR (300 MHz, DMSO-d$_6$) δ ppm 2.28-2.47 (m, 5H) 3.63-4.12 (m, 4H) 4.64 (s, 2H) 7.10 (d, J=9.47 Hz, 1H) 7.21 (s, 1H) 7.28 (d, J=7.57 Hz, 1H) 7.56 (d, J=7.57 Hz, 1H) 8.04 (d, J=9.47 Hz, 1H)

Example 177 optically active form of 1'-[6-(3-methyl-1,2,4-oxadiazol-5-yl)pyridazin-3-yl]-3H-spiro[2-benzofuran-1,3'-pyrrolidine]

(1) tert-butyl 1'H,3H-spiro[2-benzofuran-1,3'-pyrrolidine]-1'-carboxylate in an optically active form tert-Butyl 1'H,3H-spiro[2-benzofuran-1,3'-pyrrolidine]-1'-carboxylate (racemate) (24 g) obtained in Example 43(4) was optically resolved by HPLC under the following conditions to give two kinds of optically active forms having "short retention time (11.3 g)" and "long retention time (11.5 g)". specific optical rotation of "short retention time": $[α]_D^{20}$+15.8° (c 0.4910, methanol).

specific optical rotation of "long retention time": $[α]_D^{20}$–15.5° (c 0.4890, methanol).

<Preparative HPLC Conditions>
column: CHIRALPAK IC(LF001) (50 mmID×500 mL)
mobile phase: hexane:2-propanol=3:1
flow rate: 60 mL/min
column temperature: 35° C.
detection: UV 220 nm
compound injection volume: 2000 mg/120 mL (hexane:2-propanol=3:1)<
HPLC Analysis Conditions>
column: CHIRALPAK IC(LF009) (4.6 mmID×250 mmL)
mobile phase: hexane:propanol=3:1
flow rate: 0.7 mL/min
column temperature: 35° C.
detection: UV 220 nm
retention time of "short retention time": 10.344 min
retention time of "long retention time": 14.657 min (2) 3H-spiro[2-benzofuran-1,3'-pyrrolidine] hydrochloride in an optically active form tert-Butyl 1'H,3H-spiro[2-benzofuran-1,3'-pyrrolidine]-1'-carboxylate in an optically active form (short retention time) (3.0 g) obtained by the above-mentioned reaction was dissolved in 4N hydrochloric acid-ethyl acetate, and the solution was stirred at room temperature for 3 hr. The solution was concentrated, and the concentrate was dissolved in ethyl acetate. The precipitated crystals were collected by filtration, and washed with ethyl acetate to give the object product (2.0 g, 87%). This compound was used for the next reaction without purification.

(3) 1'-[6-(3-methyl-1,2,4-oxadiazol-5-yl)pyridazin-3-yl]-3H-spiro[2-benzofuran-1,3'-pyrrolidine] in an optically active form The object product (213 mg) was obtained in the same manner as in Example 1 and using 3H-spiro[2-benzofuran-1,3'-pyrrolidine] hydrochloride in an optically active form (short retention time, 200 mg) obtained by the above-mentioned reaction, 3-chloro-6-(3-methyl-1,2,4-oxadiazol-5-yl)pyridazine (186 mg) obtained in Example 43(2) and potassium carbonate (261 mg).
specific optical rotation: $[α]_D^{20}$–35.6° (c 0.4760, methanol)

$^1$H NMR (300 MHz, DMSO-d$_6$) δ ppm 2.43 (m, 5H) 3.66-3.90 (m, 4H) 5.07 (s, 2H) 7.11 (brs, 1H) 7.37 (d, J=2.83 Hz, 3H) 7.49 (dd, J=2.35, 4.99 Hz, 1H) 8.02 (d, J=9.42 Hz, 1H)

Example 178 optically active form of 1'-[6-(3-methyl-1,2,4-oxadiazol-5-yl)pyridazin-3-yl]-3H-spiro[2-benzofuran-1,3'-pyrrolidine]

The object product (193 mg) was obtained in the same manner as in Example 1 and using 3H-spiro[2-benzofuran-1,3'-pyrrolidine] hydrochloride in an optically active form (long retention time, 200 mg) obtained in Example 177(2), 3-chloro-6-(3-methyl-1,2,4-oxadiazol-5-yl)pyridazine (186 mg) obtained in Example 43(2) and potassium carbonate (261 mg).
specific optical rotation: $[α]_D^{20}$+34.6° (c 0.4690, methanol)

$^1$H NMR (300 MHz, CDCl$_3$) δ ppm 2.45 (d, J=7.54 Hz, 2H) 2.49 (s, 3H) 3.86 (brs, 4H) 5.16 (s, 2H) 6.71 (d, J=9.42 Hz, 1H) 7.08-7.52 (m, 4H) 7.95 (d, J=9.42 Hz, 1H)

Example 179 optically active form of 1'-[6-(3-methyl-1,2,4-oxadiazol-5-yl)pyridazin-3-yl]spiro[1-benzofuran-3,3'-pyrrolidine]

1'-[6-(3-Methyl-1,2,4-oxadiazol-5-yl)pyridazin-3-yl]spiro[1-benzofuran-3,3'-pyrrolidine] (racemate) (190 mg) obtained in Example 51 was optically resolved by HPLC under the following conditions to give two kinds of optically active forms having "short retention time (94 mg)" and "long retention time (94 mg)".
specific optical rotation of "short retention time": $[\alpha]_D^{25}$+34.4° (c 0.4695, N,N-dimethyl sulfoxide).
specific optical rotation of "long retention time": $[\alpha]_D^{25}$−19.7° (c 0.4800, N,N-dimethyl sulfoxide).
<Preparative HPLC Conditions>
column: CHIRALPAK IC(LF001) (50 mmID×500 mL)
mobile phase: hexane:ethanol=1:4
flow rate: 40 mL/min
column temperature: 30° C.
detection: UV 220 nm
compound injection volume: 0.1 mg/mL (hexane:ethanol=1:4)
<HPLC Analysis Conditions>
column: CHIRALPAK IC(LF009) (4.6 mmID×250 mL)
mobile phase: ethanol
flow rate: 0.4 mL/min
column temperature: 30° C.
detection: UV 220 nm
retention time of "short retention time": 37.212 min
retention time of "long retention time": 41.739 min

Example 180 optically active form of N-(3-phenylpropyl)-6-(1'H,3H-spiro[2-benzofuran-1,3'-pyrrolidin]-1'-yl)pyridazine-3-carboxamide (1) methyl 6-(1'H,3H-spiro[2-benzofuran-1,3'-pyrrolidin]-1'-yl)pyridazine-3-carboxylate in an optically active form 3H-Spiro[2-benzofuran-1,3'-pyrrolidine] hydrochloride (1.0 g, 4.72 mmol) in an optically active form obtained in Example 177(2), methyl 6-chloropyridazine-3-carboxylate (0.815 g, 4.72 mmol) and potassium carbonate (1.436 g, 10.39 mmol) were dissolved in N,N-dimethylformamide solution (50 mL), and the solution was stirred at 90° C. overnight. After cooling to room temperature, water was added, and the precipitated solid was collected by filtration and washed with water to give the object product (1.01 g, 68.7%). This compound was used for the next reaction without purification.

(2) 6-(1'H,3H-spiro[2-benzofuran-1,3'-pyrrolidin]-1'-yl)pyridazine-3-carboxylic acid in an optically active form Methyl 6-(1'H,3H-spiro[2-benzofuran-1,3'-pyrrolidin]-1'-yl)pyridazine-3-carboxylate (1.01 g) in an optically active form obtained by the above-mentioned reaction was dissolved in methanol solution (10 mL), tetrahydrofuran solution (10 mL) and 8N aqueous sodium hydroxide solution (10 mL), and the reaction solution was stirred at room temperature for 2 hr. The solvent was evaporated under reduced pressure and neutralized with hydrochloric acid. The precipitated crystals were collected by filtration, and washed with water to give the object product (1.01 g). This compound was used for the next reaction without purification.

(3) N-(3-phenylpropyl)-6-(1'H,3H-spiro[2-benzofuran-1,3'-pyrrolidin]-1'-yl)pyridazine-3-carboxamide in an optically active form 6-(1'H,3H-Spiro[2-benzofuran-1,3'-pyrrolidin]-1'-yl)pyridazine-3-carboxylic acid (100 mg) in an optically active form obtained by the above-mentioned reaction, 3-phenylpropylamine (45.5 mg), triethylamine (40.8 mg) and 2-(1H-benzotriazol-1-yl)-1,1,3,3-tetramethyluroniume trafluoroborate (130 mg) were dissolved in N,N-dimethylformamide solution, and the solution was stirred at room temperature overnight. To the reaction solution was added water, and the mixture was extracted with ethyl acetate. The organic layer was washed with saturated sodium hydrogen carbonate and brine, and dried over sodium sulfate. The desiccant was filtered off, and the filtrate was concentrated. The residue was purified by silica gel chromatography to give the object product (107 mg).
specific optical rotation: $[\alpha]_D^{20}$+18.8° (c 0.4915, methanol)
$^1$H NMR (300 MHz, CDCl$_3$) δ ppm 1.95 (qd, J=7.44, 7.25 Hz, 2H) 2.31-2.49 (m, 2H) 2.71 (d, J=8.10 Hz, 2H) 3.51 (q, J=6.91 Hz, 2H) 3.72-4.07 (m, 4H) 5.15 (s, 2H) 6.72 (d, J=9.42 Hz, 1H) 7.11-7.42 (m, 9H) 7.93-8.07 (m, 2H)

Example 181 optically active form of N-(2-oxo-2-phenylethyl)-6-(1'H,3H-spiro[2-benzofuran-1,3'-pyrrolidin]-1'-yl)pyridazine-3-carboxamide The object product (46 mg) was obtained in the same manner as in Example 180(3) and using 6-(1'H,3H-spiro[2-benzofuran-1,3'-pyrrolidin]-1'-yl)pyridazine-3-carboxylic acid (100 mg) in an optically active form obtained in Example 180(2) and 2-amino-1-phenylethanone (46.1 mg).
specific optical rotation: $[\alpha]_D^{20}$+18.1° (c 0.4785, methanol)
$^1$H NMR (300 MHz, CDCl$_3$) δ ppm 2.37-2.50 (m, 2H) 3.67-4.17 (m, 4H) 4.99 (d, J=4.90 Hz, 2H) 5.16 (s, 2H) 6.72 (d, J=9.42 Hz, 1H) 7.26 (s, 2H) 7.33-7.40 (m, 2H) 7.46-7.56 (m, 2H) 7.58-7.67 (m, 1H) 8.03 (dd, J=5.09, 8.85 Hz, 3H) 8.56-8.92 (m, 1H)

Example 182 optically active form of N-(2-phenoxyethyl)-6-(1'H,3H-spiro[2-benzofuran-1,3'-pyrrolidin]-1'-yl)pyridazine-3-carboxamide The object product (99 mg) was obtained in the same manner as in Example 180(3) and using 6-(1'H,3H-spiro[2-benzofuran-1,3'-pyrrolidin]-1'-yl)pyridazine-3-carboxylic acid (100 mg) in an optically active form obtained in Example 180(2) and 2-phenoxyethanamine (46.1 mg).
specific optical rotation: $[\alpha]_D^{20}$+20.7° (c 0.4610, methanol)
$^1$H NMR (300 MHz, CDCl$_3$) δ ppm 1.73 (s, 1H) 2.29-2.47 (m, 2H) 2.80 (s, 1H) 3.71-4.05 (m, 5H) 4.13 (q, J=5.09 Hz, 2H) 5.15 (s, 2H) 6.71 (d, J=9.42 Hz, 1H) 6.85-6.99 (m, 3H) 7.17-7.42 (m, 6H) 8.01 (d, J=9.42 Hz, 1H) 8.34 (t, J=5.84 Hz, 1H)

Example 183 optically active form of N-(3-phenylpropyl)-6-(1'H, 3H-spiro[2-benzofuran-1,3'-pyrrolidin]-1'-yl)pyridazine-3-carboxamide (1) 3H-spiro[2-benzofuran-1,3'-pyrrolidine] hydrochloride in an optically active form The object product (2.1 g) was obtained in the same manner as in Example 180(2) and using tert-butyl 1'H,3H-spiro[2-benzofuran-1,3'-pyrrolidine]-1'-carboxylate in an optically active form (long retention time, 3.0 g) obtained in Example 177(1). The compound was used for the next reaction without purification.

(2) N-(3-phenylpropyl)-6-(1'H,3H-spiro[2-benzofuran-1,3'-pyrrolidin]-1'-yl)pyridazine-3-carboxamide in an optically active form The object product (104 mg) was obtained in the same manner as in Example 180(3) and using 3H-spiro[2-benzofuran-1,3'-pyrrolidine] hydrochloride in an optically active form (100 mg) obtained by the above-mentioned reaction and 3-phenylpropylamine (45.5 mg).
specific optical rotation: $[\alpha]_D^{20}$ –22.8° (c 0.4575, methanol)
$^1$H NMR (300 MHz, CDCl$_3$) δ ppm 1.69 (brs., 1H) 1.96 (qd, J=7.44, 7.25 Hz, 2H) 2.29-2.48 (m, 2H) 2.71 (d, J=8.10 Hz, 2H) 3.51 (q, J=6.84 Hz, 2H) 3.64-4.08 (m, 4H) 5.15 (s, 2H) 6.72 (d, J=9.42 Hz, 1H) 7.02-7.44 (m, 8H) 8.02 (d, J=9.23 Hz, 2H)

Example 184 optically active form of N-(2-oxo-2-phenoxyethyl)-6-(1'H,3H-spiro[2-benzofuran-1,3'-pyrrolidin]-1'-yl)pyridazine-3-carboxamide The object product (83 mg) was obtained in the same manner as in Example 180(3) and using 3H-spiro[2-benzofuran-1,3'-pyrrolidine] hydrochloride in an optically active form (100 mg) obtained in Example 183(1) and 2-amino-1-phenylethanone (46.1 mg).
specific optical rotation: $[\alpha]_D^{20}$ –24.4° (c 0.4865, methanol)
$^1$H NMR (300 MHz, CDCl$_3$) δ ppm 2.30-2.49 (m, 2H) 3.82 (d, J=11.68 Hz, 4H) 4.98 (d, J=4.71 Hz, 2H) 5.16 (s, 2H) 6.72 (d, J=9.23 Hz, 1H) 7.19-7.32 (m, 2H) 7.33-7.40 (m, 2H) 7.44-7.56 (m, 2H) 7.57-7.66 (m, 1H) 8.03 (dd, J=5.09, 9.04 Hz, 3H) 8.77 (t, J=4.52 Hz, 1H)

Example 185 optically active form of N-(2-phenoxyethyl)-6-(1'H, 3H-spiro[2-benzofuran-1,3'-pyrrolidin]-1'-yl)pyridazine-3-carboxamide The object product (109 mg) was obtained in the same manner as in Example 180(3) and using 3H-spiro[2-benzofuran-1,3'-pyrrolidine] hydrochloride in an optically active form (100 mg) obtained in Example 183(1) and 2-phenoxyethanamine (46.1 mg).
specific optical rotation: $[\alpha]_D^{20}$ –21.5° (c 0.4730, methanol)
$^1$H NMR (300 MHz, CDCl$_3$) δ ppm 2.32-2.47 (m, 2H) 3.72-3.94 (m, 4H) 4.07-4.19 (m, 3H) 5.15 (s, 2H) 6.71 (d, J=9.42 Hz, 1H) 6.86-7.00 (m, 3H) 7.17-7.42 (m, 7H) 8.01 (d, J=9.42 Hz, 1H) 8.34 (t, J=5.84 Hz, 1H)

Experimental Example 1

Measurement of SCD Inhibitory Activity (test compounds)
(1) compound of Example 2
(2) compound of Example 4
(3) compound of Example 5
(4) compound of Example 6
(5) compound of Example 11
(6) compound of Example 15
(7) compound of Example 17
(8) compound of Example 20
(9) compound of Example 29
(10) compound of Example 31
(11) compound of Example 32
(12) compound of Example 43
(13) compound of Example 47
(14) compound of Example 50
(15) compound of Example 51
(16) compound of Example 55
(17) compound of Example 60
(18) compound of Example 74
(19) compound of Example 86
(20) compound of Example 126
(21) compound of Example 143
(22) compound of Example 146
(23) compound of Example 148
(24) compound of Example 150
(25) compound of Example 156
(26) compound of Example 157
(27) compound of Example 159
(28) compound of Example 170
(29) compound of Example 177
(30) compound of Example 178
(31) compound of Example 179
(Test Method: Measurement of SCD Inhibitory Activity Using Microsome (TLC Detection System))

A test compound (10 mM) diluted with DMSO in advance was secondarily diluted to 3/1000 with 3× buffer (300 mmol/L NaH$_2$PO$_4$ [pH 7.4], 450 mM KCl, 30 mM NaF, 9 mM MgCl$_2$, 4.5 mM glutathione [reduced form], 0.3% BSA [fatty acid free, SIGMA]). The test compound (10 μL) diluted with the assay buffer was dispensed to a PP 96-deep well block, and a microsome fraction (10 μL) diluted with a microsome buffer was added thereto. The enzyme reaction was started by the addition of 10 μL of [$^{14}$C] stearoyl-CoA (American Radiolabeled Chemicals [ARC], Inc.) diluted to 10 μCi/mL with 9 mmol/L NADH. For evaluation of the compound, an enzyme reaction using rat liver microsome (20 μg) was performed for 15 min. The reaction was quenched by the addition of 10 μL of 2.5N NaOH, a plate seal was applied, and the reaction mixture was incubated overnight in a dry heater set to 65° C. to allow saponification. Solvent extraction of fatty acid was based on the Bligh&Dyer method (1). Formic acid:methanol:chloroform (1:6:3) (200 μL) was added, the state of single layer was maintained, the mixture was sufficiently stirred, and pure water (120 μL) was added to allow separation into two layers. The lower chloroform layer (10 μL) was spotted on reversed-phase TLC plate (RP-18, 1154230001, Merck Japan, Ltd.) and developed with acetonitrile:pure water:acetic:acid (95:4.5:0.5). The TLC plate was dried and transferred onto an Imaging Plate (Fuji Photo Film Co., Ltd.) for not less than 5 hr. For detection, BAS-5000 (Fuji Photo Film Co., Ltd) was used and the obtained spot images were converted to numerical values using Multi Gauge Ver2.3 (Fuji Photo Film Co., Ltd), based on which the SCD activity inhibitory rate (%) was determined.

(Test Results)

The test results are shown in Table 1. As shown in Table 1, the compound of the present invention has a superior SCD inhibitory action.

TABLE 1

| Example No. | SCD activity inhibitory rate (%) |
|---|---|
| 2 | 99 |
| 4 | 97 |
| 5 | 100 |
| 6 | 95 |
| 11 | 93 |
| 15 | 100 |
| 17 | 100 |
| 20 | 98 |
| 29 | 99 |
| 31 | 92 |
| 32 | 94 |
| 43 | 100 |
| 47 | 93 |
| 50 | 99 |
| 51 | 97 |
| 55 | 99 |
| 60 | 98 |
| 74 | 98 |
| 86 | 100 |
| 126 | 98 |
| 143 | 100 |
| 146 | 97 |
| 148 | 100 |
| 150 | 99 |
| 156 | 100 |
| 157 | 100 |
| 159 | 99 |
| 170 | 100 |
| 177 | 99 |
| 178 | 97 |
| 179 (short retention time) | 100 |
| 179 (long retention time) | 96 |

Experimental Example 2

Antiobesity Action of the Compound of the Present Invention on Diet-Induced Obesity (DIO) Model Mouse Male C57BL/6J mice (6-week-old) were purchased from CLEA Japan, Inc. The mice were divided into two groups, and a high fat diet (Research Diets, Inc.; solid D12451) was given to one group and a general feed for rearing and breeding (CLEA Japan, Inc.; solid CE-2) was given to the other group.

Each group was reared for 4 months under full feeding, and divided into a diet-induced obesity model group and a general feed group using the body weight and plasma triglyceride concentration as indices. 10 mL of a 0.5% methylcellulose suspension of the compound of Example 15 (0.1 mg/kg body weight) was administered to each of the diet-induced obesity model group and the general feed group by gavage for 4 weeks (each group n=7). As a control of the compound, 10 mL of a 0.5% methylcellulose solution was administered to each of the diet-induced obesity model group and the general feed group by gavage for 4 weeks (each group n=7). The body weight of each group was measured during the dosing period.

After the completion of the administration by gavage for 4 weeks, the liver was isolated from each mouse, and homogenized with STE buffer in a 4-fold amount of the wet weight. 600 μL of 0.01% butylated hydroxytoluene containing chloroform:methanol (1:2) solution was added to 200 μL of the liver homogenate, and the mixture was shaken at room temperature for 30 min. 200 μL of chloroform and 200 μL of purified water were added, and the mixture was centrifuged (15,000 rpm, 2 min) and chloroform layer (50 μL) was recovered, dried to solidness under a nitrogen stream, and subjected to the following labeling reaction.

The liver total lipid sample extracted by the above-mentioned procedure was labeled using an ester type fatty acid labeling reagent (YMC). The labeled sample was dissolved in methanol (5 μL) and analyzed using YMC-Pack FA (6.0Φ× 250 mm), $CH_3CN:H_2O:0.1\%$ TFA (850:150:2) as a mobile phase at a flow rate of 1.2 mL/min. The peak area of each fatty acid in the sample was determined as a C18:1/C18:0 ratio from the peak area of each standard product and used as an unsaturation index number which is an index of the enzyme activity of SCD. The results are shown in the following Table 2. The values in the Table show mean (n=7)±standard deviation.

TABLE 2

| group | compound administration | unsaturation index number (mean ± SD) |
|---|---|---|
| general feed group | none | 29.283 ± 0.6882 |
| general feed group | yes | 29.017 ± 1.2254 |
| diet-induced obesity model group | none | 48.114 ± 1.8106 |
| diet-induced obesity model group | yes | 43.886 ± 2.0318 |

The above results show that the compound of the present invention has a superior antiobesity action.

(Formulation Example 1)

An SCD inhibitor or medicament containing compound (I) as an active ingredient (e.g., agent for the prophylaxis or treatment of diabetes, hyperlipidemia (including hypercholesterolemia, high LDL-cholesterolemia, low HDL-cholesterolemia and hypertriglycerid(TG)emia) and the like) can be produced, for example, according to the following formulations.

As the components (additives) other than the active ingredient in the following formulations, the products listed in the Japanese Pharmacopoeia, the Japanese Pharmacopoeia Japanese Pharmaceutical Codex or Japanese Pharmaceutical Excipients and the like can be used.

1. Capsule

| | |
|---|---|
| (1) compound obtained in Example 2 | 10 mg |
| (2) lactose | 90 mg |
| (3) microcrystalline cellulose | 70 mg |
| (4) magnesium stearate | 10 mg |
| 1 capsule | 180 mg |

(1), (2) and (3), and ½ of (4) are blended and granulated. The rest of (4) is added and the total amount is sealed in a gelatin capsule.

2. Tablet

| (1) compound obtained in Example 4 | 10 mg |
|---|---|
| (2) lactose | 35 mg |
| (3) cornstarch | 150 mg |
| (4) microcrystalline cellulose | 30 mg |
| (5) magnesium stearate | 5 mg |
| 1 tablet | 230 mg |

(1), (2) and (3), ⅔ of (4) and ½ of (5) are blended and granulated. The rest of (4) and (5) is added to the granules and the mixture is compression molded into a tablet.

INDUSTRIAL APPLICABILITY

Since compound (I) has an SCD inhibitory action, the compound is highly useful as an agent for the prophylaxis and/or treatment of diabetes, hyperlipidemia (including hypercholesterolemia, high LDL-cholesterolemia, low HDL-cholesterolemia and hypertriglycerid(TG)emia, particularly hypertriglyceridemia) and the like.

CITATION OF RELATED APPLICATION

This application is based on patent application Nos. 27404/2007 and 139645/2007 filed in Japan, the contents of which are hereby incorporated by reference.

The invention claimed is:
1. A compound represented by the formula (I)

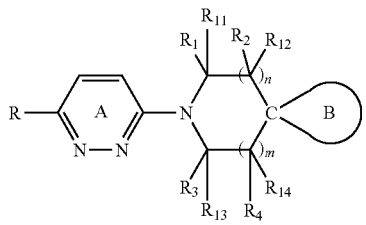

wherein
R is
(1) a cyclic group selected from the group consisting of:
    (i) an alicyclic hydrocarbon group,
    (ii) an aromatic hydrocarbon group,
    (iii) an aromatic heterocyclic group, and
    (iv) a non-aromatic heterocyclic group,
        wherein each of (i) to (iv) is optionally substituted by 1 to 5 substituent(s) selected from the following Substituent Group (a), or
(2) a carbamoyl group optionally substituted by 1 or 2 substituent(s) selected from the group consisting of:
    (i) an optionally substituted hydrocarbon group, and
    (ii) an optionally substituted heterocyclic group,
provided that R is not an optionally substituted 7-pyrido[2,3-d]pyrimidyl group;
ring A is a pyridazine ring optionally substituted by 1 or 2 substituent(s) selected from the following Substituent Group (a);
$R_1$, $R_2$, $R_3$, $R_4$, $R_{11}$, $R_{12}$, $R_{13}$ and $R_{14}$ are each independently
(1) a hydrogen atom,
(2) an optionally substituted hydrocarbon group,
(3) an optionally substituted heterocyclic group,
(4) a hydroxyl group optionally substituted by a substituent selected from the group consisting of:
    (i) an optionally substituted hydrocarbon group,
    (ii) an optionally substituted heterocyclic group, and
    (iii) an acyl group,
(5) an amino group optionally mono- or di-substituted by substituent(s) selected from the group consisting of:
    (i) an optionally substituted hydrocarbon group,
    (ii) an optionally substituted heterocyclic group, and
    (iii) an acyl group,
(6) a mercapto group optionally substituted by a substituent selected from the group consisting of:
    (i) an optionally substituted hydrocarbon group,
    (ii) an optionally substituted heterocyclic group, and
    (iii) an acyl group,
(7) a cyano group,
(8) a nitro group,
(9) an acyl group, or
(10) a halogen atom, or
$R_1$ and $R_{11}$ in combination, $R_2$ and $R_{12}$ in combination, $R_3$ and $R_{13}$ in combination, or $R_4$ and $R_{14}$ in combination optionally form an oxo group, or $R_2$ and $R_4$ in combination optionally form a bond or an alkylene cross-linkage;
m and n are each independently an integer of 0 to 2; and
ring B is a ring selected from the group consisting of:
    (i) a $C_{3-10}$ cycloalkane,
    (ii) a $C_{3-10}$ cycloalkene,
    (iii) a $C_{4-10}$ cycloalkadiene,
    (iv) a 3- to 8-membered saturated or unsaturated non-aromatic heterocycle, and
    (v) a non-aromatic ring selected from the group consisting of a $C_{3-10}$ cycloalkane, a $C_{3-10}$ cycloalkene, a $C_{4-10}$ cycloalkadiene and a 3- to 8-membered saturated or unsaturated non-aromatic heterocycle, wherein the $C_{3-10}$ cycloalkane, the $C_{3-10}$ cycloalkene, the $C_{4-10}$ cycloalkadiene and the 3- to 8-membered saturated or unsaturated non-aromatic heterocycle are each condensed with a benzene ring or a 5- or 6-membered aromatic heterocycle,
    wherein each of (i) to (v) is optionally substituted by 1 to 5 substituent(s) selected from the following Substituent Group (a), and
    provided that the two atoms constituting ring B, which are adjacent to the spiro carbon atom, are not oxygen atoms at the same time,
wherein Substituent Group (a) is:
(1) a halogen atom,
(2) a $C_{1-6}$ alkyl group,
(3) a $C_{3-6}$ cycloalkyl group,
(4) a $C_{2-6}$ alkenyl group,
(5) a $C_{2-6}$ alkynyl group,
(6) a $C_{7-12}$ aralkyl group,
(7) a $C_{6-10}$ aryl group,
(8) a $C_{1-6}$ alkoxy group,
(9) a $C_{6-10}$ aryloxy group,
(10) a formyl group or a $C_{1-6}$ alkyl-carbonyl group,
(11) a $C_{6-10}$ aryl-carbonyl group,
(12) a formyloxy group or a $C_{1-6}$ alkyl-carbonyloxy group,
(13) a $C_{6-10}$ aryl-carbonyloxy group,
(14) a carboxy group,
(15) a $C_{1-6}$ alkoxy-carbonyl group,
(16) a $C_{7-12}$ aralkyloxy-carbonyl group,
(17) a carbamoyl group,
(18) a mono-$C_{1-6}$ alkyl-carbamoyl group,
(19) a di-$C_{1-6}$ alkyl-carbamoyl group,
(20) a mono-, di- or tri-halogeno-$C_{1-6}$ alkyl group,
(21) an oxo group,

(22) an amidino group,
(23) an imino group,
(24) an amino group,
(25) a mono-$C_{1-6}$ alkylamino group,
(26) a di-$C_{1-6}$ alkylamino group,
(27) a 3- to 8-membered aromatic heterocyclic group containing, besides carbon atom(s) and one nitrogen atom, 1 to 3 heteroatom(s) selected from the group consisting of nitrogen atom(s), oxygen atom(s) and sulfur atom(s),
(28) a 3- to 8-membered non-aromatic heterocyclic group containing, besides carbon atom(s) and one nitrogen atom, 1 to 3 heteroatom(s) selected from the group consisting of nitrogen atom(s), oxygen atom(s) and sulfur atom(s),
(29) a $C_{1-3}$ alkylenedioxy group,
(30) a hydroxy group,
(31) a nitro group,
(32) a cyano group,
(33) a mercapto group,
(34) a sulfo group,
(35) a sulfino group,
(36) a phosphono group,
(37) a sulfamoyl group,
(38) a mono-$C_{1-6}$ alkylsulfamoyl group,
(39) a di-$C_{1-6}$ alkylsulfamoyl group,
(40) a $C_{1-6}$ alkylthio group,
(41) a $C_{6-10}$ arylthio group,
(42) a $C_{1-6}$ alkylsulfinyl group,
(43) a $C_{6-10}$ arylsulfinyl group,
(44) a $C_{1-6}$ alkylsulfonyl group, and
(45) a $C_{6-10}$ arylsulfonyl group;
wherein:
(A) all of the "acyl group" recited above are a group represented by a formula selected from the group consisting of —$COR^A$, —CO—$OR^A$, —$SO_3R^A$, —$SO_2R^A$, —$SOR^A$, —CO—$NR^{A'}R^{B'}$, —CS—$NR^{A'}R^{B'}$ and —$SO_2NR^{A'}R^{B'}$,
wherein
$R^A$ is a hydrogen atom, an optionally substituted hydrocarbon group or an optionally substituted heterocyclic group, and
$R^{A'}$ and $R^{B'}$ are the same or different and each is a hydrogen atom, an optionally substituted hydrocarbon group or an optionally substituted heterocyclic group, or
$R^{A'}$ and $R^{B'}$ optionally form, together with the adjacent nitrogen atom, a nitrogen-containing heterocycle optionally substituted by 1 or 2 substituent(s) selected from the Substituent Group (a);
(B) all of the "optionally substituted hydrocarbon group" recited above are a hydrocarbon group selected from the group consisting of:
(1) a $C_{1-10}$ alkyl group,
(2) a $C_{2-10}$ alkenyl group,
(3) a $C_{2-10}$ alkenyl group,
(4) a $C_{3-10}$ cycloalkyl group,
(5) a $C_{3-10}$ cycloalkenyl group,
(6) a $C_{4-10}$ cycloalkadienyl group,
(7) a $C_{6-14}$ aryl group,
(8) a $C_{7-13}$ aralkyl group,
(9) a $C_{8-13}$ arylalkenyl group,
(10) a $C_{4-13}$ cycloalkylalkyl group,
(11) a $C_{5-13}$ cycloalkylalkenyl group,
(12) a $C_{4-13}$ cycloalkenylalkyl group, and
(13) a $C_{5-13}$ cycloalkenylalkenyl group, wherein each of (1) to (13) is optionally substituted by 1 to 5 substituent(s) selected from the Substituent Group (a); and
(C) all of the "optionally substituted heterocyclic group" recited above are a heterocyclic group selected from the group consisting of an aromatic heterocyclic group and a non-aromatic heterocyclic group, wherein each of the aromatic heterocyclic group and the non-aromatic heterocyclic group is optionally substituted by 1 to 5 substituent(s) selected from the Substituent Group (a); or a salt or a prodrug thereof.

2. The compound of claim 1, wherein R is an optionally substituted 5-membered nitrogen-containing aromatic heterocyclic group selected from the group consisting of thiadiazolyl, pyrazolyl, oxadiazolyl and imidazolyl, each of which is optionally substituted by 1 to 5 substituent(s) selected from Substituent Group (a) as defined in claim 1.

3. The compound of claim 1, wherein m and n are each independently 0 or 1.

4. The compound of claim 1, wherein ring B is a ring represented by the formula:

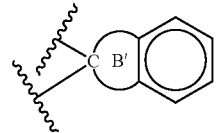

wherein ring B' is a 5- or 6-membered non-aromatic ring selected from the group consisting of a $C_{5-6}$ cycloalkane, a $C_{5-6}$ cycloalkene, a $C_{5-6}$ cycloalkadiene and a 5- or 6-membered saturated or unsaturated non-aromatic heterocycle, and ring B is optionally substituted by 1 to 5 substituents selected from Substituent Group (a) as defined in claim 1.

5. The compound of claim 1, wherein the ring of the optionally substituted ring for ring B is a monocyclic non-aromatic heterocycle selected from the group consisting of a $C_{3-10}$ cycloalkane, a $C_{3-10}$ cycloalkene, a $C_{4-10}$ cycloalkadiene and a 3- to 8-membered saturated or unsaturated non-aromatic heterocycle.

6. The compound of claim 1, wherein $R_1$, $R_2$, $R_3$, $R_4$, $R_{11}$, $R_{12}$, $R_{13}$ and $R_{14}$ are all hydrogen atoms.

7. 1'-[6-(3-methyl-1,2,4-thiadiazol-5-yl)pyridazin-3-yl]spiro[1-benzofuran-3,4'-piperidine],
1'-[6-(3-methyl-1,2,4-oxadiazol-5-yl)pyridazin-3-yl]-3H-spiro[2-benzofuran-1,3'-pyrrolidine],
1'-[6-(3-methyl-1,2,4-oxadiazol-5-yl)pyridazin-3-yl]spiro[1-benzofuran-3,3'-pyrrolidine],
{5-[6-(1'H-Spiro[1-benzofuran-3,4'-piperidin]-1'-yl)pyridazin-3-yl]-1,2,4-oxadiazol-3-yl}methanol,
1'-[6-(4-methyl-4,5-dihydro-1,3-thiazol-2-yl)pyridazin-3-yl]spiro[1-benzofuran-3,4'-piperidine],
{3-[6-(1'H-Spiro[1-benzofuran-3,4'-piperidin]-1'-yl)pyridazin-3-yl]-1,2,4-oxadiazol-5-yl}methanol,
1'-[6-(5-methyl-1,2,4-oxadiazol-3-yl)pyridazin-3-yl]-3H-spiro[2-benzofuran-1,3'-pyrrolidine],
{5-[6-(1'H,3H-spiro[2-benzofuran-1,3'-pyrrolidin]-1'-yl)pyridazin-3-yl]-1,2,4-oxadiazol-3-yl}methanol,
{5-[6-(1'H-Spiro[1-benzofuran-3,3'-pyrrolidin]-1'-yl)pyridazin-3-yl]-1,2,4-oxadiazol-3-yl}methanol,
1-methyl-1'-[6-(3-methyl-1,2,4-oxadiazol-5-yl)pyridazin-3-yl]spiro[indole-3,3'-pyrrolidin]-2(1H)-one, or
1'-[6-(3-methyl-1,2,4-oxadiazol-5-yl)pyridazin-3-yl]-3H-spiro[1-benzofuran-2,3'-pyrrolidine] or a salt thereof.

8. A prodrug of the compound of claim 1.

9. A pharmaceutical composition comprising the compound of claim 1 or a salt thereof or a prodrug thereof, and a pharmaceutically acceptable carrier.

10. A method of inhibiting a SCD in a mammal, which comprises administering the compound of claim 1 or a salt thereof or a prodrug thereof to the mammal.

11. A method for the treatment of obesity in a mammal, which comprises administering the compound of claim 1 or a salt thereof or a prodrug thereof to the mammal.

* * * * *